United States Patent
Mueller et al.

(10) Patent No.: US 7,696,195 B2
(45) Date of Patent: *Apr. 13, 2010

(54) SELECTED CGRP-ANTAGONISTS, PROCESS FOR PREPARING THEM AND THEIR USE AS PHARMACEUTICAL COMPOSITIONS

(75) Inventors: Stephan Georg Mueller, Warthausen (DE); Klaus Rudolf, Warthausen (DE); Philipp Lustenberger, Warthausen (DE); Dirk Stenkamp, Biberach (DE); Marco Santagostino, Magenta (IT); Fabio Paleari, Monza (IT); Gerhard Schaenzle, Biberach (DE); Kirsten Arndt, Biberach (DE); Henri Doods, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 958 days.

This patent is subject to a terminal disclaimer.

(21) Appl. No.: 11/109,968

(22) Filed: Apr. 20, 2005

(65) Prior Publication Data

US 2005/0256099 A1 Nov. 17, 2005

Related U.S. Application Data

(60) Provisional application No. 60/569,533, filed on May 10, 2004.

(30) Foreign Application Priority Data

Apr. 22, 2004 (DE) .................. 10 2004 019 492

(51) Int. Cl.
*A61K 31/554* (2006.01)
*C07D 417/04* (2006.01)

(52) U.S. Cl. .................. 514/221; 514/252.13; 540/500

(58) Field of Classification Search .................. 514/221, 514/252.13; 540/500
See application file for complete search history.

(56) References Cited

U.S. PATENT DOCUMENTS

| | | |
|---|---|---|
| 6,344,449 B1 | 2/2002 | Rudolf et al. |
| 6,521,609 B1 | 2/2003 | Doods et al. |
| 7,205,294 B2 * | 4/2007 | Lustenberger et al. ...... 514/221 |
| 7,439,237 B2 | 10/2008 | Rudolf et al. |
| 7,479,488 B2 | 1/2009 | Mueller et al. |
| 7,491,717 B2 | 2/2009 | Mueller et al. |
| 2004/0192729 A1 | 9/2004 | Rudolf et al. |
| 2005/0227968 A1 | 10/2005 | Lustenberger et al. |
| 2006/0079504 A1 | 4/2006 | Rudolf et al. |
| 2006/0252931 A1* | 11/2006 | Mueller et al. .............. 540/502 |
| 2007/0099903 A1* | 5/2007 | Mueller et al. .............. 514/221 |
| 2007/0244099 A1 | 10/2007 | Rudolf et al. |

FOREIGN PATENT DOCUMENTS

| | | |
|---|---|---|
| WO | 0018764 | 4/2000 |
| WO | 0110425 | 2/2001 |
| WO | 2004037810 A1 | 5/2004 |
| WO | 2004037811 A1 | 5/2004 |
| WO | 2004063171 | 7/2004 |
| WO | 2005084672 A1 | 9/2005 |
| WO | 2005092880 A1 | 10/2005 |
| WO | 2005095383 | 10/2005 |
| WO | 2005100343 A1 | 10/2005 |
| WO | 2006100009 A1 | 9/2006 |
| WO | 2006100026 A1 | 9/2006 |

OTHER PUBLICATIONS

Hoover et al. "Preparation of norstatine . . . " CA 124:87802 (1995).*
Pasternak, A., et al; "Potent, Orally Bioavailable Somatostatin Agonists: Good Absorption Achieved by Urea Backbone Cyclization"; Bioorganic & Medicinal Chemistry Letters, Bd. 9, Nr. 3, Feb. 8, 1999, Seiten 491-496.
Mueller et al.; Selected CGRP-antagonists, process for preparing them and their use as pharmaceutical compositions; U.S. Appl. No. 12/246,067, filed Oct. 6, 2008.
Mueller et al.; New CGRP-antagonists, process for preparing them and their use as pharmaceutical compositions; U.S. Appl. No. 12/363,175, filed Jan. 30, 2009.
Mueller et al.; Selected CGRP-antagonists, process for preparing them and their use as pharmaceutical compositions; U.S. Appl. No. 12/186,005, filed Aug. 5, 2008.

* cited by examiner

*Primary Examiner*—Celia Chang
(74) *Attorney, Agent, or Firm*—Michael P. Morris; Mary-Ellen M. Devlin; Alan R. Stempel

(57) ABSTRACT

The present invention relates to the CGRP antagonists of general formula

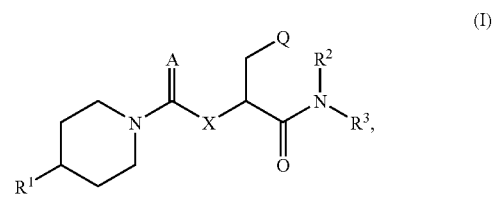

(I)

wherein A, X, Q and $R^1$ to $R^3$ are defined as in claim 1, the tautomers, the isomers, the diastereomers, the enantiomers, the hydrates, mixtures and salts thereof and the hydrates of the salts, particularly the physiologically acceptable salts thereof with inorganic or organic acids, pharmaceutical compositions containing these compounds, their use and processes for preparing them.

15 Claims, No Drawings

SELECTED CGRP-ANTAGONISTS, PROCESS FOR PREPARING THEM AND THEIR USE AS PHARMACEUTICAL COMPOSITIONS

This application claims benefit under 35 USC 119(e) of U.S. Provisional Application Ser. No. US 60/569,533, filed May 10, 2004.

The present invention relates to novel compounds which are CGRP antagonists, their use as medicaments and methods for their preparation.

In its broadest aspect, the invention includes novel compounds of the formula

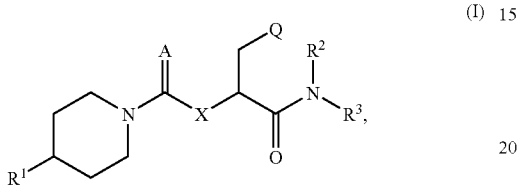

(I)

wherein,

A denotes an oxygen or sulphur atom,

X denotes an oxygen or sulphur atom,

Q denotes a heterocycle bound via a carbon or nitrogen atom consisting of two or three in each case 4- to 8-membered fused rings, saturated, partially unsaturated or totally unsaturated independently of one another, while the heterocycle comprises a total of one to five heteroatoms selected independently of one another from among O, N and S, may contain one or two carbonyl groups as ring members and each saturated nitrogen atom as a ring member of the heterocycle may be substituted by the group $R^a$ and one or two carbon atoms as ring members of the heterocycle may be substituted by the group $R^b$, $R^1$ denotes a saturated, mono- or diunsaturated 5- to 7-membered aza, diaza, triaza, oxaza, thiaza, thiadiaza or S,S-dioxido-thiadiaza heterocycle, while the above-mentioned heterocycles are linked to the piperidine ring in formula I by a carbon or nitrogen atom or are spirocyclically linked to the piperidine ring in formula I by two carbon atoms, by a carbon and a nitrogen atom, by a carbon and an oxygen atom or by a carbon and a sulphur atom, contain one or two carbonyl or thiocarbonyl groups adjacent to a nitrogen atom, may be substituted at one of the nitrogen atoms by a $C_{1-6}$-alkyl, $C_{3-6}$-alkenyl or $C_{3-6}$-alkenyl group, may be substituted at one or at two carbon atoms by a $C_{1-6}$-alkyl, $C_{2-6}$-alkenyl or $C_{2-6}$-alkynyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-($C_{1-3}$-alkyl)-pyrazolyl, imidazolyl or 1-($C_{1-3}$-alkyl)-imidazolyl group, while the substituents may be identical or different, and an olefinic double bond of one of the above-mentioned unsaturated heterocycles may be fused to a phenyl, naphthyl, pyridine, diazine, 1,3-oxazole, thienyl, furan, thiazole, pyrrole, N—$C_{1-3}$-alkyl-pyrrole or quinoline ring, to a 1H-quinolin-2-one ring optionally substituted at the nitrogen atom by a $C_{1-6}$-alkyl, $C_{3-6}$-alkenyl or $C_{3-6}$-alkynyl group or to an imidazole or N—$C_{1-3}$-alkyl-imidazole ring or two olefinic double bonds of one of the above-mentioned unsaturated heterocycles may each be fused to a phenyl or pyridine ring, while the phenyl, pyridinyl, diazinyl, furyl, thienyl, pyrrolyl, 1,3-oxazolyl, 1,3-thiazolyl, isoxazolyl, pyrazolyl, 1-$C_{1-3}$-alkyl-pyrazolyl, imidazolyl or 1-$C_{1-3}$-alkyl-imidazolyl groups contained in $R^1$ and benzo-, thieno-, pyrido- and diazino-fused heterocycles in the carbon skeleton may additionally be mono-, di- or trisubstituted by halogen atoms, $C_{1-6}$-alkyl, $C_{2-6}$-alkenyl, $C_{2-6}$-alkynyl, cyclo-$C_{3-7}$-alkyl, cyclo-$C_{3-7}$-alkenyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{3-6}$-alkenoxy-$C_{3-6}$-alkenyl, $C_{3-6}$-alkenoxy-$C_{3-6}$-alkynyl, $C_{3-6}$-alkynoxy-$C_{1-6}$-alkyl, $C_{3-6}$-alkynoxy-$C_{3-6}$-alkenyl, $C_{3-6}$-alkynoxy-$C_{3-6}$-alkynyl, thiohydroxy, $C_{1-6}$-alkylthio, $C_{3-6}$-alkenylthio, $C_{3-6}$-alkynylthio, amino, $C_{1-6}$-alkyl-amino, $C_{3-6}$-alkenyl-amino, $C_{3-6}$-alkynyl-amino, di-($C_{1-6}$-alkyl)-amino, di-($C_{3-6}$-alkenyl)-amino, di-($C_{3-6}$-alkynyl)-amino, amino-$C_{1-6}$-alkyl, $C_{1-3}$-alkyl-amino-$C_{1-6}$-alkyl, di-($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$-alkyl-amino-$C_{3-6}$-alkynyl, di-($C_{1-3}$-alkyl)-amino-$C_{3-6}$-alkynyl, hydroxycarbonyl, phenylcarbonyl, pyridylcarbonyl, $C_{1-6}$-alkyl-carbonyl, $C_{2-6}$-alkenyl-carbonyl, $C_{2-6}$-alkynyl-carbonyl, formyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{2-6}$-alkenyl-carbonylamino, $C_{2-6}$-alkynyl-carbonylamino, formyl-$C_{1-6}$-alkyl-amino, formyl-$C_{3-6}$-alkenyl-amino, formyl-$C_{3-6}$-alkynyl-amino, $C_{1-6}$-alkyl-carbonyl-$C_{1-6}$-alkyl-amino, $C_{2-6}$-alkenyl-carbonyl-$C_{1-6}$-alkyl-amino, $C_{2-6}$-alkynyl-carbonyl-$C_{1-6}$-alkyl-amino, $C_{1-6}$-alkyl-carbonyl-$C_{3-6}$-alkenyl-amino, $C_{2-6}$-alkenyl-carbonyl-$C_{3-6}$-alkenyl-amino, $C_{2-6}$-alkynyl-carbonyl-$C_{3-6}$-alkenyl-amino, $C_{1-6}$-alkyl-carbonyl-$C_{3-6}$-alkynyl-amino, $C_{2-6}$-alkenyl-carbonyl-$C_{3-6}$-alkynyl-amino, $C_{2-6}$-alkynyl-carbonyl-$C_{3-6}$-alkynyl-amino, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, $C_{1-6}$-alkyl-sulphonylamino, $C_{2-6}$-alkenyl-sulphonylamino, $C_{2-6}$-alkynyl-sulphonylamino, $C_{1-6}$-alkyl-sulphonyl-$C_{1-6}$-alkylamino, $C_{1-6}$-alkyl-sulphonyl-$C_{3-6}$-alkenylamino, $C_{1-6}$-alkyl-sulphonyl-$C_{3-6}$-alkynylamino, $C_{2-6}$-alkenyl-sulphonyl-$C_{1-6}$-alkylamino, $C_{2-6}$-alkenyl-sulphonyl-$C_{3-6}$-alkenylamino, $C_{2-6}$-alkenyl-sulphonyl-$C_{3-6}$-alkynylamino, $C_{2-6}$-alkynyl-sulphonyl-$C_{1-6}$-alkylamino, $C_{2-6}$-alkynyl-sulphonyl-$C_{3-6}$-alkenylamino, $C_{2-6}$-alkynyl-sulphonyl-$C_{3-6}$-alkynylamino, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl, di-($C_{3-6}$-alkynyl)-aminosulphonyl groups, while the substituents may be identical or different, $R^2$ denotes the hydrogen atom, a phenylmethyl group or a $C_{2-7}$-alkyl group which may be substituted in the $C_3$ position by a cyclo-$C_{3-7}$-alkyl, cyclo-$C_{3-7}$-alkenyl, phenyl, pyridinyl, diazinyl, hydroxy, amino, $C_{1-6}$-alkylamino, di-($C_{1-6}$-alkyl)-amino, $C_{3-6}$-alkenylamino, di-($C_{3-6}$-alkenyl)amino, $C_{3-6}$-alkynylamino, di-($C_{3-6}$-alkynyl)amino, hydroxycarbonyl, $C_{1-6}$alkoxycarbonyl, aminocarbonyl, aminocarbonylamino, $C_{1-6}$-alkylcarbonylamino, $C_{2-6}$-alkenylcarbonylamino, $C_{2-6}$-alkynylcarbonylamino, 4-morpholinyl, [bis-(2-hydroxyethyl)]amino, 4-($C_{1-6}$-alkyl)-1-piperazinyl or 4-(ω-hydroxy-$C_{2-7}$-alkyl)-1-piperazinyl group, a phenyl or pyridinyl group, while the phenyl, pyridinyl and diazinyl groups mentioned in the above definitions of $R^2$ or contained as substituents may additionally be mono- di- or trisubstituted in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkyl-amino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonylamino-$C_{1-3}$-alkyl, aminocarbonyl, $C_{1-3}$-alkyl-aminocarbonyl, di-($C_{1-3}$-alkyl)-aminocarbonyl, cyano, aminosulphonyl, $C_{1-3}$-alkyl-aminosulphonyl, di-($C_{1-3}$-alkyl)-aminosulphonyl, $C_{1-3}$-alkyl-thio, $C_{1-3}$-alkyl-sulphinyl or $C_{1-3}$-alkyl-sulphonyl and the substituents may be identical or different, $R^3$ denotes the hydrogen atom or a $C_{1-3}$-alkyl group substituted by a phenyl or pyridinyl group, while the $C_{1-3}$-alkyl group may be connected to an alkyl group contained in $R^2$ or a phenyl or pyridyl ring contained in $R^2$ including the nitrogen atom to which $R^2$ and $R^3$ are bound, forming a 4- to 7-membered ring, or $R^2$ and $R^3$ together with the enclosed nitrogen atom denote a group of general formula

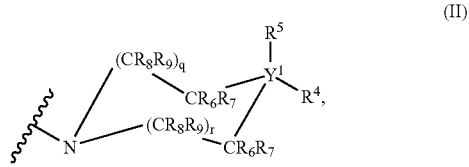

(II)

wherein $Y^1$ denotes the carbon atom or, if $R^5$ denotes a pair of free electrons, it may also denote the nitrogen atom, q and r, if $Y^1$ denotes the carbon atom, denote the numbers 0, 1 or 2, or q and r, if $Y^1$ denotes the nitrogen atom, denote the numbers 1 or 2, $R^4$ denotes the hydrogen atom, an amino, $C_{1-4}$-alkyl-amino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$-alkyl-amino)-$C_{2-7}$-alkyl, aminoiminomethyl, aminocarbonylamino, $C_{1-4}$-alkyl-aminocarbonylamino, di-($C_{1-4}$-alkyl)-aminocarbonylamino, $C_{1-4}$-alkyl-aminocarbonyl-$C_{1-4}$-alkyl-amino, di-($C_{1-4}$-alkyl)-aminocarbonyl-$C_{1-4}$-alkyl-amino, phenylaminocarbonylamino, aminocarbonyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{3-6}$-alkenoxycarbonyl, $C_{3-6}$-alkynoxycarbonyl, $C_{1-6}$-alkoxycarbonyl-$C_{1-3}$-alkyl, $C_{1-6}$-alkenoxycarbonyl-$C_{1-3}$-alkyl, $C_{1-6}$-alkynoxycarbonyl-$C_{1-3}$-alkyl or hydroxycarbonyl-$C_{1-3}$-alkyl group, a phenyl, pyridinyl, diazinyl, 1-naphthyl, 2-naphthyl, pyridinylcarbonyl or phenylcarbonyl group which may be mono- di- or trisubstituted in each case in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-4}$-alkyl-aminocarbonyl, di-($C_{1-4}$-alkyl)-aminocarbonyl, cyano, aminosulphonyl, $C_{1-4}$-alkyl-aminosulphonyl, di-($C_{1-4}$-alkyl)-aminosulphonyl, $C_{1-4}$-alkyl-thio, $C_{1-4}$-alkyl-sulphinyl or $C_{1-4}$-alkyl-sulphonyl and the substituents may be identical or different, a heterocycle selected from a 4- to 10-membered azacycloalkyl group, a 6- to 10-membered oxaza-, thiaza-, S,S-dioxothiaza- and diazacycloalkyl group as well as a 6- to 10-membered azabicycloalkyl group, a 1-alkyl-4-piperidinylcarbonyl or 4-alkyl-1-piperazinylcarbonyl group, while the above-mentioned mono- and bicyclic heterocycles are bound to $Y^1$ in formula (II) by a nitrogen or a carbon atom, in the above-mentioned mono- and bicyclic heterocycles a methyne group not directly linked to a nitrogen, oxygen or sulphur atom may be substituted by a fluorine atom and a methylene group not directly linked to a nitrogen, oxygen or sulphur atom may be substituted by one or two fluorine atoms, the above-mentioned mono- and bicyclic heterocycles as well as the 1-($C_{1-6}$-alkyl)-4-piperidinylcarbonyl- and 4-($C_{1-6}$-alkyl)-1-piperazinylcarbonyl group in the ring may be mono- to tetra-substituted by hydroxy, $C_{1-6}$-alkyl or hydroxy-$C_{1-3}$-alkyl groups, or, optionally additionally, may be monosubstituted by a cyclo-$C_{3-7}$-alkyl, hydroxy-$C_{3-7}$-cycloalkyl, cyclo-$C_{3-7}$-alkenyl, cyclo-$C_{3-7}$-alkyl-$C_{1-3}$-alkyl, phenyl-$C_{1-3}$-alkyl, pyridyl-$C_{1-3}$-alkyl, $C_{1-6}$-alkylcarbonyl, $C_{1-6}$-alkylcarbonyl-$C_{1-3}$-alkyl, hydroxy, $C_{1-6}$-alkoxy, amino, $C_{1-4}$-alkylamino, di-($C_{1-4}$-alkyl)amino, phenylcarbonyl, pyridinylcarbonyl, $C_{1-6}$-alkoxycarbonyl, hydroxycarbonyl-carbonyl, $C_{1-6}$-alkoxycarbonyl-carbonyl, hydroxycarbonyl-$C_{1-3}$-alkyl, $C_{1-6}$-alkoxycarbonyl-$C_{1-3}$-alkyl, hydroxycarbonyl-$C_{1-3}$-alkylcarbonyl, $C_{1-6}$-alkoxycarbonyl-$C_{1-3}$-alkylcarbonyl, aminocarbonyl, $C_{1-4}$-alkylaminocarbonyl, di-($C_{1-4}$-alkyl)aminocarbonyl, aminosulphonyl, $C_{1-4}$-alkylaminosulphonyl, di-($C_{1-4}$-alkyl)aminosulphonyl, $C_{1-3}$-alkylsulphonyl, cyclo-$C_{3-7}$-alkylsulphonyl, aminocarbonyl-$C_{1-3}$-alkyl, $C_{1-4}$-alkylaminocarbonyl-$C_{1-3}$-alkyl, di-($C_{1-4}$-alkyl)aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl group, by a cyclo-$C_{3-7}$-alkyl-carbonyl, azacyclo-$C_{4-7}$-alkyl-carbonyl, diazacyclo-$C_{5-7}$-alkyl-carbonyl or oxazacyclo-$C_{5-7}$-alkyl-carbonyl group optionally $C_{1-3}$-alkyl-substituted in the ring, while the substituents may be identical or different and may be bound to a cyclic carbon or cyclic nitrogen atom, while the phenyl and pyridinyl groups contained in the groups given as definitions of $R^4$ hereinbefore may in turn be mono-, di- or trisubstituted by halogen atoms, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-3}$-alkyl-aminocarbonyl, di-$C_{1-4}$-alkyl-aminocarbonyl, cyano, aminosulphonyl, $C_{1-4}$-alkyl-aminosulphonyl, di-($C_{1-4}$-alkyl)-aminosulphonyl, $C_{1-3}$-alkyl-thio, $C_{1-3}$-alkyl-sulphinyl or $C_{1-3}$-alkyl-sulphonyl, while the substituents may be identical or different, or, if $Y^1$ denotes the carbon atom, may denote the hydroxycarbonyl, aminomethyl, $C_{1-4}$-alkyl-aminomethyl or di-($C_{1-4}$-alkyl)-aminomethyl group, $R^5$ denotes a hydrogen atom or a hydroxy group, a $C_{1-4}$-alkyl group, while an unbranched alkyl group in the ω position may be substituted by a phenyl, pyridinyl, diazinyl, amino, $C_{1-4}$-alkylamino, di-($C_{1-4}$-alkyl)-amino, 4-$C_{1-4}$-alkyl-1-piperazinyl or 4-morpholinyl group, a $C_{1-6}$-alkoxycarbonyl, cyano or aminocarbonyl group or, if $Y^1$ denotes a nitrogen atom, $R^5$ also denotes a pair of free electrons, or, if $Y^1$ denotes the carbon atom, $R^5$ also denotes the fluorine atom, or $R^4$ together with $R^5$ and $Y^1$ denotes a 4- to 7-membered cycloaliphatic ring wherein a methylene group may be replaced by an —NH—, —N($C_{1-4}$-alkyl)-, —N($C_{3-4}$-alkenyl)-, —N($C_{3-4}$-alkynyl)-, —N(cyclo-$C_{3-7}$-alkyl)-, —N($C_{3-7}$-cycloalkyl-$C_{1-3}$-alkyl)-, —N(hydroxycarbonyl-$C_{1-3}$-alkyl)- or —N($C_{1-6}$-alkoxycarbonyl-$C_{1-3}$-alkyl)- group, while a hydrogen atom bound to a nitrogen atom in one of the groups defined for $R^4$ hereinbefore may be replaced by a protective group, $R^6$ and $R^7$, which may be identical or different, in each case denote a hydrogen atom, a $C_{1-4}$-alkyl group or, if $Y^1$ denotes a carbon atom, also denote the fluorine atom, an amino, $C_{1-4}$-alkylamino or di-($C_{1-4}$-alkyl)-amino group, while the two $C_{1-4}$-alkyl groups may be joined together to form a ring and $R^8$ and $R^9$, which may be identical or different, in each case denote a hydrogen atom or a $C_{1-3}$-alkyl group, while $R^a$ denotes a hydrogen atom, a straight-chain or branched $C_{1-6}$-alkyl, $C_{3-6}$-alkenyl, $C_{3-6}$-alkynyl or cyclo-$C_{3-7}$-alkyl group wherein each hydrogen atom, if it is not in the α-position to a nitrogen atom, may be replaced by fluorine, $R^b$ denotes a halogen atom, a straight-chain or branched $C_{1-6}$-alkyl, $C_{2-6}$-alkenyl, $C_{2-6}$-alkynyl, cyclo-$C_{3-7}$-alkyl, cyano, hydroxy, hydroxy-$C_{1-6}$-alkyl, $C_{1-6}$-alkoxy, $C_{1-6}$-alkoxy-$C_{1-6}$-alkyl, amino, $C_{1-6}$-alkyl-amino or di-$C_{1-6}$-alkyl-amino group, wherein each hydrogen atom, if it is not in the α-position to a nitrogen atom, may be replaced by fluorine and the two alkyl groups of the di-$C_{1-6}$-alkyl-amino substituents may be joined together to form a 4- to 8-membered ring, a methylene group in the α-position to a saturated nitrogen atom substituted by the group $R^a$ or to an oxygen or sulphur atom, as a ring member of the heterocycle of the group Q, is not substituted by a hydroxy, $C_{1-6}$-alkoxy, amino, $C_{1-6}$-alkyl-amino or di-$C_{1-6}$-alkyl-amino group, the double and triple bonds of the $C_{3-6}$-alkenyl or $C_{3-6}$-alkynyl groups contained in the groups mentioned for $R^a$, $R^b$, and $R^1$ hereinbefore are also isolated from any heteroatoms contained in these groups, and, unless otherwise stated, all the alkyl, alkenyl and alkynyl groups mentioned or contained in the groups defined hereinbefore may be straight-chain or branched, each methyne group contained in the groups defined hereinbefore may be substituted by a fluorine atom, each methylene group may be substituted by up to 2 fluorine atoms and each methyl group may be substituted by up to 3 fluorine atoms and two alkyl and alkenyl groups bound to a nitrogen atom may be joined together forming a 4- to 7-membered, saturated or unsaturated heterocyclic ring, all the aromatic and heteroaromatic groups mentioned or contained in the groups defined hereinbefore may additionally be mono-, di- or trisubstituted by halogen, by cyano or hydroxy groups and the substituents may be identical or different and by the protective groups mentioned in the definitions above and hereinafter are meant the protective groups familiar from peptide chemistry, particularly a phenylalkoxycarbonyl group with 1 to 3 carbon atoms in the alkoxy moiety optionally substituted in the phenyl nucleus by a halogen atom, by a nitro or phenyl group or by one or two methoxy groups, for example the benzyloxycarbonyl, 2-nitro-benzyloxycarbonyl, 4-nitrobenzyloxycarbonyl, 4-methoxybenzyloxycarbonyl, 2-chloro-benzyloxycarbonyl, 3-chloro-benzyloxycarbonyl, 4-chloro-benzyloxycarbonyl, 4-biphenylyl-α,αdimethyl-benzyloxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, isopropoxycarbonyl, n-butoxycarbonyl, 1-methylpropoxycarbonyl, 2-methylpropoxy-carbonyl or tert.-butyloxycarbonyl group, the allyloxycarbonyl, 2,2,2-trichloro-(1,1-dimethylethoxy) carbonyl or 9-fluorenylmethoxycarbonyl group or the formyl, acetyl or trifluoracetyl group.

In the definitions given above and hereinafter, by a group substituted in the ω position is meant a terminally substituted group, by a halogen atom is meant a fluorine, chlorine, bromine or iodine atom and by a double or triple bond isolated from a heteroatom is meant a double or triple bond which is linked to a heteroatom via at least one saturated carbon atom.

The invention also includes the tautomers, isomers, diastereomers, enantiomers, hydrates, and salts of compounds of the formula I, particularly the physiologically acceptable salts thereof with inorganic or organic acids or bases, hydrates of the salts of compounds of formula I, as well as those compounds of general formula I in which one or more hydrogen atoms are replaced by deuterium.

A second embodiment of the present invention comprises the compounds of the above general formula (I), wherein A denotes an oxygen or sulphur atom, X denotes an oxygen or sulphur atom, Q denotes a heterocycle bound via a carbon or nitrogen atom consisting of two or three in each case 4- to 8-membered fused rings, saturated, partially unsaturated or totally unsaturated independently of one another, while the heterocycle comprises a total of one to five heteroatoms selected independently of one another from among O, N and S, may contain one or two carbonyl groups as ring members and each saturated nitrogen atom as a ring member of the heterocycle may be substituted by the group $R^a$ and one or two carbon atoms as ring members of the heterocycle may be substituted by the group $R^b$, $R^1$ denotes a saturated, mono- or diunsaturated 5- to 7-membered aza, diaza, triaza, oxaza, thiaza, thiadiaza or S,S-dioxido-thiadiaza heterocycle, while the above-mentioned heterocycles are linked to the piperidine ring in formula I by a carbon or nitrogen atom or are spirocyclically linked to the piperidine ring in formula I by two carbon atoms, by a carbon and a nitrogen atom, by a carbon and an oxygen atom or by a carbon and a sulphur atom, contain one or two carbonyl or thiocarbonyl groups adjacent to a nitrogen atom, may be substituted at one of the nitrogen atoms by a $C_{1-6}$-alkyl, $C_{3-6}$-alkenyl or $C_{3-6}$-alkenyl group, may be substituted at one or at two carbon atoms by a $C_{1-6}$-alkyl, $C_{2-6}$-alkenyl or $C_{2-6}$-alkynyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-($C_{1-3}$-alkyl)-pyrazolyl, imidazolyl or 1-($C_{1-3}$-alkyl)-imidazolyl group, while the substituents may be identical or different, and an olefinic double bond of one of the above-mentioned unsaturated heterocycles may be fused to a phenyl, naphthyl, pyridine, diazine, 1,3-oxazole, thienyl, furan, thiazole, pyrrole, N—$C_{1-3}$-alkyl-pyrrole or quinoline ring , to a 1H-quinolin-2-one ring optionally substituted at the nitrogen atom by a $C_{1-6}$-alkyl, $C_{3-6}$-alkenyl or $C_{3-6}$-alkynyl group or to an imidazole or N—$C_{1-3}$-alkylimidazole ring or two olefinic double bonds of one of the above-mentioned unsaturated heterocycles may each be fused to a phenyl or pyridine ring, while the phenyl, pyridinyl, diazinyl, furyl, thienyl, pyrrolyl, 1,3-oxazolyl, 1,3-thiazolyl, isoxazolyl, pyrazolyl, 1-$C_{1-3}$-alkyl-pyrazolyl, imidazolyl or 1-$C_{1-3}$-alkylimidazolyl groups contained in $R^1$ and the benzo-, thieno-, pyrido- and diazino-fused heterocycles in the carbon skeleton may additionally be mono-, di- or trisubstituted by halogen atoms, $C_{1-6}$-alkyl, $C_{2-6}$-alkenyl, $C_{2-6}$-alkynyl, cyclo-$C_{3-7}$-alkyl, cyclo-$C_{3-7}$-alkenyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{3-6}$-alkenoxy-$C_{3-6}$-alkenyl, $C_{3-6}$-alkenoxy-$C_{3-6}$-alkynyl, $C_{3-6}$-alkynoxy-$C_{1-6}$-alkyl, $C_{3-6}$-alkynoxy-$C_{3-6}$-alkenyl, $C_{3-6}$-alkynoxy-$C_{3-6}$-alkynyl, thiohydroxy, $C_{1-6}$-alkylthio, $C_{3-6}$-alkenylthio, $C_{3-6}$-alkynylthio, amino, $C_{1-6}$-alkyl-amino, $C_{3-6}$-alkenyl-amino, $C_{3-6}$-alkynyl-amino, di-($C_{1-6}$-alkyl)-amino, di-($C_{3-6}$-alkenyl)-amino, di-($C_{3-6}$-alkynyl)-amino, amino-$C_{1-6}$-alkyl, $C_{1-3}$-alkyl-amino-$C_{1-6}$-alkyl, di-($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$-alkyl-amino-$C_{3-6}$-alkynyl, di-($C_{1-3}$-alkyl)-amino-$C_{3-6}$-alkynyl, hydroxycarbonyl, phenylcarbonyl, pyridylcarbonyl, $C_{1-6}$-alkyl-carbonyl, $C_{2-6}$-alkenyl-carbonyl, $C_{2-6}$-alkynyl-carbonyl, formyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{2-6}$-alkenyl-carbonylamino, $C_{2-6}$-alkynyl-carbonylamino, formyl-$C_{1-6}$-alkyl-amino, formyl-$C_{3-6}$-alkenyl-amino, formyl-$C_{3-6}$-alkynyl-amino, $C_{1-6}$-alkyl-carbonyl-$C_{1-6}$-alkyl-amino, $C_{2-6}$-alkenyl-carbonyl-$C_{1-6}$-alkyl-amino, $C_{2-6}$-alkynyl-carbonyl-$C_{1-6}$-alkyl-amino, $C_{1-6}$-alkyl-carbonyl-$C_{3-6}$-alkenyl-amino, $C_{2-6}$-alkenyl-carbonyl-$C_{3-6}$-alkenyl-amino, $C_{2-6}$-alkynyl-carbonyl-$C_{3-6}$-alkenyl-amino, $C_{1-6}$-alkyl-carbonyl-$C_{3-6}$-alkynyl-amino, $C_{2-6}$-alkenyl-carbonyl-$C_{3-6}$-alkynyl-amino, $C_{2-6}$-alkynyl-carbonyl-$C_{3-6}$-alkynyl-amino, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, $C_{1-6}$-alkyl-sulphonylamino, $C_{2-6}$-alkenyl-sulphonylamino, $C_{2-6}$-alkynyl-sulphonylamino, $C_{1-6}$-alkyl-sulphonyl-$C_{1-6}$-alkylamino, $C_{1-6}$-alkyl-sulphonyl-$C_{3-6}$-alkenylamino, $C_{1-6}$-alkyl-sulphonyl-$C_{3-6}$-alkynylamino, $C_{2-6}$-alkenyl-sulphonyl-$C_{1-6}$-alkylamino, $C_{2-6}$-alkenyl-sulphonyl-$C_{3-6}$-alkenylamino, $C_{2-6}$-alkenyl-sulphonyl-$C_{3-6}$-alkynylamino, $C_{2-6}$-alkynyl-sulphonyl-$C_{1-6}$-alkylamino, $C_{2-6}$-alkynyl-sulphonyl-$C_{3-6}$-alkenylamino, $C_{2-6}$-alkynyl-sulphonyl-$C_{3-6}$-alkynylamino, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl, di-($C_{3-6}$-alkynyl)-aminosulphonyl groups, while the substituents may be identical or different, $R^2$ denotes the hydrogen atom, a phenylmethyl group or a $C_{2-7}$-alkyl group which may be substituted in the ω position by a cyclo-$C_{3-7}$-alkyl, cyclo-$C_{3-7}$-alkenyl, phenyl, pyridinyl, diazinyl, hydroxy, amino, $C_{1-6}$-alkylamino, di-($C_{1-6}$-alkyl)-amino, $C_{3-6}$-alkenylamino, di-($C_{3-6}$-alkenyl)amino, $C_{3-6}$-alkynylamino, di-($C_{3-6}$-alkynyl)amino, hydroxycarbonyl, $C_{1-6}$-alkoxycarbonyl, aminocarbonyl, aminocarbonylamino, $C_{1-6}$-alkylcarbonylamino, $C_{2-6}$-alkenylcarbonylamino, $C_{2-6}$-alkynylcarbonylamino, 4-morpholinyl, [bis-(2-hydroxyethyl)]amino, 4-($C_{1-6}$-alkyl)-1-piperazinyl or 4-(ω-hydroxy-$C_{2-7}$-alkyl)-1-piperazinyl group, a phenyl or pyridinyl group, while the phenyl, pyridinyl and diazinyl groups mentioned in the groups defined for $R^2$ hereinbefore or contained as substituents may additionally be mono-, di- or trisubstituted in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkyl-amino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonylamino-$C_{1-3}$-alkyl, aminocarbonyl, $C_{1-3}$-alkyl-aminocarbonyl, di-($C_{1-3}$-alkyl)-aminocarbonyl, cyano, aminosulphonyl, $C_{1-3}$-alkyl-aminosulphonyl, di-($C_{1-3}$-alkyl)-aminosulphonyl, $C_{1-3}$-alkylthio, $C_{1-3}$-alkylsulphinyl or $C_{1-3}$-alkylsulphonyl and the substituents may be identical or different, $R^3$ denotes the hydrogen atom or a $C_{1-3}$-alkyl group substituted by a phenyl or pyridinyl group, while the $C_{1-3}$-alkyl group may be connected to an alkyl group contained in $R^2$ or a phenyl or pyridyl ring contained in $R^2$ including the nitrogen atom to which $R^2$ and $R^3$ are bound, forming a 4- to 7-membered ring, or $R^2$ and $R^3$ together with the enclosed nitrogen atom denote a group of general formula

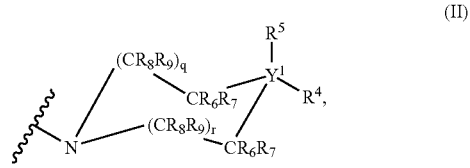

(II)

wherein $Y^1$ denotes the carbon atom or, if $R^5$ denotes a pair of free electrons, $Y^1$ may also denote the nitrogen atom, q and r, if $Y^1$ denotes the carbon atom, denote the numbers 0, 1 or 2, or q and r, if $Y^1$ denotes the nitrogen atom, denote the numbers 1 or 2, $R^4$ denotes the hydrogen atom, an amino, $C_{1-4}$-alkyl-amino, di-($C_{1-4}$-alkyl)-alkylamino, $C_{1-6}$-alkyl, cyclo-$C_{3-7}$-alkyl, cyclo-$C_{3-7}$-alkenyl, amino-$C_{2-7}$-alkyl, $C_{1-4}$-alkyl-amino-$C_{2-7}$-alkyl, di-($C_{1-4}$-alkyl-amino)-$C_{2-7}$-alkyl, aminoiminomethyl, aminocarbonylamino, $C_{1-4}$-alkyl-aminocarbonylamino, di-($C_{1-4}$-alkyl)-aminocarbonylamino, $C_{1-4}$-alkyl-aminocarbonyl-$C_{1-4}$-alkyl-amino, di-($C_{1-4}$-alkyl)-aminocarbonyl-$C_{1-4}$-alkyl-amino, phenylaminocarbonylamino, aminocarbonyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{3-6}$-alkenoxycarbonyl, $C_{3-6}$-alkynoxycarbonyl, $C_{1-6}$-alkoxycarbonyl-$C_{1-3}$-alkyl, $C_{1-6}$-alkenoxycarbonyl-$C_{1-3}$-alkyl, $C_{1-6}$-alkynoxycarbonyl-$C_{1-3}$-alkyl or hydroxycarbonyl-$C_{1-3}$-alkyl group, a phenyl, pyridinyl, diazinyl, 1-naphthyl, 2-naphthyl, pyridinylcarbonyl or phenylcarbonyl group which may be mono-, di- or trisubstituted in the carbon skeleton in each case by halogen, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-4}$-alkyl-aminocarbonyl, di-($C_{1-4}$-alkyl)-aminocarbonyl, cyano, aminosulphonyl, $C_{1-4}$-alkyl-aminosulphonyl, di-($C_{1-4}$-alkyl)-aminosulphonyl, $C_{1-4}$-alkyl-thio, $C_{1-4}$-alkyl-sulphinyl or $C_{1-4}$-alkyl-sulphonyl, and the substituents may be identical or different, a heterocycle selected from a 4- to 10-membered azacycloalkyl group, a 6- to 10-membered oxaza, thiaza- and diazacycloalkyl group as well as a 6- to 10-membered azabicycloalkyl group, a 1-alkyl-4-piperidinylcarbonyl or 4-alkyl-1-piperazinylcarbonyl group, while the above-mentioned mono- and bicyclic heterocycles are bound to $Y^1$ by a nitrogen or a carbon atom in formula (II), in the above-mentioned mono- and bicyclic heterocycles a methyne group not directly linked to a nitrogen, oxygen or sulphur atom may be substituted by a fluorine atom and a methylene group not directly linked to a nitrogen, oxygen or sulphur atom may be substituted by one or two fluorine atoms, the above-mentioned mono- and bicyclic heterocycles as well as the 1-($C_{1-6}$-alkyl)-4-piperidinylcarbonyl and 4-($C_{1-6}$-alkyl)-1-piperazinylcarbonyl group in the ring may be mono- to tetra-substituted by $C_{1-6}$-alkyl groups, or may optionally additionally be monosubstituted by a cyclo-$C_{3-7}$-alkyl, cyclo-$C_{3-7}$-alkenyl, cyclo-$C_{3-7}$-alkyl-$C_{1-3}$-alkyl, phenyl-$C_{1-3}$-alkyl, pyridyl-$C_{1-3}$-alkyl, $C_{1-6}$-alkylcarbonyl, hydroxy, $C_{1-6}$-alkoxy, amino, $C_{1-4}$-alkylamino, di-($C_{1-4}$-alkyl)amino, phenylcarbonyl, pyridinylcarbonyl, hydroxycarbonyl, hydroxycarbonyl-$C_{1-3}$-alkyl, $C_{1-6}$-alkoxycarbonyl, $C_{1-6}$-alkoxycarbonyl-$C_{1-3}$-alkyl, aminocarbonyl, $C_{1-4}$-alkylaminocarbonyl, di-($C_{1-4}$-alkyl)aminocarbonyl or $C_{1-3}$-alkylsulphonyl group, by a cyclo-$C_{3-7}$-alkyl-carbonyl, azacyclo-$C_{4-7}$-alkyl-carbonyl, diazacyclo-$C_{5-7}$-alkyl-carbonyl or oxazacyclo-$C_{5-7}$-alkyl-carbonyl group optionally $C_{1-3}$-alkyl-substituted in the ring, while the substituents may be identical or different and may be bound to a cyclic carbon or cyclic nitrogen atom, while the phenyl and pyridinyl groups contained in the groups mentioned for $R^4$ hereinbefore may in turn be mono-, di- or trisubstituted by halogen atoms, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-3}$-alkyl-aminocarbonyl, di-$C_{1-4}$-alkyl-aminocarbonyl, cyano, aminosulphonyl, $C_{1-4}$-alkyl-aminosulphonyl, di-($C_{1-4}$-alkyl)-aminosulphonyl, $C_{1-3}$-alkyl-thio, $C_{1-3}$-alkyl-sulphinyl or $C_{1-3}$-alkyl-sulphonyl, while the substituents may be identical or different, or, if $Y^1$ denotes the carbon atom, $R^4$ may denote the hydroxycarbonyl, aminomethyl, $C_{1-4}$-alkyl-aminomethyl or di-($C_{1-4}$-alkyl)-aminomethyl group, $R^5$ denotes a hydrogen atom, a $C_{1-4}$-alkyl group, while an unbranched alkyl group may be substituted in the ω position by a phenyl, pyridinyl, diazinyl, amino, $C_{1-4}$-alkylamino, di-($C_{1-4}$-alkyl)-amino, 4-$C_{1-4}$-alkyl-1-piperazinyl or 4-morpholinyl group, a $C_{1-6}$-alkoxycarbonyl, cyano or aminocarbonyl group or, if $Y^1$ denotes a nitrogen atom, $R^5$ may denote a pair of free electrons, or, if $Y^1$ denotes the carbon atom, $R^5$ may denote the fluorine atom, or $R^4$ together with $R^5$ and $Y^1$ denote a 4- to 7-membered cycloaliphatic ring wherein a methylene group may be replaced by a —NH—, —N($C_{1-4}$-alkyl)-, —N($C_{3-4}$-alkenyl)-, —N($C_{3-4}$-alkynyl)-, —N(cyclo-$C_{3-7}$-alkyl)- or —N($C_{3-7}$-cycloalkyl-$C_{1-3}$-alkyl)- group, while a hydrogen atom bound to a nitrogen atom in one of the groups defined for $R^4$ hereinbefore may be replaced by a protective group, $R^6$ and $R^7$, which may be identical or different, in each case denote a hydrogen atom, a $C_{1-4}$-alkyl group or, if $Y^1$ denotes a carbon atom, the fluorine atom, a $C_{1-4}$-alkylamino or di-($C_{1-4}$-alkyl)-amino group, while the two $C_{1-4}$-alkyl groups may be joined together to form a ring and $R^8$ and $R^9$, which may be identical or different, in each case denote a hydrogen atom or a $C_{1-3}$-alkyl group, while $R^a$ denotes a hydrogen atom, a straight-chain or branched $C_{1-6}$-alkyl, $C_{3-6}$-alkenyl, $C_{3-6}$-alkynyl or cyclo-$C_{3-7}$-alkyl group wherein each hydrogen atom, if it is not in the α-position to a nitrogen atom, may be replaced by fluorine, $R^b$ denotes a halogen atom, a straight-chain or branched $C_{1-6}$-alkyl, $C_{2-6}$-alkenyl, $C_{2-6}$-alkynyl, cyclo-$C_{3-7}$-alkyl, cyano, hydroxy, hydroxy-$C_{1-6}$-alkyl, $C_{1-6}$-alkoxy, $C_{1-6}$-alkoxy-$C_{1-6}$-alkyl, amino, $C_{1-6}$-alkyl-amino or di-$C_{1-6}$-alkyl-amino group, wherein each hydrogen atom, if it is not in the α-position to a nitrogen atom, may be replaced by fluorine and the two alkyl groups of the di-$C_{1-6}$-alkyl-amino substituents may be joined together to form a 4- to 8-membered ring, a methylene group in the α-position to a saturated nitrogen atom substituted by the group $R^a$, or to an oxygen or sulphur atom, as a ring member of the heterocycle of the group Q, is not substituted by hydroxy, $C_{1-6}$-alkoxy, amino, $C_{1-6}$-alkyl-amino or di-$C_{1-6}$-alkyl-amino group, the double and triple bonds of the $C_{3-6}$-alkenyl or $C_{3-6}$-alkynyl groups contained in the groups defined hereinbefore for $R^a$, $R^b$, and $R^1$ are isolated from any heteroatoms which may be contained in these groups, the tautomers, the diastereomers, the enantiomers, the hydrates, mixtures and salts thereof and the hydrates of the salts, particularly the physiologically acceptable salts thereof with inorganic or organic acids or bases.

A third embodiment of the present invention comprises the compounds of the above general formula (I), wherein A, X, Q, $R^2$ and $R^3$ are defined as hereinbefore in the first or second embodiment and $R^1$ denotes a mono- or diunsaturated 5- to 7-membered aza, diaza, triaza or thiaza heterocycle, while the above-mentioned heterocycles are linked by a carbon or nitrogen atom or are spirocyclically linked by a carbon and a nitrogen atom, by a carbon and an oxygen atom or by a carbon and a sulphur atom, contain one or two carbonyl groups adjacent to a nitrogen atom, may be substituted at a carbon atom by a phenyl, pyridinyl, diazinyl, thienyl, pyrrolyl, 1,3-thiazolyl, isoxazolyl, pyrazolyl or 1-($C_{1-4}$-alkyl)-pyrazolyl group and an olefinic double bond of one of the above-mentioned unsaturated heterocycles may be fused to a phenyl, naphthyl, pyridine, diazine, thienyl or quinoline ring or to a 1H-quinolin-2-one ring optionally substituted at the nitrogen atom by a methyl group, while the phenyl, pyridinyl, diazinyl, thienyl, pyrrolyl, 1,3-thiazolyl, isoxazolyl, pyrazolyl or 1-($C_{1-4}$-alkyl)-pyrazolyl groups contained in $R^1$ as well as the benzo-, pyrido- and diazino-fused heterocycles in the carbon skeleton may additionally be mono-, di- or trisubstituted by halogen, by $C_{1-6}$-alkyl, cyclo-$C_{3-7}$-alkyl, cyclo-$C_{3-7}$-alkenyl, $C_{1-6}$-alkoxy, hydroxycarbonyl, $C_{1-6}$-alkoxycarbonyl, cyano, hydroxy, amino, $C_{1-4}$-alkylamino, di-$C_{1-4}$-alkylamino, $C_{1-4}$-alkylcarbonylamino or $C_{1-4}$-alkylcarbonyl groups, while the substituents may be identical or different, while, unless otherwise stated, all the alkyl, alkenyl and alkynyl groups mentioned or contained in the groups defined hereinbefore under $R^1$ may be straight-chain or branched, every methyne group contained in the groups defined hereinbefore may be substituted by a fluorine atom, each methylene group may be substituted by up to 2 fluorine atoms and each methyl group may be substituted by up to 3 fluorine atoms and two alkyl and alkenyl groups bound to a nitrogen atom may be joined together forming a 4- to 7-membered, saturated or unsaturated heterocyclic ring, and all the aromatic and heteroaromatic groups mentioned or contained in the groups defined hereinbefore under $R^1$ may additionally be mono-, di- or trisubstituted by halogen or by cyano or hydroxy groups and the substituents may be identical or different, the tautomers, the isomers, the diastereomers, the enantiomers, the hydrates, mixtures and salts thereof and the hydrates of the salts, particularly the physiologically acceptable salts thereof with inorganic or organic acids or bases.

A fourth embodiment of the present invention comprises the compounds of the above general formula (I), wherein A, X, Q, $R^2$ and $R^3$ are as hereinbefore defined in the first or second embodiment and $R^1$ denotes a monounsaturated 5- to 7-membered diaza or triaza heterocycle, while the above-mentioned heterocycles are linked via a nitrogen atom or are spirocyclically linked by a carbon and a nitrogen atom or by a carbon and an oxygen atom, contain a carbonyl group adjacent to a nitrogen atom, may additionally be substituted at a carbon atom by a phenyl group and an olefinic double bond of one of the above-mentioned unsaturated heterocycles may be fused to a phenyl, thienyl or quinoline ring, while the phenyl groups contained in $R^1$ and benzo-fused heterocycles in the carbon skeleton may additionally be mono-, di- or trisubstituted by halogen, by methyl, methoxy, difluoromethyl, trifluoromethyl, hydroxy, amino, $C_{1-4}$-alkylamino, di-($C_{1-4}$-alkyl)-amino, acetylamino, acetyl, hydroxycarbonyl, $C_{1-6}$-alkoxycarbonyl, cyano-difluoromethoxy or trifluoromethoxy groups, while the substituents may be identical or different, but are preferably unsubstituted or monosubstituted by a halogen atom or by a methyl or methoxy group, while, unless otherwise stated, all the alkyl groups mentioned or contained in the groups defined hereinbefore under $R^1$ may be straight-chain or branched, every methyne group contained in the groups defined hereinbefore may be substituted by a fluorine atom, each methylene group may be substituted by up to 2 fluorine atoms and each methyl group may be substituted by up to 3 fluorine atoms, the tautomers, the isomers, the diastereomers, the enantiomers, the hydrates, mixtures and salts thereof and the hydrates of the salts, particularly the physiologically acceptable salts thereof with inorganic or organic acids or bases.

A fifth embodiment of the present invention comprises the compounds of the above general formula (I), wherein A, X, Q, $R^2$ and $R^3$ are as hereinbefore defined in the first or second embodiment and $R^1$ denotes a 1,3,4,5-tetrahydro-1,3-benzodiazepin-2-on-3-yl, 3,4-dihydro-1H-quinazolin-2-on-3-yl, 5-phenyl-2,4-dihydro-1,2,4-triazol-3-on-2-yl, 1,3-dihydro-imidazo[4,5-c]quinolin-2-on-3-yl, 1,3-dihydro-naphth[1,2-d]imidazol-2-on-3-yl, 1,3-dihydro-benzimidazol-2-on-3-yl, 4-phenyl-1,3-dihydro-imidazol-2-on-1-yl, 3,4-dihydro-1H-thieno[3,2-d]pyrimidin-2-on-3-yl or 3,4-dihydro-1H-thieno[3,4-d]pyrimidin-2-on-3-yl group or together with the piperidine ring in formula (I) denotes the 1',2'-dihydro-2'-oxospiro-4H-3',1-benzoxazin'-4,4'-piperidin-1-yl group, while the heterocycles mentioned hereinbefore under $R^1$ in the carbon skeleton may additionally be monosubstituted by a methoxy group, all the aromatic and heteroaromatic groups mentioned or contained in the groups defined hereinbefore under $R^1$ may additionally be mono-, di- or trisubstituted by halogen atoms or by cyano or hydroxy groups and the substituents may be identical or different, the tautomers, the isomers, the diastereomers, the enantiomers, the hydrates, mixtures and salts thereof and the hydrates of the salts, particularly the physiologically acceptable salts thereof with inorganic or organic acids or bases.

A sixth embodiment of the present invention comprises the compounds of the above general formula (I), wherein A, X, $R^1$, $R^2$ and $R^3$ are as hereinbefore defined in the first, second, third, fourth or fifth embodiment and Q denotes a heterocycle bound via a carbon or nitrogen atom consisting of a ring A and a ring B, which is fused by two adjacent carbon atoms or by a carbon atom and an adjacent nitrogen atom to the ring A, while the rings A and B are selected independently of one another from a 4-membered, saturated or monounsaturated carbocycle, in which a ring member may be replaced by an >$NR^a$ group, an oxygen or sulphur atom or, in the case of an unsaturated ring member, by a nitrogen atom, a 5-membered, saturated, mono- or diunsaturated carbocycle, in which one, two or three ring members may be replaced independently of one another in each case by an >$NR^a$ group, an oxygen or sulphur atom or, in the case of unsaturated ring members, may be replaced by a nitrogen atom, while in each case two or three oxygen or sulphur atoms may not be directly linked to one another, or a 6-membered, saturated, mono-, di- or triunsaturated carbocycle, in which one, two or three ring members may be replaced independently of one another in each case by an >$NR\alpha$ group, an oxygen or sulphur atom or, in the case of unsaturated ring members, by a nitrogen atom, while in each case two or three oxygen or sulphur atoms may not be directly linked to one another, and optionally additionally a fourth, unsaturated ring member may be replaced by a nitrogen atom, or a 7-membered, saturated, mono-, di- or triunsaturated carbocycle, in which one, two, three or four ring members may each independently of one another be replaced by an >$NR^a$ group, an oxygen or sulphur atom or, in the case of unsaturated ring members, may be replaced by a nitrogen atom, while in each case two or three oxygen or sulphur atoms may not be directly linked to one another, or an 8-membered, saturated, mono-, di-, tri- or tetra-unsaturated carbocycle, in which one, two, three or four ring members may each independently of one another be replaced by an >$NR^a$ group, an oxygen or sulphur atom or, in the case of unsaturated ring members, may be replaced by a nitrogen atom, while in each case two or three oxygen or sulphur atoms may not be directly linked to one another, while at least one of the fused rings A and B contains at least one heteroatom as a ring member, a methylene group as a ring member in the 4-membered rings A and B may in each case be replaced independently of one another by a carbonyl group, one or two methylene groups as ring members in the 5- to 8-membered rings A and B may in each case be replaced independently of one another by carbonyl groups, one or two carbon atoms as ring members of the rings A and B may be substituted by $R^b$, while the substituents may be identical or different, two hydrogen atoms bound to adjacent carbon or nitrogen atoms or to a carbon and an adjacent nitrogen atom as ring members of the rings A or B may be replaced by a $C_{3-6}$-n-alkylene bridge and thus form a tricyclic group, or a hydrogen atom bound to a carbon or nitrogen atom as a ring member of the ring A and another hydrogen atom bound to a carbon or nitrogen atom as a ring member of the ring B, where the above-mentioned ring members are separated from one another by two bonds, may be replaced by a $C_{2-5}$-n-alkylene bridge and thus form a tricyclic group, while in the above-mentioned $C_{3-6}$-n-alkylene bridges and $C_{2-5}$-n-alkylene bridges a methylene group may be replaced by a carbonyl group and/or one or two methylene groups may each be replaced independently of one another by an >$NR^a$ group, an oxygen or sulphur atom and/or a carbon atom may be substituted by $R^b$, with the proviso that two oxygen and two sulphur atoms are not directly linked together, $R^a$ denotes a hydrogen atom, a straight-chain or branched $C_{1-6}$-alkyl, $C_{3-6}$-alkenyl, $C_{3-6}$-alkynyl or cyclo-$C_{3-7}$-alkyl group, wherein each hydrogen atom, if it is not in the α-position to a nitrogen atom, may be replaced by fluorine, $R^b$ denotes a halogen atom, a straight-chain or branched $C_{1-6}$-alkyl, $C_{2-6}$-alkenyl, $C_{2-6}$-alkynyl, cyclo-$C_{3-7}$-alkyl, cyano, hydroxy, hydroxy-$C_{1-6}$-alkyl, $C_{1-6}$-alkoxy, $C_{1-6}$-alkoxy-$C_{1-6}$-alkyl, amino, $C_{1-6}$-alkyl-amino or di-$C_{1-6}$-alkyl-amino group, wherein each hydrogen atom, if it is not in the α-position to a nitrogen atom, may be replaced by fluorine and the two alkyl groups of the di-$C_{1-6}$-alkyl-amino substituents may be joined together to form a 4- to 8-membered ring, with the provisos that (i) the group Q contains a total of not more than five heteroatoms as ring members, (ii) the group Q contains a total of not more than two carbonyl groups as ring members and (iii) a group $R^b$ bound to a saturated carbon atom in the α-position to a saturated nitrogen atom substituted by the group $R^a$, or to an oxygen or sulphur atom as a ring member of a bi- or tricyclic heterocycle of the group Q does not take on the meanings of a hydroxy, $C_{1-6}$-alkoxy, amino, $C_{1-6}$-alkyl-amino or di-$C_{1-6}$-alkyl-amino group, the tautomers, the isomers, the diastereomers, the enantiomers, the hydrates, mixtures and salts thereof and the hydrates of the salts, particularly the physiologically acceptable salts thereof with inorganic or organic acids.

A seventh embodiment of the present invention comprises the compounds of the above general formula (I), wherein A, X, $R^1$, $R^2$ and $R^3$ are as hereinbefore defined in the first, second, third, fourth or fifth embodiment and Q denotes a heterocycle bound via a carbon or nitrogen atom consisting of a ring A and a ring B, which is fused via two adjacent carbon atoms or via a carbon atom and an adjacent nitrogen atom to the ring A, while the rings A and B are selected independently of one another from a 5-membered, saturated, mono- or diunsaturated carbocycle, in which one, two or three ring members may each be replaced independently of one another by an >$NR^a$ group, an oxygen or sulphur atom or, in the case of unsaturated ring members, by a nitrogen atom, while a maximum of two ring members denote oxygen or sulphur atoms and these may not be directly linked to one another, or a 6-membered, saturated, mono-, di- or triunsaturated carbocycle, in which one, two or three ring members may each independently of one another be replaced by an >$NR^a$ group, an oxygen or sulphur atom or, in the case of unsaturated ring members, by a nitrogen atom, while a maximum of two ring members denote oxygen or sulphur atoms and these may not be directly linked to one another, or a 7-membered, saturated, mono-, di- or triunsaturated carbocycle, in which one, two or three ring members may each independently of one another be replaced by an >$NR^a$ group, an oxygen or sulphur atom or, in the case of unsaturated ring members, by a nitrogen atom, while a maximum of two ring members denote oxygen or sulphur atoms and these may not be directly linked to one another, or at least one of the fused rings A and B contains at least one heteroatom as a ring member, one or two methylene groups as ring members in the 5- to 7-membered rings A and B may each be replaced independently of one another by carbonyl groups, one or two carbon atoms as ring members of the rings A and B may be substituted by $R^b$, while the substituents may be identical or different, two hydrogen atoms bound to adjacent carbon or nitrogen atoms or to a carbon and an adjacent nitrogen atom as ring members of the rings A or B may be replaced by a $C_{3-5}$-n-alkylene bridge and thus form a tricyclic group, or a hydrogen atom bound to a carbon or nitrogen atom as a ring member of the ring A and another hydrogen atom bound to a carbon or nitrogen atom as a ring member of the ring B, where the above-mentioned ring members are separated from one another by two bonds, may be replaced by a $C_{2-4}$-n-alkylene bridge and thus form a tricyclic group, while in the above-mentioned $C_{3-5}$-n-alkylene bridges and $C_{2-4}$-n-alkylene bridges one or two methylene groups may each be replaced independently of one another by an >$NR^a$ group or an oxygen atom and/or a carbon atom may be substituted by $R^b$, with the proviso that two oxygen atoms are not directly linked together, $R^a$ denotes a hydrogen atom, a straight-chain or branched $C_{1-3}$-alkyl, $C_3$-alkenyl, $C_3$-alkynyl or cyclo-$C_{3-6}$-alkyl group, wherein each hydrogen atom, if it is not in the α-position to a nitrogen atom, may be replaced by fluorine, $R^b$ denotes a halogen atom, a straight-chain or branched $C_{1-3}$-alkyl, $C_{2-3}$-alkenyl, $C_{2-3}$-alkynyl, cyclo-$C_{3-6}$-alkyl, cyano, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkyl-amino or di-$C_{1-3}$-alkyl-amino group, wherein each hydrogen atom, if it is not in the α-position to a nitrogen atom, may be replaced by fluorine and the two alkyl groups of the di-$C_{1-3}$-alkyl-amino substituents may be joined together to form a 5- to 7-membered ring, with the provisos that (i) the group Q contains a total of not more than three heteroatoms as ring members, (ii) the group Q contains a total of not more than two carbonyl groups as ring members and (iii) a group $R^b$ bound to a saturated carbon atom in the α-position to a saturated nitrogen atom substituted by the group $R^a$, or to an oxygen or sulphur atom as a ring member of a bi- or tricyclic heterocycle of the group Q does not take on the meanings of a hydroxy, $C_{1-3}$-alkoxy, amino, $C_{1-3}$-alkyl-amino or di-$C_{1-3}$-alkyl-amino group, the tautomers, the isomers, the diastereomers, the enantiomers, the hydrates, mixtures and salts thereof and the hydrates of the salts, particularly the physiologically acceptable salts thereof with inorganic or organic acids.

An eighth embodiment of the present invention comprises the compounds of the above general formula (I), wherein A, X, $R^1$, $R^2$ and $R^3$ are as hereinbefore defined in the first, second, third, fourth or fifth embodiment and Q denotes a heterocycle bound via a carbon or nitrogen atom consisting of a ring A and a ring B, which is fused to the ring A via two adjacent carbon atoms or via a carbon atom and an adjacent nitrogen atom, while, with the proviso that A is a 5- or 6-membered ring and B is a 6- or 7-membered ring, the rings A and B are selected from a 5-membered, saturated, mono- or diunsaturated carbocycle, in which one, two or three ring members may each independently of one another be replaced by an >$NR^a$ group, an oxygen or sulphur atom or, in the case of unsaturated ring members, by a nitrogen atom, while a maximum of two ring members denote an oxygen atom, which may not be directly linked to one another, and a maximum of one ring member denotes a sulphur atom, or a 6-membered, saturated, mono-, di- or triunsaturated carbocycle, in which one, two or three ring members may each independently of one another be replaced by an >$NR^a$ group, an oxygen or sulphur atom or, in the case of unsaturated ring members, by a nitrogen atom, while a maximum of two ring members denote oxygen atoms which may not be directly linked to one another denote and a maximum of one ring member denotes a sulphur atom, or a 7-membered, saturated, mono-, di- or triunsaturated carbocycle, in which one, two or three ring members may each independently of one another be replaced by an >NR$^a$ group, an oxygen or sulphur atom or, in the case of unsaturated ring members, by a nitrogen atom, while a maximum of two ring members denote oxygen or sulphur atoms and these may not be directly linked to one another, or at least one of the fused rings A and B contains at least one heteroatom as a ring member, one or two methylene groups as ring members in the 5- to 7-membered rings A and B may each be replaced independently of one another by carbonyl groups, one or two carbon atoms as ring members of the rings A and B may be substituted by R$^b$, while the substituents may be identical or different, two hydrogen atoms bound to adjacent carbon or nitrogen atoms or to a carbon and an adjacent nitrogen atom as ring members of the rings A or B may be replaced by a $C_{3-4}$-n-alkylene bridge and thus form a tricyclic group, or a hydrogen atom bound to a carbon or nitrogen atom as a ring member of the ring A and another hydrogen atom bound to a carbon or nitrogen atom as a ring member of the ring B, where the above-mentioned ring members are separated from one another by two bonds, may be replaced by a $C_{2-3}$-n-alkylene bridge and thus form a tricyclic group, while in the above-mentioned $C_{3-4}$-n-alkylene bridges and $C_{2-3}$-n-alkylene bridges one or two methylene groups may be substituted by R$^b$ independently of one another, R$^a$ denotes a hydrogen atom or a straight-chain or branched $C_{1-3}$-alkyl group, wherein each hydrogen atom, if it is not in the α-position to a nitrogen atom, may be replaced by fluorine, R$^b$ denotes a halogen atom or a straight-chain or branched $C_{1-3}$-alkyl group, wherein each hydrogen atom, if it is not in the α-position to a nitrogen atom, may be replaced by fluorine, with the provisos that (i) the group Q contains a total of not more than three heteroatoms as ring members, (ii) the group Q contains a total of not more than two carbonyl groups as ring members and the tautomers, the isomers, the diastereomers, the enantiomers, the hydrates, mixtures and salts thereof and the hydrates of the salts, particularly the physiologically acceptable salts thereof with inorganic or organic acids.

A ninth embodiment of the present invention comprises the compounds of the above general formula (I), wherein A, X, Q and R$^1$ are as hereinbefore defined in the first, second, third, fourth, fifth, sixth, seventh or eighth embodiment and R$^2$ denotes the hydrogen atom or a phenylmethyl group or a $C_{2-7}$-alkyl group which may be substituted in the ω position by a cyclo-$C_{3-7}$-alkyl, cyclo-$C_{3-7}$-alkenyl, phenyl, pyridinyl, hydroxy, amino, $C_{1-6}$-alkylamino, di-($C_{1-6}$-alkyl)-amino, hydroxycarbonyl, $C_{1-6}$-alkoxycarbonyl, aminocarbonyl, aminocarbonylamino, $C_{1-6}$-alkylamino, 4-morpholinyl group, while the phenyl and pyridinyl groups mentioned in the groups defined hereinbefore for R$^2$ or contained as substituents may additionally be mono-, di- or trisubstituted in the carbon skeleton by halogen, by $C_{1-3}$-alkyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonyl-$C_{1-3}$-alkylamino, aminocarbonyl, $C_{1-3}$-alkylaminocarbonyl or di-($C_{1-3}$-alkyl)-aminocarbonyl groups and the substituents may be identical or different, R$^3$ denotes the hydrogen atom or a $C_{1-3}$-alkyl group or R$^2$ and R$^3$ together with the enclosed nitrogen atom denote a group of general formula

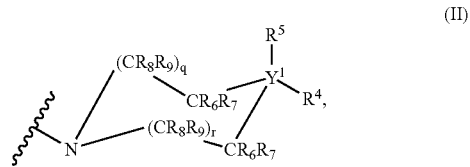

(II)

wherein

Y$^1$ denotes the carbon atom or, if R$^5$ denotes a pair of free electrons, Y$^1$ may also be the nitrogen atom, q and r, if Y$^1$ denotes the carbon atom, denote the numbers 0 or 1 or q and r, if Y$^1$ denotes the nitrogen atom, denote the numbers 1 or 2, R$^4$ denotes the hydrogen atom, an amino, $C_{1-4}$-alkyl-amino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group, a phenyl, pyridinyl or diazinyl group which may be substituted in each case by a halogen, by a $C_{1-3}$-alkyl, $C_{1-3}$-alkoxy, hydroxy, amino, $C_{1-4}$-alkyl-amino, di-($C_{1-4}$-alkyl)-amino-amino-$C_{1-3}$-alkyl, $C_{1-4}$-alkyl-amino-$C_{1-3}$-alkyl, di-($C_{1-4}$-alkyl)-amino-$C_{1-3}$-alkyl group, a heterocycle selected from a 4- to 7-membered azacycloalkyl group, a 6- to 7-membered oxaza, S,S-dioxothiaza or diazacycloalkyl group and a 7- to 9-membered azabicycloalkyl group, while the above-mentioned mono- and bicyclic heterocycles are bound to Y$^1$ in formula (II) by a nitrogen or a carbon atom, in the above-mentioned mono- and bicyclic heterocycles a methylene group not directly linked to a nitrogen, oxygen or sulphur atom may be substituted by one or two fluorine atoms and the above-mentioned mono- and bicyclic heterocycles may be mono- or disubstituted by hydroxy, $C_{1-3}$-alkyl or hydroxy-$C_{1-3}$-alkyl groups or may be monosubstituted by a benzyl, cyclo-$C_{3-6}$-alkyl, hydroxycyclo-$C_{3-6}$-alkyl, cyclo-$C_{3-6}$-alkyl-$C_{1-3}$-alkyl, $C_{1-4}$-alkylcarbonyl, $C_{1-4}$-alkylcarbonyl-$C_{1-3}$-alkyl, hydroxy, $C_{1-4}$-alkoxy, amino, $C_{1-4}$-alkylamino, di-($C_{1-4}$-alkyl)-amino, $C_{1-3}$-alkoxycarbonyl, hydroxycarbonyl-carbonyl, $C_{1-3}$-alkoxycarbonyl-carbonyl, hydroxycarbonyl-$C_{1-3}$-alkyl, $C_{1-3}$-alkoxycarbonyl-$C_{1-3}$-alkyl, hydroxycarbonyl-$C_{1-3}$-alkylcarbonyl, $C_{1-3}$-alkoxycarbonyl-$C_{1-3}$-alkylcarbonyl, aminosulphonyl, $C_{1-4}$-alkylaminosulphonyl, di-($C_{1-4}$-alkyl)-aminosulphonyl, $C_{1-3}$-alkylsulphonyl, cyclo-$C_{3-7}$-alkylsulphonyl, aminocarbonyl-$C_{1-3}$-alkyl, $C_{1-4}$-alkylaminocarbonyl-$C_{1-3}$-alkyl, di-($C_{1-4}$-alkyl)-aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl groups, or, if $Y^1$ denotes the carbon atom, also denotes the hydroxycarbonyl, aminomethyl, $C_{1-4}$-alkyl-aminomethyl or di-($C_{1-4}$-alkyl)-aminomethyl group, $R^5$ denotes a hydrogen atom, a $C_{1-3}$-alkyl group or, if $Y^1$ denotes a nitrogen atom, also denotes a pair of free electrons, $R^6$ and $R^7$, which may be identical or different, in each case denote a hydrogen atom, a $C_{1-3}$-alkyl group or, if $Y^1$ denotes a carbon atom, they may also denote an amino, $C_{1-3}$-alkylamino or di-($C_{1-3}$-alkyl)-amino group, while the two $C_{1-3}$-alkyl groups may be joined together to form a ring and $R^8$ and $R^9$, which may be identical or different, in each case denote a hydrogen atom or a $C_{1-3}$-alkyl group, while, unless otherwise stated, all the alkyl, alkenyl and alkynyl groups mentioned or contained in the groups defined hereinbefore may be straight-chain or branched, every methyne group contained in the groups defined hereinbefore may be substituted by a fluorine atom, each methylene group may be substituted by up to 2 fluorine atoms and each methyl group may be substituted by up to 3 fluorine atoms and two alkyl and alkenyl groups bound to a nitrogen atom may be joined together forming a 4- to 7-membered, saturated or unsaturated heterocyclic ring, all the aromatic and heteroaromatic groups mentioned or contained in the groups defined hereinbefore may additionally be mono-, di- or trisubstituted by halogen, by cyano or hydroxy groups and the substituents may be identical or different, the tautomers, the isomers, the diastereomers, the enantiomers, the hydrates, mixtures and salts thereof and the hydrates of the salts, particularly the physiologically acceptable salts thereof with inorganic or organic acids or bases.

A tenth embodiment of the present invention comprises the compounds of the above general formula (I), wherein A, X, Q and $R^1$ are as hereinbefore defined in the first, second, third, fourth, fifth, sixth, seventh or eighth embodiment and $R^2$ denotes the hydrogen atom or a phenylmethyl group or a $C_{2-7}$-alkyl group which may be substituted in the ω position by a cyclo-$C_{3-7}$-alkyl, cyclo-$C_{3-7}$-alkenyl, phenyl, pyridinyl, hydroxy, amino, $C_{1-6}$-alkylamino, di-($C_{1-6}$-alkyl)-amino, hydroxycarbonyl, $C_{1-6}$-alkoxycarbonyl, aminocarbonyl, aminocarbonylamino, $C_{1-6}$-alkylamino, 4-morpholinyl group, while the phenyl and pyridinyl groups mentioned in the groups defined hereinbefore for $R^2$ or contained as substituents may additionally be mono-, di- or trisubstituted in the carbon skeleton by halogen, by $C_{1-3}$-alkyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonyl-$C_{1-3}$-alkylamino, aminocarbonyl, $C_{1-3}$-alkylaminocarbonyl or di-($C_{1-3}$-alkyl)-aminocarbonyl groups and the substituents may be identical or different, $R^3$ denotes the hydrogen atom or a $C_{1-3}$-alkyl group or $R^2$ and $R^3$ together with the enclosed nitrogen atom denote a group of general formula

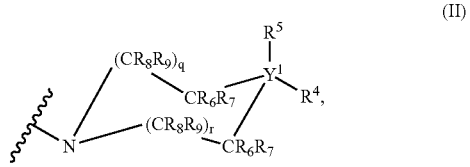

wherein $Y^1$ denotes the carbon atom or, if $R^5$ denotes a pair of free electrons, may also represent the nitrogen atom, q and r, if $Y^1$ denotes the carbon atom, denote the numbers 0 or 1 or q and r, if $Y^1$ denotes the nitrogen atom, denote the numbers 1 or 2, $R^4$ denotes the hydrogen atom, an amino, $C_{1-4}$-alkyl-amino, di-($C_{1-4}$-alkyl)-alkylamino, $C_{1-6}$-alkyl, cyclo-$C_{3-7}$-alkyl, cyclo-$C_{3-7}$-alkenyl, amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group, a phenyl, pyridinyl or diazinyl group which may be substituted in each case by a halogen, by a $C_{1-3}$-alkyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkylamino-$C_{1-3}$-alkyl, di-($C_{1-4}$-alkyl)-amino-$C_{1-3}$-alkyl group, a heterocycle selected from a 4- to 7-membered azacycloalkyl group, a 6- to 7-membered oxaza or diazacycloalkyl group and a 7- to 9-membered azabicycloalkyl group, while the above-mentioned mono- and bicyclic heterocycles are bound to $Y^1$ in formula (II) by a nitrogen or a carbon atom, in the above-mentioned mono- and bicyclic heterocycles a methylene group not directly linked to a nitrogen, oxygen or sulphur atom may be substituted by one or two fluorine atoms and the above-mentioned mono- and bicyclic heterocycles may be mono- or polysubstituted, for example mono- to trisubstituted, by $C_{1-3}$-alkyl groups or monosubstituted by a benzyl, cyclo-$C_{3-6}$-alkyl, cyclo-$C_{3-6}$-alkyl-$C_{1-3}$-alkyl, $C_{1-4}$-alkylcarbonyl, hydroxy, $C_{1-4}$-alkoxy, amino, $C_{1-4}$-alkylamino, di-($C_{1-4}$-alkyl)-amino, hydroxycarbonyl, $C_{1-3}$-alkoxycarbonyl, hydroxycarbonyl-$C_{1-3}$-alkyl, $C_{1-3}$-alkoxycarbonyl-$C_{1-3}$-alkyl or $C_{1-3}$-alkylsulphonyl group, or also, if $Y^1$ denotes the carbon atom, the hydroxycarbonyl, aminomethyl, $C_{1-4}$-alkylaminomethyl or di-($C_{1-4}$-alkyl)-aminomethyl group, $R^5$ denotes a hydrogen atom, a $C_{1-3}$-alkyl group or, if $Y^1$ denotes a nitrogen atom, also a pair of free electrons, $R^6$ and $R^7$, which may be identical or different, in each case represent a hydrogen atom, a $C_{1-3}$-alkyl group or also, if $Y^1$ denotes a carbon atom, a $C_{1-3}$-alkylamino or di-($C_{1-3}$-alkyl)-amino group, while the two $C_{1-3}$-alkyl groups may be joined together to form a ring and $R^8$ and $R^9$, which may be identical or different, in each case represent a hydrogen atom or a $C_{1-3}$-alkyl group, while, unless otherwise stated, all the alkyl, alkenyl and alkynyl groups mentioned or contained in the groups defined hereinbefore may be straight-chain or branched, every methyne group contained in the groups defined hereinbefore may be substituted by a fluorine atom, each methylene group may be substituted by up to 2 fluorine atoms and each methyl group may be substituted by up to 3 fluorine atoms and two alkyl and alkenyl groups bound to a nitrogen atom may be joined together forming a 4- to 7-membered, saturated or unsaturated heterocyclic ring, all the aromatic and heteroaromatic groups mentioned or contained in the groups defined hereinbefore may additionally be mono-, di- or trisubstituted by halogen, by cyano or hydroxy groups and the substituents may be identical or different, the tautomers, the diastereomers, the enantiomers, the hydrates, mixtures and salts thereof and the hydrates of the salts, particularly the physiologically acceptable salts thereof with inorganic or organic acids or bases.

An eleventh embodiment of the present invention comprises the compounds of the above general formula (I), wherein A, X, Q and $R^1$ are as hereinbefore defined in the first, second, third, fourth, fifth, sixth, seventh or eighth embodiment and $R^2$ denotes the hydrogen atom or a phenylmethyl group or a $C_{2-7}$-alkyl group which may be substituted in the ω position by a phenyl, amino, $C_{1-6}$-alkylamino, di-($C_{1-6}$-alkyl)-amino group, while the phenyl and phenylmethyl group mentioned hereinbefore may additionally be mono- or disubstituted at an aromatic carbon atom by halogen, by $C_{1-3}$-alkyl, $C_{1-3}$-alkoxy, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different, $R^3$ denotes the hydrogen atom or a $C_{1-3}$-alkyl group or $R^2$ and $R^3$ together with the enclosed nitrogen atom denote a group of general formula

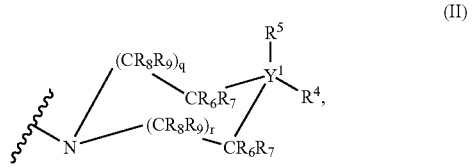

(II)

wherein $Y^1$ denotes the carbon atom or, if $R^5$ denotes a pair of free electrons, may also represent the nitrogen atom, q and r, if $Y^1$ denotes the carbon atom, denote the numbers 0 or 1 or q and r, if $Y^1$ denotes the nitrogen atom, denote the numbers 1 or 2, $R^4$ denotes a hydrogen atom, an amino, $C_{1-4}$-alkyl-amino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group, a phenyl or pyridyl group which may be substituted in each case by a halogen, by a $C_{1-3}$-alkyl, $C_{1-3}$-alkoxy, amino, $C_{1-4}$-alkyl-amino, di-($C_{1-4}$-alkyl)-amino group, a heterocycle selected from a 6- to 7-membered azacycloalkyl group, a 6- to 7-membered S,S,dioxothiaza- and diazacycloalkyl group and a 7- to 9-membered azabicycloalkyl group, while the above-mentioned mono- and bicyclic heterocycles are bound to $Y^1$ in formula (II) by a nitrogen or a carbon atom, in the above-mentioned mono- and bicyclic heterocycles a methylene group not directly linked to a nitrogen, oxygen or sulphur atom may be substituted by one or two fluorine atoms and the above-mentioned mono- and bicyclic heterocycles may be mono- or disubstituted by a hydroxy, $C_{1-3}$-alkyl or hydroxy-$C_{1-3}$-alkyl group, by a benzyl, cyclo-$C_{3-6}$-alkyl, hydroxy-$C_{3-6}$-cycloalkyl, cyclo-$C_{3-6}$-alkyl-$C_{1-3}$-alkyl, $C_{1-3}$-alkylcarbonyl-$C_{1-3}$-alkyl, amino, $C_{1-4}$-alkylamino or di-($C_{1-4}$-alkyl)-amino, hydroxycarbonyl-carbonyl, $C_{1-6}$-alkoxycarbonyl-carbonyl, hydroxycarbonyl-$C_{1-3}$-alkylcarbonyl, $C_{1-3}$-alkoxycarbonyl-$C_{1-3}$-alkylcarbonyl, aminosulphonyl, $C_{1-4}$-alkylaminosulphonyl, di-($C_{1-4}$-alkyl)-aminosulphonyl, cyclo-$C_{3-7}$-alkylsulphonyl, aminocarbonyl-$C_{1-3}$-alkyl, $C_{1-4}$-alkylaminocarbonyl-$C_{1-3}$-alkyl, di-($C_{1-4}$-alkyl)-aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl groups, or, if $Y^1$ denotes the carbon atom, the hydroxycarbonyl, aminomethyl, $C_{1-4}$-alkyl-aminomethyl or di-($C_{1-4}$-alkyl)-aminomethyl group, $R^5$ denotes a hydrogen atom or, if $Y^1$ denotes a nitrogen atom, it may also denote a pair of free electrons, $R^6$ and $R^7$, which may be identical or different, in each case represent a hydrogen atom, a $C_{1-3}$-alkyl group or, if $Y^1$ denotes a carbon atom, may also represent a $C_{1-3}$-alkylamino or di-($C_{1-3}$-alkyl)-amino group, while the two $C_{1-3}$-alkyl groups may be joined together to form a ring and $R^8$ and $R^9$, which may be identical or different, in each case represent a hydrogen atom or a $C_{1-3}$-alkyl group, the tautomers, the isomers, the diastereomers, the enantiomers, the hydrates, mixtures and salts thereof and the hydrates of the salts, particularly the physiologically acceptable salts thereof with inorganic or organic acids or bases.

A twelfth embodiment of the present invention comprises the compounds of the above general formula (I), wherein A, X, Q and $R^1$ are as hereinbefore defined in the first, second, third, fourth, fifth, sixth, seventh or eighth embodiment and $R^2$ denotes a phenylmethyl group or a $C_{2-7}$-alkyl group which may be substituted in the ω position by a phenyl, amino, $C_{1-6}$-alkylamino, di-($C_{1-6}$-alkyl)-amino group, while the above-mentioned phenyl and phenylmethyl group may be substituted at an aromatic carbon atom by an amino-$C_{1-3}$-alkyl, $C_{1-3}$-alkylamino-$C_{1-3}$-alkyl or di-($C_{1-3}$-alkyl)-amino-$C_{1-3}$-alkyl group, $R^3$ denotes the hydrogen atom or a $C_{1-3}$-alkyl group or $R^2$ and $R^3$ together with the enclosed nitrogen atom denote a group of general formula

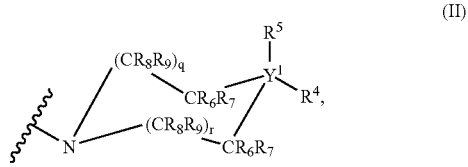

(II)

wherein $R^6$ and $R^7$ in each case denote a hydrogen atom or a dimethylamino group, $R^8$ and $R^9$ in each case denote the hydrogen atom and (a) $Y^1$ denotes the carbon atom, q and r denote the numbers 0 or 1, $R^4$ denotes the hydrogen atom, a phenyl, pyridinyl or pyrimidinyl group which may be substituted in each case by a halogen, by an amino, methylamino, dimethylamino, methyl or methoxy group, a hydroxy, 2-diethylaminoethyl, amino, methylamino, dimethylamino, diethylamino, pyrrolidin-1-yl, piperidin-1-yl, 4-amino-piperidin-1-yl, 4-methylamino-piperidin-1-yl, 4-dimethylamino-piperidin-1-yl, 4-hydroxymethyl-piperidin-1-yl, 4-hydroxy-piperidin-1-yl, 4-methoxy-piperidin-1-yl, 4-hydroxy-4-methyl-piperidin-1-yl, 4-hydroxy-4-trifluoromethyl-piperidin-1-yl, 4-ethyl4-hydroxy-piperidin-1-yl, 4,4-dimethylpiperidin-1-yl, 4-amino4-methyl-piperidin-1-yl, 4-hydroxy-4-hydroxymethyl-piperidin1-yl, 3-amino-piperidin-1-yl, 3-methylamino-piperidin-1-yl, 3-dimethylamino-piperidin-1-yl, perhydro-azepin-1-yl, perhydro-1,4-diazepin-1-yl, 4-methyl-perhydro-1,4-diazepin-1-yl, 1-methyl-piperidin-4-yl, piperidin-4-yl, 1-ethylpiperidin-4-yl, 1-(2-hydroxyethyl)-piperidin-4-yl, 1-cyclopropyl-piperidin-4-yl, 1-cyclopropylmethyl-piperidin-4-yl, 1-hydroxycarbonylmethyl-piperidin-4-yl, 1-ethoxycarbonylmethyl-piperidin-4-yl, 1-hydroxycarbonylethyl-piperidin-4-yl, 1-ethoxycarbonylethyl-piperidin-4-yl, 1-hydroxycarbonylethylcarbonyl-piperidin-4-yl, 1-ethoxycarbonylethylcarbonyl-piperidin-4-yl, 1-methylsulphonyl-piperidin-4-yl, 1-aminosulphonyl-piperidin-4-yl, 1-hydroxycarbamoylmethyl-piperidin-4-yl, 1-(hydroxy-methyl-carbamoyl)-piperidin-4-yl, 1-(methoxycarbamoyl-methyl)-piperidin-4-yl, piperazin-1-yl, 4-methyl-piperazin-1-yl, 4-methylsulphonyl-piperazin-1-yl, 4-aminosulphonyl-piperazin-1-yl, 4-cyclopropylmethyl-piperazin-1-yl, 4-ethyl-piperazin-1-yl, 4-(2-hydroxyethyl)-piperazin-1-yl, 4-cyclopropyl-piperazin-1-yl, 4-hydroxycarbonylmethyl-piperazin-1-yl, 4-ethoxycarbonylmethyl-piperazin-1-yl, 4-hydroxycarbonylethyl-piperazin-1-yl, 4-ethoxycarbonylethyl-piperazin-1-yl, 4-hydroxycarbonylethylcarbonyl-piperazin-1-yl, 4-ethoxycarbonylethylcarbonyl-piperazin-1-yl, 1,2-dimethyl-piperazin-1-yl, 3-methyl-piperazin-1-yl, 3,4,5-trimethyl-piperazin-1-yl, 3,5-dimethyl-piperazin-1-yl, 3,3,4-trimethyl-piperazin-1-yl, 3,3-dimethyl-piperazin-1-yl, 3,3,4,5,5-pentamethyl-piperazin-1-yl, 3,3,5,5-tetramethyl-piperazin-1-yl, morpholin-4-yl, 4,4-difluoro-piperidin-1-yl, 8-methyl-8-aza-bicyclo[3.2.1]oct-3-yl, 8-aza-bicyclo[3.2.1]oct-3-yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-hydroxycarbonylmethyl-piperidin-4-yl or 4-hydroxycarbonylmethyl-piperazin-1-yl group, and $R^5$ denotes a hydrogen atom, or (b) $Y^1$ denotes a nitrogen atom, q and r denote the numbers 1 or 2, $R^4$ denotes the hydrogen atom, a phenyl, pyridinyl or pyrimidinyl group which may be substituted in each case by a halogen, by an amino, methylamino, dimethylamino, methyl or methoxy group, a methyl, ethyl, isopropyl, cyclopropyl, cyclopentyl, cyclohexyl, cycloheptyl, cyclopropylmethyl, 2-diethylaminopropyl, 1-quinuclidin-3-yl, piperidin-4-yl, 1-methyl-piperidin-4-yl, 1-ethyl-piperidin-4-yl, 1-(2-hydroxyethyl)-piperidin-4-yl, 1-cyclopropyl-piperidin-4-yl, 1-cyclopropylmethyl-piperidin-4-yl, 1-hydroxycarbonylmethyl-piperidin-4-yl, 1-ethoxycarbonylmethyl-piperidin-4-yl, 1-hydroxycarbonylethyl-piperidin-4-yl, 1-ethoxycarbonylethyl-piperidin-4-yl, 1-hydroxycarbonylethylcarbonyl-piperidin-4-yl, 1-ethoxycarbonylethylcarbonyl-piperidin-4-yl, 1-ethoxycarbonylmethyl-piperidin-4-yl, 1-methylsulphonyl-piperidin-4-yl, 1-aminosulphonyl-piperidin-4-yl, tetrahydropyran4-yl, 8-methyl-8-aza-bicyclo[3.2.1]oct-3-yl, 5-methyl-2,5-diaza-bicyclo[2.2.1]hept-2-yl or 1-aza-bicyclo[2.2.2]oct-3-yl group and $R^5$ denotes a pair of free electrons, the tautomers, the isomers, the diastereomers, the enantiomers, the hydrates, mixtures and salts thereof and the hydrates of the salts, particularly the physiologically acceptable salts thereof with inorganic or organic acids or bases.

A thirteenth embodiment of the present invention comprises the compounds of the above general formula (I), wherein A, X, Q and $R^1$ are as hereinbefore defined in the first, second, third, fourth, fifth, sixth, seventh or eighth embodiment and $R^2$ denotes a phenylmethyl group or a $C_{2-7}$-alkyl group which may be substituted in the ω position by a phenyl, amino, $C_{1-6}$-alkylamino, di-($C_{1-6}$-alkyl)-amino group, while the phenyl and phenylmethyl group mentioned hereinbefore may be substituted at an aromatic carbon atom by an amino-$C_{1-3}$-alkyl, $C_{1-3}$-alkylamino-$C_{1-3}$-alkyl or di-($C_{1-3}$-alkyl)-amino-$C_{1-3}$-alkyl group, $R^3$ denotes the hydrogen atom or a $C_{1-3}$-alkyl group or $R^2$ and $R^3$ together with the enclosed nitrogen atom denote a group of general formula

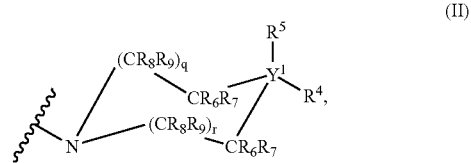

(II)

wherein $R^6$ and $R^7$ in each case denote a hydrogen atom or a dimethylamino group, $R^8$ and $R^9$ in each case denote the hydrogen atom and (a) $Y^1$ denotes the carbon atom, q and r denote the numbers 0 or 1, $R^4$ denotes the hydrogen atom, a phenyl, pyridinyl or pyrimidinyl group which may be substituted in each case by a halogen, by an amino, methylamino, dimethylamino, methyl or methoxy group, a hydroxy, 2-diethylaminoethyl, amino, methylamino, dimethylamino, diethylamino, pyrrolidin-1-yl, piperidin-1-yl, 4-amino-piperidin-1-yl, 4-methylamino-piperidin-1-yl, 4-dimethylamino-piperidin-1-yl, 3-amino-piperidin-1-yl, 3-methylamino-piperidin-1-yl, 3-dimethylamino-piperidin-1-yl, perhydro-azepin-1-yl, perhydro-1,4-diazepin-1-yl, 4-methyl-perhydro-1,4-diazepin-1-yl, 1-methyl-piperidin-4-yl, piperidin-4-yl, 1-ethylpiperidin-4-yl, 1-cyclopropyl-piperidin-4-yl, 1-cyclopropylmethyl-piperidin-4-yl, piperazin-1-yl, 4-methyl-piperazin-1-yl, 4-cyclopropylmethyl-piperazin-1-yl, 4-ethyl-piperazin-1-yl, 4-cyclopropyl-piperazin-1-yl, 1,2-dimethyl-piperazin-1-yl, 3-methyl-piperazin-1-yl, 3,4,5-trimethyl-piperazin-1-yl, 3,5-dimethyl-piperazin-1-yl, 3,3,4-trimethyl-piperazin-1-yl, 3,3-dimethyl-piperazin-1-yl, 3,3,4,5,5-pentamethyl-piperazin-1-yl, 3,3,5,5-tetramethyl-piperazin-1-yl, morpholin-4-yl, 4,4-difluoro-piperidin-1-yl, 8-methyl-8-aza-bicyclo[3.2.1]oct-3-yl, 8-aza-bicyclo[3.2.1]oct-3-yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-hydroxycarbonylmethyl-piperidin-4-yl or 4-hydroxycarbonylmethyl-piperazin-1-yl group, and $R^5$ denotes a hydrogen atom, or (b) $Y^1$ denotes a nitrogen atom, q and r denote the numbers 1 or 2, $R^4$ denotes the hydrogen atom, a phenyl, pyridinyl or pyrimidinyl group which may be substituted in each case by a halogen, by an amino, methylamino, dimethylamino, methyl or methoxy group, a methyl, ethyl, isopropyl, cyclopropyl, cyclopropylmethyl, 2-diethylamino-propyl, 1-quinuclidin-3-yl, 1-piperidin-4-yl, 1-methyl-piperidin-4-yl, 1-ethyl-piperidin-4-yl, 1-cyclopropyl-piperidin-4-yl, 1-cyclopropylmethyl-piperidin-4-yl, 1-hydroxycarbonylmethyl-piperidin-4-yl or 1-ethoxycarbonylmethyl-piperidin-4-yl group and $R^5$ denotes a pair of free electrons, the tautomers, the diastereomers, the enantiomers, the hydrates, mixtures and salts thereof and the hydrates of the salts, particularly the physiologically acceptable salts thereof with inorganic or organic acids or bases.

Other preferred embodiments of the present invention consist of the compounds of the above general formula (I), wherein Q, $R^1$, $R^2$ and $R^3$ are as hereinbefore defined in the first, second, third, fourth, fifth, sixth, seventh, eighth, ninth, tenth, eleventh or twelfth embodiment and A and X in each case denote an oxygen atom, the tautomers, the isomers, the diastereomers, the enantiomers, the hydrates, mixtures and salts thereof and the hydrates of the salts, particularly the physiologically acceptable salts thereof with inorganic or organic acids or bases.

A fourteenth embodiment of the present invention comprises the compounds of the above general formula (I), wherein A and X in each case denote an oxygen atom, $R^1$ denotes a 1,3,4,5-tetrahydro-1,3-benzodiazepin-2-on-3-yl, 3,4-dihydro-1H-quinazolin-2-on-3-yl, 5-phenyl-2,4-dihydro-1,2,4-triazol-3-on-2-yl, 1,3-dihydro-imidazo[4,5-c]quinolin-2-on-3-yl, 1,3-dihydro-naphth[1,2-d]imidazol-2-on-3-yl, 1,3-dihydro-benzimidazol-2-on-3-yl, 4-phenyl-1,3-dihydro-imidazol-2-on-1-yl, 3,4-dihydro-1H-thieno[3,2-d]pyrimidin-2-on-3-yl or 3,4-dihydro-1H-thieno[3,4-d]pyrimidin-2-on-3-yl group or together with the piperidine ring in formula (I) denotes the 1',2'-dihydro-2'-oxospiro-4H-3',1-benzoxazin'-4,4'-piperidin-1-yl group, and $R^2$ and $R^3$ are as hereinbefore defined in the first or second embodiment, while the heterocycles mentioned hereinbefore under $R^1$ may additionally be monosubstituted in the carbon skeleton by a methoxy group, and all the aromatic and heteroaromatic groups and parts of molecules mentioned or contained in the groups defined under $R^1$ may additionally be mono-, di- or trisubstituted by halogen atoms or by cyano or hydroxy groups and the substituents may be identical or different, and in this and all the embodiments mentioned previously, in each case the compounds wherein Q is defined as in the seventh embodiment
are of exceptional importance,
the compounds wherein
Q is defined as in the eighth embodiment
are of particularly outstanding importance, the tautomers, the isomers, the diastereomers, the enantiomers, the hydrates, mixtures and salts thereof and the hydrates of the salts, particularly the physiologically acceptable salts thereof with inorganic or organic acids or bases.

A fifteenth embodiment of the present invention comprises the compounds of the above general formula (I), wherein
A and X in each case denote an oxygen atom,
$R^1$ is defined as in the fifth embodiment hereinbefore, Q is defined as in the eighth embodiment hereinbefore, and in this and all the embodiments mentioned previously, in each case the compounds wherein $R^2$ and $R^3$ are defined as in the ninth or tenth embodiment hereinbefore, are of exceptional importance, the compounds in which $R^2$ and $R^3$ are as defined in the eleventh embodiment hereinbefore are of particularly outstanding importance, and the compounds in which $R^2$ and $R^3$ are defined as in the twelfth embodiment hereinbefore are of most particularly outstanding importance, the tautomers, the isomers, the diastereomers, the enantiomers, the hydrates, mixtures and salts thereof and the hydrates of the salts, particularly the physiologically acceptable salts thereof with inorganic or organic acids or bases.

A sixteenth embodiment of the present invention comprises the compounds of the above general formula (I), wherein A and X in each case denote an oxygen atom, $R^1$ is defined as in the fifth embodiment, Q is defined as in the eighth embodiment, $R^2$ and $R^3$ are defined as in the twelfth embodiment, the tautomers, the isomers, the diastereomers, the enantiomers, the hydrates, mixtures and salts thereof and the hydrates of the salts, particularly the physiologically acceptable salts thereof with inorganic or organic acids or bases.

Q may be, for example, the bi- and tricyclic heterocycles mentioned in Table I, which may be substituted at a saturated nitrogen atom by the group $R^{a'}$ and, independently thereof, may be substituted in the carbon skeleton by the group $R^b$ and $R^{a'}$ denotes the methyl, ethyl or 2,2,2-trifluoroethyl group and $R^b$ denotes the chlorine or bromine atom, the methyl, difluoromethyl, trifluoromethyl, ethyl, propyl, isopropyl, cyclopropyl, hydroxy, methoxy, difluoromethoxy, trifluoromethoxy, amino, methylamino or dimethylamino group.

In all the embodiments described above Q may represent the groups shown in Table I, either unsubstituted as explicitly shown or optionally substituted, as mentioned above, by the groups $R^{a'}$ and/or $R^b$.

TABLE I

| | Q | Name |
|---|---|---|
| (1) | | 1H-indol-5-yl |
| (2) | | 1H-indazol-5-yl |
| (3) | | 1H-indol-6-yl |

TABLE I-continued
| Q | | Name |
|---|---|---|
| (4) | 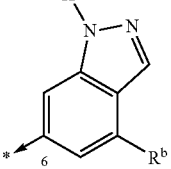 | 1H-indazol-6-yl |
| (5) | 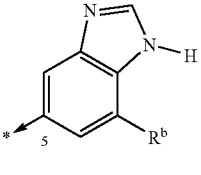 | 1H-benzimidazol-5-yl |
| (6) | 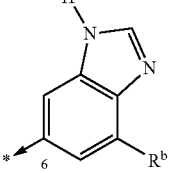 | 1H-benzimidazol-6-yl |
| (7) | 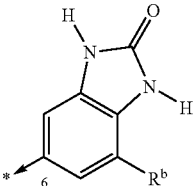 | 1,3-dihydro-benzimidazol-2-on-6-yl |
| (8) | 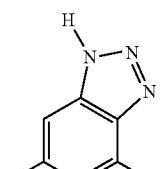 | 1H-benzotriazol-6-yl |
| (9) | 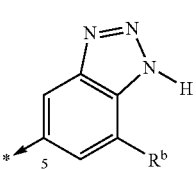 | 1H-benzotriazol-5-yl |
| (10) | 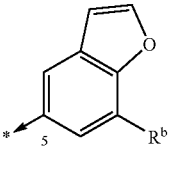 | benzofuran-5-yl |
| (11) | 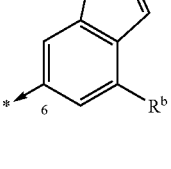 | benzofuran-6-yl |
| (12) | 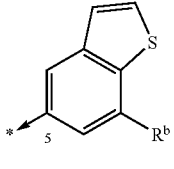 | benzothiophen-5-yl |
| (13) | 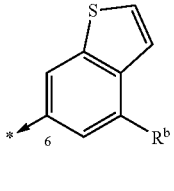 | benzothiophen-6-yl |
| (14) | 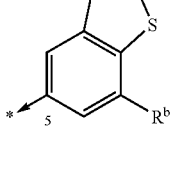 | benzothiazol-5-yl |
| (15) | 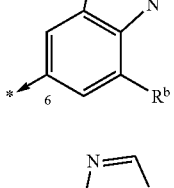 | benzothiazol-6-yl |
| (16) | 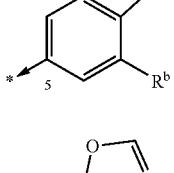 | benzoxazol-5-yl |
| (17) | 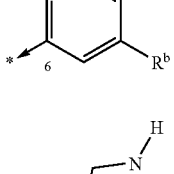 | benzoxazol-6-yl |
| (18) | 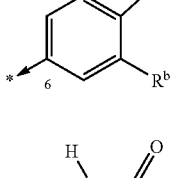 | 2,3-dihydro-1H-isoindol-6-yl |
| (19) | 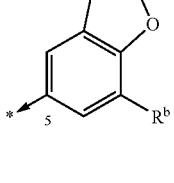 | 3H-benzooxazol-2-on-5-yl |

TABLE I-continued
| Q | Name |
|---|---|
| (20) 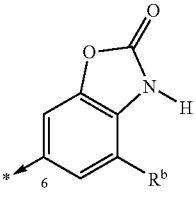 | 3H-benzooxazol-2-on-6-yl |
| (21) 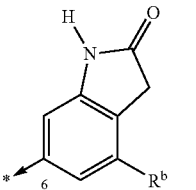 | 1,3-dihydro-indol-2-on-6-yl |
| (22) 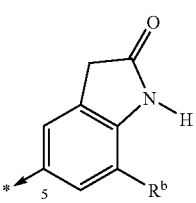 | 1,3-dihydro-indol-2-on-5-yl |
| (23) 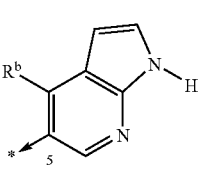 | 1H-pyrrolo[2,3-b]pyridin-5-yl |
| (24) 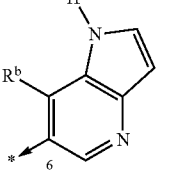 | 1H-pyrrolo[3,2-b]pyridin-6-yl |
| (25) 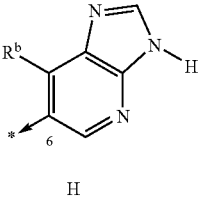 | 3H-imidazo[4,5-b]pyridin-6-yl |
| (26) 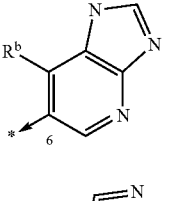 | 1H-imidazo[4,5-b]pyridin-6-yl |
| (27) 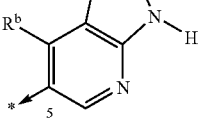 | 1H-pyrazolo[3,4-b]pyridin-5-yl |
| (28) 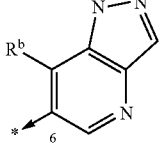 | 1H-pyrazolo[4,3-b]pyridin-6-yl |
| (29) 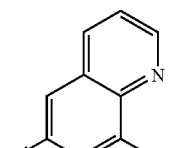 | quinolin-6-yl |
| (30) 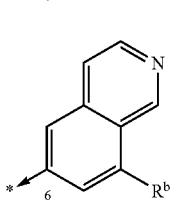 | isoquinolin-6-yl |
| (31) 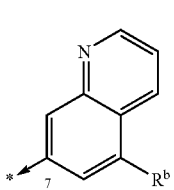 | quinolin-7-yl |
| (32) 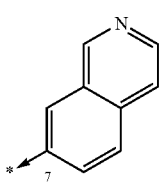 | isoquinolin-7-yl |
| (33) 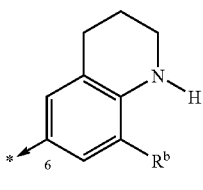 | 1,2,3,4-tetrahydroquinolin-6-yl |
| (34) 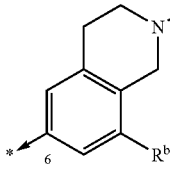 | 1,2,3,4-tetrahydroisoquinolin-6-yl |
| (35)  | 1,2,3,4-tetrahydroquinolin-7-yl |

TABLE I-continued

| Q | | Name |
|---|---|---|
| (36) | 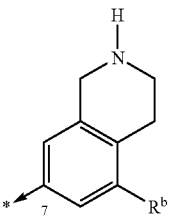 | 1,2,3,4-tetrahydroisoquinolin-7-yl |
| (37) | 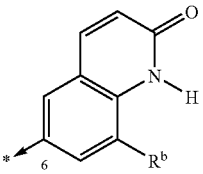 | 1H-quinolin-2-on-6-yl |
| (38) | 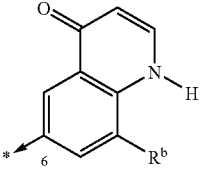 | 1H-quinolin-4-on-6-yl |
| (39) | 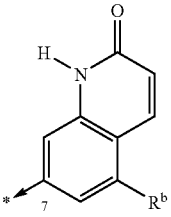 | 1H-quinolin-2-on-7-yl |
| (40) | 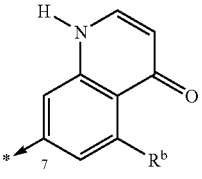 | 1H-quinolin-4-on-7-yl |
| (41) | 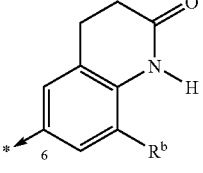 | 3,4-dihydro-1H-quinolin-2-on-6-yl |
| (42) | 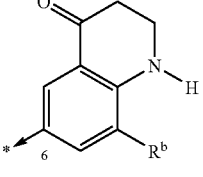 | 2,3-dihydro-1H-quinolin-4-on-6-yl |
| (43) | 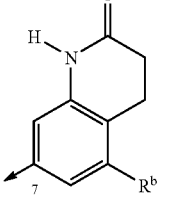 | 3,4-dihydro-1H-quinolin-2-on-7-yl |
| (44) | 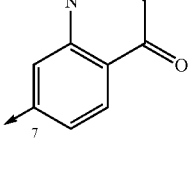 | 2,3-dihydro-1H-quinolin-4-on-7-yl |
| (45) | 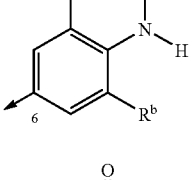 | 1,4-dihydro-3,1-benzoxazin-2-on-6-yl |
| (46) | 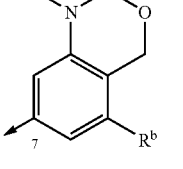 | 1,4-dihydro-3,1-benzoxazin-2-on-7-yl |
| (47) | 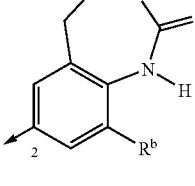 | 8,9-dihydro-5H-7-oxa-5-aza-benzcyclohepten-6-on-2-yl |
| (48) | 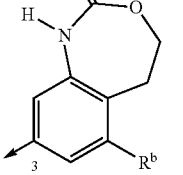 | 8,9-dihydro-5H-7-oxa-5-aza-benzcyclohepten-6-on-3-yl |
| (49) | 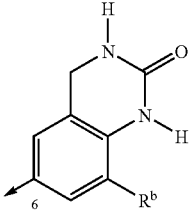 | 3,4-dihydro-1H-quinazolin-2-on-6-yl |

TABLE I-continued
| Q | | Name |
|---|---|------|
| (50) | 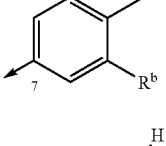 | 3,4-dihydro-1H-quinazolin-2-on-7-yl |
| (51) | 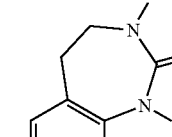 | 1,3,4,5-tetrahydro-1,3-benzodiazepin-2-on-7-yl |
| (52) | 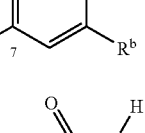 | 1,3,4,5-tetrahydro-1,3-benzodiazepin-2-on-8-yl |
| (53) | 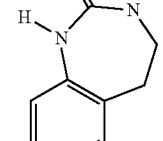 | 1,4-dihydro-quinoxalin-2,3-dion-6-yl |
| (54) | 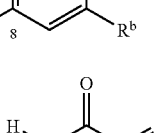 | chroman-2-on-6-yl |
| (55) | 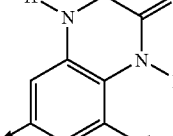 | chroman-4-on-6-yl |
| (56) | 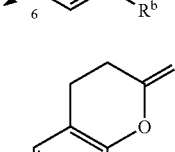 | chroman-2-on-7-yl |
| (57) | 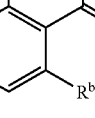 | chroman-4-on-7-yl |
| (58) | 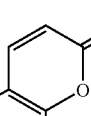 | chromen-2-on-6-yl |
| (59) | 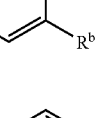 | chromen-4-on-6-yl |
| (60) | 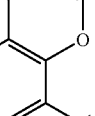 | chromen-2-on-7-yl |
| (61) | 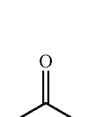 | chromen-4-on-7-yl |
| (62) | 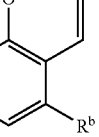 | 3H-benzofuran-2-on-5-yl |
| (63) | 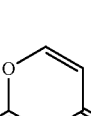 | 3H-benzofuran-2-on-6-yl |

TABLE I-continued
| Q | | Name |
|---|---|---|
| (64) | 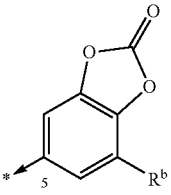 | 1,3-benzodioxol-2-on-5-yl |
| (65) | 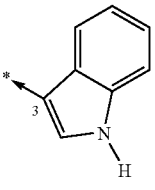 | indol-3-yl |
| (66) | 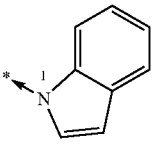 | indol-1-yl |
| (67) | 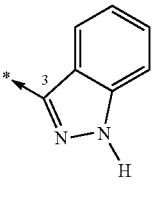 | indazol-3-yl |
| (68) | 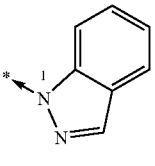 | indazol-1-yl |
| (69) | 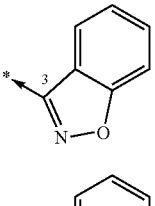 | 1,2-benzisoxazol-3-yl |
| (70) | 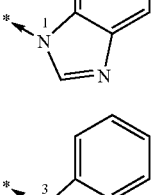 | benzimidazol-1-yl |
| (71) | 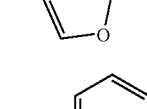 | benzofuran-3-yl |
| (72) | 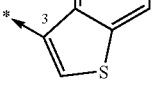 | benzothiophen-3-yl |
| (73) | 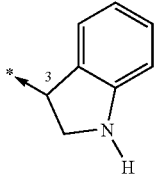 | 2,3-dihydro-1H-indol-3-yl |
| (74) | 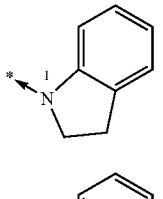 | 2,3-dihydro-1H-indol-1-yl |
| (75) | 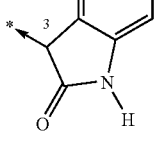 | 1,3-dihydro-indol-2-on-3-yl |
| (76) | 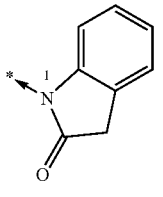 | 1,3-dihydro-indol-2-on-1-yl |
| (77) | 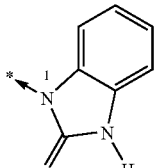 | 1,3-dihydro-benzimidazol-2-on-1-yl |
| (78) | 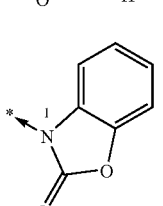 | 3H-benzoxazol-2-on-1-yl |
| (79) | 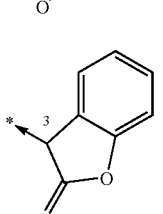 | 3H-benzofuran-2-on-3-yl |
| (80) | 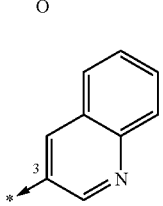 | quinolin-3-yl |

TABLE I-continued
| Q | Name |
|---|---|
| (81) 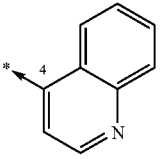 | quinolin-4-yl |
| (82) 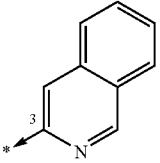 | isoquinolin-3-yl |
| (83) 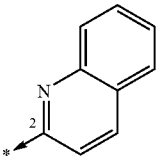 | quinolin-2-yl |
| (84) 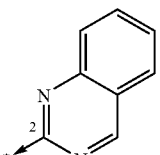 | quinazolin-2-yl |
| (85) 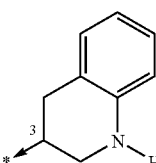 | 1,2,3,4-tetrahydro-quinolin-3-yl |
| (86) 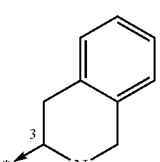 | 1,2,3,4-tetrahydro-isoquinolin-3-yl |
| (87) 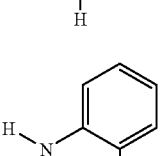 | 1,2,3,4-tetrahydro-quinoiin-2-yl |
| (88) 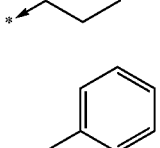 | 3,4-dihydro-1H-quinolin-2-on-3-yl |
TABLE I-continued
| Q | Name |
|---|---|
| (89) 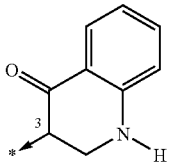 | 2,3-dihydro-1H-quinolin-4-on-3-yl |
| (90) 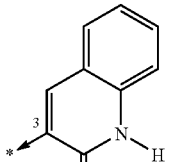 | 1H-quinolin-2-on-3-yl |
| (91) 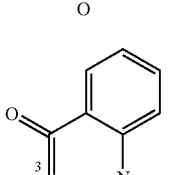 | 1H-quinolin-4-on-3-yl |
| (92) 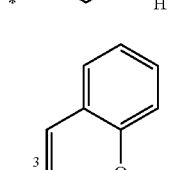 | chromen-2-on-3-yl |
| (93) 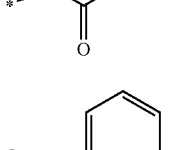 | chromen-4-on-3-yl |
| (94) 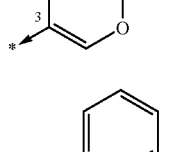 | chroman-2-on-3-yl |
| (95) 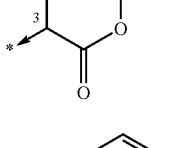 | chroman-4-on-3-yl |
| (96) 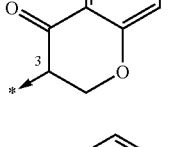 | 2,3-dihydro-benzofuran-3-yl |

TABLE I-continued

| Q | | Name |
|---|---|---|
| (97) | (benzotriazole structure, attachment at N1) | benzotriazol-1-yl |
| (98) | (6-bromo-imidazopyridine structure) | 6-bromo-3H-imidazo[4,5-b]pyridin-3-yl |
| (99) | (pyrroloquinoline structure) | 5,6-dihydro-4H-pyrrolo[3,2,1-ij]quinolin-8-yl |
| (100) | (tetrahydropyrroloquinoline structure) | 1,2,5,6-tetrahydro-4H-pyrrolo[3,2,1-ij]quinolin-8-yl |
| (101) | (benzodioxin structure) | 2,3-dihydro-1,4-benzodioxin-6-yl |
| (102) | (pyrazolopyridine structure with R$^b$) | pyrazolo[1,5-a]pyridin-5-yl |
| (103) | (imidazopyridine structure with R$^b$) | imidazo[1,2-a]pyridin-6-yl |
| (104) | (quinoxaline structure with R$^b$) | quinoxalin-7-yl |
| (105) | (benzoxazine structure with R$^b$) | 3,4-dihydro-2H-1,4-benzoxazin-7-yl |
| (106) | (imidazopyridine structure with R$^b$) | 2,3-dihydro-1,4-benzodioxin-7-yl |

The following compounds are mentioned by way of example as most particularly preferred compounds of the above general formula (I):

| | Structure | Name |
|---|---|---|
| (1) | 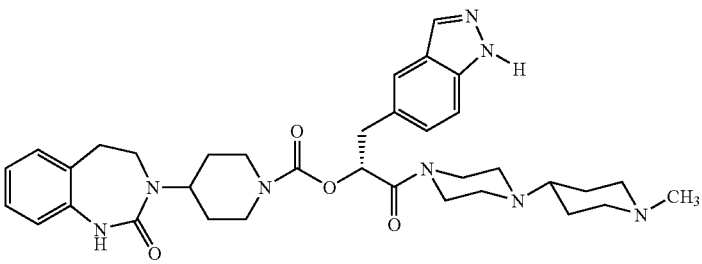 | (R)-1-(1H-indazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (2) | 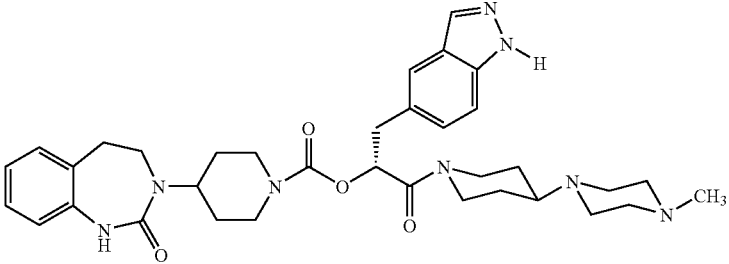 | (R)-1-(1H-indazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| Structure | Name |
|---|---|
| (3) 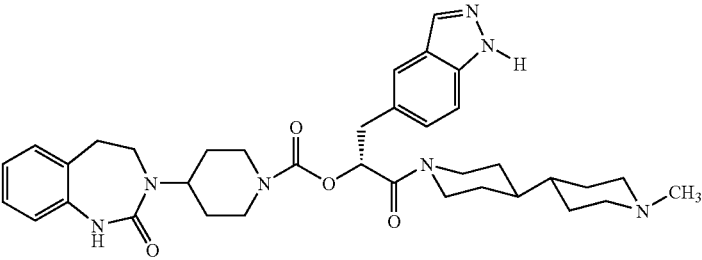 | (R)-1-(1H-indazol-5-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (4) 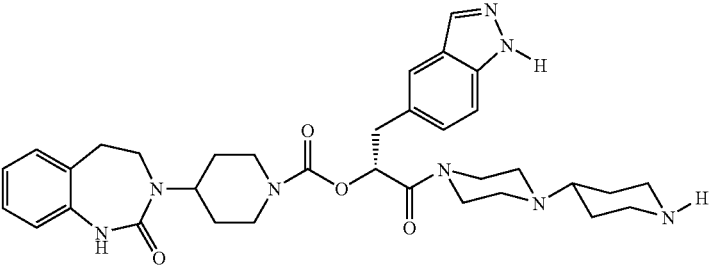 | (R)-1-(1H-indazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (5) 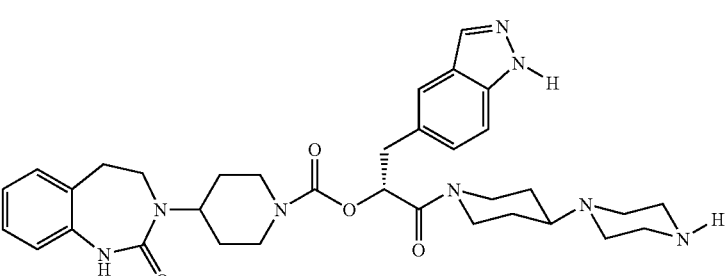 | (R)-1-(1H-indazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (6) 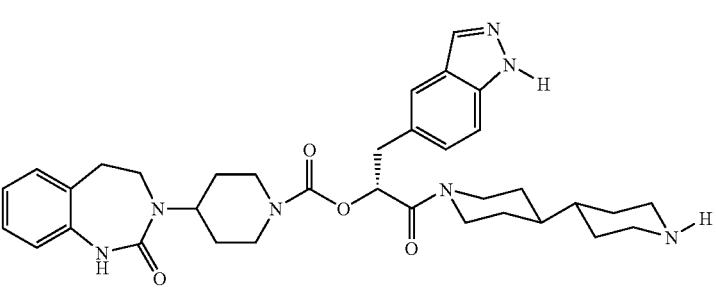 | (R)-2-4,4'-bipiperidinyl-1-yl-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (7) 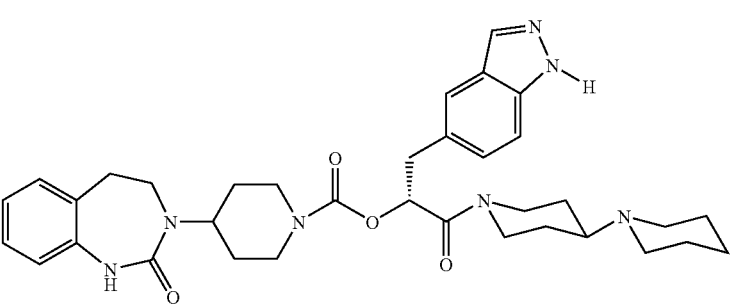 | (R)-2-1,4'-bipiperidinyl-1'-yl-1-(1H-indazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (8) 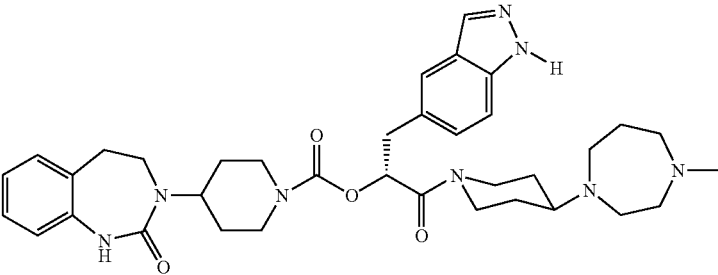 | (R)-1-(1H-indazol-5-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (9) 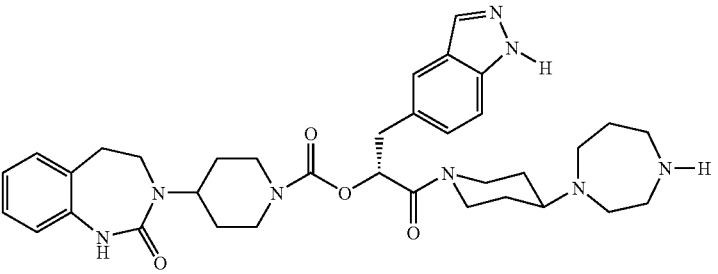 | (R)-1-(1H-indazol-5-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (10) 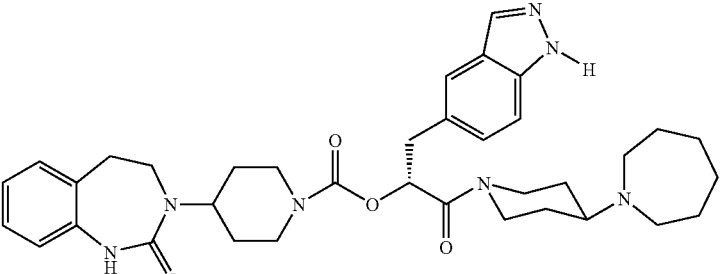 | (R)-1-(1H-indazol-5-ylmethyl)-2-oxo-2-(4-perhydro-azepin-1-yl-piperidin-1-yl)-ethyl 4-(2-oxo-1,2,4,5-tetrahydro-1,3-benzodiazepin-3-yl)-piperidine-1-carboxylate |
| (11) 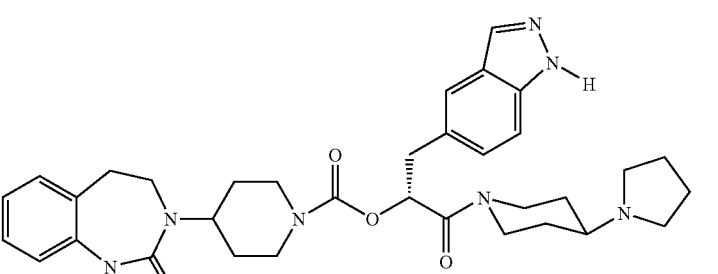 | (R)-1-(1H-indazol-5-ylmethyl)-2-oxo-2-(4-pyrrolidin-1-yl-piperidin-1-yl)-ethyl 4-(2-oxo-1,2,4,5-tetrahydro-1,3-benzodiazepin-3-yl)-piperidine-1-carboxylate |
| (12) 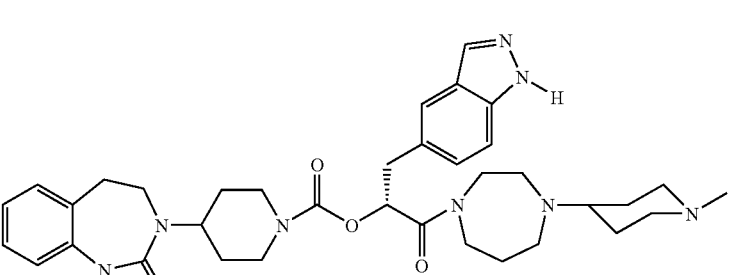 | (R)-1-(1H-indazol-5-ylmethyl)-2-[4-(1-methyl-piperidin-4-yl)-perhydro-1,4-diazepin-1-yl]-2-oxo-ethyl 4-(2-oxo-1,2,4,5-tetrahydro-1,3-benzodiazepin-3-yl)-piperidine-1-carboxylate |

-continued

| Structure | Name |
|---|---|
| (13) 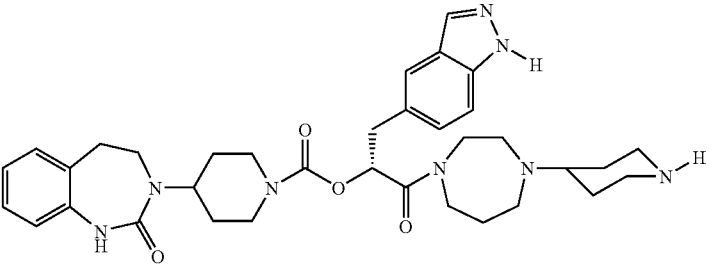 | (R)-1-(1H-indazol-5-ylmethyl)-2-oxo-2-(4-piperidin-4-yl-perhydro-1,4-diazepin-1-yl)-ethyl 4-(2-oxo-1,2,4,5-tetrahydro-1,3-benzodiazepin-3-yl)-piperidine-1-carboxylate |
| (14) 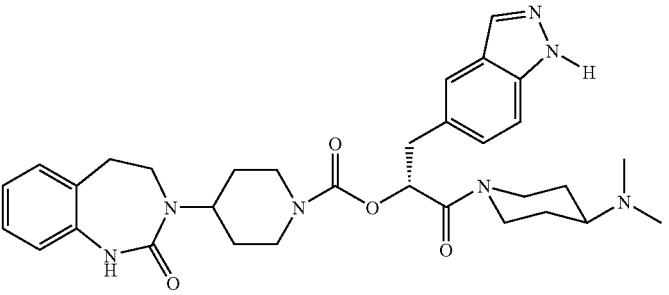 | (R)-2-(4-dimethylamino-piperidin-1-yl)-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (15) 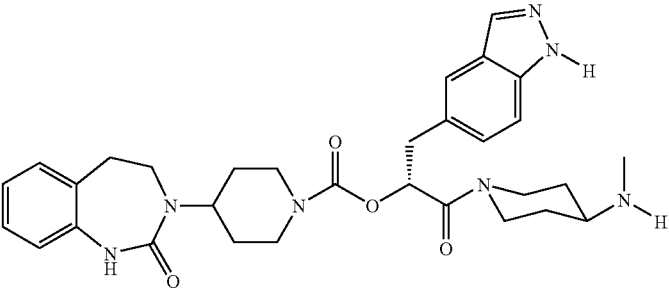 | (R)-1-(1H-indazol-5-ylmethyl)-2-(4-methyl-amino-piperidin-1-yl)-2-oxo-ethyl 4-(2-oxo-1,2,4,5-tetrahydro-1,3-benzodiazepin-3-yl)-piperidine-1-carboxylate |
| (16) 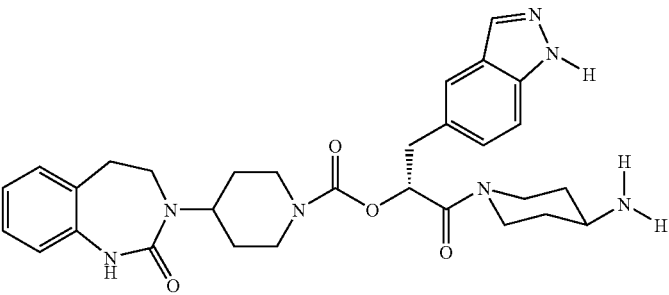 | (R)-2-(4-amino-piperidin-1-yl)-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (17) 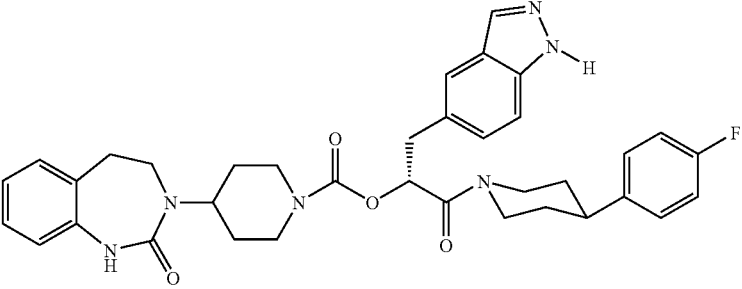 | (R)-2-[4-(4-fluoro-phenyl)-piperidin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (18) 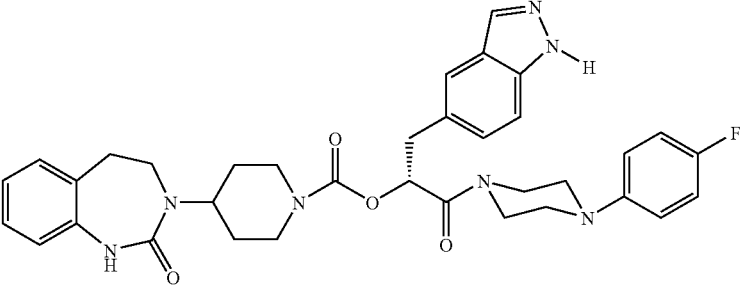 | (R)-2-[4-(4-fluoro-phenyl)-piperazin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (19) 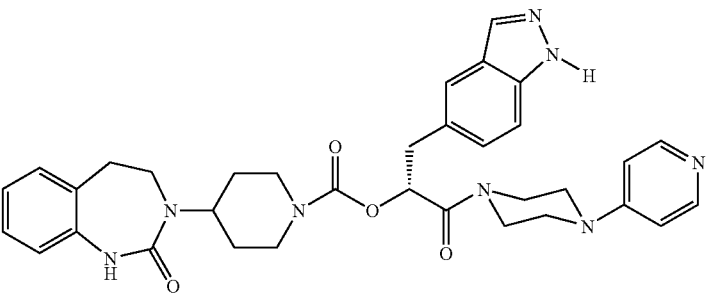 | (R)-1-(1H-indazol-5-ylmethyl)-2-oxo-2-(4-pyridin-4-yl-piperazin-1-yl)-ethyl 4-(2-oxo-1,2,4,5-tetrahydro-1,3-benzodiazepin-3-yl)-piperidine-1-carboxylate |
| (20) 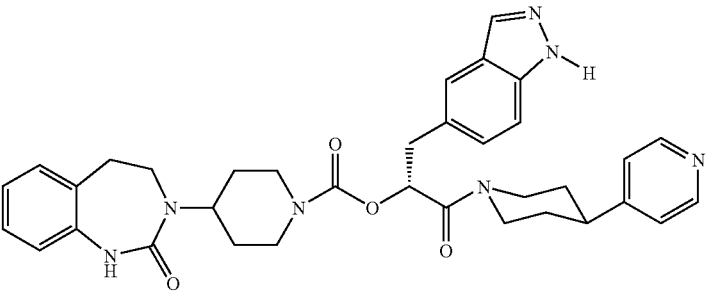 | (R)-1-(1H-indazol-5-ylmethyl)-2-oxo-2-(3,4,5,6-tetrahydro-2H-4,4'-bipyridinyl-1-yl)-ethyl 4-(2-oxo-1,2,4,5-tetrahydro-1,3-benzodiazepin-3-yl)-piperidine-1-carboxylate |
| (21) 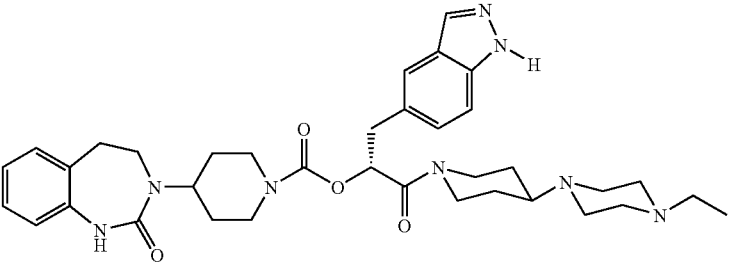 | (R)-2-[4-(4-ethyl-piperazin-1-yl)-piperidin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (22) 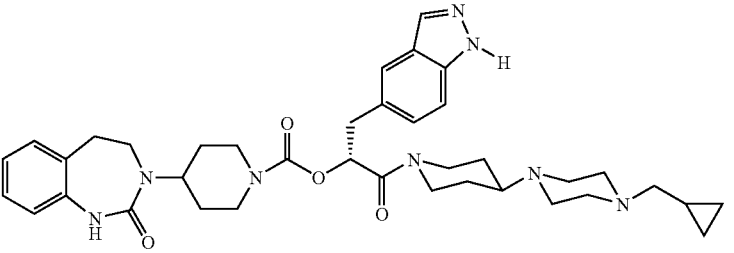 | (R)-2-[4-(4-cyclopropylmethyl-piperazin-1-yl)-piperidin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (23) 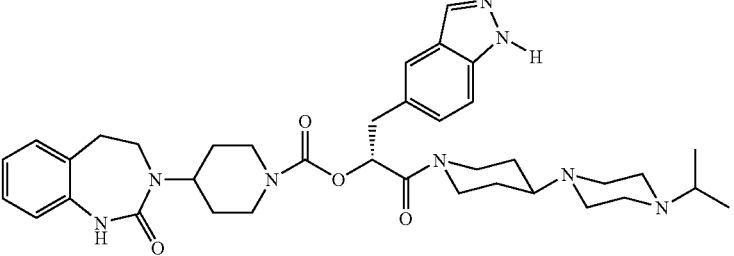 | (R)-1-(1H-indazol-5-ylmethyl)-2-[4-(4-isopropyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (24) 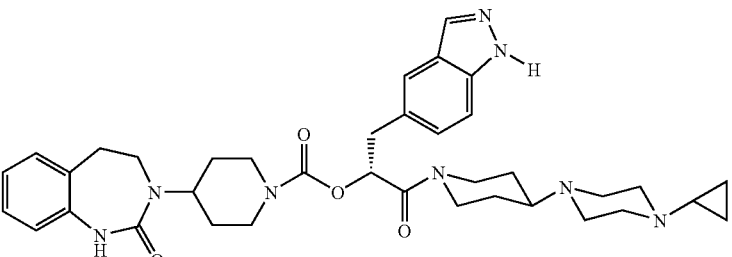 | (R)-2-[4-(4-cyclopropyl-piperazin-1-yl)-piperidin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (25) 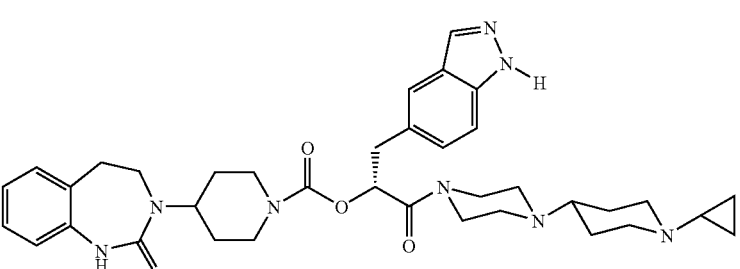 | (R)-2-[4-(1-cyclopropyl-piperidin-4-yl)-piperazin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (26) 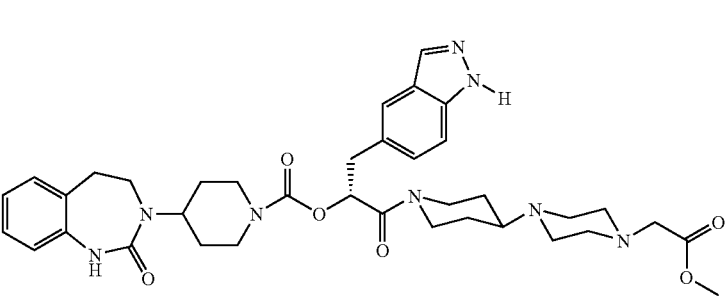 | (R)-1-(1H-indazol-5-ylmethyl)-2-[4-(4-methoxycarbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (27) 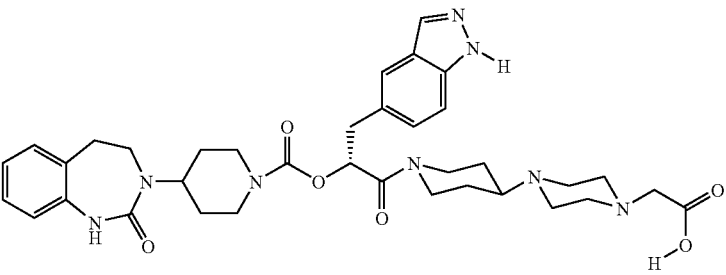 | (R)-2-[4-(4-carboxymethyl-piperazin-1-yl)-piperidin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (28) | 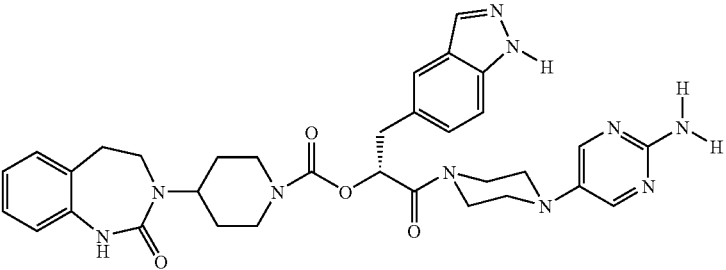 | (R)-2-[4-(2-amino-pyrimidine-5-yl)-piperazin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (29) | 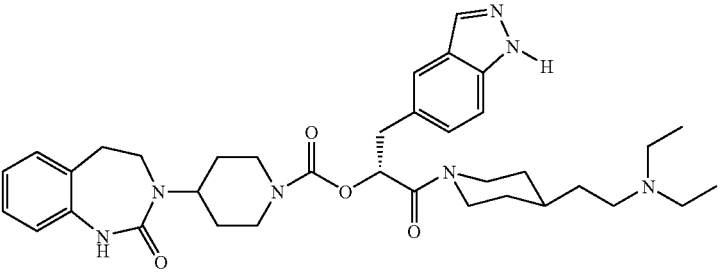 | (R)-2-[4-(2-diethylamino-ethyl)-piperidin-1-yl]-1-(1H-indazol-5-ylmethyl )-2-oxo-ethyl 4-(2-oxo-1,2,4, 5-tetrahydro-1,3-benzodiazepin-3-yl)-piperidine-1-carboxylate |
| (30) | 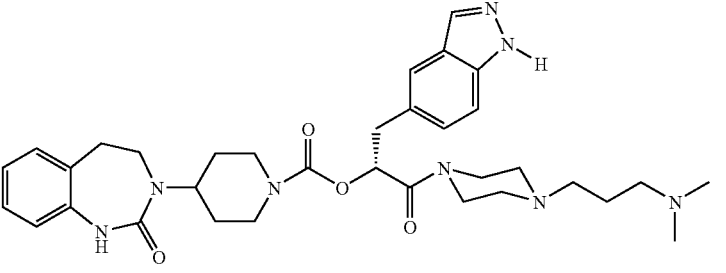 | (R)-2-[4-(3-dimethylamino-propyl)-piperazin-1-yl]-1-(1H-indazol-5-ylmethyl)-2-oxo-ethyl 4-(2-oxo-1,2,4,5-tetrahydro-1,3-benzodiazepin-3-yl)-piperidine-1-carboxylate |
| (31) | 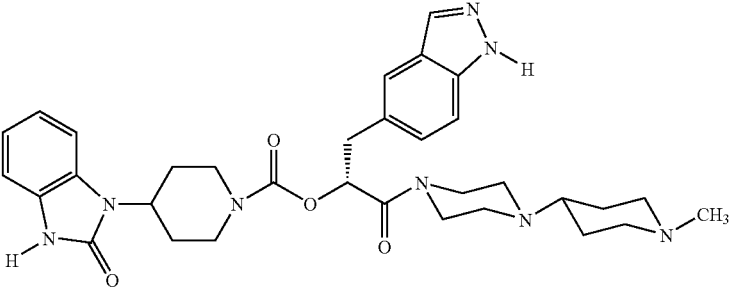 | (R)-1-(1H-indazol-5-ylmethyl)-2-[4-(1-methyl-piperidin-4-yl)-piperazin-1-yl]-2-oxo-ethyl 4-(2-oxo-2,3-dihydro-benzimidazol-1-yl)-piperidine-1-carboxylate |
| (32) | 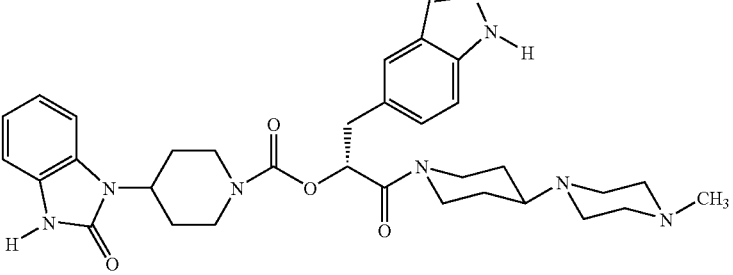 | (R)-1-(1H-indazol-5-ylmethyl)-2-[4-(4-methyl-piperazin-1-yl)-piperidin-1-yl]-2-oxo-ethyl 4-(2-oxo-2,3-dihydro-benzimidazol-1-yl)-piperidine-1-carboxylate |

-continued

| Structure | Name |
|---|---|
| (33) 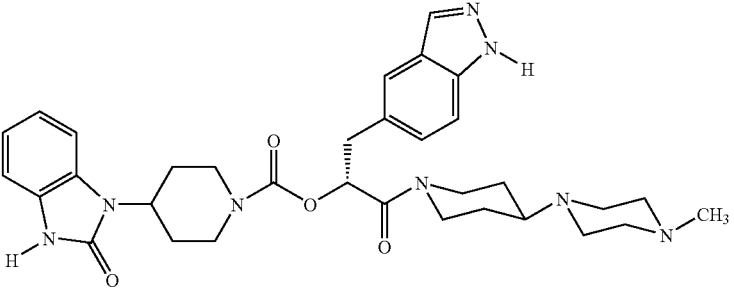 | (R)-1-(1H-indazol-5-ylmethyl)-2-(1'-methyl-4,4'-bipiperidinyl-1-yl)-2-oxo-ethyl 4-(2-oxo-2,3-dihydro-benzimidazol-1-yl)-piperidine-1-carboxylate |
| (34) 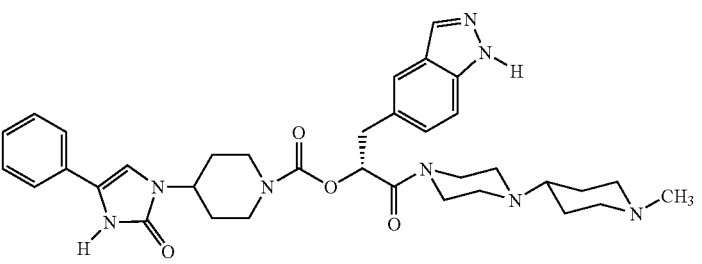 | (R)-1-(1H-indazol-5-ylmethyl)-2-[4-(1-methyl-piperidin-4-yl)-piperazin-1-yl]-2-oxo-ethyl 4-(2-oxo-4-phenyl-2,3-dihydro-imiadazol-1-yl)-piperidine-1-carboxylate |
| (35) 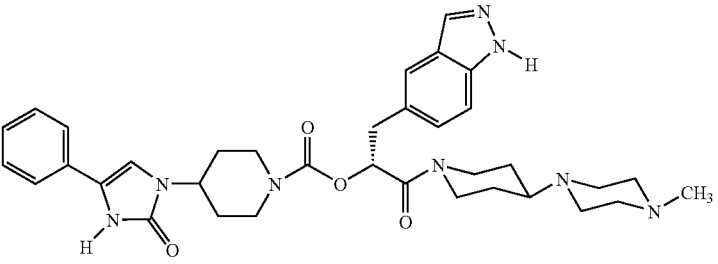 | (R)-1-(1H-indazol-5-ylmethyl)-2-[4-(4-methyl-piperazin-1-yl)-piperidin-1-yl]-2-oxo-ethyl 4-(2-oxo-4-phenyl-2,3-dihydro-imidazol-1-yl)-piperidine-1-carboxylate |
| (36) 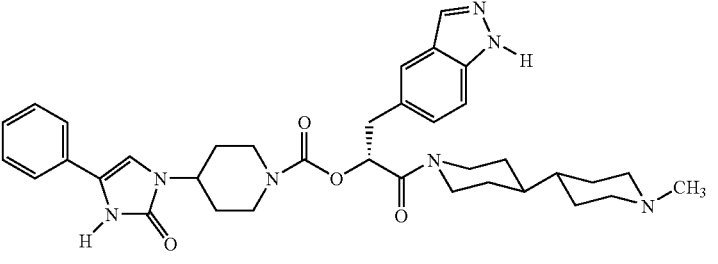 | (R)-1-(1H-indazol-5-ylmethyl)-2-(1'-methyl-[4,4']bipiperidinyl-1-yl)-2-oxo-ethyl 4-(2-oxo-4-phenyl-2,3-dihydro-imidazol-1-yl)-piperidine-1-carboxylate |
| (37) 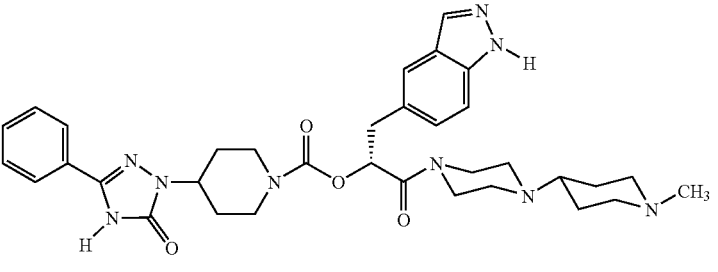 | (R)-1-(1H-indazol-5-ylmethyl)-2-[4-(1-methyl-piperidin-4-yl)-piperazin-1-yl]-2-oxo-ethyl 4-(5-oxo-3-phenyl-4,5-dihydro-1,2,4-triazol-1-yl)-piperidine-1-carboxylate |

-continued

| Structure | Name |
|---|---|
| (38) 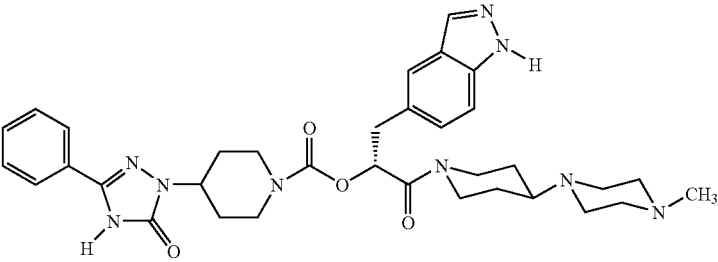 | (R)-1-(1H-indazol-5-ylmethyl)-2-[4-(4-methyl-piperazin-1-yl)-piperidin-1-yl]-2-oxo-ethyl 4-(5-oxo-3-phenyl-4,5-dihydro-1,2,4-triazol-1-yl)-piperidine-1-carboxylate |
| (39) 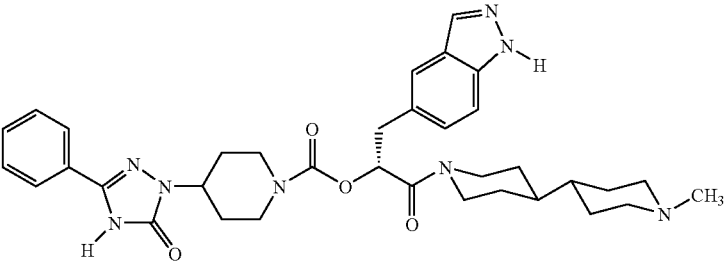 | (R)-1-(1H-indazol-5-ylmethyl)-2-(1'-methyl-4,4'-bipiperidinyl-1-yl)-2-oxo-ethyl 4-(5-oxo-3-phenyl-4,5-dihydro-1,2,4-triazol-1-yl)-piperidine-1-carboxylate |
| (40) 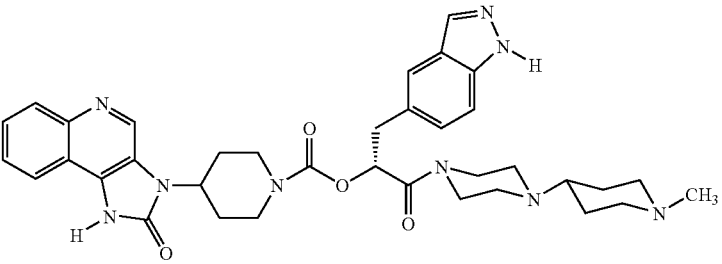 | (R)-1-(1H-indazol-5-ylmethyl)-2-[4-(1-methyl-piperidin-4-yl)-piperazin-1-yl]-2-oxo-ethyl 4-(2-oxo-1,2-dihydro-imidazo[4,5-c]quinolin-3-yl)-piperidine-1-carboxylate |
| (41) 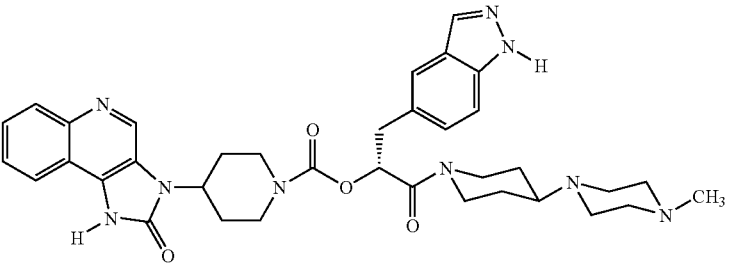 | (R)-1-(1H-indazol-5-ylmethyl)-2-[4-(4-methyl-piperazin-1-yl)-piperidin-1-yl]-2-oxo-ethyl 4-(2-oxo-1,2-dihydro-imidazo[4,5-c]quinolin-3-yl)-piperidine-1-carboxylate |
| (42) 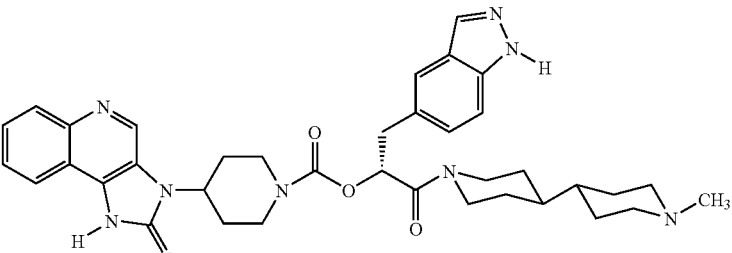 | (R)-1-(1H-indazol-5-ylmethyl)-2-(1'-methyl-[4,4']bipiperidinyl-1-yl)-2-oxo-ethyl 4-(2-oxo-1,2-dihydro-imidazo[4,5-c]quinolin-3-yl)-piperidine-1-carboxylate |

| Structure | Name |
|---|---|
| (43) 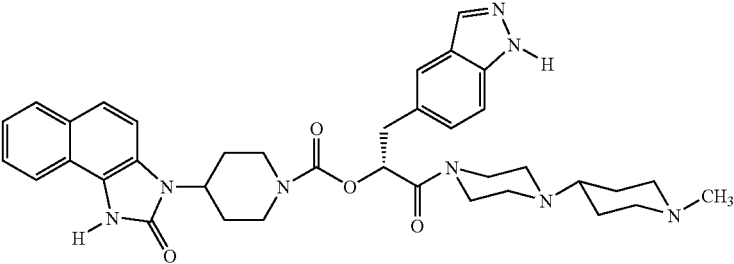 | (R)-1-(1H-indazol-5-ylmethyl)-2-[4-(1-methyl-piperidin-4-yl)-piperazin-1-yl]-2-oxo-ethyl 4-(2-oxo-1,2-dihydro-naphth[1,2-d]imidazol-3-yl)-piperidine-1-carboxylate |
| (44) 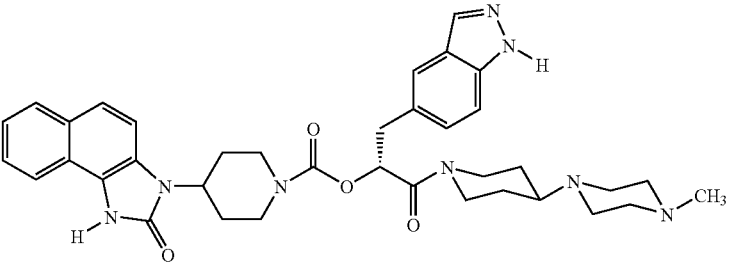 | (R)-1-(1H-indazol-5-ylmethyl)-2-[4-(4-methyl-piperazin-1-yl)-piperidin-1-yl]-2-oxo-ethyl 4-(2-oxo-1,2-dihydro-naphth[1,2-d]imidazol-3-yl)-piperidine-1-carboxylate |
| (45) 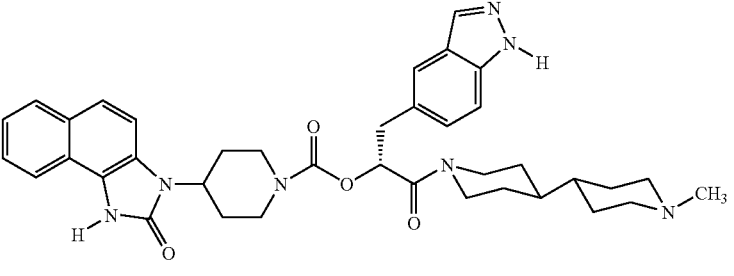 | (R)-1-(1H-indazol-5-ylmethyl)-2-(1'-methyl-4,4'-bipiperidinyl-1-yl)-2-oxo-ethyl 4-(2-oxo-1,2-dihydro-naphth[1,2-d]imidazol-3-yl)-piperidine-1-carboxylate |
| (46) 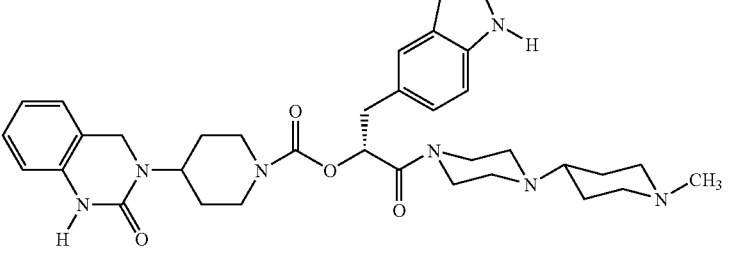 | (R)-1-(1H-indazol-5-ylmethyl)-2-[4-(1-methyl-piperidin-4-yl)-piperazin-1-yl]-2-oxo-ethyl 4-(2-oxo-1,4-dihydro-2H-quinazolin-3-yl)-piperidine-1-carboxylate |
| (47) 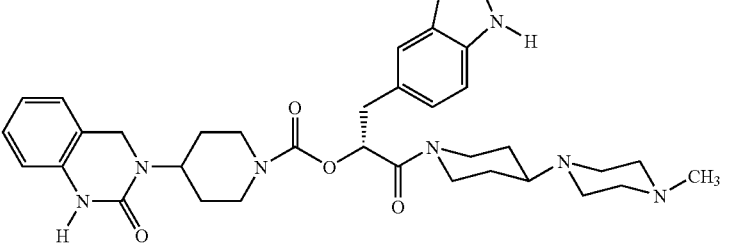 | (R)-1-(1H-indazol-5-ylmethyl)-2-[4-(4-methyl-piperazin-1-yl)-piperidin-1-yl]-2-oxo-ethyl 4-(2-oxo-1,4-dihydro-2H-quinazolin-3-yl)-piperidine-1-carboxylate |

-continued

| Structure | Name |
|---|---|
| (48) 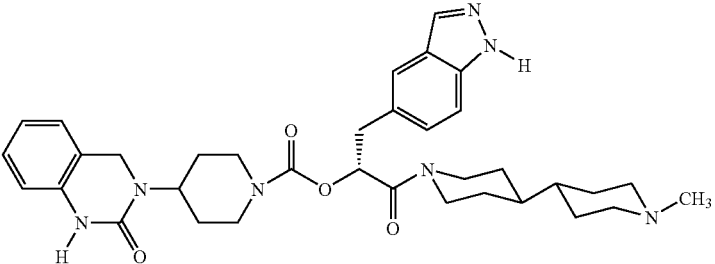 | (R)-1-(1H-indazol-5-ylmethyl)-2-(1'-methyl-[4,4']bipiperidinyl-1-yl)-2-oxo-ethyl 4-(2-oxo-1,4-dihydro-2H-quinazolin-3-yl)-piperidine-1-carboxylate |
| (49) 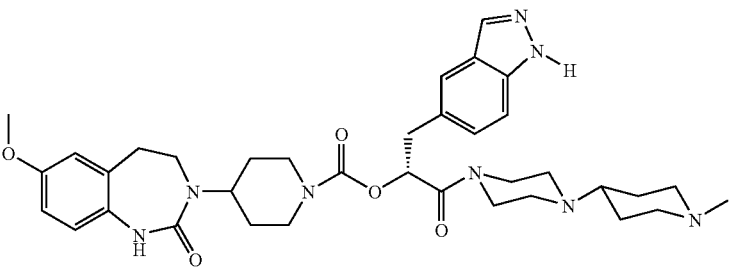 | (R)-1-(1H-indazol-5-ylmethyl)-2-[4-(1-methyl-piperidin-4-yl)-piperazin-1-yl]-2-oxo-ethyl 4-(7-methoxy-2-oxo-1,2,4,5-tetrahydro-1,3-benzodiazepin-3-yl)-piperidine-1-carboxylate |
| (50) 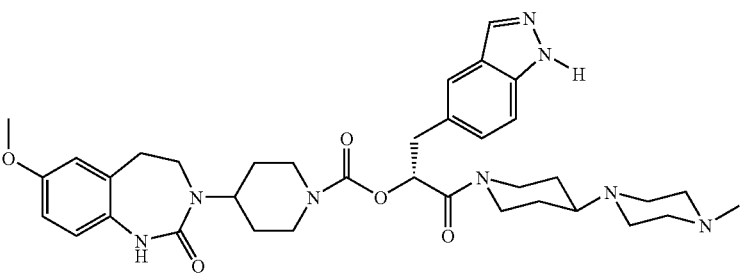 | (R)-1-(1H-indazol-5-ylmethyl)-2-[4-(4-methyl-piperazin-1-yl)-piperidin-1-yl]-2-oxo-ethyl 4-(7-methoxy-2-oxo-1,2,4,5-tetrahydro-1,3-benzodiazepin-3-yl)-piperidine-1-carboxylate |
| (51) 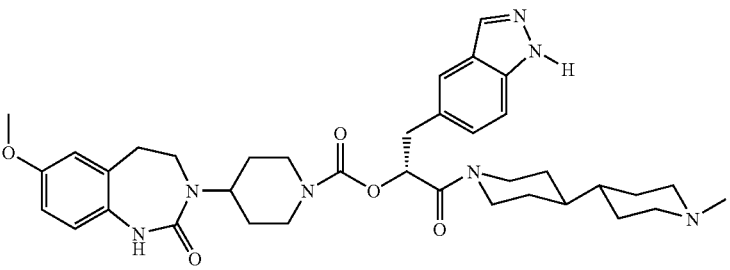 | (R)-1-(1H-indazol-5-ylmethyl)-2-(1'-methyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate |
| (52) 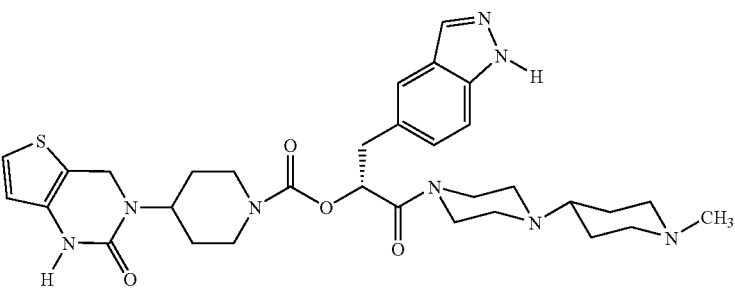 | (R)-1-(1H-indazol-5-ylmethyl)-2-[4-(1-methyl-piperidin-4-yl)-piperazin-1-yl]-2-oxo-ethyl 4-(2-oxo-1,4-dihydro-2H-thieno[3,2-d]pyrimidin-3-yl)-piperidine-1-carboxylate |

-continued

| | Structure | Name |
|---|---|---|
| (53) | 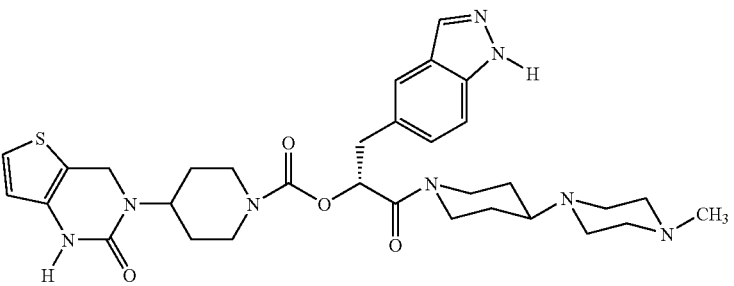 | (R)-1-(1H-indazol-5-ylmethyl)-2-[4-(4-methyl-piperazin-1-yl)-piperidin-1-yl]-2-oxo-ethyl 4-(2-oxo-1,4-dihydro-2H-thieno[3,2-d]pyrimidin-3-yl)-piperidine-1-carboxylate |
| (54) | 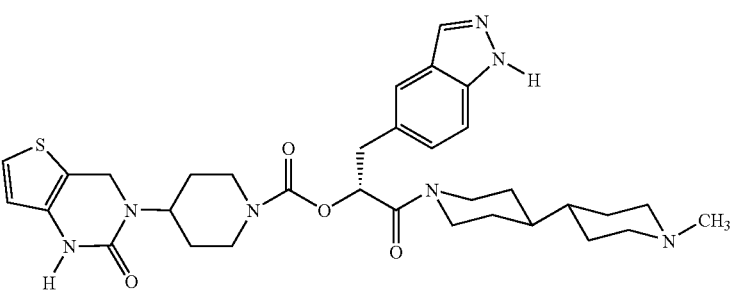 | (R)-1-(1H-indazol-5-ylmethyl)-2-(1'-methyl-[4,4']bipiperidinyl-1-yl)-2-oxo-ethyl 4-(2-oxo-1,4-dihydro-2H-thieno[3,2-d]pyrimidin-3-yl)-piperidine-1-carboxylate |
| (55) | 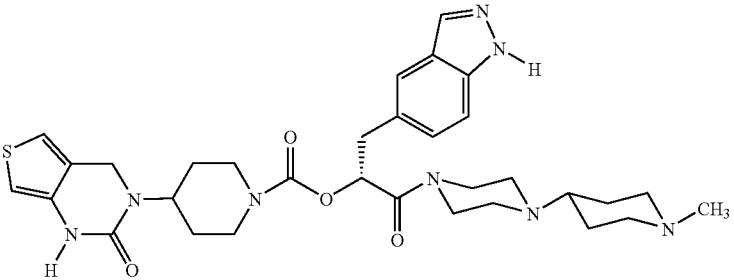 | (R)-1-(1H-indazol-5-ylmethyl)-2-[4-(1-methyl-piperidin-4-yl)-piperazin-1-yl]-2-oxo-ethyl 4-(2-oxo-1,2-dihydro-4H-thieno[3,4-d]pyrimidin-3-yl)-piperidine-1-carboxylate |
| (56) | 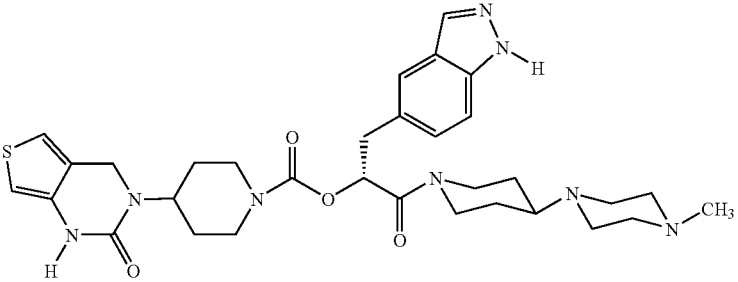 | (R)-1-(1H-indazol-5-ylmethyl)-2-[4-(4-methyl-piperazin-1-yl)-piperidin-1-yl]-2-oxo-ethyl 4-(2-oxo-1,2-dihydro-4H-thieno[3,4-d]pyrimidin-3-yl)-piperidine-1-carboxylate |
| (57) | 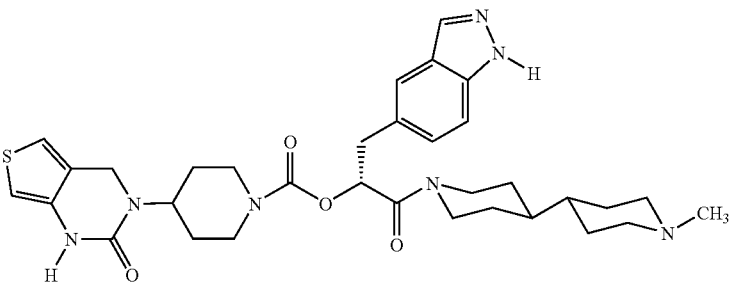 | (R)-1-(1H-indazol-5-ylmethyl)-2-(1'-methyl-[4,4']bipiperidinyl-1-yl)-2-oxo-ethyl 4-(2-oxo-1,2-dihydro-4H-thieno[3,4-d]pyrimidin-3-yl)-piperidine-1-carboxylate |

-continued

| | Structure | Name |
|---|---|---|
| (58) | 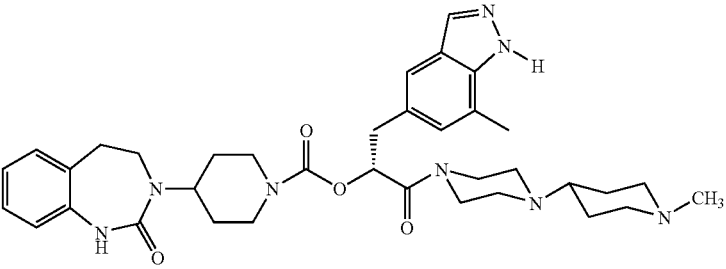 | (R)-1-(7-methyl-1H-indazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (59) | 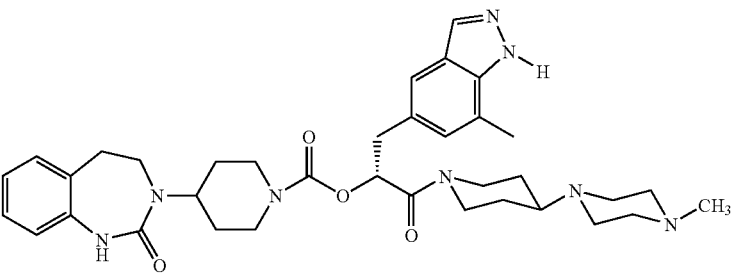 | (R)-1-(7-methyl-1H-indazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (60) | 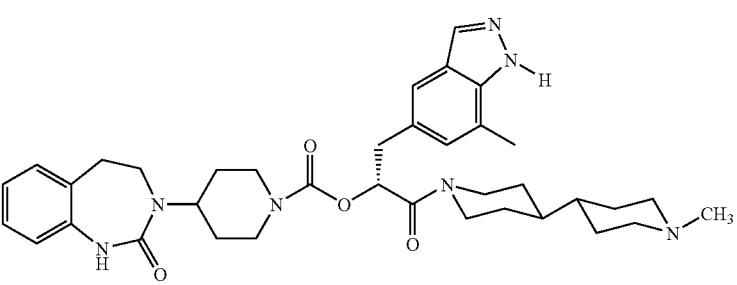 | (R)-2-(1'-methyl-4,4'-bipiperidinyl-1-yl)-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (61) | 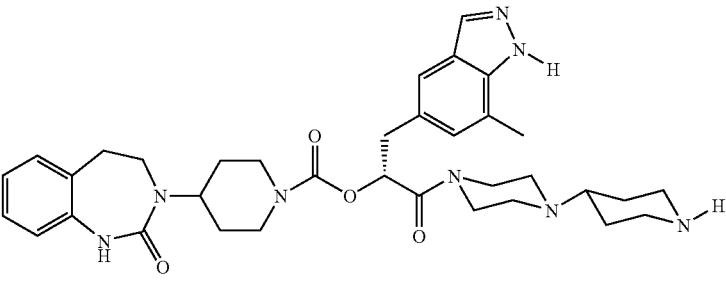 | (R)-1-(7-methyl-1H-indazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (62) | 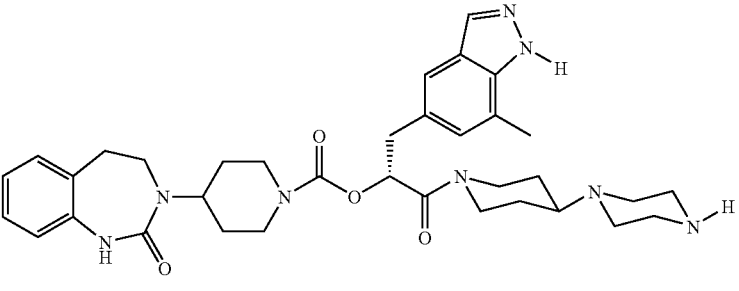 | (R)-1-(7-methyl-1H-indazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (63) 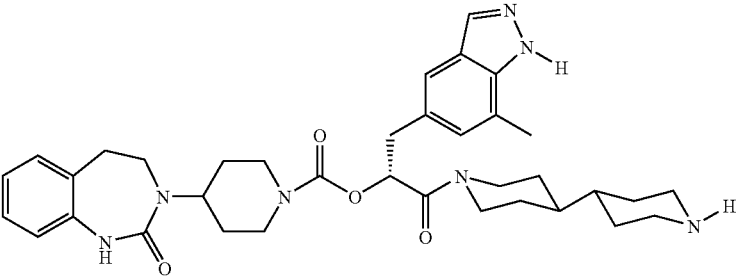 | (R)-2-4,4'-bipiperidinyl-1-yl-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (64) 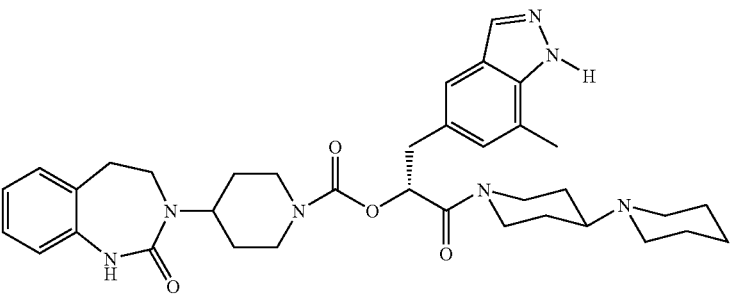 | (R)-2-1,4'-bipiperidinyl-1'-yl-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (65) 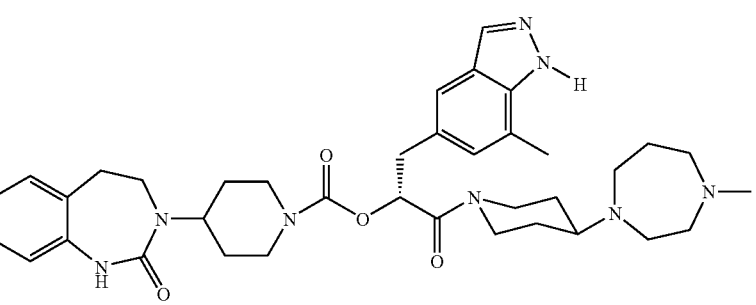 | (R)-1-(7-methyl-1H-indazol-5-yl methyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (66) 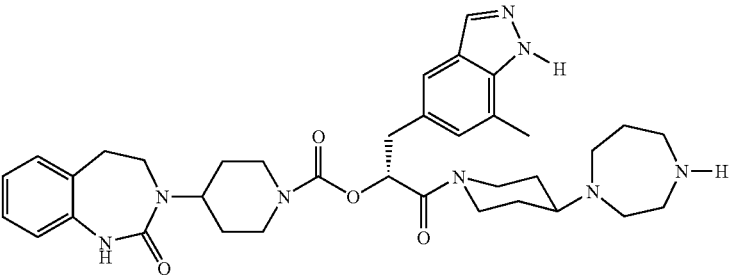 | (R)-1-(7-methyl-1H-indazol-5-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (67) 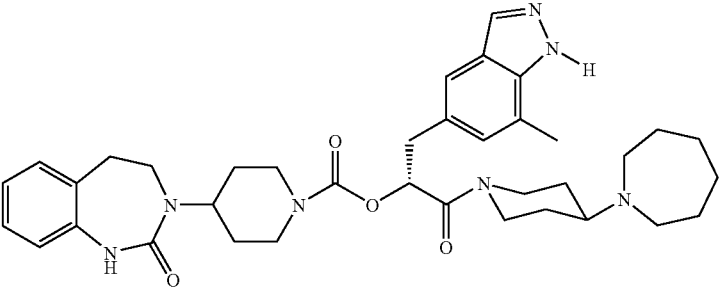 | (R)-1-(7-methyl-1H-indazol-5-ylmethyl)-2-oxo-2-(4-perhydro-azepin-1-yl-piperidin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (68) 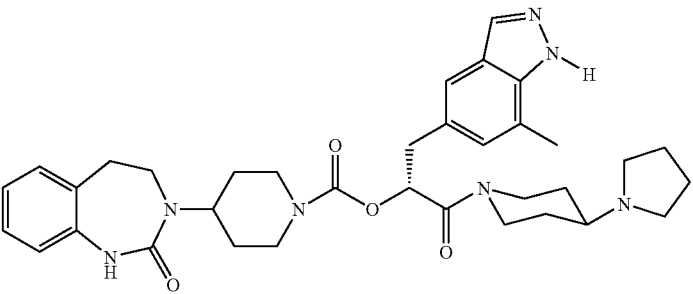 | (R)-1-(7-methyl-1H-indazol-5-ylmethyl)-2-oxo-2-(4-pyrrolidin-1-yl-piperidin-1-yl)-ethyl 4-(2-oxo-1,2,4, 5-tetrahydro-1,3-benzodiazepin-3-yl)-piperidine-1-carboxylate |
| (69) 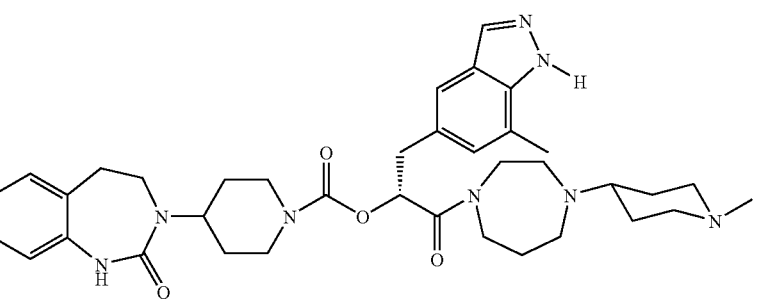 | (R)-1-(7-methyl-1H-indazol-5-ylmethyl)-2-[4-(1-methyl-piperidin-4-yl)-perhydro-1,4-diazepin-1-yl]-2-oxo-ethyl 4-(2-oxo-1,2,4,5-tetrahydro-1,3-benzodiazepin-3-yl)-piperidine-1-carboxylate |
| (70) 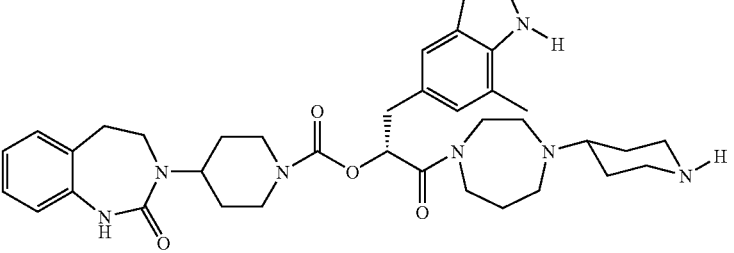 | (R)-1-(7-methyl-1H-indazol-5-ylmethyl)-2-oxo-2-(4-piperidin-4-yl-perhydro-1,4-diazepin-1-yl)-ethyl 4-(2-oxo-1,2,4,5-tetrahydro-1,3-benzodiazepin-3-yl)-piperidine-1-carboxylate |
| (71) 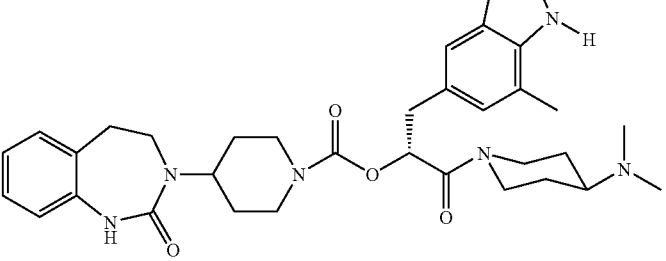 | (R)-2-(4-dimethylamino-piperidin-1-yl)-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (72) 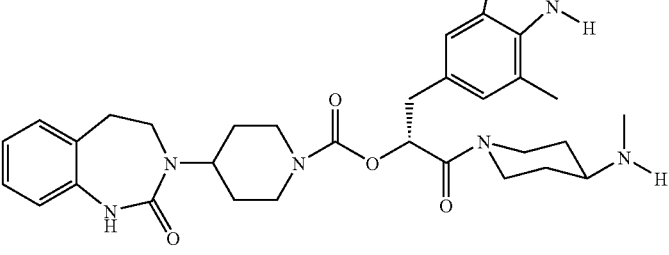 | (R)-2-(4-methylamino-piperidin-1-yl)-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (73) | (R)-2-(4-amino-piperidin-1-yl)-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (74) | (R)-2-[4-(4-fluoro-phenyl)-piperidin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (75) | (R)-2-[4-(4-fluoro-phenyl)-piperazin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (76) | (R)-1-(7-methyl-1H-indazol-5-ylmethyl)-2-oxo-2-(4-pyridin-4-yl-piperazin-1-yl)-ethyl 4-(2-oxo-1,2,4,5-tetrahydro-1,3-benzodiazepin-3-yl)-piperidine-1-carboxylate |
| (77) | (R)-1-(7-methyl-1H-indazol-5-ylmethyl)-2-oxo-2-(3,4,5,6-tetrahydro-2H-4,4'-bipyridinyl-1-yl)-ethyl 4-(2-oxo-1,2,4,5-tetrahydro-1,3-benzodiazepin-3-yl)-piperidine-1-carboxylate |

-continued

| Structure | Name |
|---|---|
| (78) 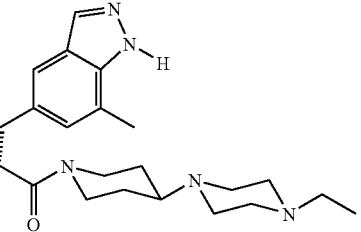 | (R)-2-[4-(4-ethyl-piperazin-1-yl)-piperidin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (79) 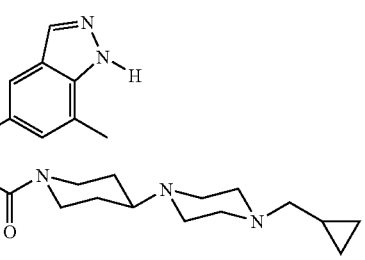 | (R)-2-[4-(4-cyclopropylmethyl-piperazin-1-yl)-piperidin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (80) 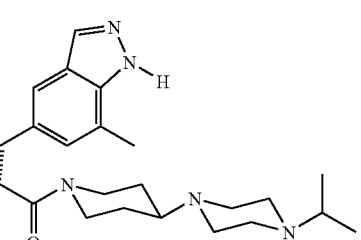 | (R)-2-[4-(4-isopropyl-piperazin-1-yl)-piperidin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (81) 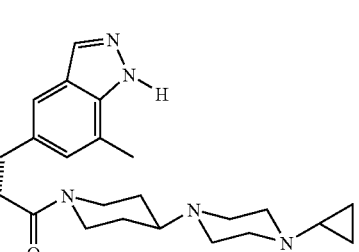 | (R)-2-[4-(4-cyclopropyl-piperazin-1-yl)-piperidin-1-yl]-1-(7-methyl-1H-indazol-5-yl-methyl)-2-oxo-ethyl 4-(2-oxo-1,2,4,5-tetrahydro-1,3-benzodiazepin-3-yl)-piperidine-1-carboxylate |
| (82) 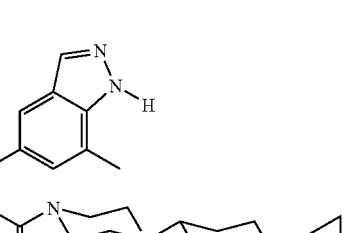 | (R)-2-[4-(1-cyclopropyl-piperidin-4-yl)-piperazin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |

| Structure | Name |
|---|---|
| (83) 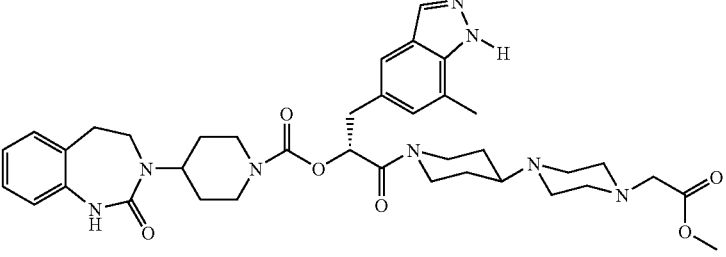 | (R)-2-[4-(4-methoxycarbonylmethyl-piperazin-1-yl)-piperidin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (84) 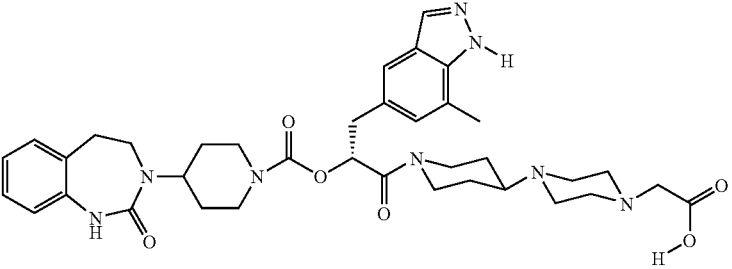 | (R)-2-[4-(4-carboxymethyl-piperazin-1-yl)-piperidin-1-yl]-1-(7-methyl-1H-indazol-5-yl-methyl)-2-oxo-ethyl 4-(2-oxo-1,2,4,5-tetrahydro-1,3-benzodiazepin-3-yl)-piperidine-1-carboxylate |
| (85) 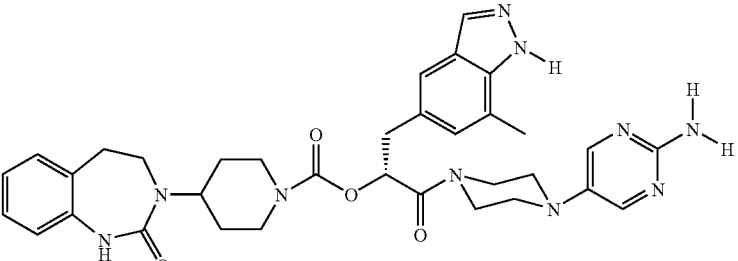 | (R)-2-[4-(2-amino-pyrimidin-5-yl)-piperazin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (86) 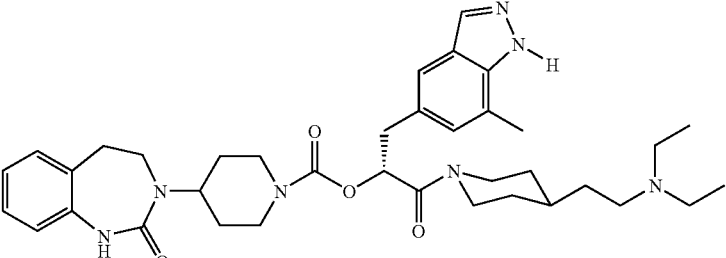 | (R)-2-[4-(2-diethylamino-ethyl)-piperidin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (87) 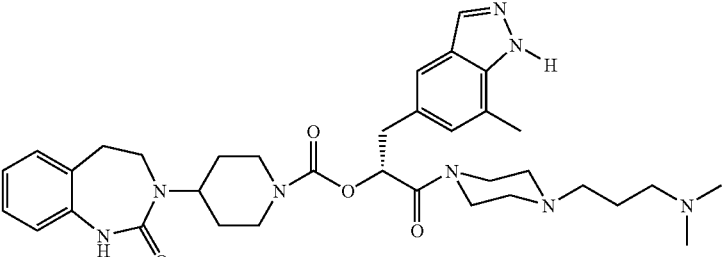 | (R)-2-[4-(3-dimethylamino-propyl)-piperazin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (88) 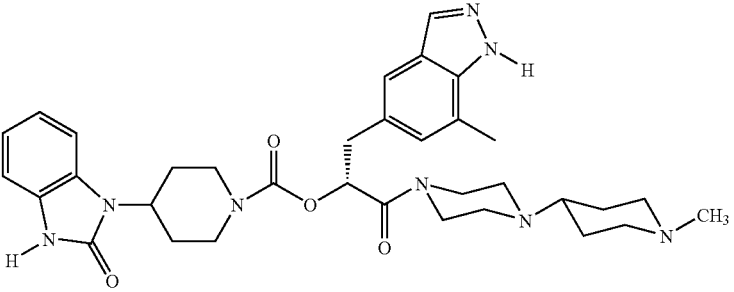 | (R)-1-(7-methyl-1H-indazol-5-ylmethyl)-2-[4-(1-methyl-piperidin-4-yl)-piperazin-1-yl]-2-oxo-ethyl 4-(2-oxo-2,3-dihydro-benzimidazol-1-yl)-piperidine-1-carboxylate |
| (89) 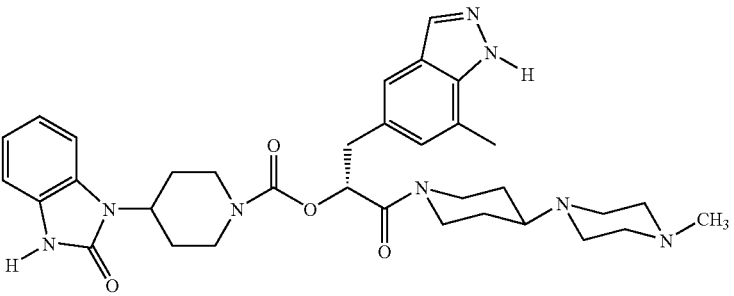 | (R)-1-(7-methyl-1H-indazol-5-ylmethyl)-2-[4-(4-methyl-piperazin-1-yl)-piperidin-1-yl]-2-oxo-ethyl 4-(2-oxo-2,3-dihydro-benzimidazol-1-yl)-piperidine-1-carboxylate |
| (90) 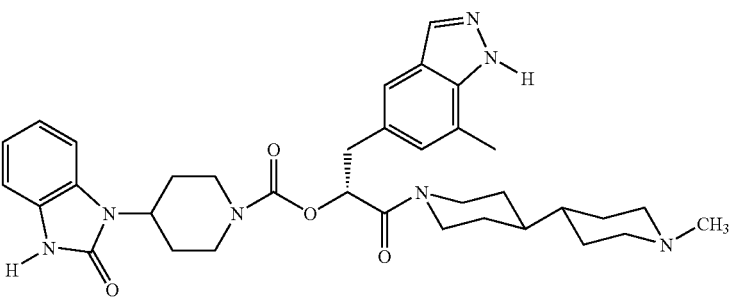 | (R)-2-(1'-methyl-4,4'-bipiperidinyl-1-yl)-1-(7-methyl-1H-indazol-5-ylmethyl)-2-oxo-ethyl 4-(2-oxo-2,3-dihydro-benzimidazol-1-yl)-piperidine-1-carboxylate |
| (91) 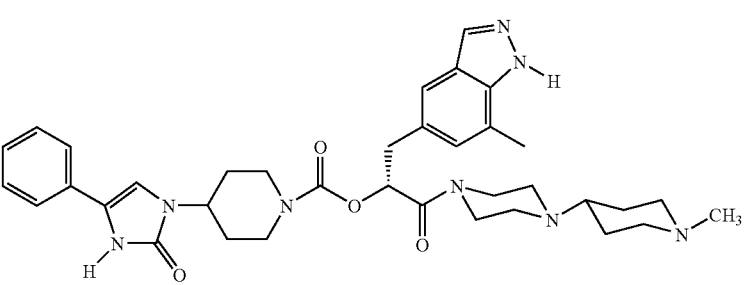 | (R)-1-(7-methyl-1H-indazol-5-ylmethyl)-2-[4-(1-methyl-piperidin-4-yl)-piperazin-1-yl]-2-oxo-ethyl 4-(2-oxo-4-phenyl-2,3-dihydro-imidazol-1-yl)-piperidine-1-carboxylate |
| (92) 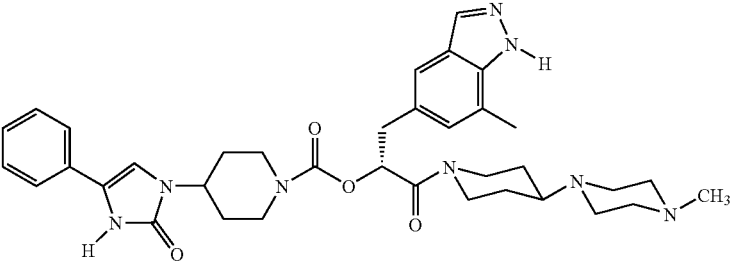 | (R)-1-(7-methyl-1H-indazol-5-ylmethyl)-2-[4-(4-methyl-piperazin-1-yl)-piperidin-1-yl]-2-oxo-ethyl 4-(2-oxo-4-phenyl-2,3-dihydro-imidazol-1-yl)-piperidine-1-carboxylate |

-continued

| Structure | Name |
|---|---|
| (93) | (R)-2-(1'-methyl-[4,4']bipiperidinyl-1-yl)-1-(7-methyl-1H-indazol-5-ylmethyl)-2-oxo-ethyl 4-(2-oxo-4-phenyl-2,3-dihydro-imidazol-1-yl)-piperidine-1-carboxylate |
| (94) | (R)-1-(7-methyl-1H-indazol-5-ylmethyl)-2-[4-(1-methyl-piperidin-4-yl)-piperazin-1-yl]-2-oxo-ethyl 4-(5-oxo-3-phenyl-4,5-dihydro-1,2,4-triazol-1-yl)-piperidine-1-carboxylate |
| (95) | (R)-1-(7-methyl-1H-indazol-5-ylmethyl)-2-[4-(4-methyl-piperazin-1-yl)-piperidin-1-yl]-2-oxo-ethyl 4-(5-oxo-3-phenyl-4,5-dihydro-1,2,4-triazol-1-yl)-piperidine-1-carboxylate |
| (96) | (R)-2-(1'-methyl-4,4'-bipiperidinyl-1-yl)-1-(7-methyl-1H-indazol-5-ylmethyl)-2-oxo-ethyl 4-(5-oxo-3-phenyl-4,5-dihydro-1,2,4-triazol-1-yl)-piperidine-1-carboxylate |
| (97) | (R)-1-(7-methyl-1H-indazol-5-ylmethyl)-2-[4-(1-methyl-piperidin-4-yl)-piperazin-1-yl]-2-oxo-ethyl 4-(2-oxo-1,2-dihydro-imidazo[4,5-c]quinolin-3-yl)-piperidine-1-carboxylate |

-continued

| Structure | Name |
|---|---|
| (98) 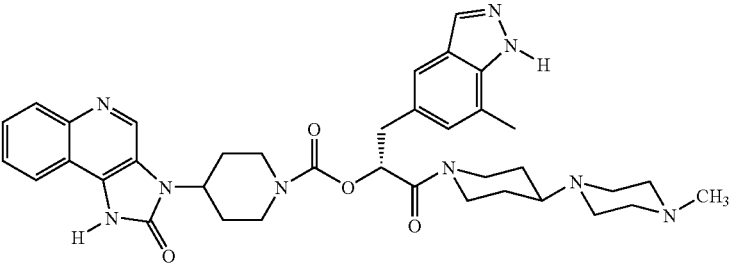 | (R)-1-(7-methyl-1H-indazol-5-ylmethyl)-2-[4-(4-methyl-piperazin-1-yl)-piperidin-1-yl]-2-oxo-ethyl 4-(2-oxo-1,2-dihydro-imidazo[4,5-c]quinolin-3-yl)-piperidine-1-carboxylate |
| (99) 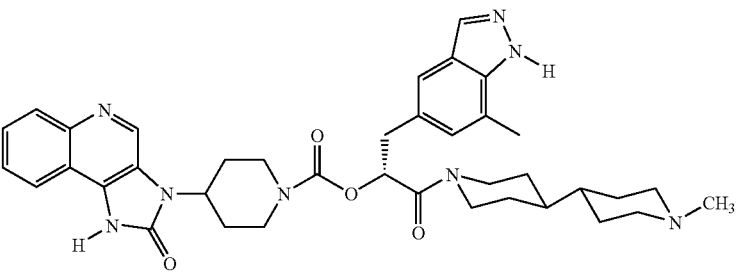 | (R)-2-(1'-methyl-[4,4']bipiperidinyl-1-yl)-1-(7-methyl-1H-indazol-5-ylmethyl)-2-oxo-ethyl 4-(2-oxo-1,2-dihydro-imidazo[4,5-c]-quinolin-3-yl)-piperidine-1-carboxylate |
| (100) 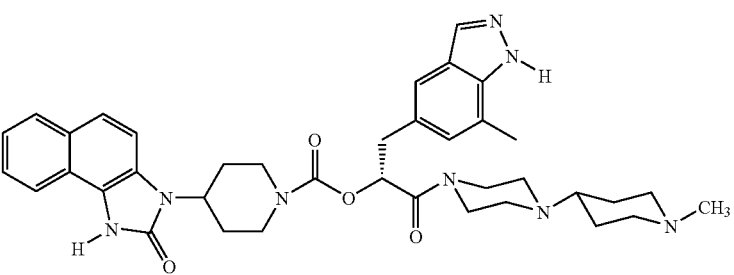 | (R)-1-(7-methyl-1H-indazol-5-ylmethyl)-2-[4-(1-methyl-piperidin-4-yl)-piperazin-1-yl]-2-oxo-ethyl 4-(2-oxo-1,2-dihydro-naphth[1,2-d]imidazol-3-yl)-piperidine-1-carboxylate |
| (101) 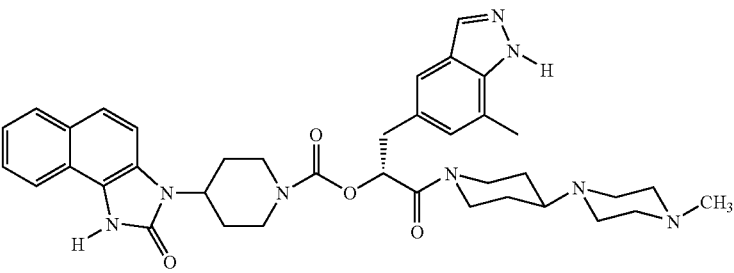 | (R)-1-(7-methyl-1H-indazol-5-ylmethyl)-2-[4-(4-methyl-piperazin-1-yl)-piperidin-1-yl]-2-oxo-ethyl 4-(2-oxo-1,2-dihydro-naphth[1,2-d]imidazol-3-yl)-piperidine-1-carboxylate |
| (102) 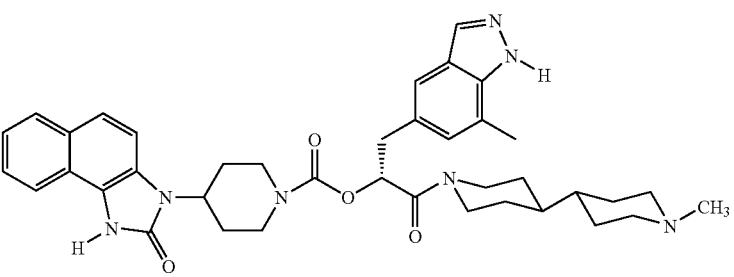 | (R)-2-(1'-methyl-4,4'-bipiperidinyl-1-yl)-1-(7-methyl-1H-indazol-5-ylmethyl)-2-oxo-ethyl 4-(2-oxo-1,2-dihydro-naphth[1,2-d]-imidazol-3-yl)-piperidine-1-carboxylate |

| Structure | Name |
|---|---|
| (103) 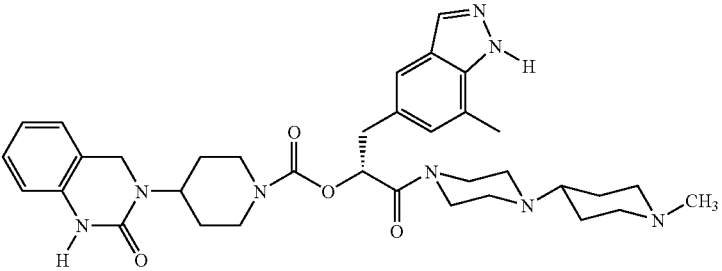 | (R)-1-(7-methyl-1H-indazol-5-ylmethyl)-2-[4-(1-methyl-piperidin-4-yl)-piperazin-1-yl]-2-oxo-ethyl 4-(2-oxo-1,4-dihydro-2H-quinazolin-3-yl)-piperidine-1-carboxylate |
| (104) 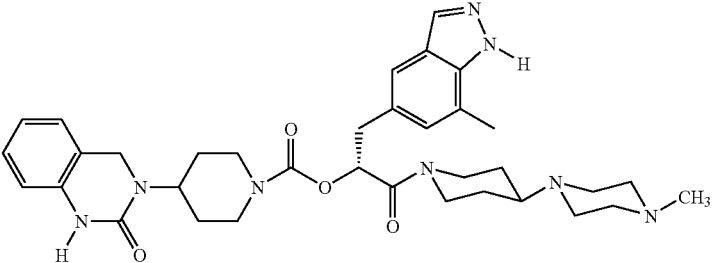 | (R)-1-(7-methyl-1H-indazol-5-ylmethyl)-2-[4-(4-methyl-piperazin-1-yl)-piperidin-1-yl]-2-oxo-ethyl 4-(2-oxo-1,4-dihydro-2H-quinazolin-3-yl)-piperidine-1-carboxylate |
| (105) 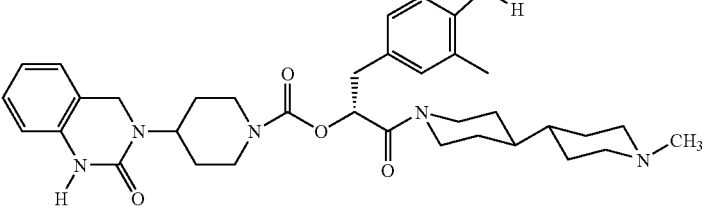 | (R)-2-(1'-methyl-[4,4']bipiperidinyl-1-yl)-1-(7-methyl-1H-indazol-5-ylmethyl)-2-oxo-ethyl 4-(2-oxo-1,4-dihydro-2H-quinazolin-3-yl)-piperidine-1-carboxylate |
| (106) 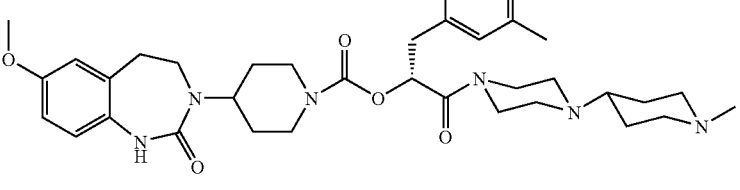 | (R)-1-(7-methyl-1H-indazol-5-ylmethyl)-2-[4-(1-methyl-piperidin-4-yl)-piperazin-1-yl]-2-oxo-ethyl 4-(7-methoxy-2-oxo-1,2,4,5-tetrahydro-1,3-benzodiazepin-3-yl)-piperidine-1-carboxylate |
| (107) 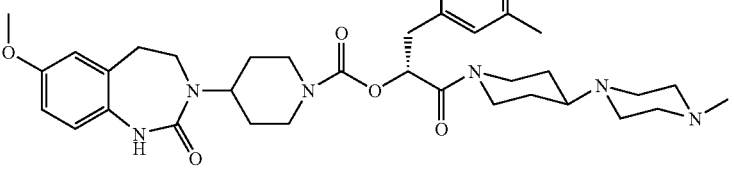 | (R)-1-(7-methyl-1H-indazol-5-ylmethyl)-2-[4-(4-methyl-piperazin-1-yl)-piperidin-1-yl]-2-oxo-ethyl 4-(7-methoxy-2-oxo-1,2,4,5-tetrahydro-1,3-benzodiazepin-3-yl)-piperidine-1-carboxylate |

-continued

| Structure | Name |
|---|---|
| (108) 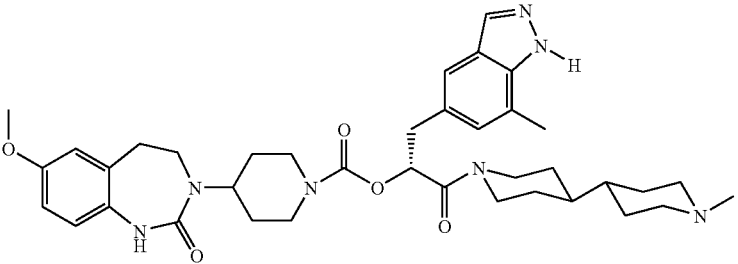 | (R)-2-(1'-methyl-4,4'-bipiperidinyl-1-yl)-1-(7-methyl-1H-indazol-5-ylmethyl)-2-oxo-ethyl 4-(7-methoxy-2-oxo-1,2,4,5-tetrahydro-1,3-benzodiazepin-3-yl)-piperidine-1-carboxylate |
| (109) 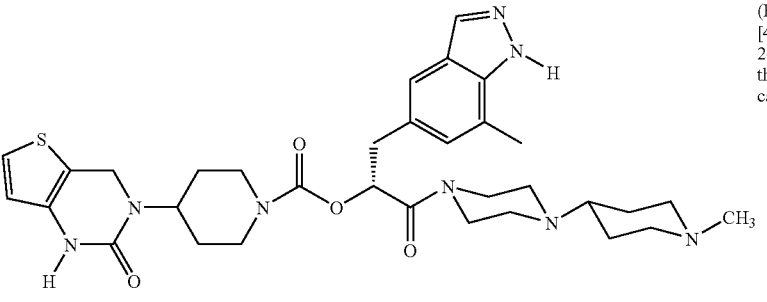 | (R)-1-(7-methyl-1H-indazol-5-ylmethyl)-2-[4-(1-methyl-piperidin-4-yl)-piperazin-1-yl]-2-oxo-ethyl 4-(2-oxo-1,4-dihydro-2H-thieno[3,2-d]pyrimidin-3-yl)-piperidine-1-carboxylate |
| (110) 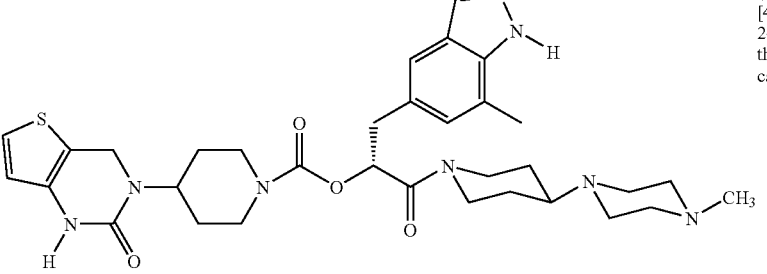 | (R)-1-(7-methyl-1H-indazol-5-ylmethyl)-2-[4-(4-methyl-piperazin-1-yl)-piperidin-1-yl]-2-oxo-ethyl 4-(2-oxo-1,4-dihydro-2H-thieno[3,2-d]pyrimidin-3-yl)-piperidine-1-carboxylate |
| (111) 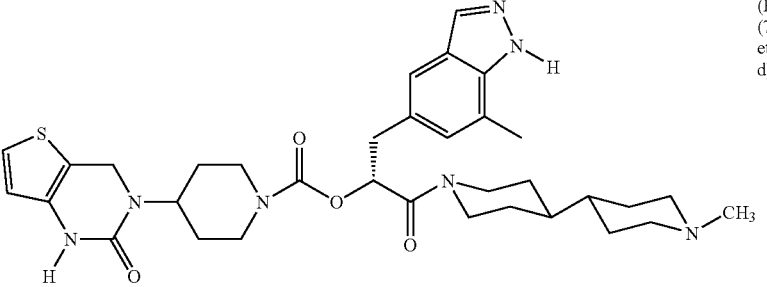 | (R)-2-(1'-methyl-[4,4']bipiperidinyl-1-yl)-1-(7-methyl-1H-indazol-5-ylmethyl)-2-oxo-ethyl 4-(2-oxo-1,4-dihydro-2H-thieno[3,2-d]pyrimidin-3-yl)-piperidine-1-carboxylate |
| (112) 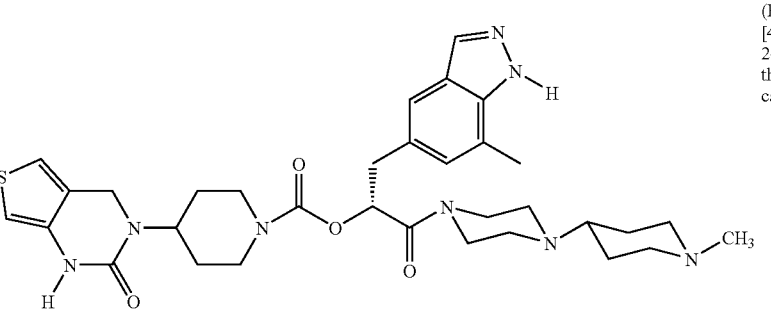 | (R)-1-(7-methyl-1H-indazol-5-ylmethyl)-2-[4-(1-methyl-piperidin-4-yl)-piperazin-1-yl]-2-oxo-ethyl 4-(2-oxo-1,2-dihydro-4H-thieno[3,4-d]pyrimidin-3-yl)-piperidine-1-carboxylate |

| Structure | Name |
|---|---|
| (113) 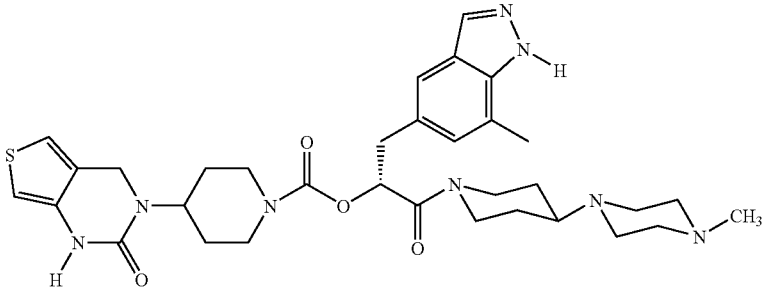 | (R)-1-(7-methyl-1H-indazol-5-ylmethyl)-2-[4-(4-methyl-piperazin-1-yl)-piperidin-1-yl]-2-oxo-ethyl 4-(2-oxo-1,2-dihydro-4H-thieno[3,4-d]pyrimidin-3-yl)-piperidine-1-carboxylate |
| (114) 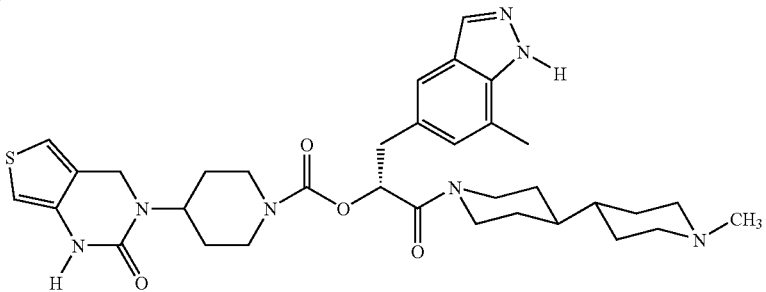 | (R)-2-(1'-methyl-[4,4']bipiperidinyl-1-yl)-1-(7-methyl-1H-indazol-5-ylmethyl)-2-oxo-ethyl 4-(2-oxo-1,2-dihydro-4H-thieno[3,4-d]pyrimidin-3-yl)-piperidine-1-carboxylate |
| (115) 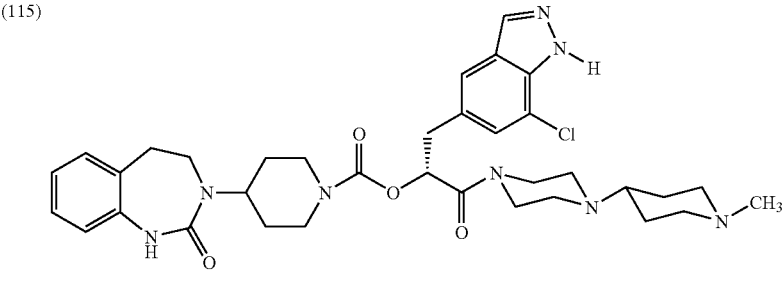 | (R)-1-(7-chloro-1H-indazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (116) 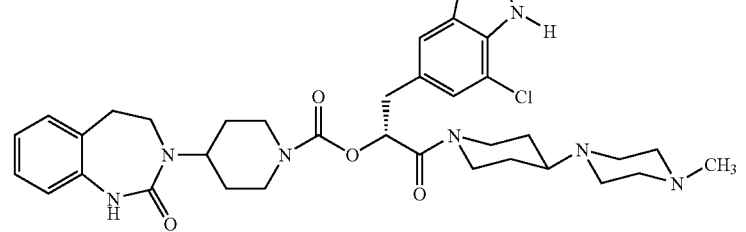 | (R)-1-(7-chloro-1H-indazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (117) 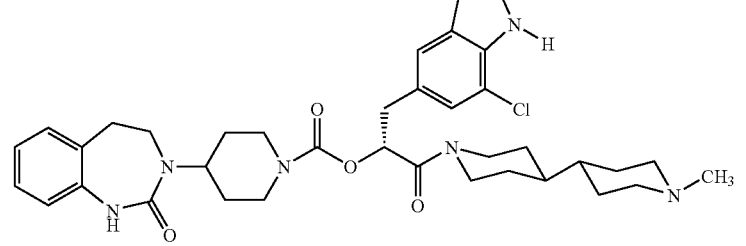 | (R)-1-(7-chloro-1H-indazol-5-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| Structure | Name |
|---|---|
| (118) 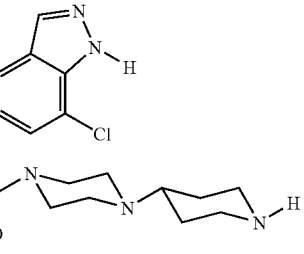 | (R)-1-(7-chloro-1H-indazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (119) 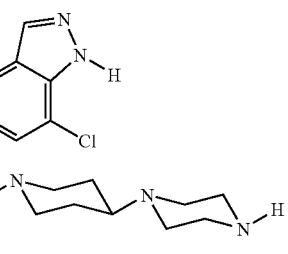 | (R)-1-(7-chloro-1H-indazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (120) 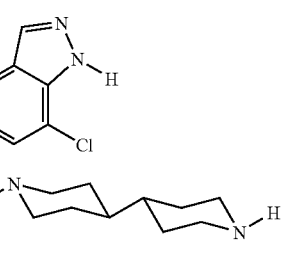 | (R)-2-4,4'-bipiperidinyl-1-yl-1-(7-chloro-1H-indazol-5-ylmethyl)-2-oxo-ethyl 4-(2-oxo-1,2,4,5-tetrahydro-1,3-benzodiazepin-3-yl)-piperidine-1-carboxylate |
| (121) 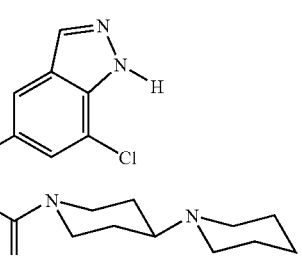 | (R)-2-1,4'-bipiperidinyl-1'-yl-1-(7-chloro-1H-indazol-5-ylmethyl)-2-oxo-ethyl 4-(2-oxo-1,2,4,5-tetrahydro-1,3-benzodiazepin-3-yl)-piperidine-1-carboxylate |
| (122) 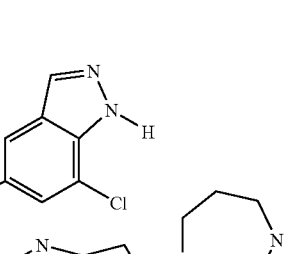 | (R)-1-(7-chloro-1H-indazol-5-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (123) | 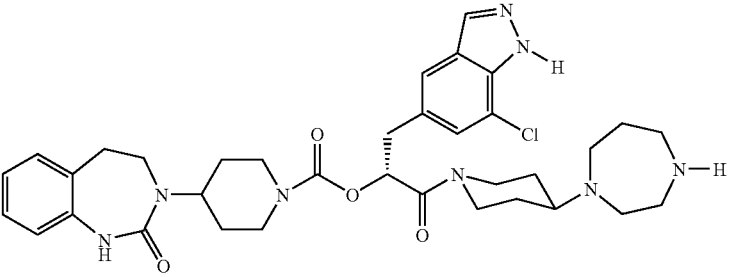 | (R)-1-(7-chloro-1H-indazol-5-ylmethyl)-2-oxo-2-(4-perhydro-1,4-diazepin-1-yl-tetrahydro-1,3-benzodiazepin-3-yl)-piperidine-1-carboxylate |
| (124) | 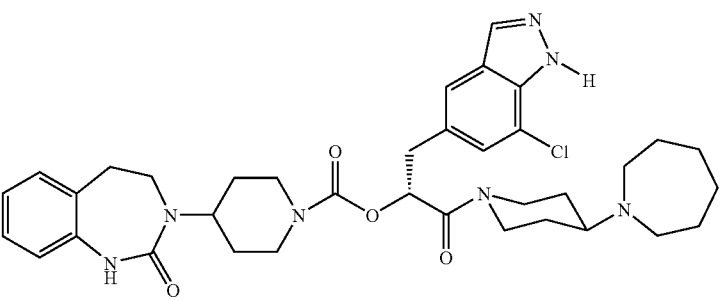 | (R)-1-(7-chloro-1H-indazol-5-ylmethyl)-2-oxo-2-(4-perhydro-azepin-1-yl-piperidin-1-yl)-ethyl 4-(2-oxo-1,2,4,5-tetrahydro-1,3-benzodiazepin-3-yl)-piperidine-1-carboxylate |
| (125) | 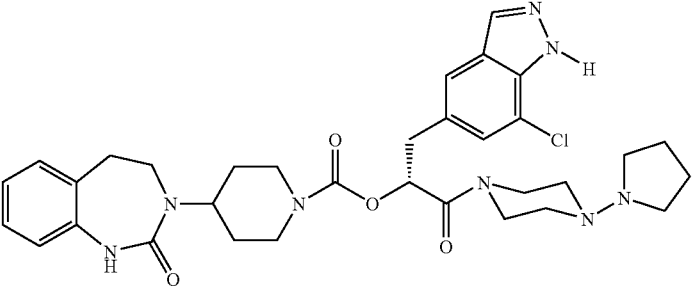 | (R)-1-(7-chloro-1H-indazol-5-ylmethyl)-2-oxo-2-(4-pyrrolidin-1-yl-piperidin-1-yl)-ethyl 4-(2-oxo-1,2,4,5-tetrahydro-1,3-benzodiazepin-3-yl)-piperidine-1-carboxylate |
| (126) | 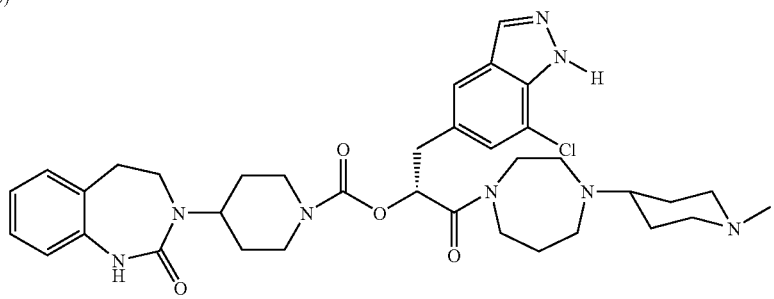 | (R)-1-(7-chloro-1H-indazol-5-ylmethyl)-2-[4-(1-methyl-piperidin-4-yl)-perhydro-1,4-diazepin-1-yl]-2-oxo-ethyl 4-(2-oxo-1,2,4,5-tetrahydro-1,3-benzodiazepin-3-yl)-piperidine-1-carboxylate |
| (127) | 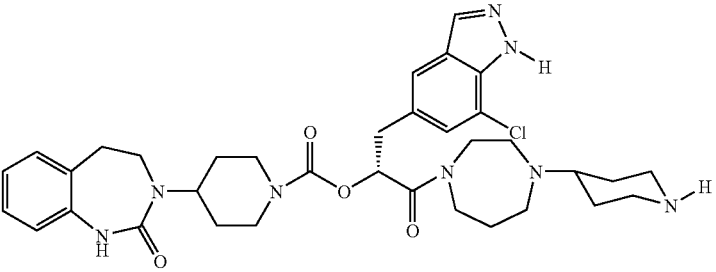 | (R)-1-(7-chloro-1H-indazol-5-ylmethyl)-2-oxo-2-(4-piperidin-4-yl-perhydro-1,4-diazepin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (128) 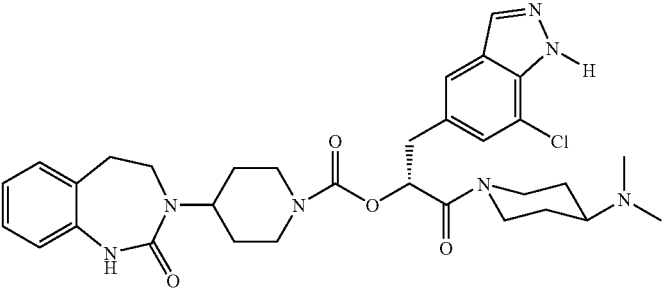 | (R)-1-(7-chloro-1H-indazol-5-ylmethyl)-2-(4-dimethylamino-piperidin-1-yl)-2-oxo-ethyl 4-(2-oxo-1,2,4,5-tetrahydro-1,3-benzodiazepin-3-yl)-piperidine-1-carboxylate |
| (129) 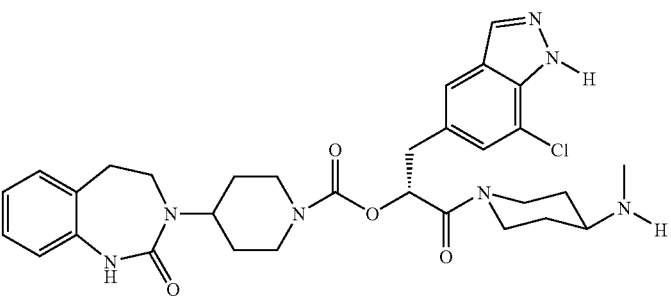 | (R)-1-(7-chloro-1H-indazol-5-ylmethyl)-2-(4-methylamino-piperidin-1-yl)-2-oxo-ethyl 4-(2-oxo-1,2,4,5-tetrahydro-1,3-benzodiazepin-3-yl)-piperidine-1-carboxylate |
| (130) 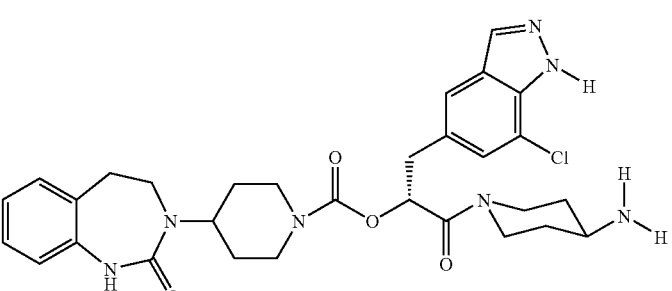 | (R)-2-(4-amino-piperidin-1-yl)-1-(7-chloro-1H-indazol-5-ylmethyl)-2-oxo-ethyl 4-(2-oxo-1,2,4,5-tetrahydro-1,3-benzodiazepin-3-yl)-piperidine-1-carboxylate |
| (131) 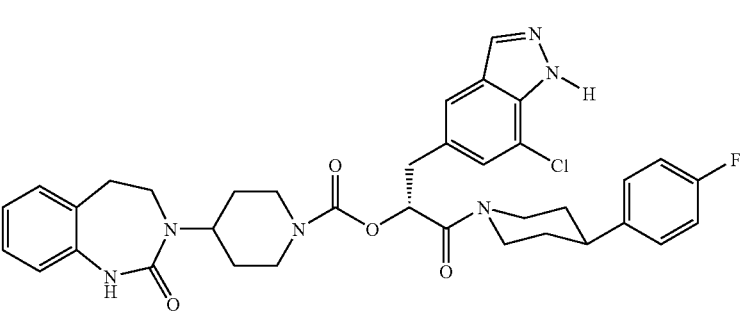 | (R)-1-(7-chloro-1H-indazol-5-ylmethyl)-2-[4-(4-fluoro-phenyl)-piperidin-1-yl]-2-oxo-ethyl 4-(2-oxo-1,2,4,5-tetrahydro-1,3-benzodiazepin-3-yl)-piperidine-1-carboxylate |
| (132) 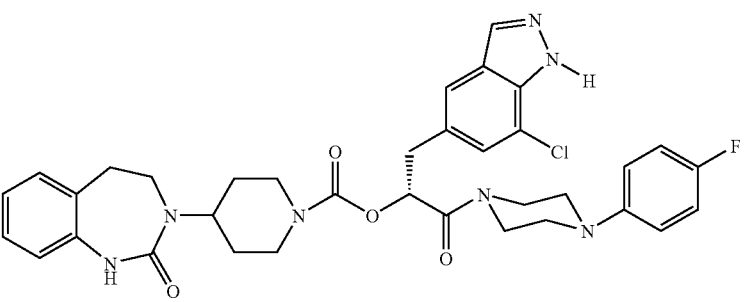 | (R)-1-(7-chloro-1H-indazol-5-ylmethyl)-2-[4-(4-fluoro-phenyl)-piperazin-1-yl]-2-oxo-ethyl 4-(2-oxo-1,2,4,5-tetrahydro-1,3-benzodiazepin-3-yl)-piperidine-1-carboxylate |

| Structure | Name |
|---|---|
| (133) 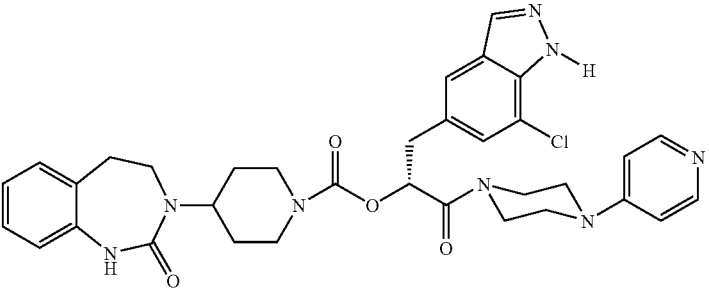 | (R)-1-(7-chloro-1H-indazol-5-ylmethyl)-2-oxo-2-(4-pyridin-4-yl-piperazin-1-yl)-ethyl 4-(2-oxo-1,2,4,5-tetrahydro-1,3-benzodiazepin-3-yl)-piperidine-1-carboxylate |
| (134) 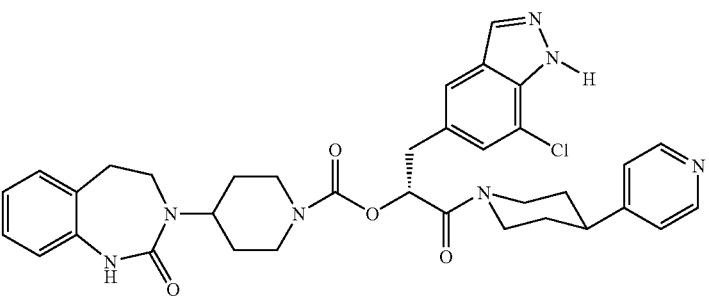 | (R)-1-(7-chloro-1H-indazol-5-ylmethyl)-2-oxo-2-(3,4,5,6-tetrahydro-2H-4,4'-bipyridinyl-1-yl)-ethyl 4-(2-oxo-1,2,4,5-tetrahydro-1,3-benzodiazepin-3-yl)-piperidine-1-carboxylate |
| (135) 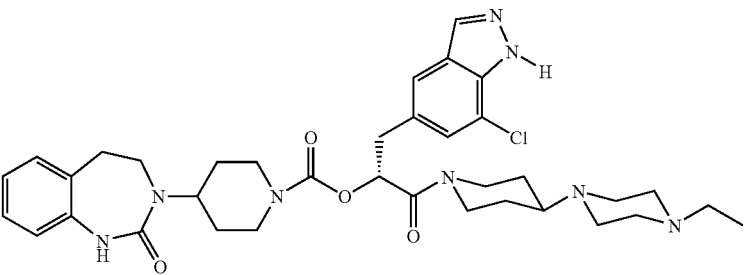 | (R)-1-(7-chloro-1H-indazol-5-ylmethyl)-2-[4-(4-ethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (136) 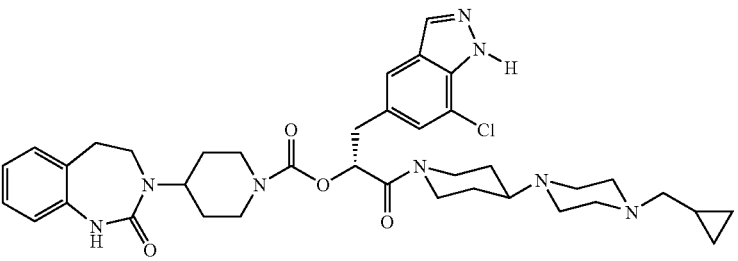 | (R)-1-(7-chloro-1H-indazol-5-ylmethyl)-2-[4-(4-cyclopropylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (137) 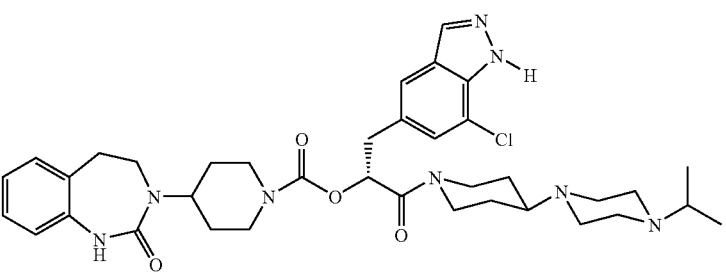 | (R)-1-(7-chloro-1H-indazol-5-ylmethyl)-2-[4-(4-isopropyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| Structure | Name |
|---|---|
| (138) | (R)-1-(7-chloro-1H-indazol-5-ylmethyl)-2-[4-(4-cyclopropyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (139) | (R)-1-(7-chloro-1H-indazol-5-ylmethyl)-2-[4-(1-cyclopropyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (140) | (R)-1-(7-chloro-1H-indazol-5-ylmethyl)-2-[4-(4-methoxycarbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (141) | (R)-2-[4-(4-carboxymethyl-piperazin-1-yl)-piperidin-1-yl]-1-(7-chloro-1H-indazol-5-yl-tetrahydro-1,3-benzodiazepin-3-yl)-piperidine-1-carboxylate |
| (142) | (R)-2-[4-(2-amino-pyrimidine-5-yl)-piperazin-1-yl]-1-(7-chloro-1H-indazol-5-ylmethyl)-2-oxo-ethyl 4-(2-oxo-1,2,4,5-tetrahydro-1,3-benzodiazepin-3-yl)-piperidine-1-carboxylate |

| Structure | Name |
|---|---|
| (143) 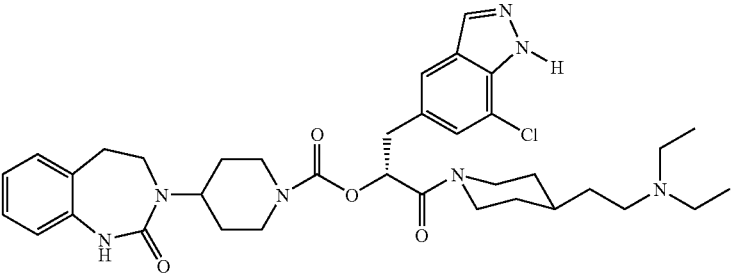 | (R)-1-(7-chloro-1H-indazol-5-ylmethyl)-2-[4-(2-diethylamino-ethyl)-piperidin-1-yl]-2-oxo-ethyl 4-(2-oxo-1,2,4,5-tetrahydro-1,3-benzodiazepin-3-yl)-piperidine-1-carboxylate |
| (144) 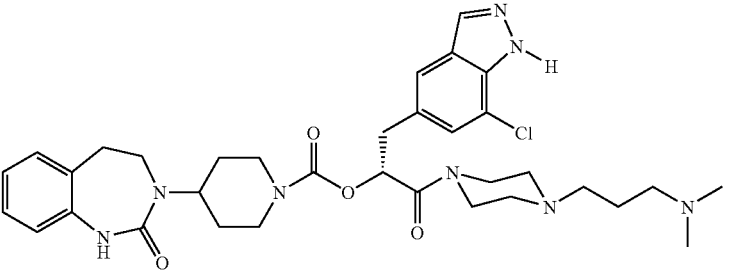 | (R)-1-(7-chloro-1H-indazol-5-ylmethyl)-2-[4-(3-dimethylamino-propyl)-piperazin-1-yl]-2-oxo-ethyl 4-(2-oxo-1,2,4,5-tetrahydro-1,3-benzodiazepin-3-yl)-piperidine-1-carboxylate |
| (145) 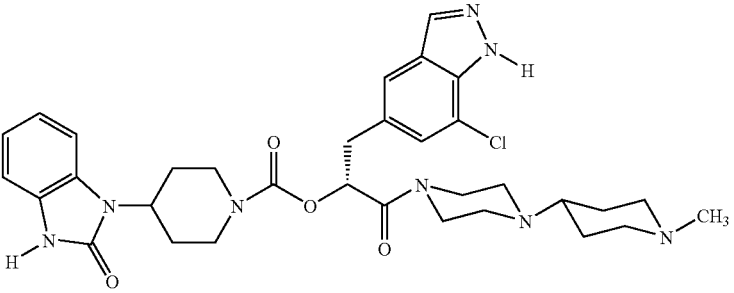 | (R)-1-(7-chloro-1H-indazol-5-ylmethyl)-2-[4-(1-methyl-piperidin-4-yl)-piperazin-1-yl]-2-oxo-ethyl 4-(2-oxo-2,3-dihydro-benzimidazol-1-yl)-piperidine-1-carboxylate |
| (146) 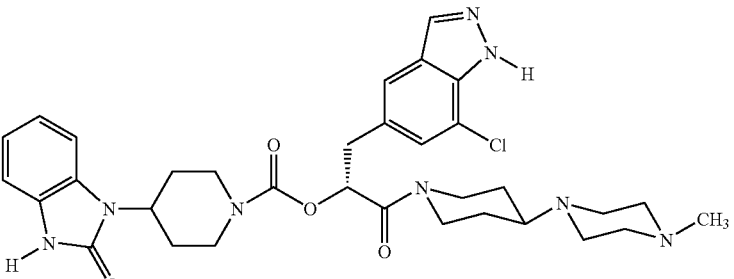 | (R)-1-(7-chloro-1H-indazol-5-ylmethyl)-2-[4-(4-methyl-piperazin-1-yl)-piperidin-1-yl]-2-oxo-ethyl 4-(2-oxo-2,3-dihydro-benzimidazol-1-yl)-piperidine-1-carboxylate |
| (147) 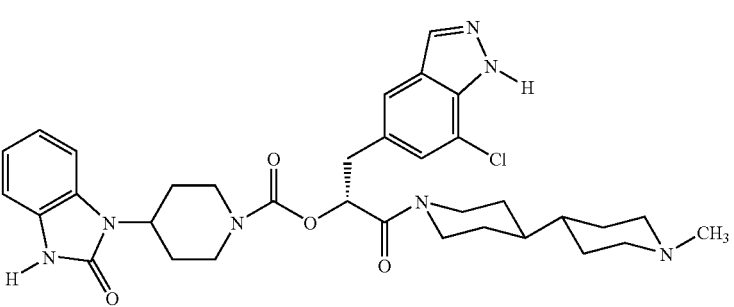 | (R)-1-(7-chloro-1H-indazol-5-ylmethyl)-2-(1'-methyl-4,4'-bipiperidinyl-1-yl)-2-oxo-ethyl 4-(2-oxo-2,3-dihydro-benzimidazol-1-yl)-piperidine-1-carboxylate |

| Structure | Name |
|---|---|
| (148) | (R)-1-(7-chloro-1H-indazol-5-ylmethyl)-2-[4-(1-methyl-piperidin-4-yl)-piperazin-1-yl]-2-oxo-ethyl 4-(2-oxo-4-phenyl-2,3-dihydro-imidazol-1-yl)-piperidine-1-carboxylate |
| (149) | (R)-1-(7-chloro-1H-indazol-5-ylmethyl)-2-[4-(4-methyl-piperazin-1-yl)-piperidin-1-yl]-2-oxo-ethyl 4-(2-oxo-4-phenyl-2,3-dihydro-imidazol-1-yl)-piperidine-1-carboxylate |
| (150) | (R)-1-(7-chloro-1H-indazol-5-ylmethyl)-2-(1'-methyl-[4,4']bipiperidinyl-1-yl)-2-oxo-ethyl 4-(2-oxo-4-phenyl-2,3-dihydro-imidazol-1-yl)-piperidine-1-carboxylate |
| (151) | (R)-1-(7-chloro-1H-indazol-5-ylmethyl)-2-[4-(1-methyl-piperidin-4-yl)-piperazin-1-yl]-2-oxo-ethyl 4-(5-oxo-3-phenyl-4,5-dihydro-1,2,4-triazol-1-yl)-piperidine-1-carboxylate |
| (152) | (R)-1-(7-chloro-1H-indazol-5-ylmethyl)-2-[4-(4-methyl-piperazin-1-yl)-piperidin-1-yl]-2-oxo-ethyl 4-(5-oxo-3-phenyl-4,5-dihydro-1,2,4-triazol-1-yl)-piperidine-1-carboxylate |

-continued

| Structure | Name |
|---|---|
| (153) | (R)-1-(7-chloro-1H-indazol-5-ylmethyl)-2-(1'-methyl-4,4'-bipiperidinyl-1-yl)-2-oxo-ethyl 4-(5-oxo-3-phenyl-4,5-dihydro-1,2,4-triazol-1-yl)-piperidine-1-carboxytate |
| (154) | (R)-1-(7-chloro-1H-indazol-5-ylmethyl)-2-[4-(1-methyl-piperidin-4-yl)-piperazin-1-yl]-2-oxo-ethyl 4-(2-oxo-1,2-dihydro-imidazo[4,5-c]quinolin-3-yl)-piperidine-1-carboxylate |
| (155) | (R)-1-(7-chloro-1H-indazol-5-ylmethyl)-2-[4-(4-methyl-piperazin-1-yl)-piperidin-1-yl]-2-oxo-ethyl 4-(2-oxo-1,2-dihydro-imidazo[4,5-c]quinolin-3-yl)-piperidine-1-carboxylate |
| (156) | (R)-1-(7-chloro-1H-indazol-5-ylmethyl)-2-(1'-methyl-[4,4']bipiperidinyl-1-yl)-2-oxo-ethyl 4-(2-oxo-1,2-dihydro-imidazo[4,5-c]-quinolin-3-yl)-piperidine-1-carboxylate |
| (157) | (R)-1-(7-chloro-1H-indazol-5-ylmethyl)-2-[4-(1-methyl-piperidin-4-yl)-piperazin-1-yl]-2-oxo-ethyl 4-(2-oxo-1,2-dihydro-naphth[1,2-d]imidazol-3-yl)-piperidine-1-carboxylate |

-continued

| Structure | Name |
|---|---|
| (158) 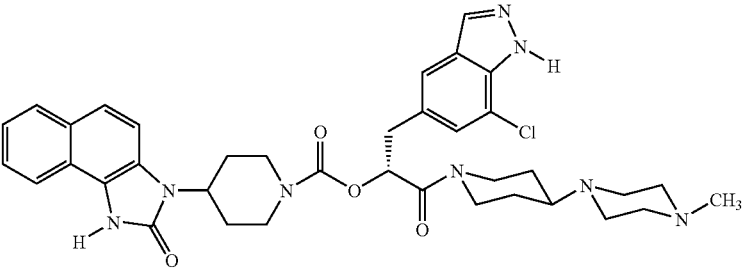 | (R)-1-(7-chloro-1H-indazol-5-ylmethyl)-2-[4-(4-methyl-piperazin-1-yl)-piperidin-1-yl]-2-oxo-ethyt 4-(2-oxo-1,2-dihydro-naphth[1,2-d]imidazol-3-yl)-piperidine-1-carboxylate |
| (159) 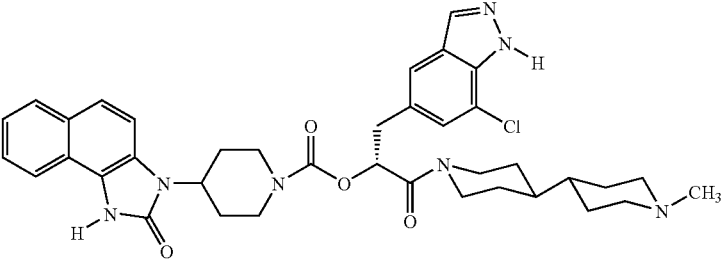 | (R)-1-(7-chloro-1H-indazol-5-ylmethyl)-2-(1'-methyl-4,4'-bipiperidinyl-1-yl)-2-oxo-ethyl 4-(2-oxo-1,2-dihydro-naphth[1,2-d]-imidazol-3-yl)-piperidine-1-carboxylate |
| (160) 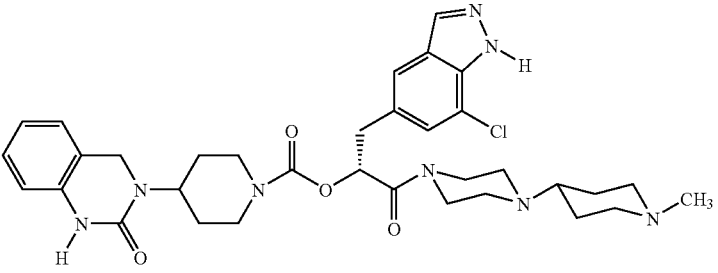 | (R)-1-(7-chloro-1H-indazol-5-ylmethyl)-2-[4-(1-methyl-piperidin-4-yl)-piperazin-1-yl]-2-oxo-ethyl 4-(2-oxo-1,4-dihydro-2H-quinazolin-3-yl)-piperidine-1-carboxylate |
| (161) 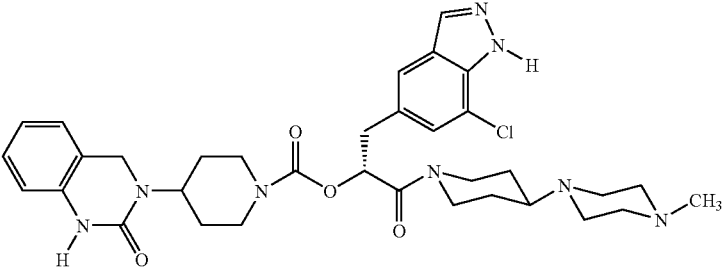 | (R)-1-(7-chloro-1H-indazol-5-ylmethyl)-2-[4-(4-methyl-piperazin-1-yl)-piperidin-1-yl]-2-oxo-ethyl 4-(2-oxo-1,4-dihydro-2H-quinazolin-3-yl)-piperidine-1-carboxylate |
| (162) 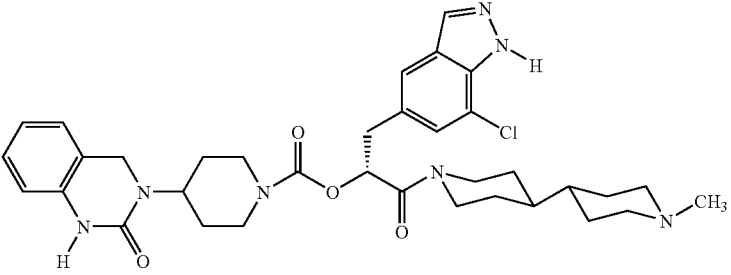 | (R)-1-(7-chloro-1H-indazol-5-ylmethyl)-2-(1'-methyl-[4,4']bipiperidinyl-1-yl)-2-oxo-ethyl 4-(2-oxo-1,4-dihydro-2H-quinazolin-3-yl)-piperidine-1-carboxylate |

-continued

| Structure | Name |
|---|---|
| (163) 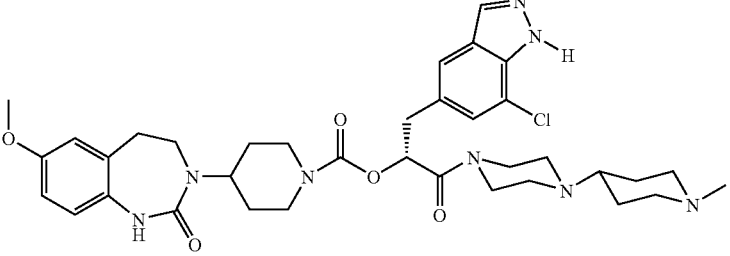 | (R)-1-(7-chloro-1H-indazol-5-ylmethyl)-2-[4-(1-methyl-piperidin-4-yl)-piperazin-1-yl]-2-oxo-ethyl 4-(7-methoxy-2-oxo-1,2,4,5-tetrahydro-1,3-benzodiazepin-3-yl)-piperidine-1-carboxylate |
| (164) 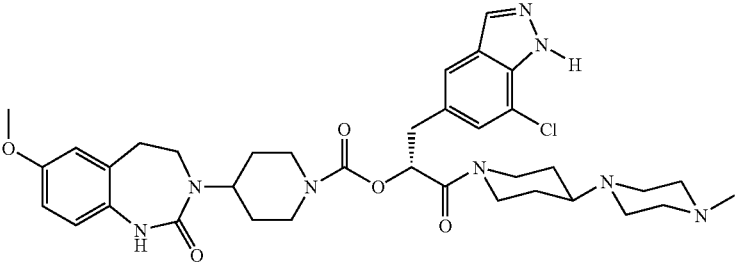 | (R)-1-(7-chloro-1H-indazol-5-ylmethyl)-2-[4-(4-methyl-piperazin-1-yl)-piperidin-1-yl]-2-oxo-ethyl 4-(7-methoxy-2-oxo-1,2,4,5-tetrahydro-1,3-benzodiazepin-3-yl)-piperidine-1-carboxylate |
| (165) 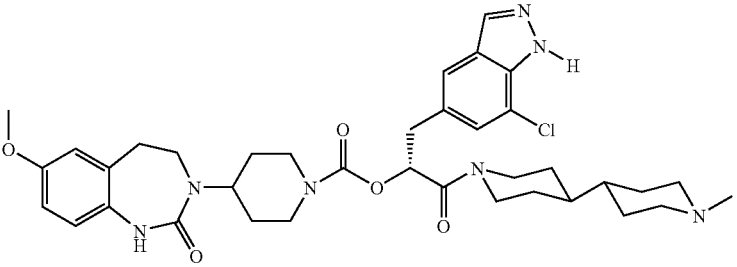 | (R)-1-(7-chloro-1H-indazol-5-ylmethyl)-2-(1'-methyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate |
| (166) 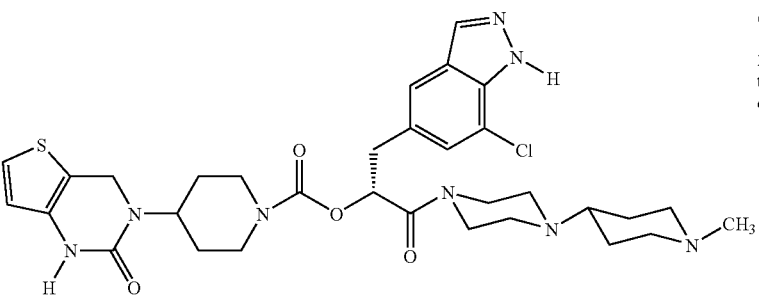 | (R)-1-(7-chloro-1H-indazol-5-ylmethyl)-2-[4-(1-methyl-piperidin-4-yl)-piperazin-1-yl]-2-oxo-ethyl 4-(2-oxo-1,4-dihydro-2H-thieno[3,2-d]pyrimidin-3-yl)-piperidine-1-carboxylate |
| (167) 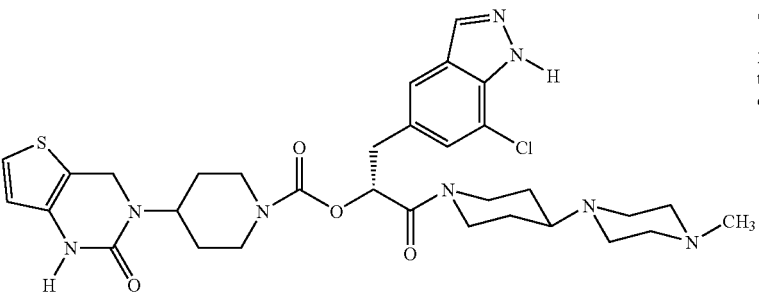 | (R)-1-(7-chloro-1H-indazol-5-ylmethyl)-2-[4-(4-methyl-piperazin-1-yl)-piperidin-1-yl]-2-oxo-ethyl 4-(2-oxo-1,4-dihydro-2H-thieno[3,2-d]pyrimidin-3-yl)-piperidine-1-carboxylate |

-continued

| Structure | Name |
|---|---|
| (168) 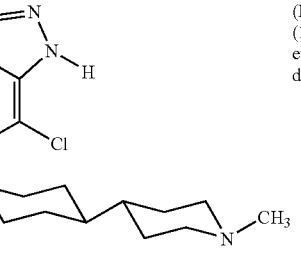 | (R)-1-(7-chloro-1H-indazol-5-ylmethyl)-2-(1'-methyl-[4,4']bipiperidinyl-1-yl)-2-oxo-ethyl 4-(2-oxo-1,4-dihydro-2H-thieno[3,2-d]pyrimidin-3-yl)-piperidine-1-carboxylate |
| (169) 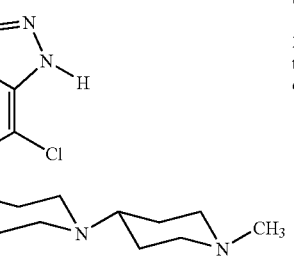 | (R)-1-(7-chloro-1H-indazol-5-ylmethyl)-2-[4-(1-methyl-piperidin-4-yl)-piperazin-1-yl]-2-oxo-ethyl 4-(2-oxo-1,2-dihydro-4H-thieno[3,4-d]pyrimidin-3-yl)-piperidine-1-carboxylate |
| (170) 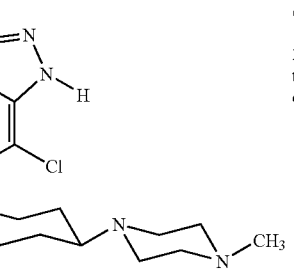 | (R)-1-(7-chloro-1H-indazol-5-ylmethyl)-2-[4-(4-methyl-piperazin-1-yl)-piperidin-1-yl]-2-oxo-ethyl 4-(2-oxo-1,2-dihydro-4H-thieno[3,4-d]pyrimidin-3-yl)-piperidine-1-carboxylate |
| (171) 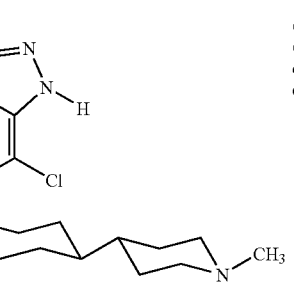 | (R)-1-(7-chloro-1H-indazol-5-ylmethyl)-2-(1'-methyl-[4,4']bipiperidinyl-1-yl)-2-oxo-ethyl 4-(2-oxo-1,2-dihydro-4H-thieno[3,4-d]pyrimidin-3-yl)-piperidine-1-carboxylate |
| (172) 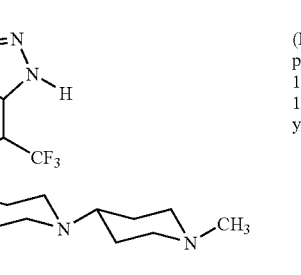 | (R)-2-[4-(1-methyl-piperidin-4-yl)-piperazin-1-yl]-2-oxo-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |

-continued

| Structure | Name |
|---|---|
| (173) 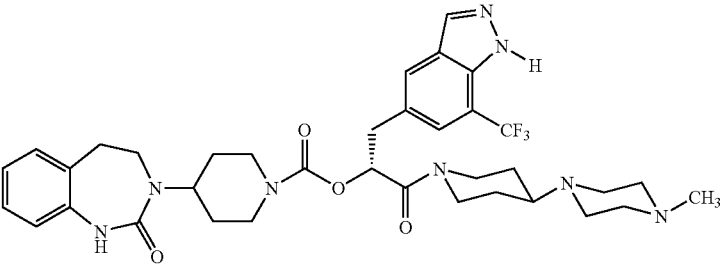 | (R)-2-[4-(4-methyl-piperazin-1-yl)-piperidin-1-yl]-2-oxo-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |
| (174) 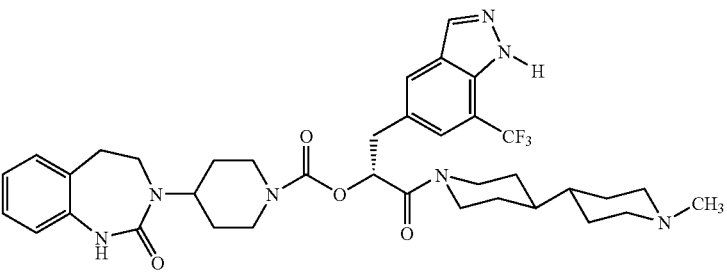 | (R)-2-(1'-methyl-4,4'-bipiperidinyl-1-yl)-2-oxo-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |
| (175) 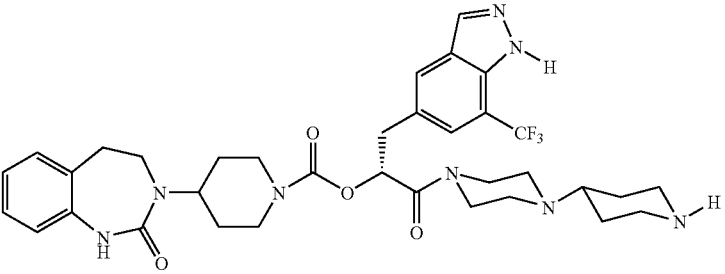 | (R)-2-oxo-2-(4-piperidin-4-yl-piperazin-1-yl)-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |
| (176) 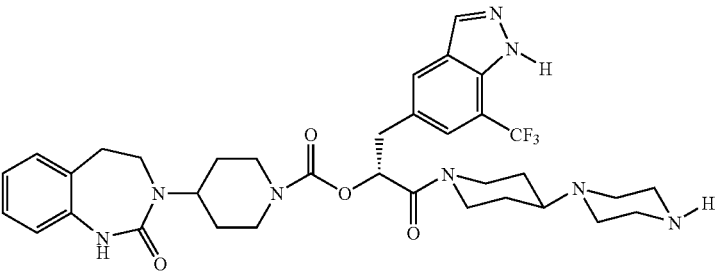 | (R)-2-oxo-2-(4-piperazin-1-yl-piperidin-1-yl)-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |
| (177) 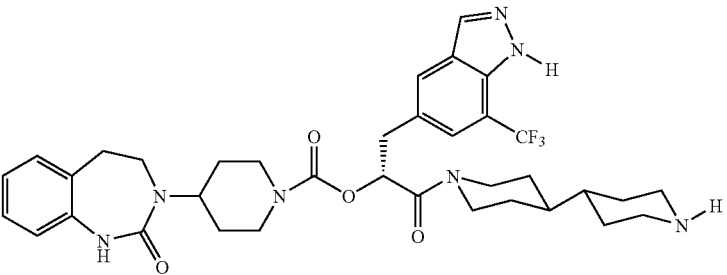 | (R)-2-4,4'-bipiperidinyl-1-yl-2-oxo-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |

-continued

| Structure | Name |
|---|---|
| (178) 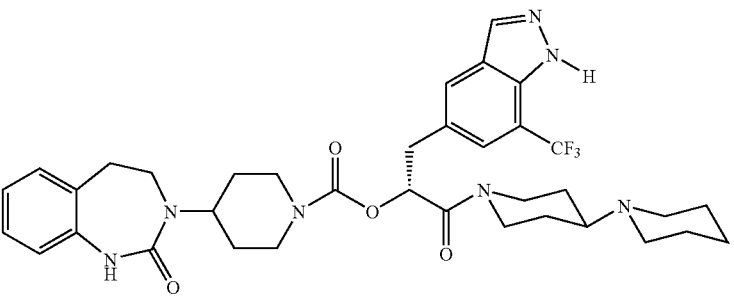 | (R)-2-1,4'-bipiperidinyl-1'-yl-2-oxo-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |
| (179) 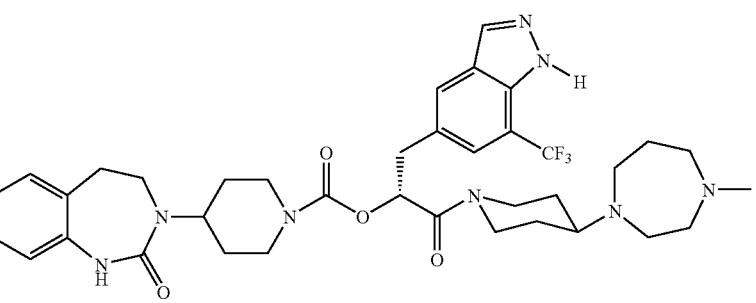 | (R)-2-[4-(4-methyl-perhydro-1,4-diazepin-1-yl)-piperidin-1-yl]-2-oxo-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |
| (180) 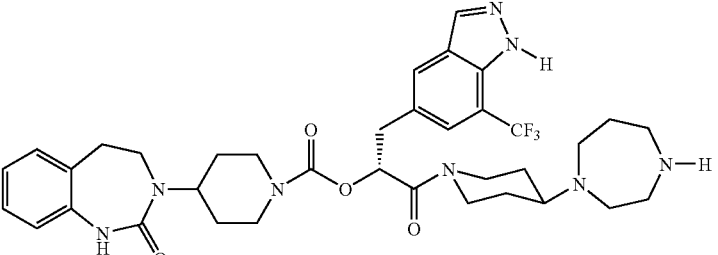 | (R)-2-oxo-2-(4-perhydro-1,4-diazepin-1-yl-piperidin-1-yl)-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |
| (181) 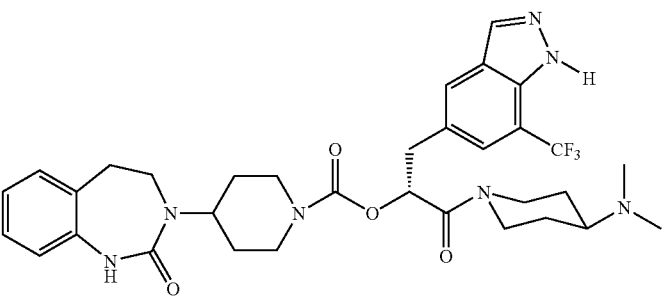 | (R)-2-(4-dimethylamino-piperidin-1-yl)-2-oxo-1-(7-trifluoromethyl-1H-indazol-5-ylmethyl)-ethyl 4-(2-oxo-1,2,4,5-tetrahydro-1,3-benzodiazepin-3-yl)-piperidine-1-carboxylate |
| (182) 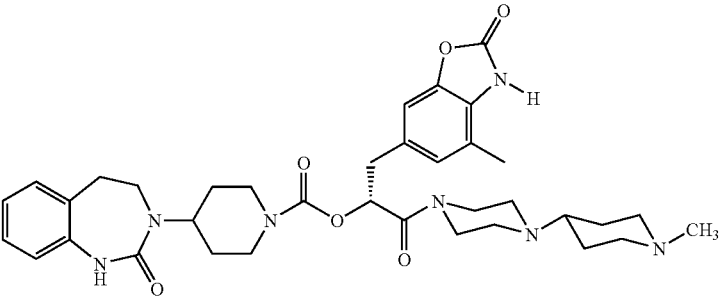 | (R)-1-(4-methyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| Structure | Name |
|---|---|
| (183) 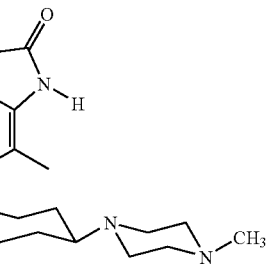 | (R)-1-(4-methyl-2-oxo-2,3-dihydro-benzoxazol-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (184) 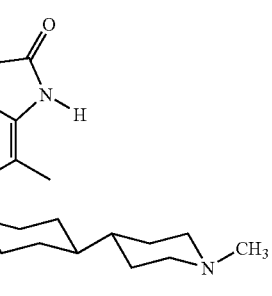 | (R)-2-(1'-methyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (185) 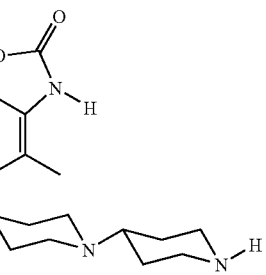 | (R)-1-(4-methyl-2-oxo-2,3-dihydro-benzoxazol-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (186) 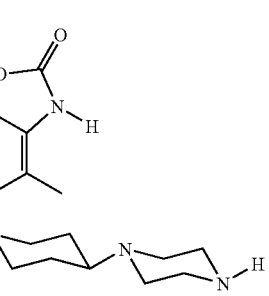 | (R)-1-(4-methyl-2-oxo-2,3-dihydro-benzoxazol-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (187) 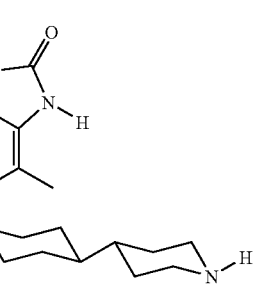 | (R)-2-4,4'-bipiperidinyl-1-yl-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (188) 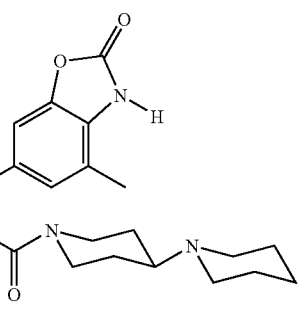 | (R)-2-1,4'-bipiperidinyl-1'-yl-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (189) 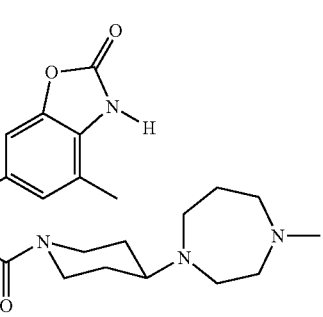 | (R)-1-(4-methyl-2-oxo-2,3-dihydro-benzoxazol-6-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (190) 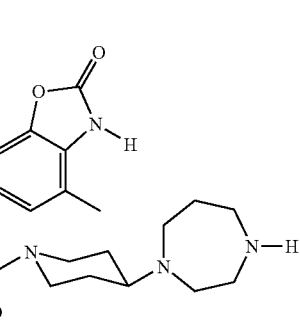 | (R)-1-(4-methyl-2-oxo-2,3-dihydro-benzoxazol-6-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (191) 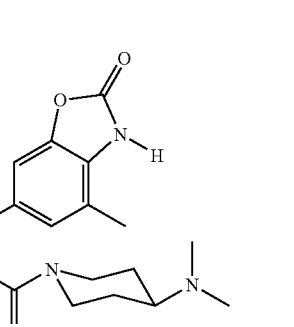 | (R)-2-(4-dimethylamino-piperidin-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (192) 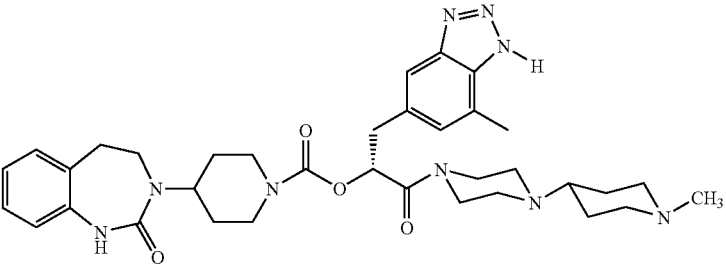 | (R)-1-(7-methyl-1H-benzotriazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (193) 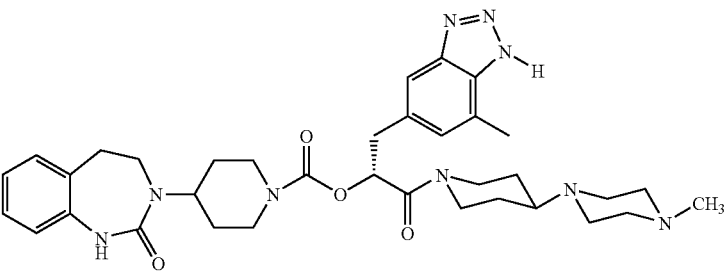 | (R)-1-(7-methyl-1H-benzotriazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (194) 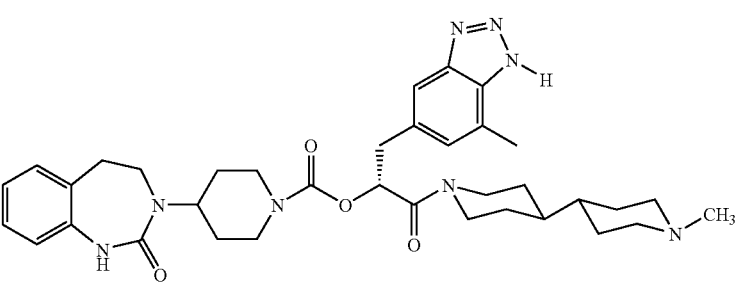 | (R)-1-(7-methyl-1H-benzotriazol-5-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (195) 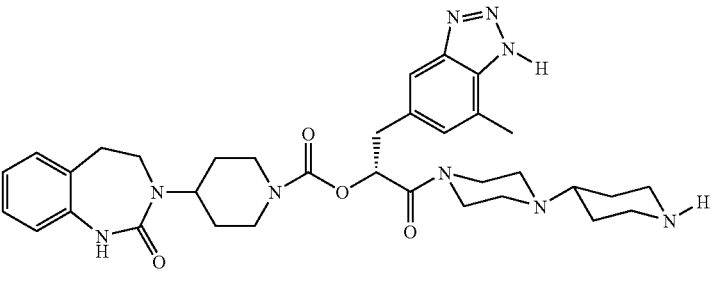 | (R)-1-(7-methyl-1H-benzotriazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (196) 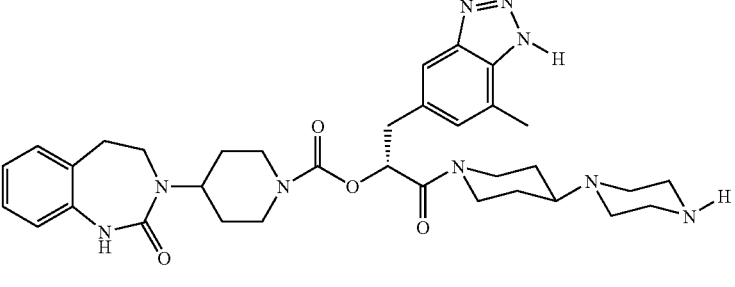 | (R)-1-(7-methyl-1H-benzotriazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

-continued

| | Structure | Name |
|---|---|---|
| (197) | 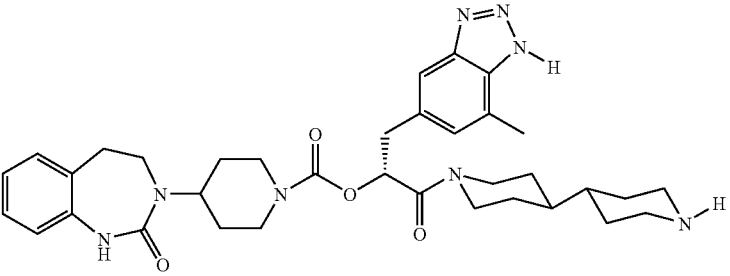 | (R)-2-4,4'-bipiperidinyl-1-yl-1-(7-methyl-1H-benzotriazol-5-ylmethyl)-2-oxo-ethyl 4-(2-oxo-1,2,4,5-tetrahydro-1,3-benzo-diazepin-3-yl)-piperidine-1-carboxylate |
| (198) | 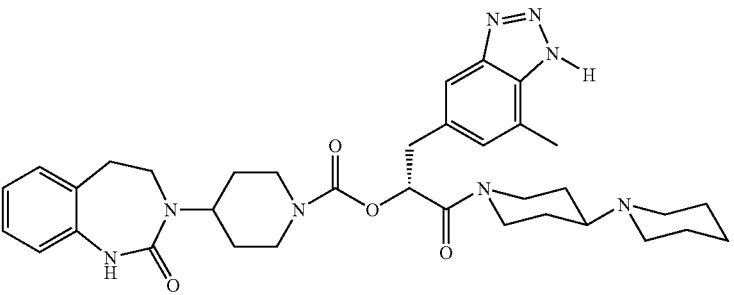 | (R)-2-1,4'-bipiperidinyl-1'-yl-1-(7-methyl-1H-benzotriazol-5-ylmethyl)-2-oxo-ethyl 4-(2-oxo-1,2,4,5-tetrahydro-1,3-benzo-diazepin-3-yl)-piperidine-1-carboxylate |
| (199) | 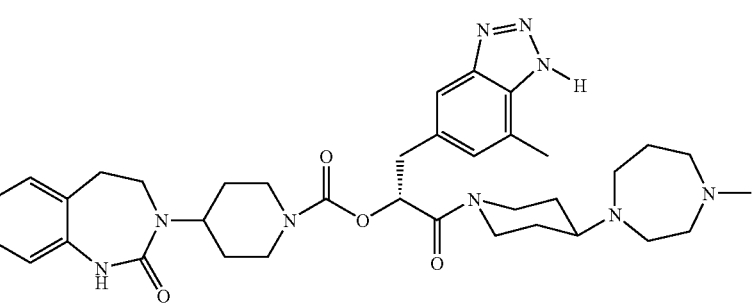 | (R)-1-(7-methyl-1H-benzotriazol-5-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzo-diazepin-3-yl)-piperidine-1-carboxylate |
| (200) | 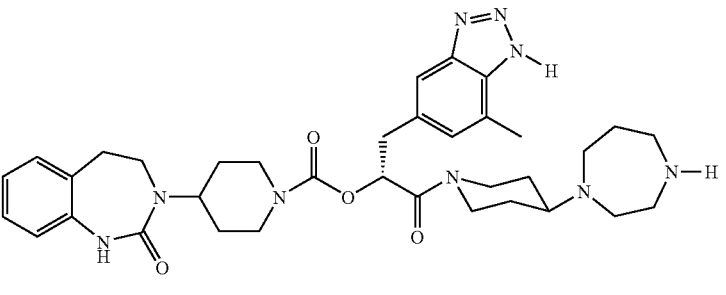 | (R)-1-(7-methyl-1H-benzotriazol-5-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (201) | 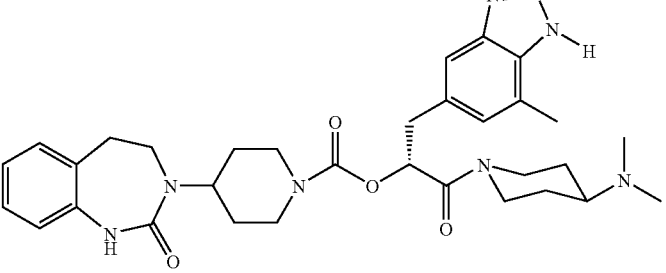 | (R)-2-(4-dimethylamino-piperidin-1-yl)-1-(7-methyl-1H-benzotriazol-5-ylmethyl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (202) | 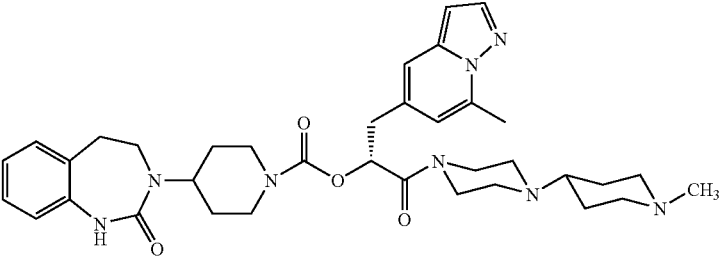 | (R)-2-[4-(1-methyl-piperidin-4-yl)-piperazin-1-yl]-1-(7-methyl-pyrazolo[1,5-a]pyridin-5-ylmethyl)-2-oxo-ethyl 4-(2-oxo-1,2,4,5-tetrahydro-1,3-benzodiazepin-3-yl)-piperidine-1-carboxylate |
| (203) | 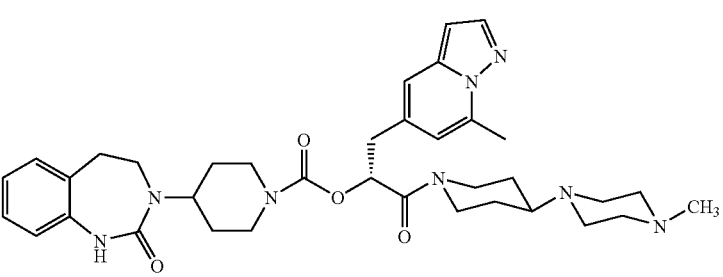 | (R)-2-[4-(4-methyl-piperazin-1-yl)-piperidin-1-yl]-1-(7-methyl-pyrazolo[1,5-a]pyridin-5-ylmethyl)-2-oxo-ethyl 4-(2-oxo-1,2,4,5-tetrahydro-1,3-benzodiazepin-3-yl)-piperidine-1-carboxylate |
| (204) | 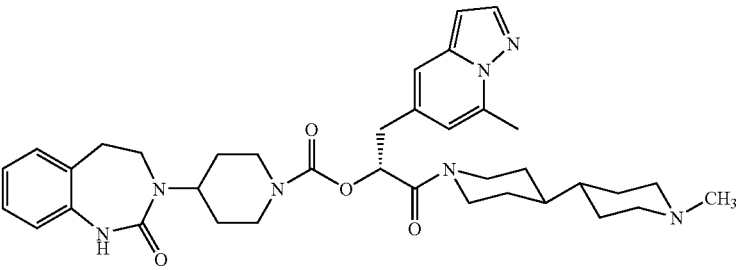 | (R)-2-(1'-methyl-4,4'-bipiperidinyl-1-yl)-1-(7-methyl-pyrazolo[1,5-a]pyridin-5-ylmethyl)-2-oxo-ethyl 4-(2-oxo-1,2,4,5-tetrahydro-1,3-benzodiazepin-3-yl)-piperidine-1-carboxylate |
| (205) | 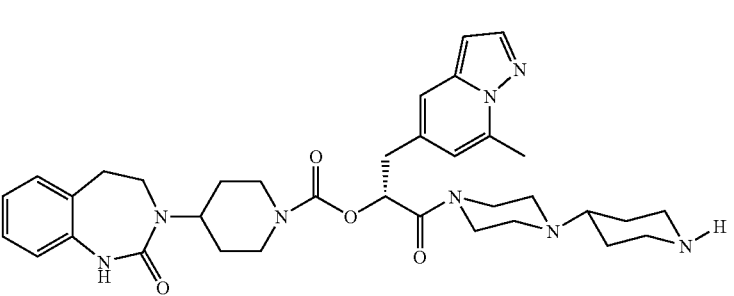 | (R)-1-(7-methyl-pyrazolo[1,5-a]pyridin-5-yl-methyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (206) | 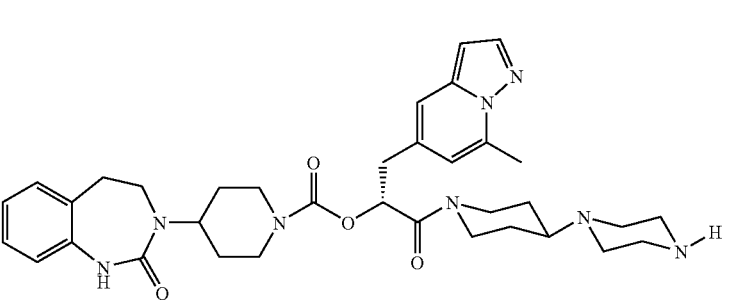 | (R)-1-(7-methyl-pyrazolo[1,5-a]pyridin-5-yl-methyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (207) | (R)-2-4,4'-bipiperidinyl-1-yl-1-(7-methyl-pyrazolo[1,5-a]pyridin-5-ylmethyl)-2-oxo-ethyl 4-(2-oxo-1,2,4,5-tetrahydro-1,3-benzodiazepin-3-yl)-piperidine-1-carboxylate |
| (208) | (R)-2-1,4'-bipiperidinyl-1'-yl-1-(7-methyl-pyrazolo[1,5-a]pyridin-5-ylmethyl)-2-oxo-ethyl 4-(2-oxo-1,2,4,5-tetrahydro-1,3-benzodiazepin-3-yl)-piperidine-1-carboxylate |
| (209) | (R)-2-[4-(4-methyl-perhydro-1,4-diazepin-1-yl)-piperidin-1-yl]-1-(7-methyl-pyrazolo[1,5-a]pyridin-5-ylmethyl)-2-oxo-ethyl 4-(2-oxo-1,2,4,5-tetrahydro-1,3-benzodiazepin-3-yl)-piperidine-1-carboxylate |
| (210) | (R)-1-(7-methyl-pyrazolo[1,5-a]pyridin-5-yl-methyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (211) | (R)-2-(4-dimethylamino-piperidin-1-yl)-1-(7-methyl-pyrazolo[1,5-a]pyridin-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (212) 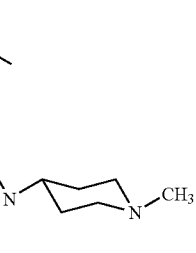 | (R)-1-(1,7-dimethyl-1H-indazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (213) 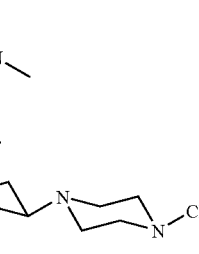 | (R)-1-(1,7-dimethyl-1H-indazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (214) 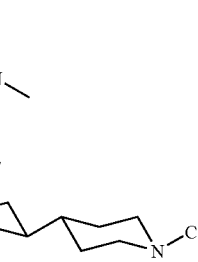 | (R)-1-(1,7-dimethyl-1H-indazol-5-ylmethyl)-2-(1'-methyl-4,4'-bipiperidinyl-1-yl)-2-oxo-ethyl 4-(2-oxo-1-1,3-benzodiazepin-3-yl)-piperidine-1-carboxylate |
| (215) 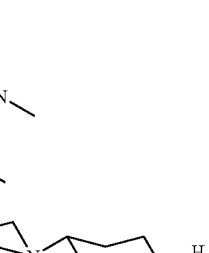 | (R)-1-(1,7-dimethyl-1H-indazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (216) 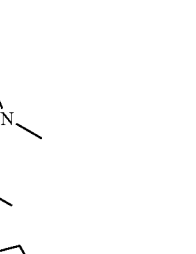 | (R)-1-(1,7-dimethyl-1H-indazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

| Structure | Name |
|---|---|
| (217) 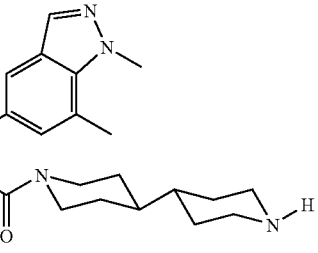 | (R)-2-4,4'-bipiperidinyl-1-yl-1-(1,7-dimethyl-1H-indazol-5-ylmethyl)-2-oxo-ethyl 4-(2-oxo-1,2,4,5-tetrahydro-1,3-benzodiazepin-3-yl)-piperidine-1-carboxylate |
| (218) 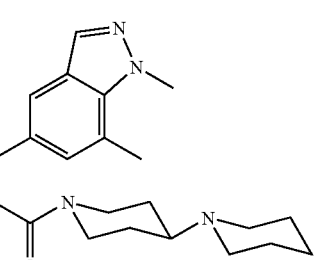 | (R)-2-1,4'-bipiperidinyl-1'-yl-1-(1,7-dimethyl-1H-indazol-5-ylmethyl)-2-oxo-ethyl 4-(2-oxo-1,2,4,5-tetrahydro-1,3-benzodiazepin-3-yl)-piperidine-1-carboxylate |
| (219) 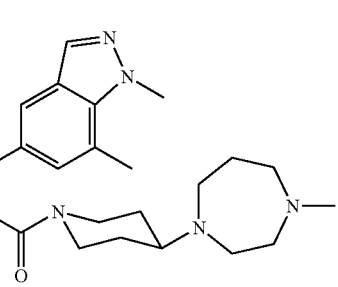 | (R)-1-(1,7-dimethyl-1H-indazol-5-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (220) 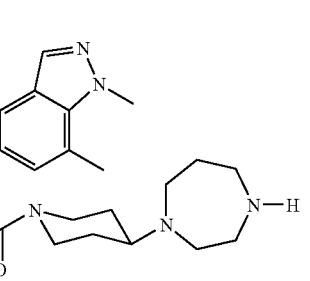 | (R)-1-(1,7-dimethyl-1H-indazol-5-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (221) 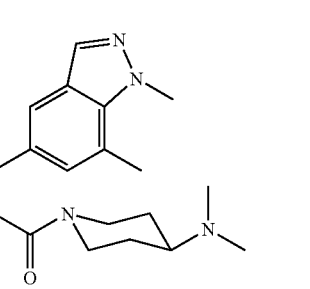 | (R)-2-(4-dimethylamino-piperidin-1-yl)-1-(1,7-dimethyl-1H-indazol-5-ylmethyl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (222) | 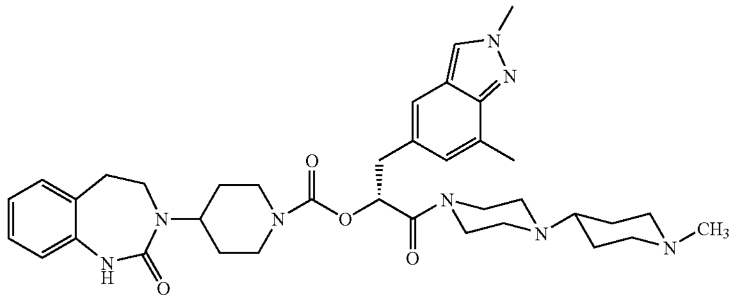 | (R)-1-(2,7-dimethyl-2H-indazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (223) | 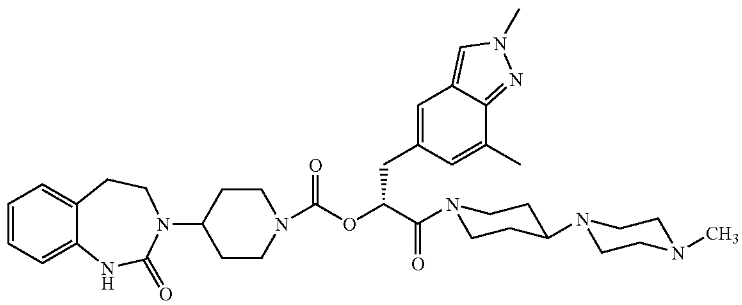 | (R)-1-(2,7-dimethyl-2H-indazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (224) | 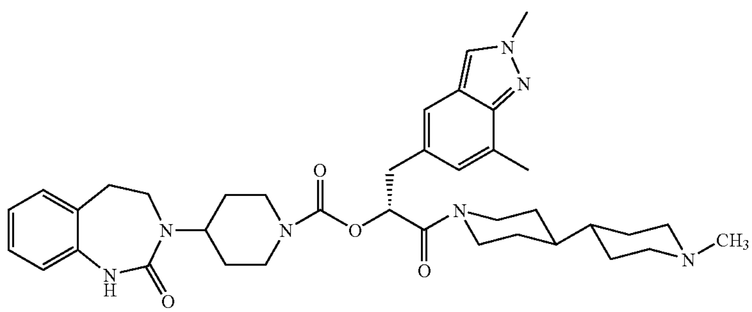 | (R)-1-(2,7-dimethyl-2H-indazol-5-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (225) | 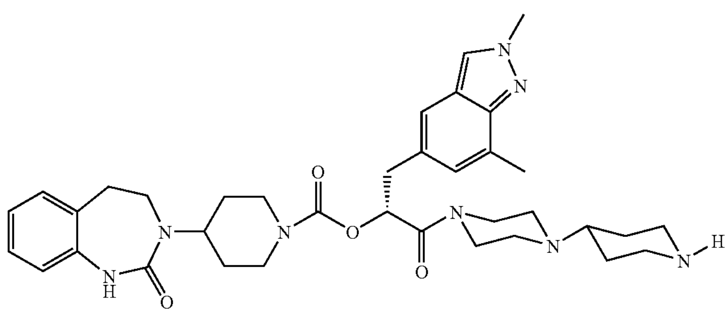 | (R)-1-(2,7-dimethyl-2H-indazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (226) | 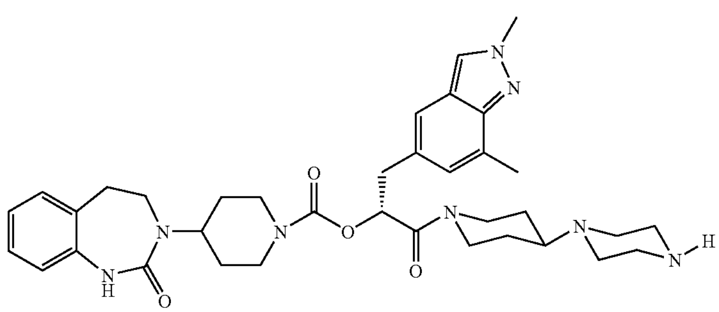 | (R)-1-(2,7-dimethyl-2H-indazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (227) | (R)-2-4,4'-bipiperidinyl-1-yl-1-(2,7-dimethyl-2H-indazol-5-ylmethyl)-2-oxo-ethyl 4-(2-oxo-1,2,4,5-tetrahydro-1,3-benzodiazepin-3-yl)-piperidine-1-carboxylate |
| (228) | (R)-2-1,4'-bipiperidinyl-1'-yl-1-(2,7-dimethyl-2H-indazol-5-ylmethyl)-2-oxo-ethyl 4-(2-oxo-1,2,4,5-tetrahydro-1,3-benzodiazepin-3-yl)-piperidine-1-carboxylate |
| (229) | (R)-1-(2,7-dimethyl-2H-indazol-5-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzo-diazepin-3-yl)-piperidine-1-carboxylate |
| (230) | (R)-1-(2,7-dimethyl-2H-indazol-5-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (231) | (R)-2-(4-dimethylamino-piperidin-1-yl)-1-(2,7-dimethyl-2H-indazol-5-ylmethyl)-2-oxo-ethyl 4-(2-oxo-1,2,4,5-tetrahydro-1,3-benzodiazepin-3-yl)-piperidine-1-carboxylate |
| (232) | (R)-1-(4-methyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,4-dihydro-2H-quinazolin-3-yl)-piperidine-1-carboxylate |
| (233) | (R)-1-(4-methyl-2-oxo-2,3-dihydro-benzoxazol-6-ylmethyl)-2-[4-(4-methyl-piperazin-1-yl)-piperidin-1-yl]-2-oxo-ethyl 4-(2-oxo-1,4-dihydro-2H-quinazolin-3-yl)-piperidine-1-carboxylate |
| (234) | (R)-2-(1'-methyl-4,4'-bipiperidinyl-1-yl)-1-(4-methyl-2-oxo-2,3-dihydro-benzoxazol-6-ylmethyl)-2-oxo-ethyl 4-(2-oxo-1,4-dihydro-2H-quinazolin-3-yl)-piperidine-1-carboxylate |
| (235) | (R)-1-(7-methyl-1H-benzotriazol-5-ylmethyl)-2-[4-(1-methyl-piperidin-4-yl)-piperazin-1-yl]-2-oxo-ethyl 4-(2-oxo-1,4-dihydro-2H-quinazolin-3-yl)-piperidine-1-carboxylate |

-continued

| Structure | Name |
|---|---|
| (236) 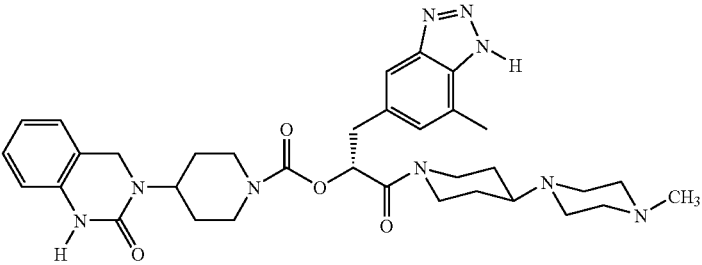 | (R)-1-(7-methyl-1H-benzotriazol-5-ylmethyl)-2-[4-(4-methyl-piperazin-1-yl)-piperidin-1-yl]-2-oxo-ethyl 4-(2-oxo-1,4-dihydro-2H-quinazolin-3-yl)-piperidine-1-carboxylate |
| (237) 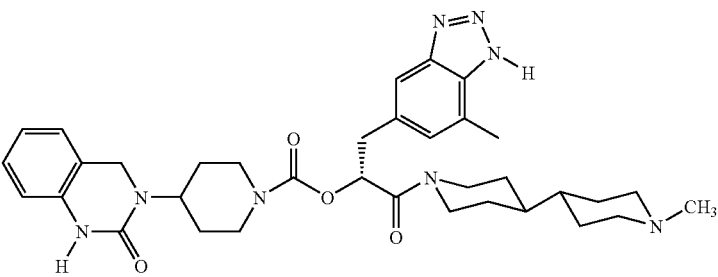 | (R)-1-(7-methyl-1H-benzotriazol-5-ylmethyl)-2-(1'-methyl-[4,4']bipiperidinyl-1-yl)-2-oxo-ethyl 4-(2-oxo-1,4-dihydro-2H-quinazolin-3-yl)-piperidine-1-carboxylate |
| (238) 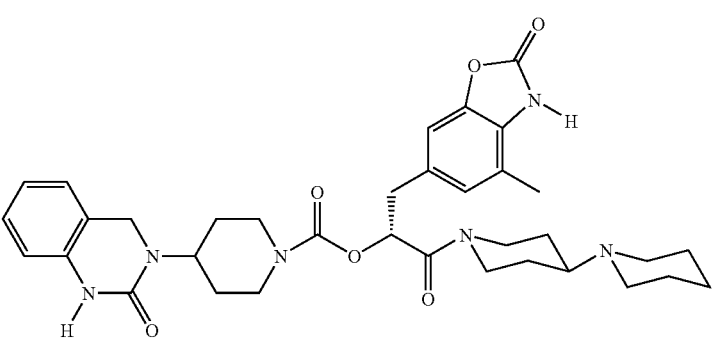 | (R)-2-1,4'-bipiperidinyl-1'-yl-1-(4-methyl-2-oxo-2,3-dihydro-benzoxazol-6-ylmethyl)-2-oxo-ethyl 4-(2-oxo-1,4-dihydro-2H-quinazolin-3-yl)-piperidine-1-carboxylate |
| (239) 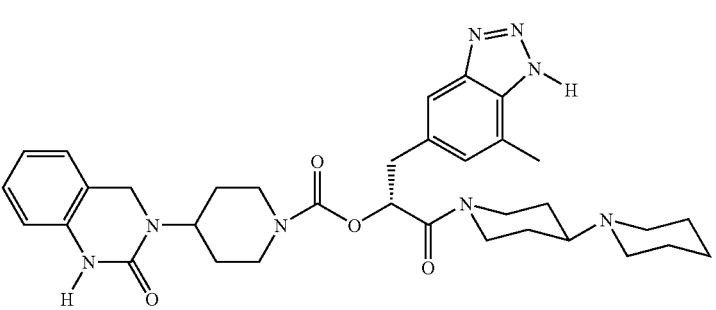 | (R)-2-[1,4']bipiperidinyl-1'-yl-1-(7-methyl-1H-benzotriazol-5-ylmethyl)-2-oxo-ethyl 4-(2-oxo-1,4-dihydro-2H-quinazolin-3-yl)-piperidine-1-carboxylate |
| (240) 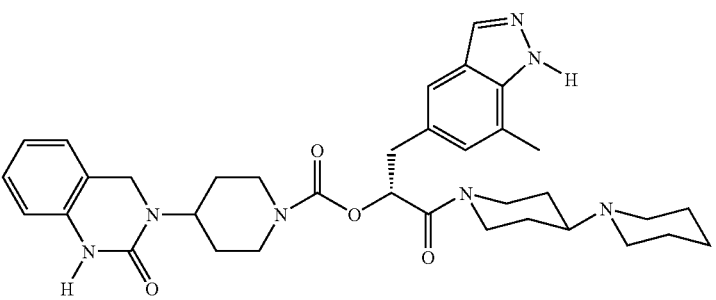 | (R)-2-[1,4']bipiperidinyl-1'-yl-1-(7-methyl-1H-indazol-5-ylmethyl)-2-oxo-ethyl 4-(2-oxo-1,4-dihydro-2H-quinazolin-3-yl)-piperidine-1-carboxylate |

-continued

| Structure | Name |
|---|---|
| (241) 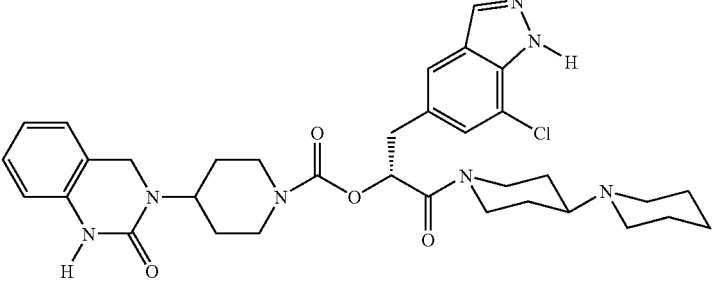 | (R)-2-[1,4']bipiperidinyl-1'-yl-1-(7-chloro-1H-indazol-5-ylmethyl)-2-oxo-ethyl 4-(2-oxo-1,4-dihydro-2H-quinazolin-3-yl)-piperidine-1-carboxylate |
| (242) 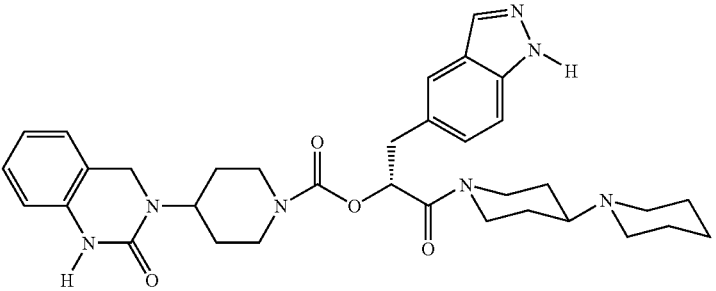 | (R)-2-[1,4']bipiperidinyl-1'-yl-1-(1H-indazol-5-ylmethyl)-2-oxo-ethyl 4-(2-oxo-1,4-dihydro-2H-quinazolin-3-yl)-piperidine-1-carboxylate |
| (243) 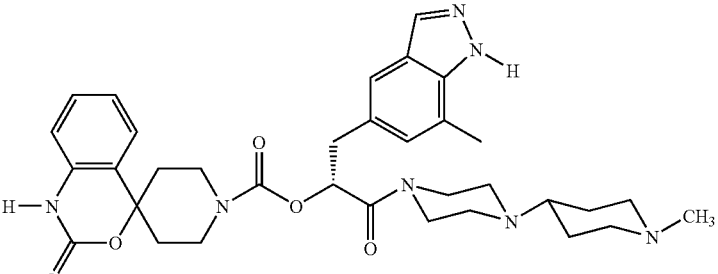 | (R)-1-(7-methyl-1H-indazol-5-ylmethyl)-2-[4-(1-methyl-piperidin-4-yl)-piperazin-1-yl]-2-oxo-ethyl 1',2'-dihydro-2'-oxospiro-4H-3',1-benzoxazin '-4,4 '-piperidine-1-carboxylate |
| (244) 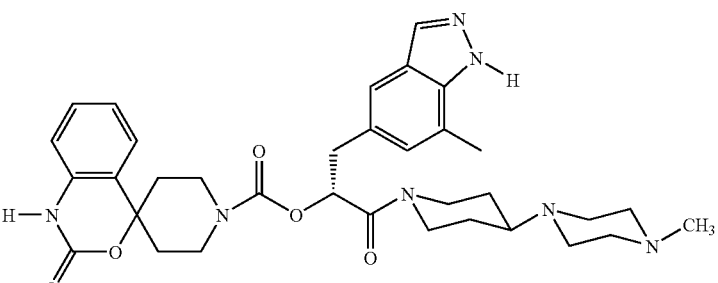 | (R)-1-(7-methyl-1H-indazol-5-ylmethyl)-2-[4-(4-methyl-piperazin-1-yl)-piperidin-1-yl]-2-oxo-ethyl 1',2'-dihydro-2'-oxospiro-4H-3',1-benzoxazin '-4,4 '-piperidine-1-carboxylate |
| (245) 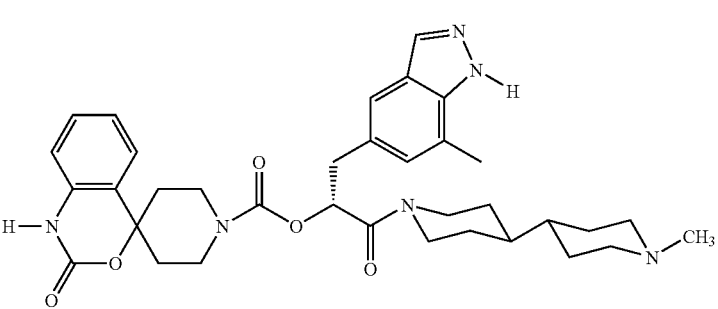 | (R)-2-(1'-methyl-4,4'-bipiperidinyl-1-yl)-1-(7-methyl-1H-indazol-5-ylmethyl)-2-oxo-ethyl 1',2'-dihydro-2-oxospiro-4H-3',1-benzoxazin '-4,4 '-piperidine-1-carboxylate |

-continued

| | Structure | Name |
|---|---|---|
| (246) | 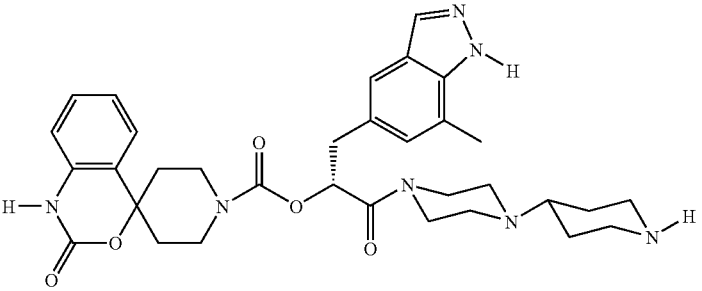 | (R)-1-(7-methyl-1H-indazol-5-ylmethyl)-2-oxo-2-(4-piperidin-4-yl-piperazin-1-yl)-ethyl 1',2'-dihydro-2'-oxospiro-4H-3',1-benzoxazin'-4,4'-piperidine-1-carboxylate |
| (247) | 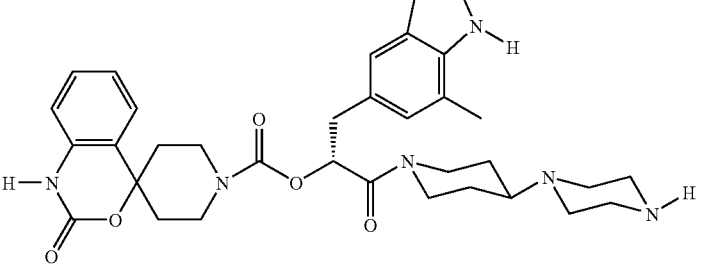 | (R)-1-(7-methyl-1H-indazol-5-ylmethyl)-2-oxo-2-(4-piperazin-1-yl-piperidin-1-yl)-ethyl 1',2'-dihydro-2 -oxospiro-4H-3',1-benzoxazin '-4,4 '-piperidine-1-carboxylate |
| (248) | 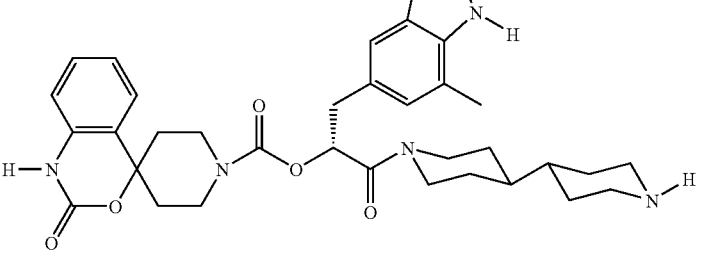 | (R)-2-4,4'-bipiperidinyl-1-yl-1-(7-methyl-1H-indazol-5-ylmethyl)-2-oxo-ethyl 1',2'-dihydro-2 '-oxospiro-4H-3 ',1-benzoxazin'-4,4'-piperidine-1-carboxylate |
| (249) | 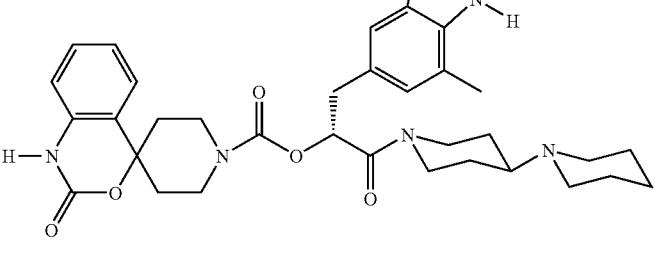 | (R)-2-1,4'-bipiperidinyl-1'-yl-1-(7-methyl-1H-indazol-5-ylmethyl)-2-oxo-ethyl 1',2'-dihydro-2 '-oxospiro-4H-3, 1-benzoxazin'-4,4'-piperidine-1-carboxylate |
| (250) | 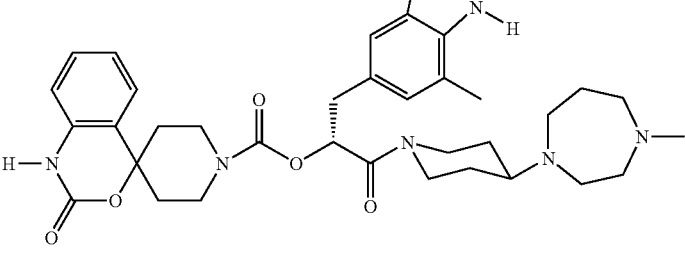 | (R)-1-(7-methyl-1H-indazol-5-ylmethyl)-2-[4-(4-methyl-perhydro-1,4-diazepin-1-yl)-piperidin-1-yl]-2-oxo-ethyl 1',Z-dihydro-2'-oxospiro-4H-3',1-benzoxazin-4,4'-piperidine-1-carboxylate |

-continued

| Structure | Name |
|---|---|
| (251) 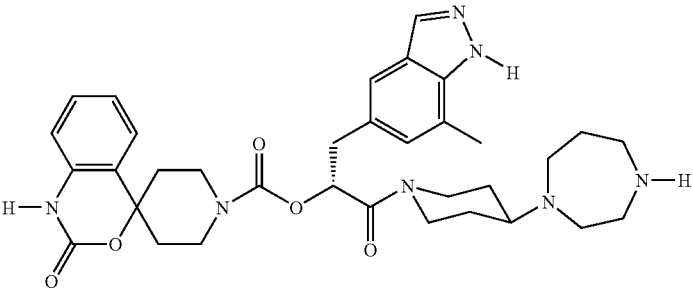 | (R)-1-(7-methyl-1H-indazol-5-ylmethyl)-2-oxo-2-(4-perhydro-1,4-diazepin-1-yl-piperidin-1-yl)-ethyl 1,2'-dihydro-2'-oxospiro-4H-3',1-benzoxazin'-4,4-piperidine-1-carboxylate |
| (252) 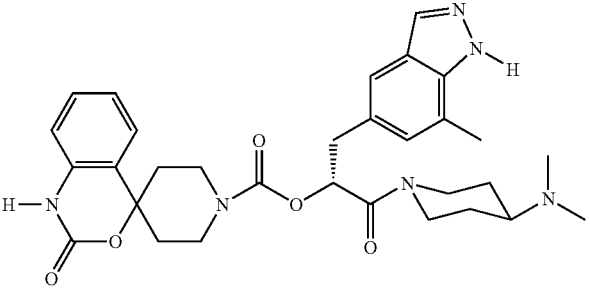 | (R)-2-(4-dimethylamino-piperidin-1-yl)-1-(7-methyl-1H-indazol-5-ylmethyl)-2-oxo-ethyl 1',Z-dihydro-2'-oxospiro-4H-3',1-benzoxazin'-4,4'-piperidine-1-carboxylate |
| (253) 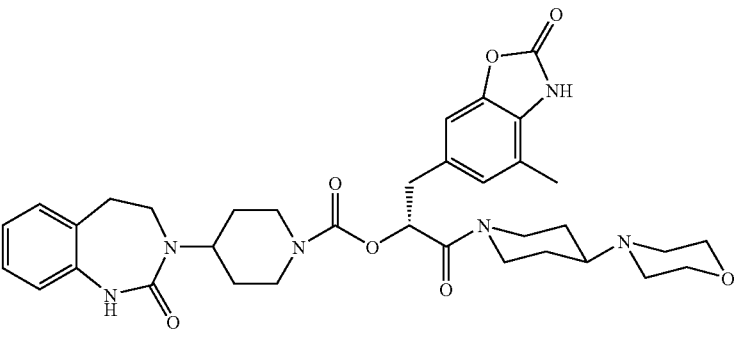 | 4-(2-oxo-1,2,4,5-tetrahydro-1,3-benzodi-(R)-1-(4-methyl-2-oxo-2,3-dihydro-benzoxazol-6-ylmethyl)-2-(4-morpholin-4-yl-piperidin-1-yl)-2-oxo-ethyl azepin-3-yl)-piperidine-1-carboxylate |
| (254) 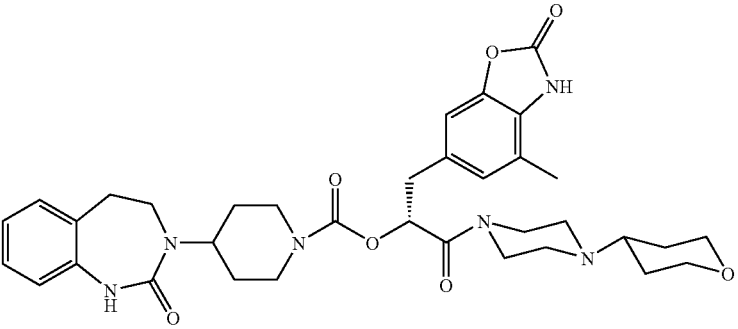 | (R)-1-(4-methyl-2-oxo-2,3-dihydro-benzoxazol-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |

-continued

| Structure | Name |
|---|---|
| (255) 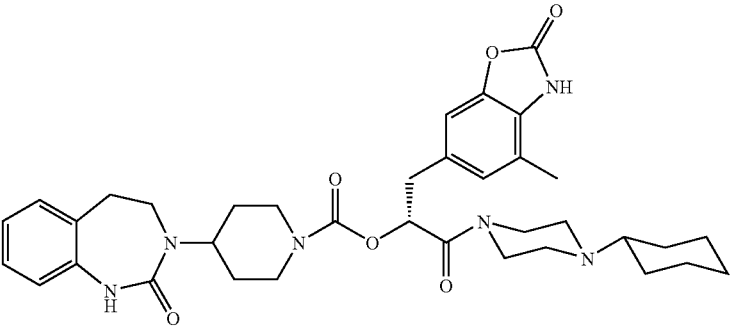 | (R)-2-(4-cyclohexyl-piperazin-1-yl)-1-(4-methyl-2-oxo-2,3-dihydro-benzoxazol-6-yl-methyl)-2-oxo-ethyl 4-(2-oxo-1,2,4,5-tetrahydro-1,3-benzodiazepin-3-yl)-piperidine-1-carboxylate |
| (256) 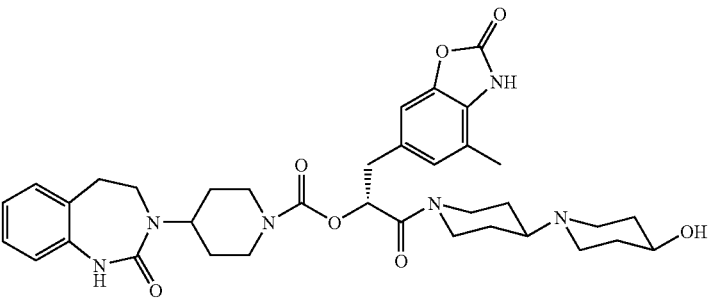 | (R)-2-(4-hydroxy-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (257) 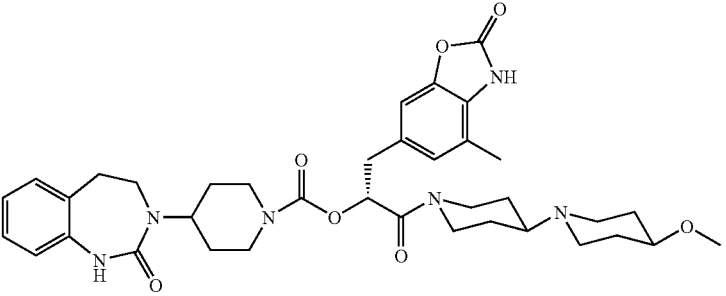 | (R)-2-(4-methoxy-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (258) 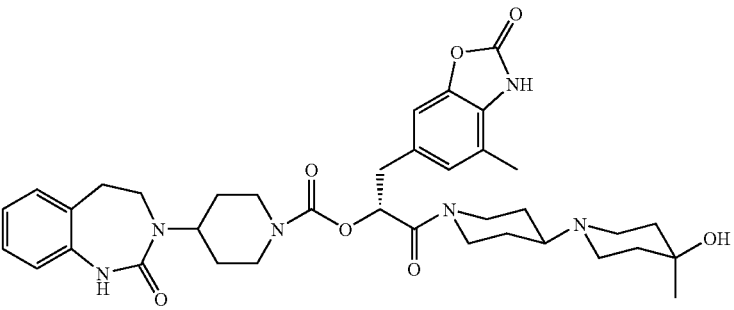 | (R)-2-(4-hydroxy-4-methyl-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (259) 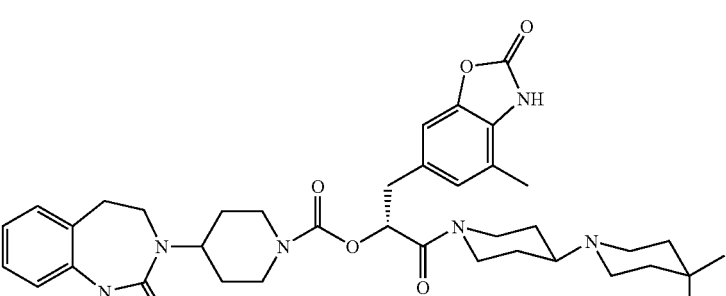 | (R)-2-(4,4-dimethyl-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (260) | 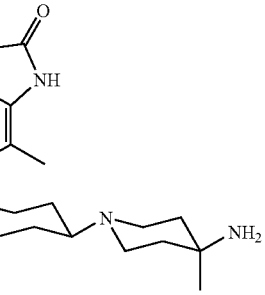 | (R)-2-(4-amino-4-methyl-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (261) | 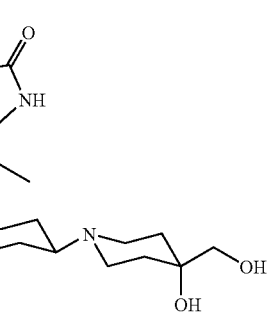 | (R)-2-(4-hydroxy-4-hydroxymethyl-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (262) | 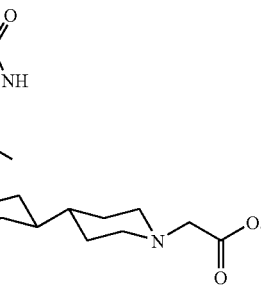 | (R)-2-(1'-ethoxycarbonylmethyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (263) | 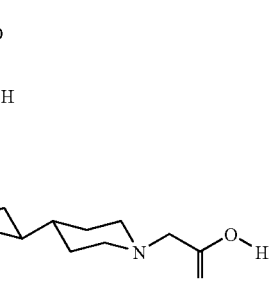 | (R)-2-(1'-carboxymethyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (264) | 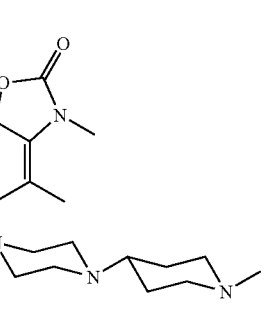 | (R)-1-(3,4-dimethyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| Structure | Name |
|---|---|
| (265) 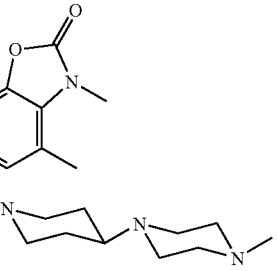 | (R)-1-(3,4-dimethyl-2-oxo-2,3-dihydro-benzoxazol-6-ylmethyl)-2-[4-(4-methyl-piperazin-1-yl)-piperidin-1-yl]-2-oxo-ethyl 4-(2-oxo-1,2,4,5-tetrahydro-1,3-benzo-diazepin-3-yl)-piperidine-1-carboxylate |
| (266) 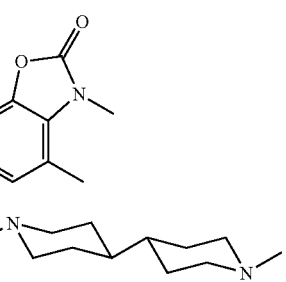 | (R)-1-(3,4-dimethyl-2-oxo-2,3-dihydro-benzoxazol-6-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (267) 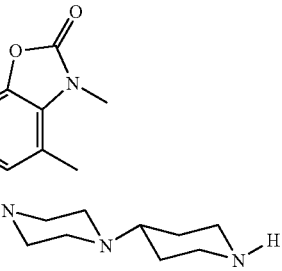 | (R)-1-(3,4-dimethyl-2-oxo-2,3-dihydro-benzoxazol-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (268) 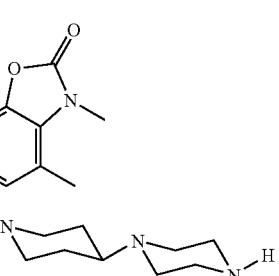 | (R)-1-(3,4-dimethyl-2-oxo-2,3-dihydro-benzoxazol-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (269) 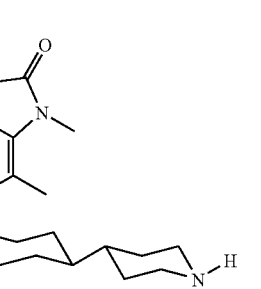 | (R)-2-4,4'-bipiperidinyl-1-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (270) 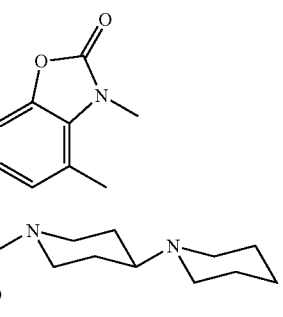 | (R)-2-1,4'-bipiperidinyl-1'-yl-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (271) 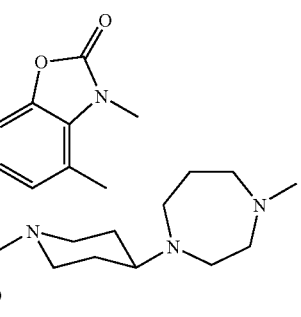 | (R)-1-(3,4-dimethyl-2-oxo-2,3-dihydro-benzoxazol-6-ylmethyl)-2-[4-(4-methyl-per-hydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate |
| (272) 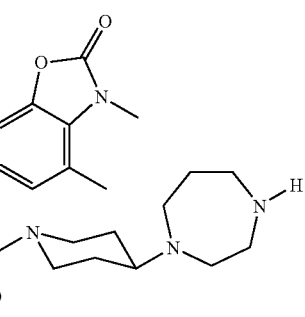 | (R)-1-(3,4-dimethyl-2-oxo-2,3-dihydro-benzoxazol-6-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate |
| (273) 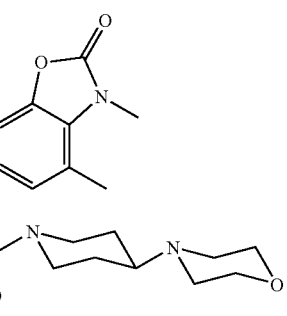 | (R)-1-(3,4-dimethyl-2-oxo-2,3-dihydro-benzoxazol-6-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (274) 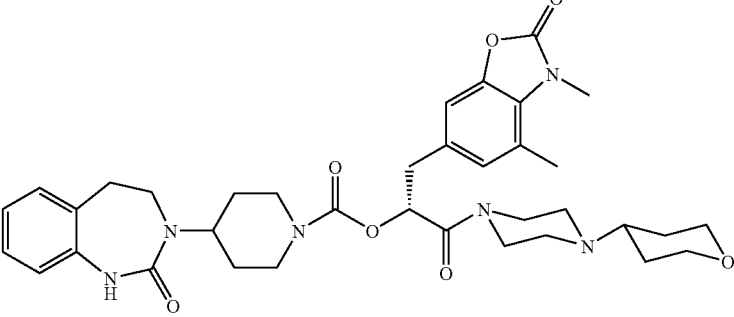 | (R)-1-(3,4-dimethyl-2-oxo-2,3-dihydro-benzoxazol-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (275) 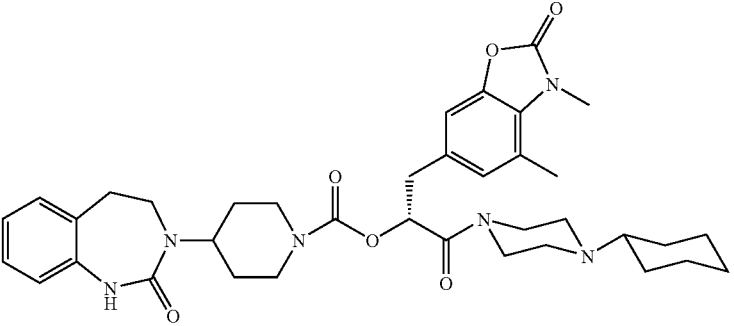 | (R)-2-(4-cyclohexyl-piperazin-1-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (276) 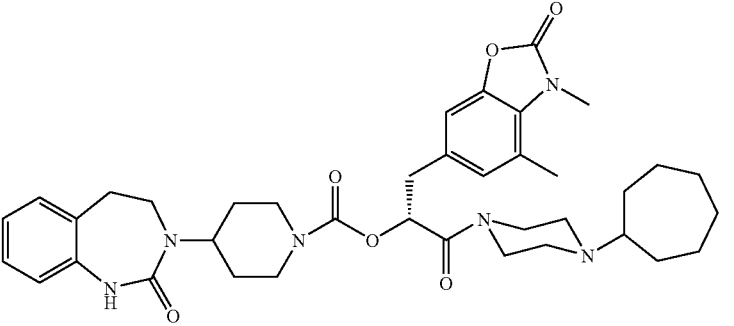 | (R)-2-(4-cycloheptyl-piperazin-1-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (277) 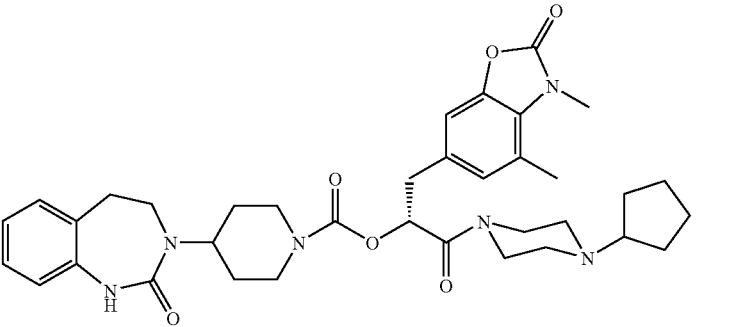 | (R)-2-(4-cyclopentyl-piperazin-1-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (278) 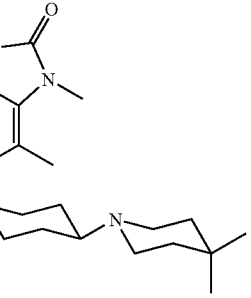 | (R)-2-(4,4-dimethyl-1,4'-bipiperidinyl-1'-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (279) 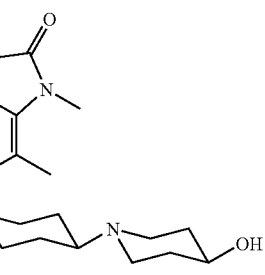 | (R)-1-(3,4-dimethyl-2-oxo-2,3-dihydro-benzoxazol-6-ylmethyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (280) 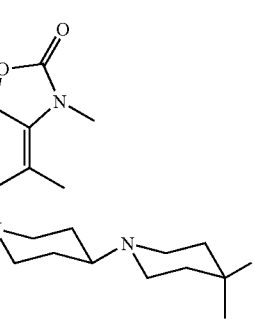 | (R)-1-(3,4-dimethyl-2-oxo-2,3-dihydro-benzoxazol-6-ylmethyl)-2-(4-hydroxy-4-methyl-1,4'-bipiperidinyl-1'-yl)-2-oxo-ethyl 4-(2-oxo-1,2,4,5-tetrahydrD-i,3-benzo-diazepin-3-yl)-piperidine-1-carboxylate |
| (281) 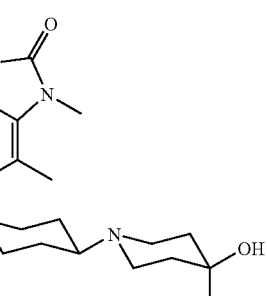 | (R)-1-(3,4-dimethyl-2-oxo-2,3-dihydro-benzoxazol-6-ylmethyl)-2-(4-ethyl-4-hydroxy-1,4'-bipiperidinyl-I '-yl)-2-oxo-ethyl 4-(2-oxo-1,2,4,5-tetrahydro-1,3-benzo-diazepin-3-yl)-piperidine-1-carboxytate |
| (282) 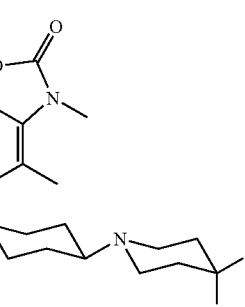 | (R)-1-(3,4-dimethyl-2-oxo-2,3-dihydro-benzoxazol-6-ylmethyl)-2-(4-hydroxy-4-trifluoromethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (283) | 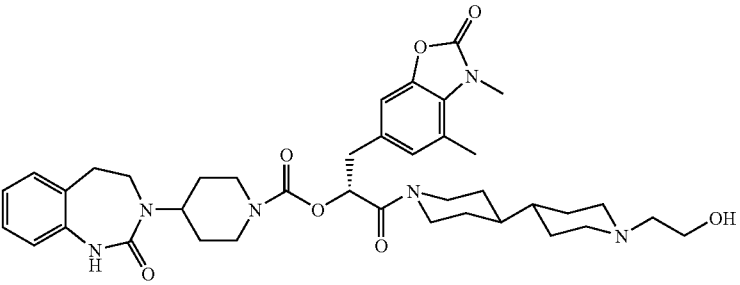 | (R)-1-(3,4-dimethyl-2-oxo-2,3-dihydro-benzoxazol-6-ylmethyl)-2-[1'-(2-hydroxy-ethyl)-4,4'-bipiperidinyl-1-yl]-2-oxo-ethyl 4-(2-oxo-1,2,4,5-tetrahydro-1,3-benzo-diazepin-3-yl)-piperidine-1-carboxylate |
| (284) | 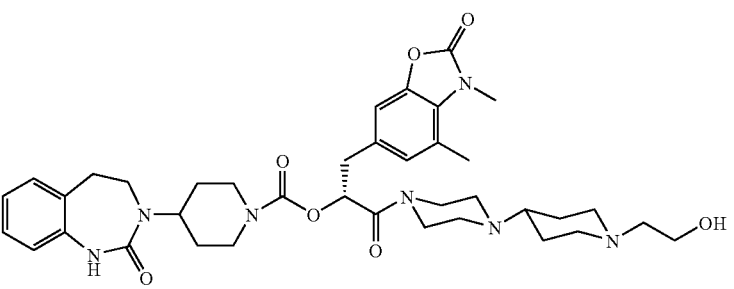 | (R)-1-(3,4-dimethyl-2-oxo-2,3-dihydro-benzoxazol-6-ylmethyl)-2-{4-[1-(2-hydroxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (285) | 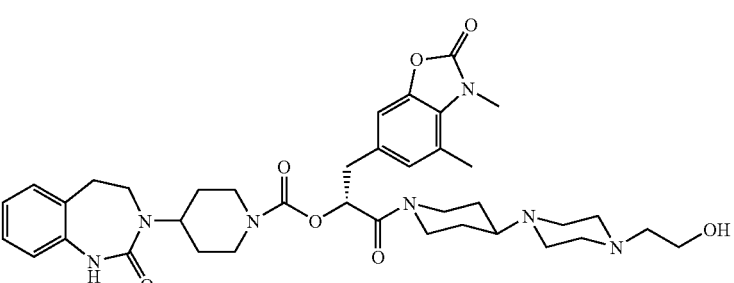 | (R)-1-(3,4-dimethyl-2-oxo-2,3-dihydro-benzoxazol-6-ylmethyl)-2-{4-[4-(2-hydroxy-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (286) | 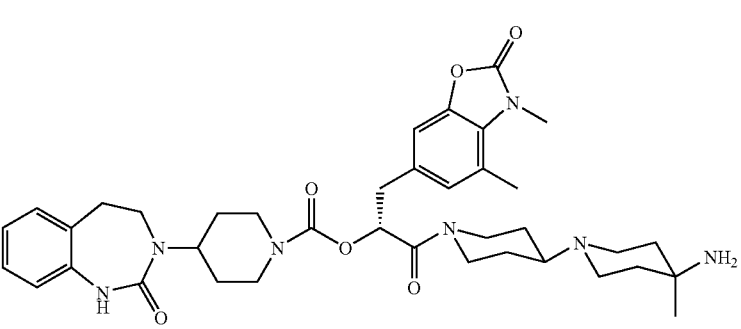 | (R)-2-(4-amino-4-methyl-1,4'-bipiperidinyl-1'-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (287) | 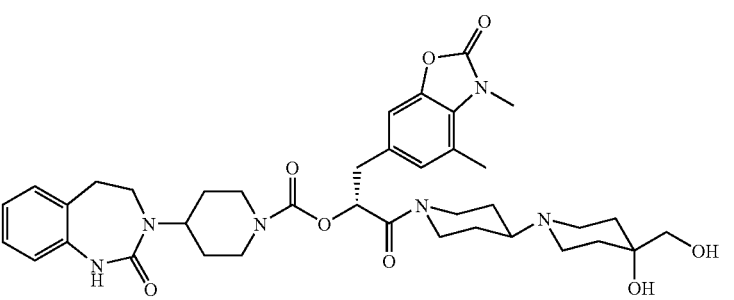 | (R)-1-(3,4-dimethyl-2-oxo-2,3-dihydro-benzoxazol-6-ylmethyl)-2-(4-hydroxy-4-hy-droxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (288) 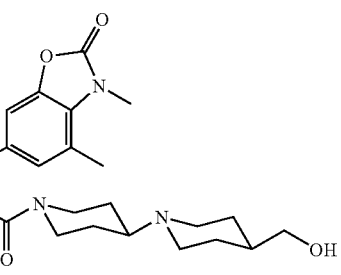 | (R)-1-(3,4-dimethyl-2-oxo-2,3-dihydro-benzoxazol-6-ylmethyl)-2-(4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (289) 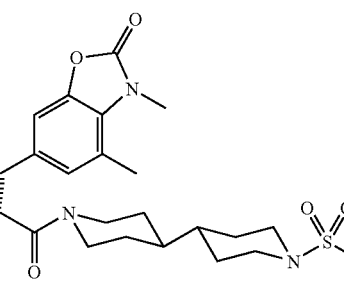 | (R)-1-(3,4-dimethyl-2-oxo-2,3-dihydro-benzoxazol-6-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (290) 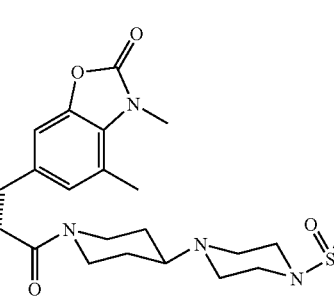 | (R)-1-(3,4-dimethyl-2-oxo-2,3-dihydro-benzoxazol-6-ylmethyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (291) 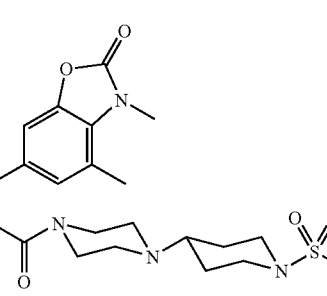 | (R)-1-(3,4-dimethyl-2-oxo-2,3-dihydro-benzoxazol-6-ylmethyl)-2-[4-(1-methanesulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (292) 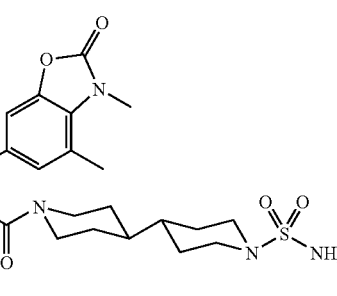 | (R)-1-(3,4-dimethyl-2-oxo-2,3-dihydro-benzoxazol-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |

| Structure | Name |
|---|---|
| (293) 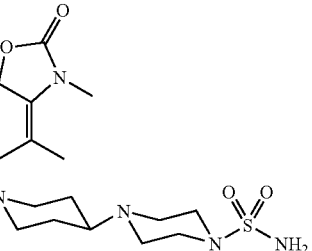 | (R)-1-(3,4-dimethyl-2-oxo-2,3-dihydro-benzoxazol-6-ylmethyl)-2-oxo-2-[4-(4-sulphamoyl-piperazin-1-yl)-piperidin-1-yl]-ethyl 4-(2-oxo-1,2,4,5-tetrahydro-1,3-benzodiazepin-3-yl)-piperidine-1-carboxylate |
| (294) 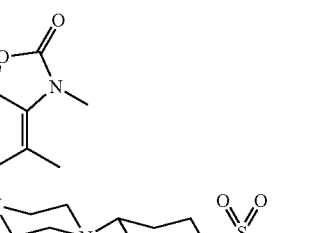 | (R)-1-(3,4-dimethyl-2-oxo-2,3-dihydro-benzoxazol-6-ylmethyl)-2-oxo-2-[4-(1-sulphamoyl-piperidin-4-yl)-piperazin-1-yl]-ethyl 4-(2-oxo-1,2,4,5-tetrahydro-1,3-benzodiazepin-3-yl)-piperidine-1-carboxylate |
| (295) 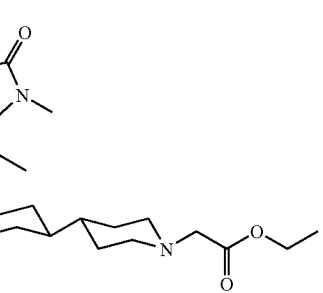 | (R)-1-(3,4-dimethyl-2-oxo-2,3-dihydro-benzoxazol-6-ylmethyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (296) 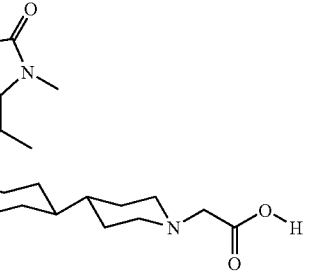 | (R)-2-(1'-carboxymethyl-4,4'-bipiperidinyl-1-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (297) 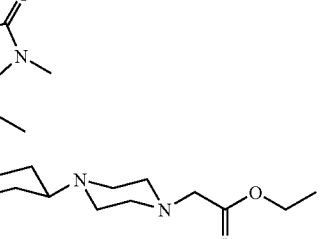 | (R)-1-(3,4-dimethyl-2-oxo-2,3-dihydro-benzoxazol-6-ylmethyl)-2-[4-(4-ethoxycarbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| Structure | Name |
|---|---|
| (298) 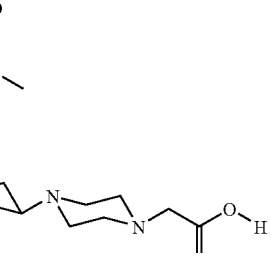 | (R)-2-[4-(4-carboxymethyl-piperazin-1-yl)-piperidin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (299) 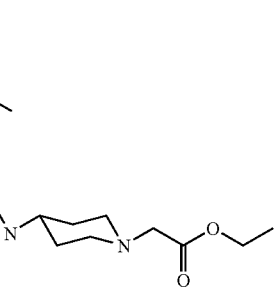 | (R)-1-(3,4-dimethyl-2-oxo-2,3-dihydro-benzoxazol-6-ylmethyl)-2-[4-(1-ethoxycarbonylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (300) 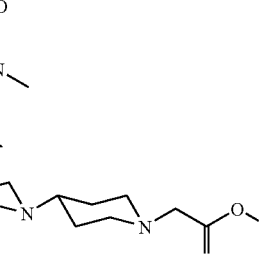 | (R)-2-[4-(1-carboxymethyl-piperidin-4-yl)-piperazin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (301) 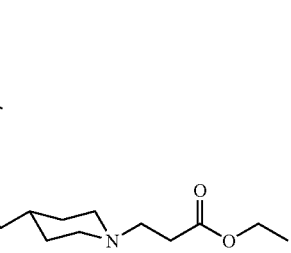 | (R)-1-(3,4-dimethyl-2-oxo-2,3-dihydro-benzoxazol-6-ylmethyl)-2-[1'-(2-ethoxycarbonyl-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (302) 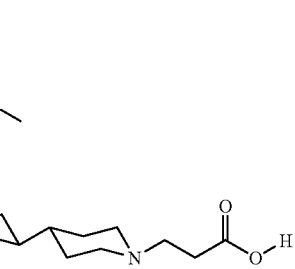 | (R)-2-[1'-(2-carboxy-ethyl)-4,4'-bipiperidinyl-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (303) | | (R)-1-(3,4-dimethyl-2-oxo-2,3-dihydro-benzoxazol-6-ylmethyl)-2-{4-[1-(2-ethoxycarbonyl-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (304) | | (R)-2-{4-[1-(2-carboxy-ethyl)-piperidin-4-yl]-piperazin-1-yl}-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (305) | | (R)-1-(3,4-dimethyl-2-oxo-2,3-dihydro-benzoxazol-6-ylmethyl)-2-{4-[4-(2-ethoxycarbonyl-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (306) | | (R)-2-{4-[4-(2-carboxy-ethyl)-piperazin-1-yl]-piperidin-1-yl}-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (307) | | (R)-1-(3,4-dimethyl-2-oxo-2,3-dihydro-benzoxazol-6-ylmethyl)-2-[1'-(3-ethoxycarbonyl-propionyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |

| Structure | Name |
|---|---|
| (308) 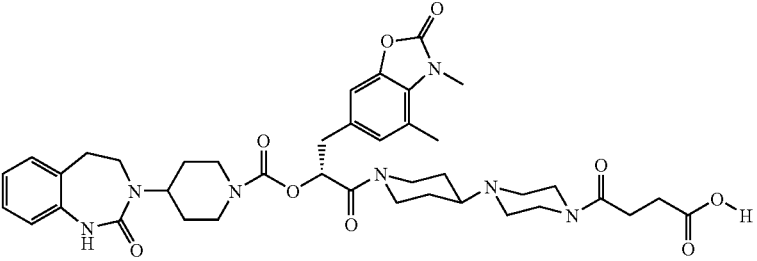 | (R)-2-[1'-(3-carboxy-propionyl)-4,4'-bipiperidinyl-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (309) 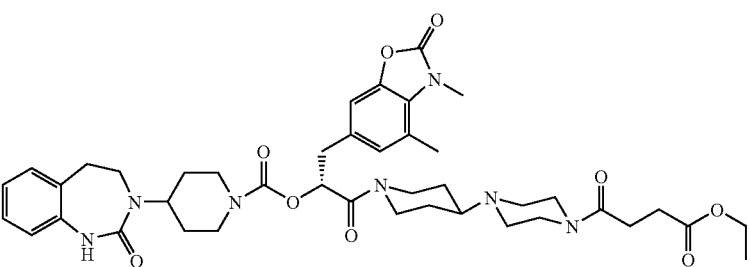 | (R)-1-(3,4-dimethyl-2-oxo-2,3-dihydro-benzoxazol-6-ylmethyl)-2-{4-[4-(3-ethoxycarbonyl-propionyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate |
| (310) 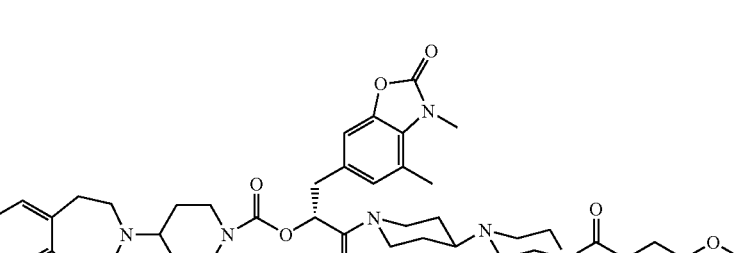 | (R)-2-{4-[4-(3-carboxy-propionyl)-piperazin-1-yl]-piperidin-1-yl}-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (311) 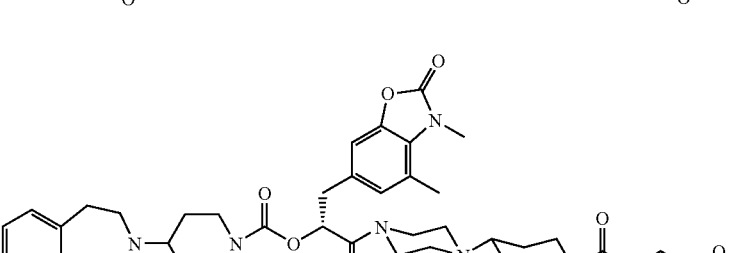 | (R)-1-(3,4-dimethyl-2-oxo-2,3-dihydro-benzoxazol-6-ylmethyl)-2-{4-[1-(3-ethoxycarbonyl-propionyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate |
| (312) 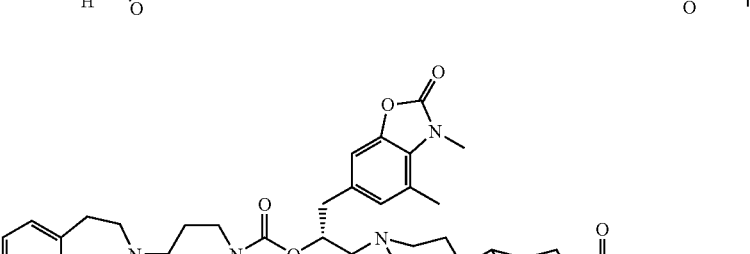 | (R)-2-{4-[1-(3-carboxy-propionyl)-piperidin-4-yl]-piperazin-1-yl}-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (313) | (R)-1-(3,4-dimethyl-2-oxo-2,3-dihydro-benzoxazol-6-ylmethyl)-2-(1'-hydroxycarbamoylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (314) | (R)-1-(3,4-dimethyl-2-oxo-2,3-dihydro-benzoxazol-6-ylmethyl)-2-{1'-[(hydroxy-methyl-carbamoyl)-methyl]-4,4'-bipiperidinyl-1-yl}-2-oxo-ethyl 4-(2-oxo-1,2,4,5-tetrahydro-1,3-benzodiazepin-3-yl)-piperidine-1-carboxylate |
| (315) | (R)-1-(3,4-dimethyl-2-oxo-2,3-dihydro-benzoxazol-6-ylmethyl)-2-[1'-(methoxycarbamoyl-methyl)-4,4'-bipiperidinyl-1-yl]-2-oxo-ethyl 4-(2-oxo-1,2,4,5-tetrahydro-1,3-benzodiazepin-3-yl)-piperidine-1-carboxylate |
| (316) | (R)-1-(8-methyl-2-oxo-1,2-dihydro-quinolin-6-ylmethyl)-2-[4-(4-methyl-piperazin-1-yl)-piperidin-1-yl]-2-oxo-ethyl 4-(2-oxo-1,2,4,5-tetrahydro-1,3-benzo-diazepin-3-yl)-piperidine-1-carboxylate |
| (317) | (R)-1-(8-methyl-2-oxo-1,2-dihydro-quinolin-6-ylmethyl)-2-[4-(1-methyl-piperidin-4-yl)-piperazin-1-yl]-2-oxo-ethyl 4-(2-oxo-1,2,4,5-tetrahydro-1,3-benzo-diazepin-3-yl)-piperidine-1-carboxylate |

-continued

| Structure | Name |
|---|---|
| (318) 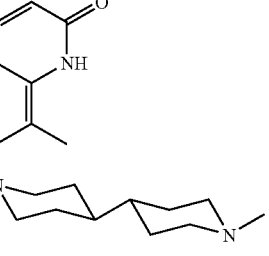 | (R)-2-(1'-methyl-4,4'-bipiperidinyl-1-yl)-1-(8-methyl-2-oxo-1,2-dihydro-quinolin-6-yl-methyl)-2-oxo-ethyl 4-(2-oxo-1,2,4,5-tetrahydro-1,3-benzodiazepin-3-yl)-piperidine-1-carboxylate |
| (319) 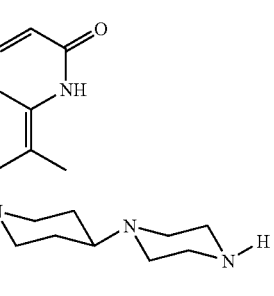 | (R)-1-(8-methyl-2-oxo-1,2-dihydro-quinolin-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (320) 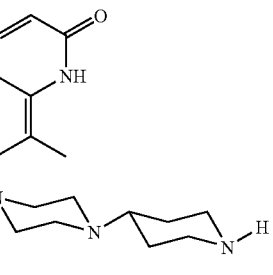 | (R)-1-(8-methyl-2-oxo-1,2-dihydro-quinolin-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (321) 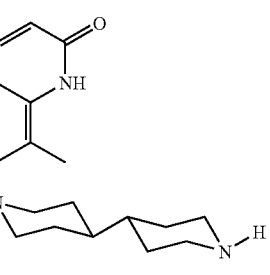 | (R)-2-4,4'-bipiperidinyl-1-yl-1-(8-methyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (322) 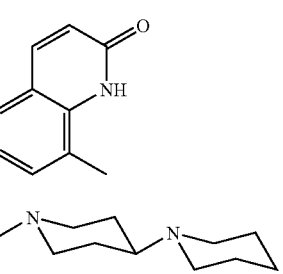 | (R)-2-1,4'-bipiperidinyl-1'-yl-1-(8-methyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (323) 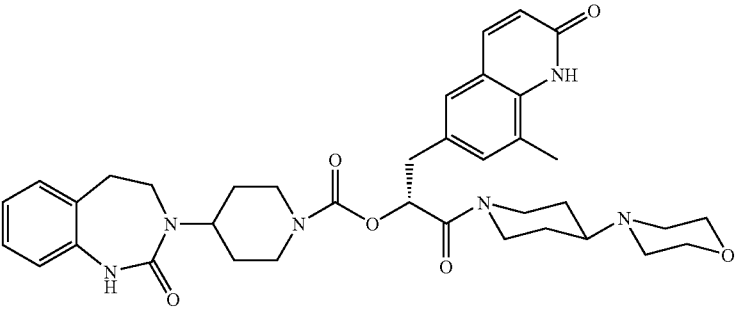 | (R)-1-(8-methyl-2-oxo-1,2-dihydro-quinolin-6-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (324) 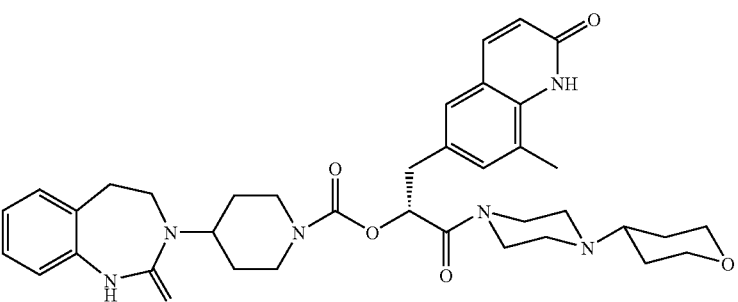 | (R)-1-(8-methyl-2-oxo-1,2-dihydro-quinolin-6-ylmethyl)-2-oxo-2-[4-(tetrahydro-pyran-4-yl)-piperazin-1-yl]-ethyl 4-(2-oxo-1 12,4,5-tetrahydro-1,3-benzodiazepin-3-yl)-piperidine-1-carboxylate |
| (325) 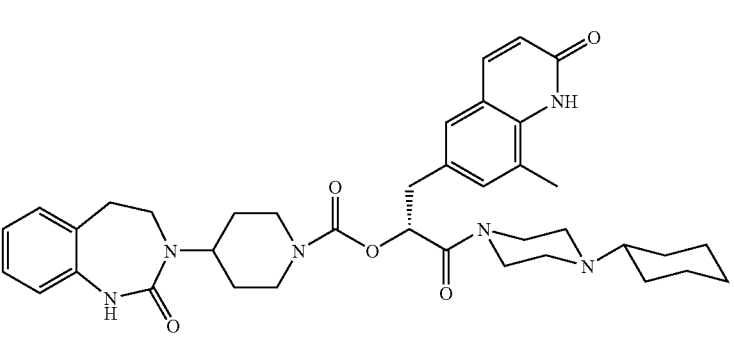 | (R)-2-(4-cyclohexyl-piperazin-1-yl)-1-(8-methyl-2-oxo-1,2-dihydro-quinolin-6-yl-methyl)-2-oxo-ethyl 4-(2-oxo-1,2,4,5-tetrahydro-1,3-benzodiazepin-3-yl)-piperidine-1-carboxylate |
| (326) 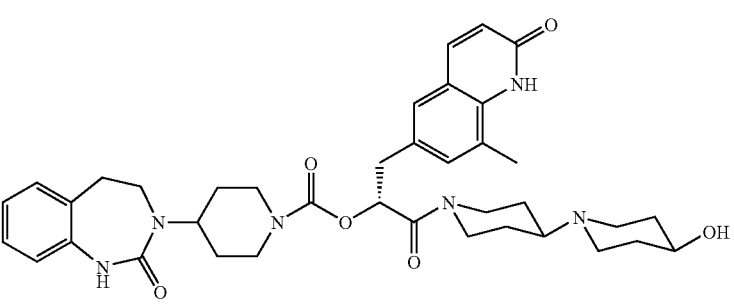 | (R)-2-(4-hydroxy-1,4'-bipiperidinyl-1'-yl)-1-(8-methyl-2-oxo-1,2-dihydro-quinolin-6-yl-methyl)-2-oxo-ethyl 4-(2-oxo-1,2,4,5-tetrahydro-1,3-benzodiazepin-3-yl)-piperidine-1-carboxylate |
| (327) 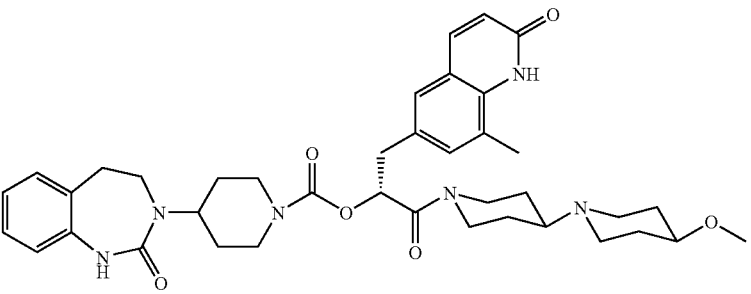 | (R)-2-(4-methoxy-1,4'-bipiperidinyl-1'-yl)-1-(8-methyl-2-oxo-1,2-dihydro-quinolin-6-yl-methyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (328) 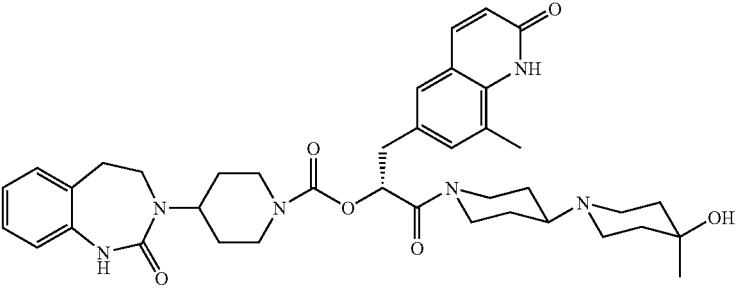 | (R)-2-(4-hydroxy-4-methyl-1,4'-bipiperidinyl-1'-yl)-1-(8-methyl-2-oxo-1,2-dihydro-quinolin-6-ylmethyl)-2-oxo-ethyl 4-(2-oxo-1,2,4,5-tetrahydro-1,3-benzo-diazepin-3-yl)-piperidine-1-carboxylate |
| (329) 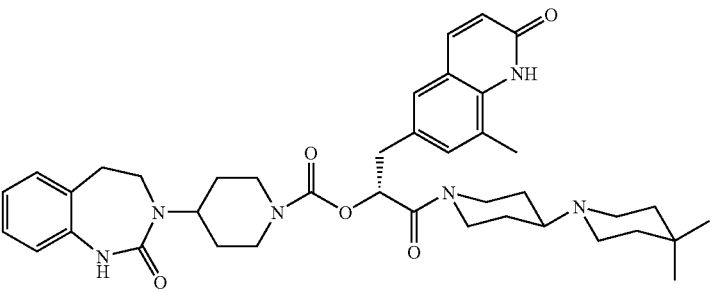 | (R)-2-(4,4-dimethyl-1,4'-bipiperidinyl-1'-yl)-1-(8-methyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (330) 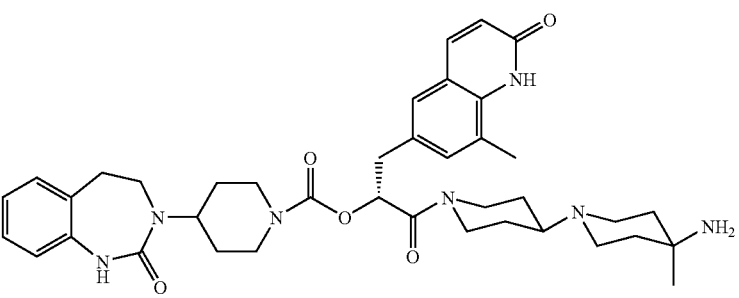 | (R)-2-(4-amino-4-methyl-1,4'-bipiperidinyl-1'-yl)-1-(8-methyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (331) 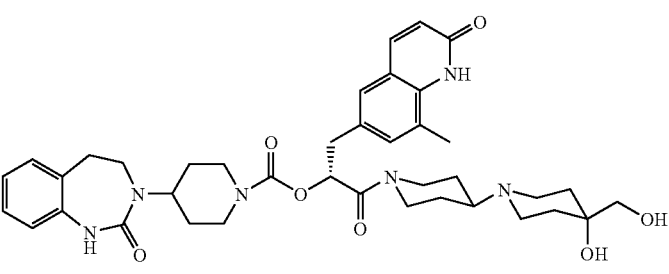 | (R)-2-(4-hydroxy-4-hydroxymethyl-1,4'-bipiperidinyl-1'-yl)-1-(8-methyl-2-oxo-1,2-dihydro-quinolin-6-ylmethyl)-2-oxo-ethyl 4-(2-oxo-1,2,4,5-tetrahydro-1,3-benzo-diazepin-3-yl)-piperidine-1-carboxylate |
| (332) 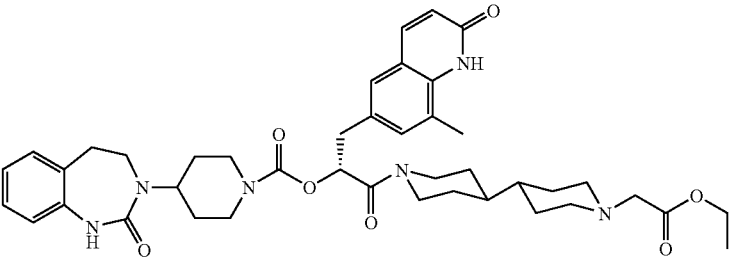 | (R)-2-(1'-ethoxycarbonylmethyl-4,4'-bipiperidinyl-1-yl)-1-(8-methyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |

| Structure | Name |
|---|---|
| (333) | (R)-2-(1'-carboxymethyl-4,4'-bipiperidinyl-1-yl)-1-(8-methyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (334) | (R)-1-(1,8-dimethyl-2-oxo-1,2-dihydro-quinolin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (335) | (R)-1-(1,8-dimethyl-2-oxo-1,2-dihydro-quinolin-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (336) | (R)-1-(1,8-dimethyl-2-oxo-1,2-dihydro-quinolin-6-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (337) | (R)-1-(1,8-dimethyl-2-oxo-1,2-dihydro-quinolin-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (338) 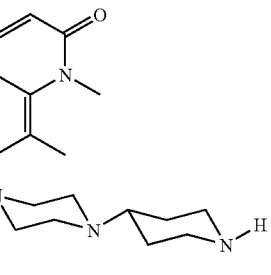 | (R)-1-(1,8-dimethyl-2-oxo-1,2-dihydro-quinolin-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (339) 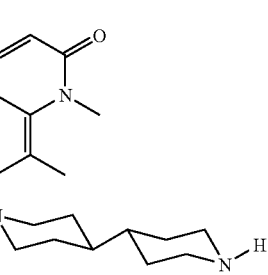 | (R)-2-4,4'-bipiperidinyl-1-yl-1-(1,8-dimethyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (340) 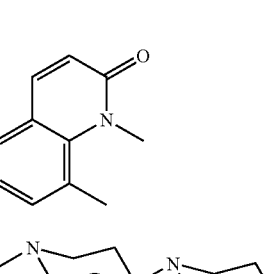 | (R)-2-1,4'-bipiperidinyl-1'-yl-1-(1,8-dimethyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (341) 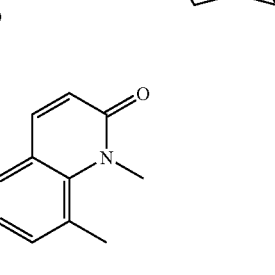 | (R)-1-(1,8-dimethyl-2-oxo-1,2-dihydro-quinolin-6-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (342) 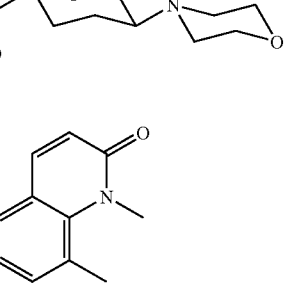 | (R)-1-(1,8-dimethyl-2-oxo-1,2-dihydro-quinolin-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |

-continued

| | Structure | Name |
|---|---|---|
| (343) | 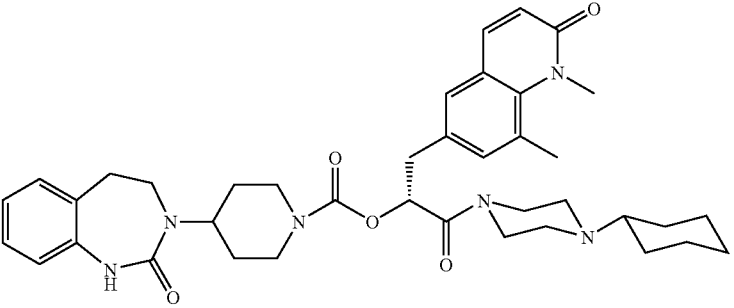 | (R)-2-(4-cyclohexyl-piperazin-1-yl)-1-(1,8-dimethyl-2-oxo-1,2-dihydro-quinolin-6-yl-methyl)-2-oxo-ethyl 4-(2-oxo-1,2,4,5-tetrahydro-1,3-benzodiazepin-3-yl)-piperidine-1-carboxylate |
| (344) | 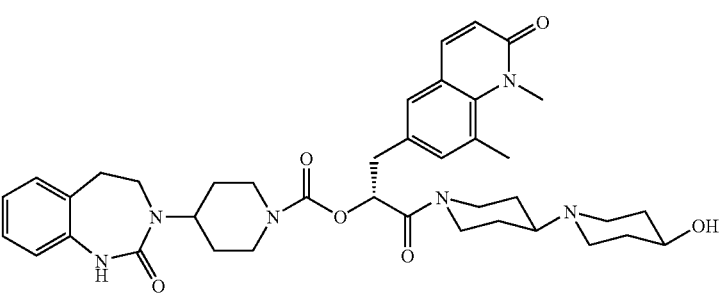 | (R)-1-(1,8-dimethyl-2-oxo-1,2-dihydro-quinolin-6-ylmethyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (345) | 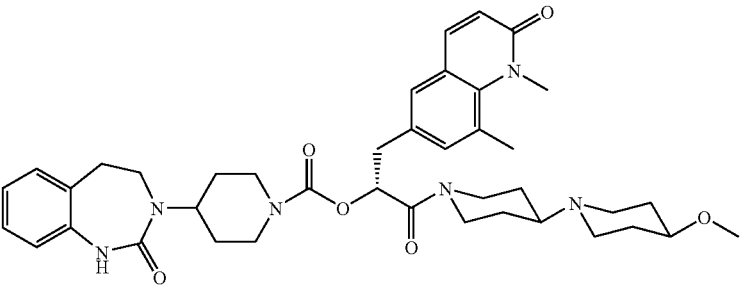 | (R)-1-(1,8-dimethyl-2-oxo-1,2-dihydro-quinolin-6-ylmethyl)-2-(4-methoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (346) | 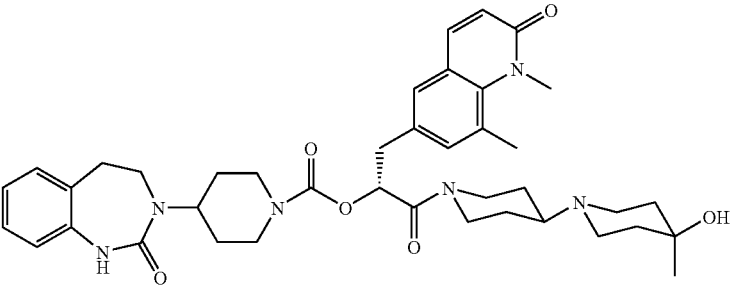 | (R)-1-(1,8-dimethyl-2-oxo-1,2-dihydro-quinolin-6-ylmethyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (347) | 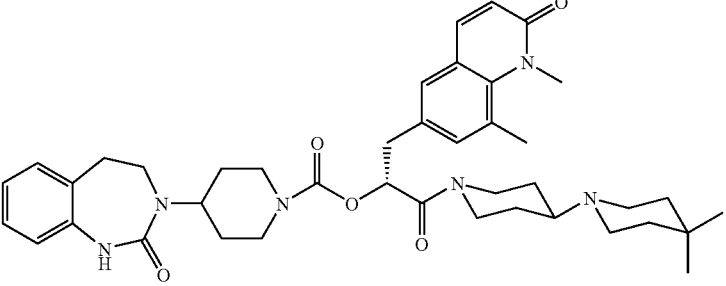 | (R)-2-(4,4-dimethyl-1,4'-bipiperidinyl-1'-yl)-1-(1,8-dimethyl-2-oxo-1,2-dihydro-quinolin-6-ylmethyl)-2-oxo-ethyl 4-(2-oxo-1,2,4,5-tetrahydro-1,3-benzodiazepin-3-yl)-piperiaine-1-carDoxylate |

-continued

| Structure | Name |
|---|---|
| (348) 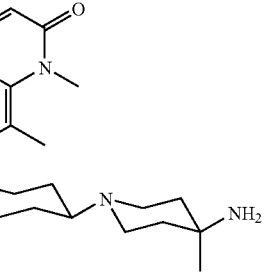 | (R)-2-(4-amino-4-methyl-1,4'-bipiperidinyl-1'-yl)-1-(1,8-dimethyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (349) 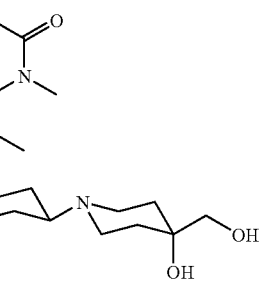 | (R)-1-(1,8-dimethyl-2-oxo-1,2-dihydro-quinolin-6-ylmethyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (350) 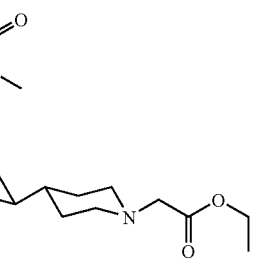 | (R)-1-(1,8-dimethyl-2-oxo-1,2-dihydro-quinolin-6-ylmethyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (351) 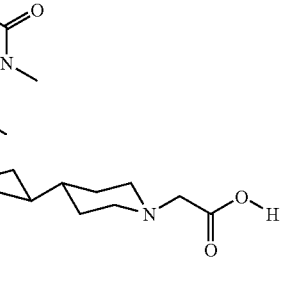 | (R)-2-(1'-carboxymethyl-4,4'-bipiperidinyl-1-yl)-1-(1,8-dimethyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (352) 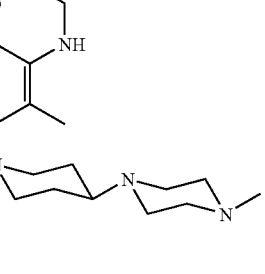 | (R)-1-(5-methyl-3,4-dihydro-2H-1,4-benzoxazin-7-ylmethyl)-2-[4-(4-methyl-piperazin-1-yl)-piperidin-1-yl]-2-oxo-ethyl 4-(2-oxo-1,2,4,5-tetrahydro-1,3-benzo-diazepin-3-yl)-piperidine-1-carboxylate |

| Structure | Name |
|---|---|
| (353) 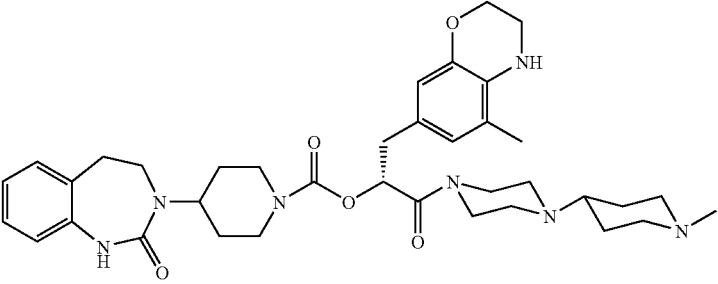 | (R)-1-(5-methyl-3,4-dihydro-2H-1,4-benzoxazin-7-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (354) 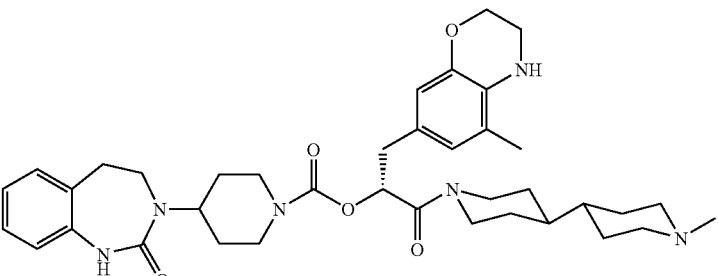 | (R)-2-(1'-methyl-4,4'-bipiperidinyl-1-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (355) 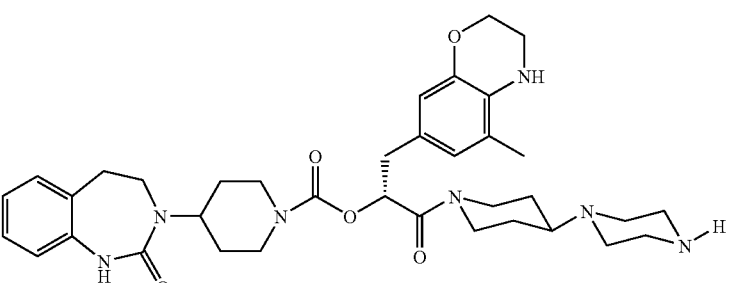 | (R)-1-(5-methyl-3,4-dihydro-2H-1,4-benzoxazin-7-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (356) 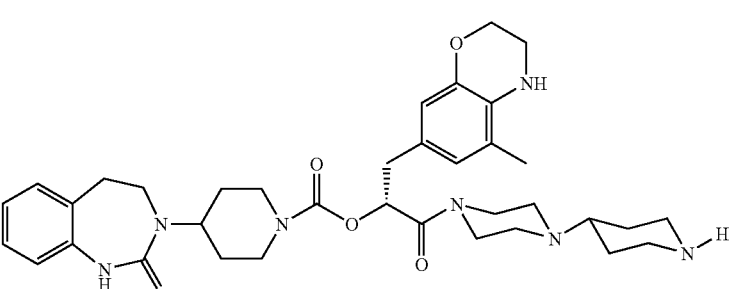 | (R)-1-(5-methyl-3,4-dihydro-2H-1,4-benzoxazin-7-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (357) 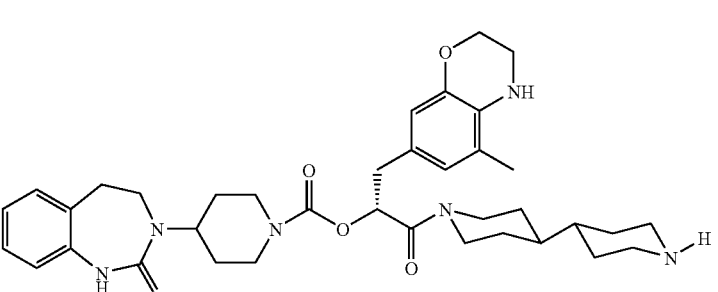 | (R)-2-4,4'-bipiperidinyl-1-yl-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |

| Structure | Name |
|---|---|
| (358) 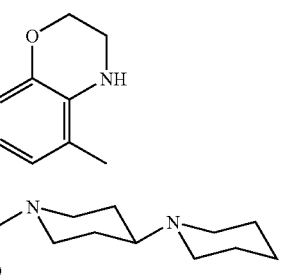 | (R)-2-1,4'-bipiperidinyl-1'-yl-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (359) 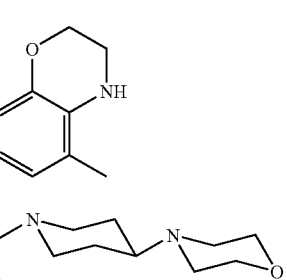 | (R)-1-(5-methyl-3,4-dihydro-2H-1,4-benzoxazin-7-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (360) 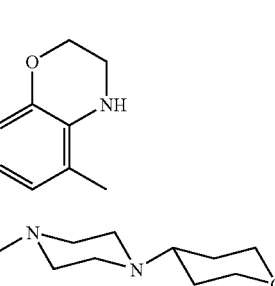 | (R)-1-(5-methyl-3,4-dihydro-2H-1,4-benzoxazin-7-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (361) 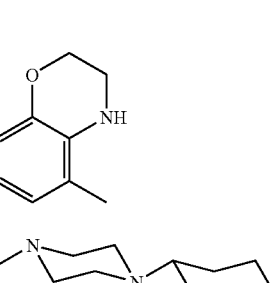 | (R)-2-(4-cyclohexyl-piperazin-1-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (362) 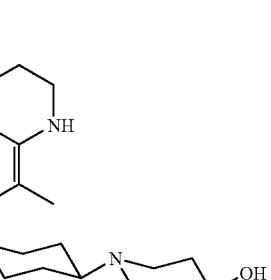 | (R)-2-(4-hydroxy-1,4'-bipiperidinyl-1'-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |

| Structure | Name |
|---|---|
| (363) | (R)-2-(4-methoxy-1,4'-bipiperidinyl-1'-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (364) | (R)-2-(4-hydroxy-4-methyl-1,4'-bipiperidinyl-1'-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (365) | (R)-2-(4,4-dimethyl-1,4'-bipiperidinyl-1'-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (366) | (R)-2-(4-amino-4-methyl-1,4'-bipiperidinyl-1'-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (367) | (R)-2-(4-hydroxy-4-hydroxymethyl-1,4'-bipiperidinyl-1'-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (368) | 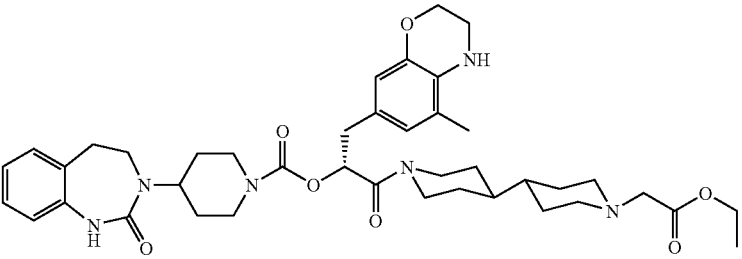 | (R)-2-(1'-ethoxycarbonylmethyl-4,4'-bipiperidinyl-1-yl)-1-(4-ethylamino-3-methoxy-5-methyl-benzyl)-2-oxo-ethyl 4-(2-oxo-1,2,4,5-tetrahydro-1,3-benzo-diazepin-3-yl)-piperidine-1-carboxylate |
| (369) | 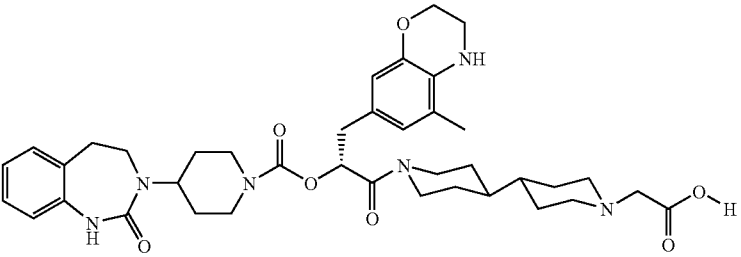 | (R)-2-(1'-carboxymethyl-4,4-bipiperidinyl-1-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (370) | 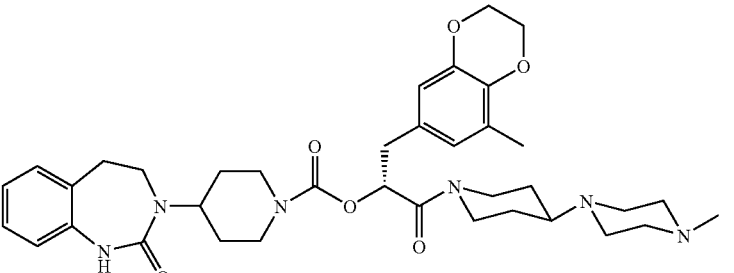 | (R)-1-(8-methyl-2,3-dihydro-1,4-benzodioxin-6-ylmethyl)-2-[4-(4-methyl-piperazin-1-yl)-piperidin-1-yl]-2-oxo-ethyl 4-(2-oxo-1,2,4,5-tetrahydro-1,3-benzo-diazepin-3-yl)-piperidine-1-carboxylate |
| (371) | 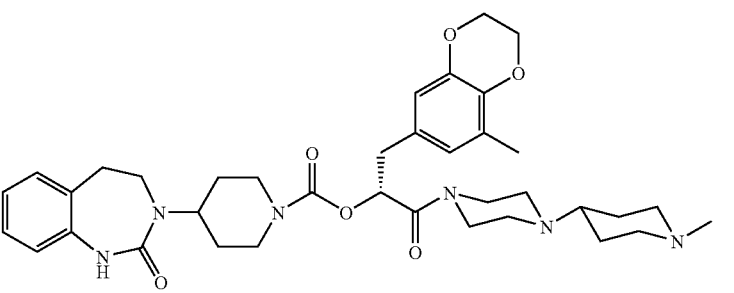 | (R)-1-(8-methyl-2,3-dihydro-1,4-benzodioxin-6-ylmethyl)-2-[4-(1-methyl-piperidin-4-yl)-piperazin-1-yl]-2-oxo-ethyl 4-(2-oxo-1,2,4,5-tetrahydro-1,3-benzo-diazepin-3-yl)-piperidine-1-carboxylate |
| (372) | 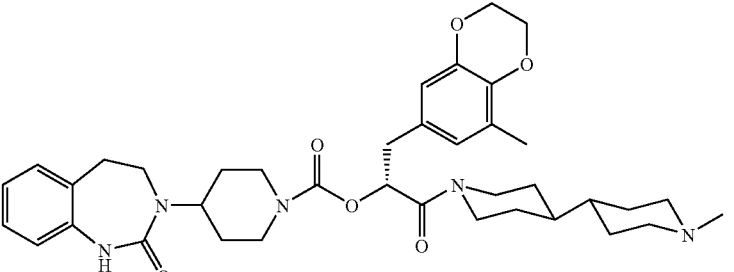 | (R)-2-(1'-methyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (373) 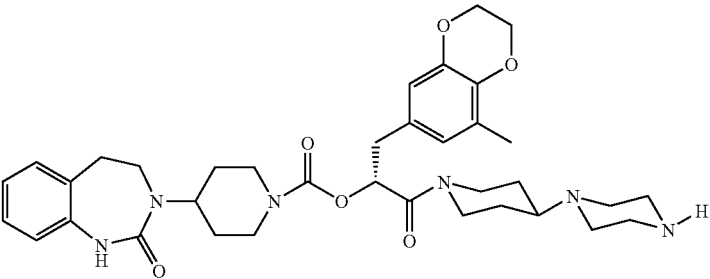 | (R)-1-(8-methyl-2,3-dihydro-1,4-benzodioxin-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (374) 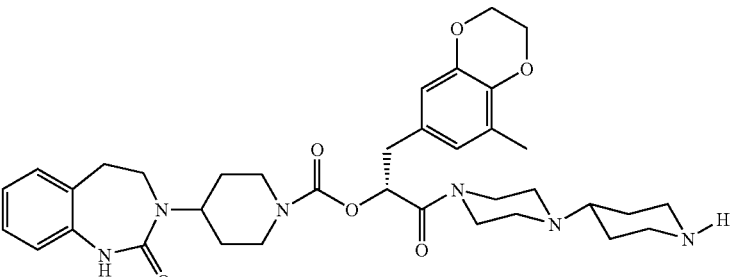 | (R)-1-(8-methyl-2,3-dihydro-1,4-benzodioxin-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (375) 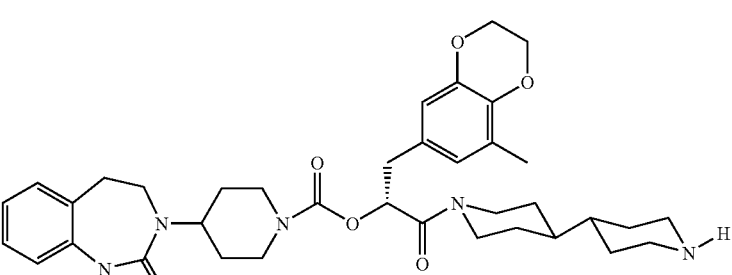 | (R)-2-4,4'-bipiperidinyl-1-yl-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (376) 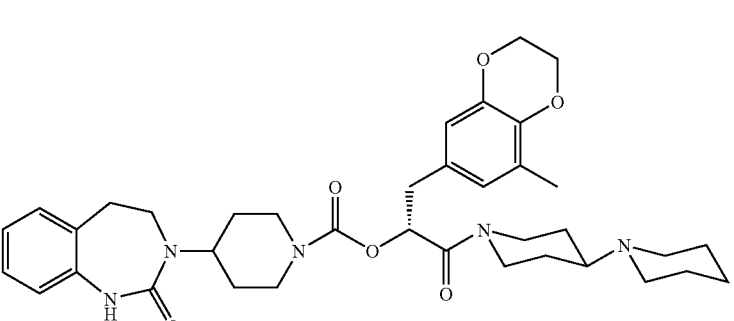 | (R)-2-1,4'-bipiperidinyl-1'-yl-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (377) 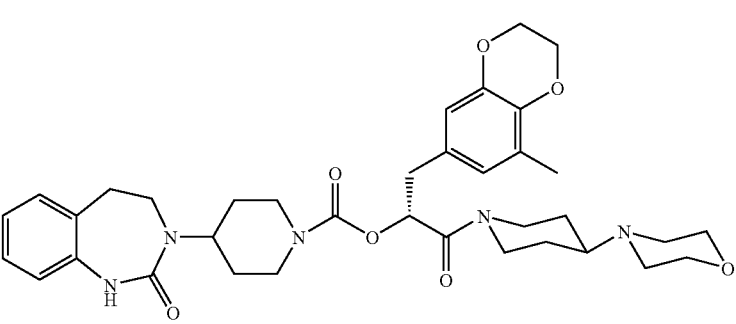 | (R)-1-(8-methyl-2,3-dihydro-1,4-benzodioxin-6-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (378) 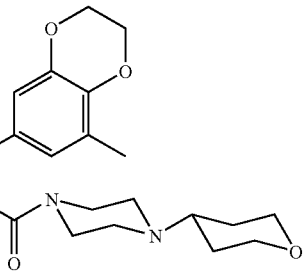 | (R)-1-(8-methyl-2,3-dihydro-1,4-benzodioxin-6-ylmethyl)-2-oxo-2-(4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (379) 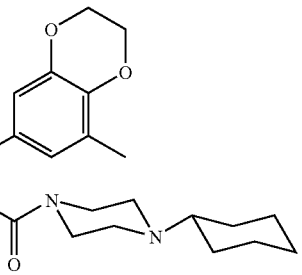 | (R)-2-(4-cyclohexyl-piperazin-1-yl)-1-(8-methyl-2,3-dihydro-1,4-benzodioxin-6-yl-methyl)-2-oxo-ethyl 4-(2-oxo-1,2,4,5-tetrahydro-1,3-benzodiazepin-3-yl)-piperidine-1-carboxylate |
| (380) 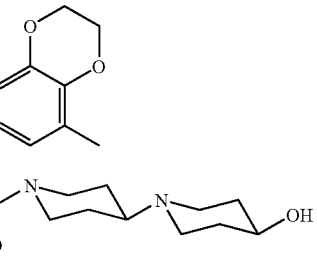 | (R)-2-(4-hydroxy-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (381) 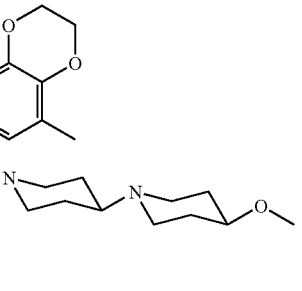 | (R)-2-(4-methoxy-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (382) 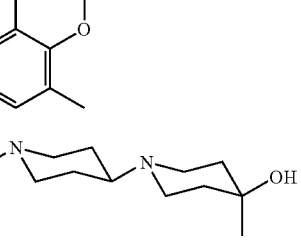 | (R)-2-(4-hydroxy-4-methyl-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (383) | | (R)-2-(4,4-dimethyl-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (384) | | (R)-2-(4-amino-4-methyl-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (385) | | (R)-2-(4-hydroxy-4-hydroxymethyl-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (386) | | (R)-2-(1'-ethoxycarbonylmethyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (387) | | (R)-2-(1'-carboxymethyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |

| Structure | Name |
|---|---|
| (388) 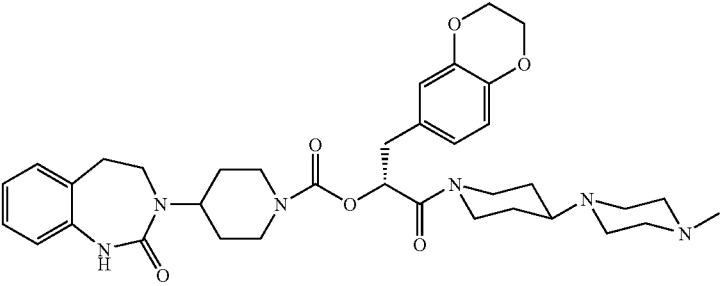 | (R)-1-(2,3-dihydro-1,4-benzodioxin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (389) 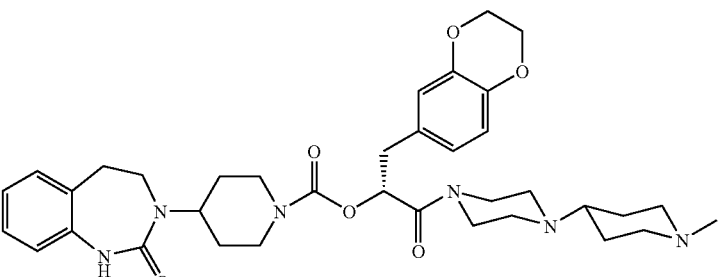 | (R)-1-(2,3-dihydro-1,4-benzodioxin-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (390) 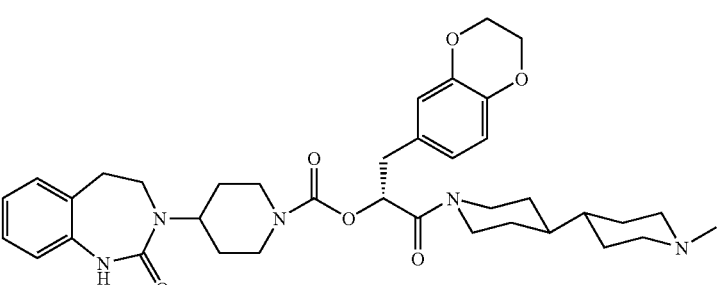 | (R)-1-(2,3-dihydro-1,4-benzodioxin-6-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (391) 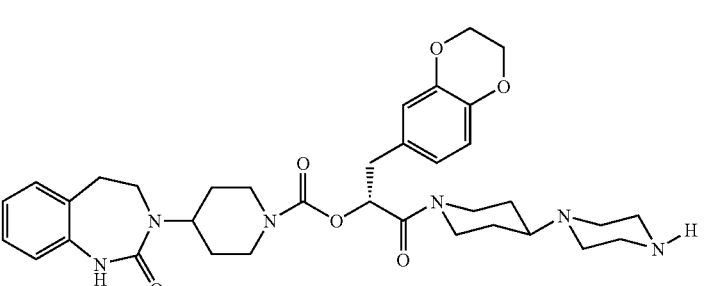 | (R)-1-(2,3-dihydro-1,4-benzodioxin-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (392) 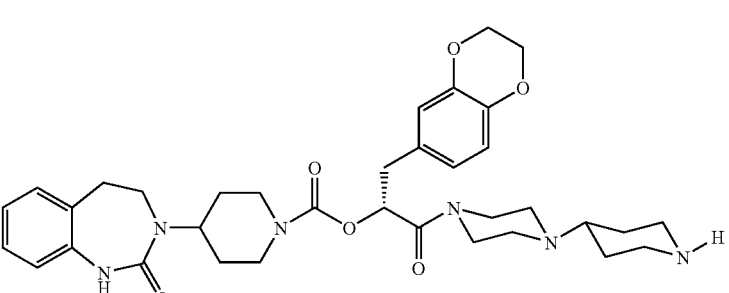 | (R)-1-(2,3-dihydro-1,4-benzodioxin-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (393) 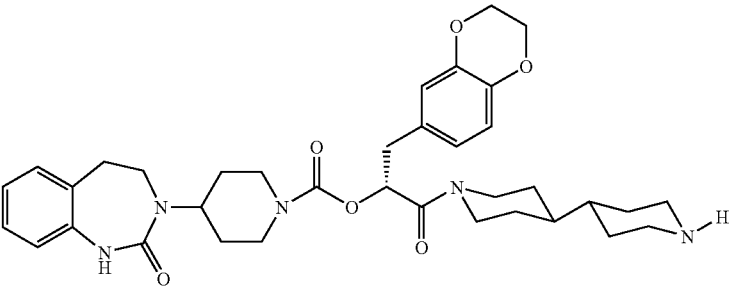 | (R)-2-4,4'-bipiperidinyl-1-yl-1-(2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (394) 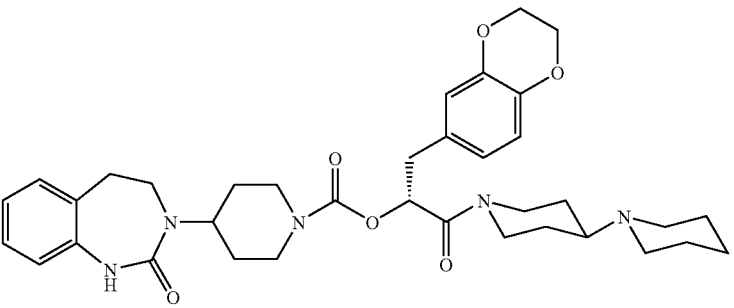 | (R)-2-1,4'-bipiperidinyl-1'-yl-1-(2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (395) 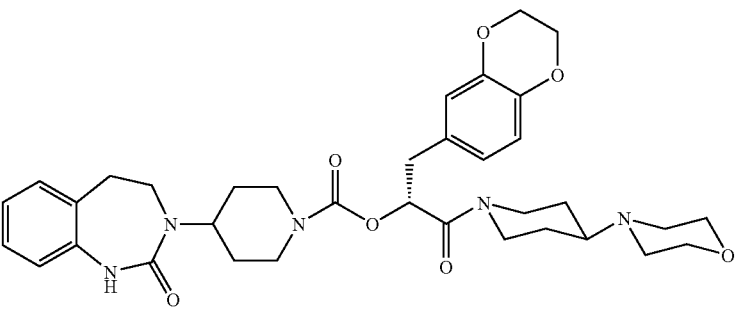 | (R)-1-(2,3-dihydro-1,4-benzodioxin-6-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (396) 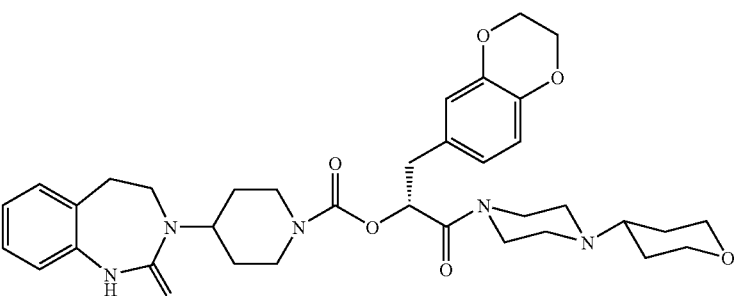 | (R)-1-(2,3-dihydro-1,4-benzodioxin-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (397) 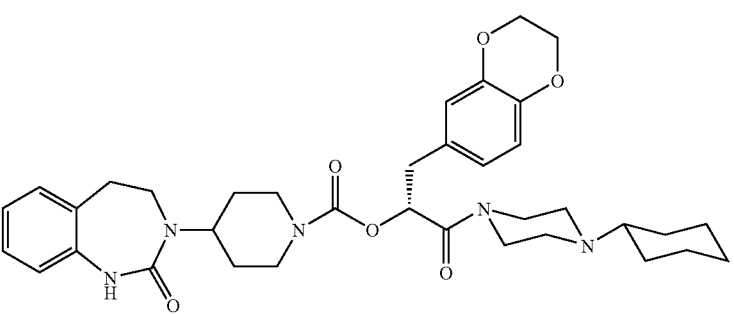 | (R)-2-(4-cyclohexyl-piperazin-1-yl)-1-(2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (398) | (R)-1-(2,3-dihydro-1,4-benzodioxin-6-ylmethyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (399) | (R)-1-(2,3-dihydro-1,4-benzodioxin-6-ylmethyl)-2-(4-methoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (400) | (R)-1-(2,3-dihydro-1,4-benzodioxin-6-ylmethyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (401) | (R)-1-(2,3-dihydro-1,4-benzodioxin-6-ylmethyl)-2-(4,4-dimethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (402) | (R)-2-(4-amino-4-methyl-1,4'-bipiperidinyl-1'-yl)-1-(2,3-dihydro-1,4-benzodioxin-6-yl-methyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (403) | (R)-1-(2,3-dihydro-1,4-benzodioxin-6-ylmethyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (404) | (R)-1-(2,3-dihydro-1,4-benzodioxin-6-ylmethyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (405) | (R)-2-(1'-carboxymethyl-4,4'-bipiperidinyl-1-yl)-1-(2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (406) | (R)-1-(7-methyl-2-oxo-2,3-dihydro-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (407) | (R)-1-(7-methyl-2-oxo-2,3-dihydro-1H-benzimidazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (408) | | (R)-2-(1'-methyl-4,4'-bipiperidinyl-1-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (409) | | (R)-1-(7-methyl-2-oxo-2,3-dihydro-1H-benzimidazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (410) | | (R)-1-(7-methyl-2-oxo-2,3-dihydro-1H-benzimidazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (411) | | (R)-2-4,4'-bipiperidinyl-1-yl-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (412) 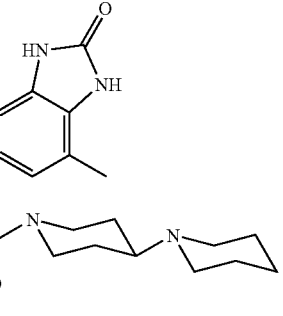 | (R)-2-1,4'-bipiperidinyl-1'-yl-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (413) 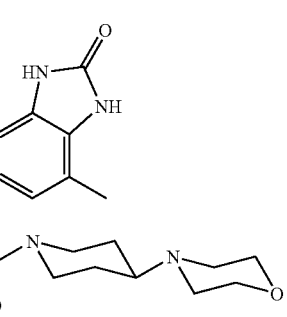 | (R)-1-(7-methyl-2-oxo-2,3-dihydro-1H-benzimidazol-5-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (414) 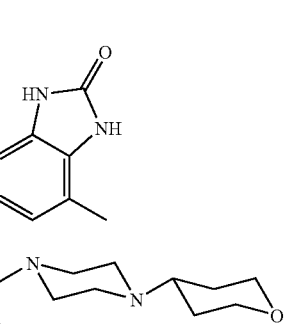 | (R)-1-(7-methyl-2-oxo-2,3-dihydro-1H-benzimidazol-5-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (415) 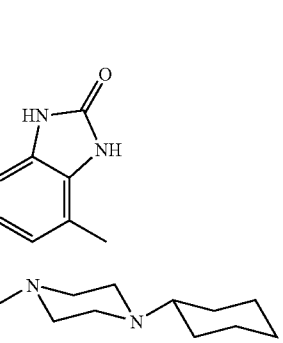 | (R)-2-(4-cyclohexyl-piperazin-1-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (416) 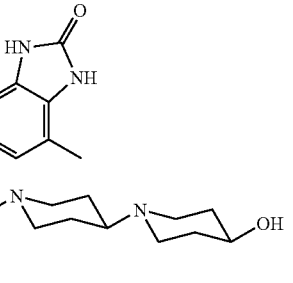 | (R)-2-(4-hydroxy-1,4'-bipiperidinyl-1'-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (417) 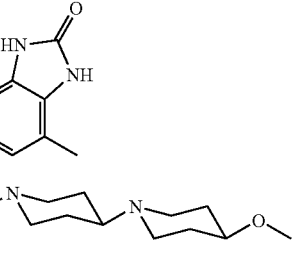 | (R)-2-(4-methoxy-1,4'-bipiperidinyl-1'-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (418) 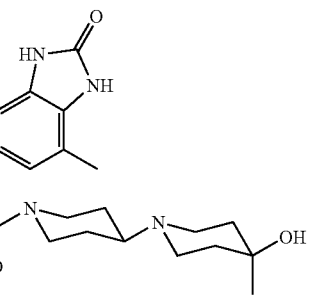 | (R)-2-(4-hydroxy-4-methyl-1,4'-bipiperidinyl-1'-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (419) 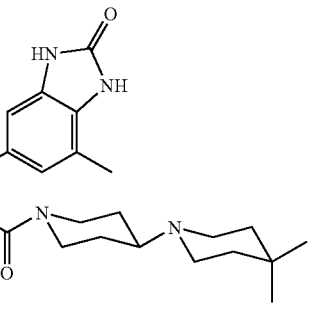 | (R)-2-(4,4-dimethyl-1,4'-bipiperidinyl-1'-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (420) 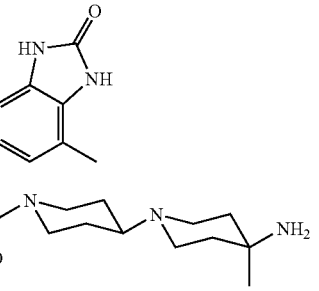 | (R)-2-(4-amino-4-methyl-1,4'-bipiperidinyl-1'-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (421) 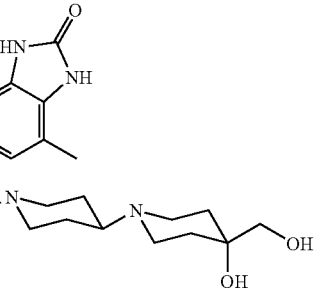 | (R)-2-(4-hydroxy-4-hydroxymethyl-1,4'-bipiperidinyl-1'-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (422) 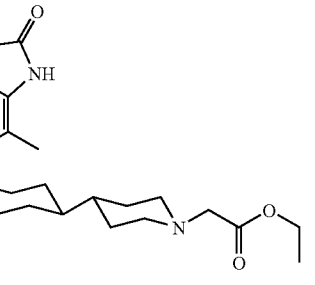 | (R)-2-(1'-ethoxycarbonylmethyl-4,4'-bipiperidinyl-1-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (423) 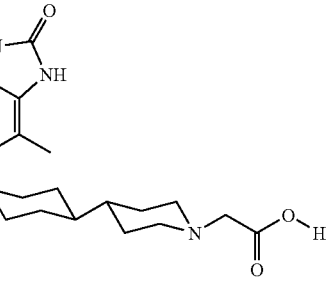 | (R)-2-(1'-carboxymethyl-4,4'-bipiperidinyl-1-yl)-1-(7-methyl-2-oxo-2,3-dihydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (424) 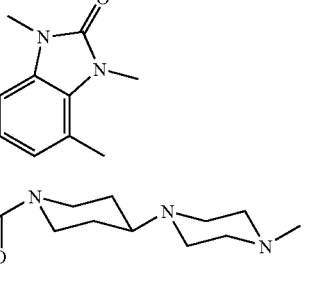 | (R)-2-[4-(4-methyl-piperazin-1-yl)-piperidin-1-yl]-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (425) 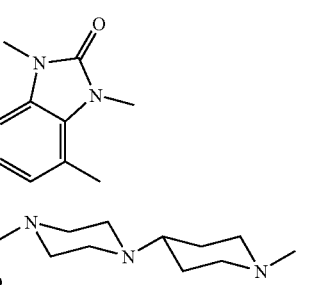 | (R)-2-(4-(1-methyl-piperidin-4-yl)-piperazin-1-yl]-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |

-continued

| | Structure | Name |
|---|---|---|
| (426) | 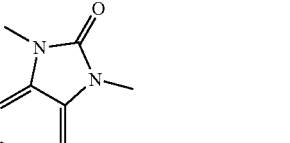 | (R)-2-(1'-methyl-4,4'-bipiperidinyl-1-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (427) | 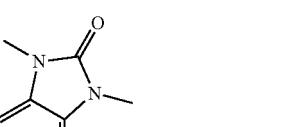 | (R)-2-oxo-2-(4-piperazin-1-yl-piperidin-1-yl)-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (428) | 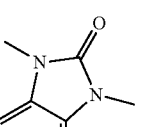 | (R)-2-oxo-2-(4-piperidin-4-yl-piperazin-1-yl)-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (429) | 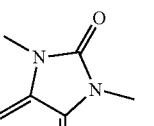 | (R)-2-4,4'-bipiperidinyl-1-yl-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |

-continued

| Structure | Name |
|---|---|
| (430) 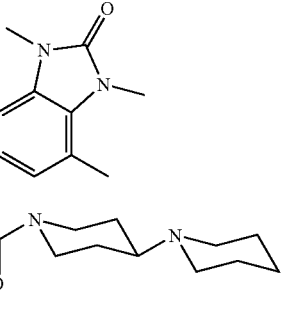 | (R)-2-1,4'-bipiperidinyl-1'-yl-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (431) 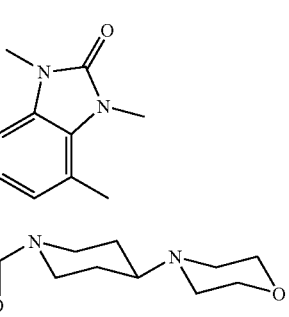 | (R)-2-(4-morpholin-4-yl-piperidin-1-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (432) 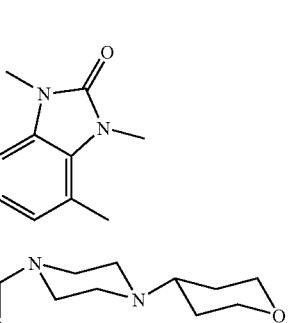 | (R)-2-oxo-2-[4-(tetrahydro-pyran-4-yl)-piperazin-1-yl]-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (433) 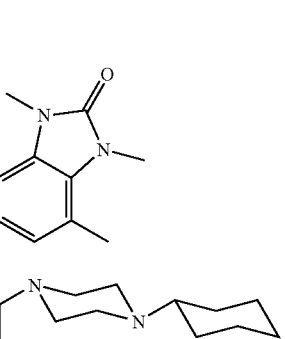 | (R)-2-(4-cyclohexyl-piperazin-1-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |

-continued

| Structure | Name |
|---|---|
| (434) 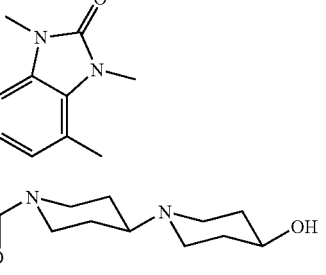 | (R)-2-(4-hydroxy-1,4'-bipiperidinyl-1'-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (435) 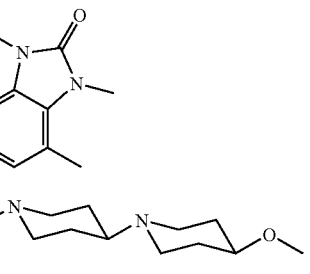 | (R)-2-(4-methoxy-1,4'-bipiperidinyl-1'-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (436) 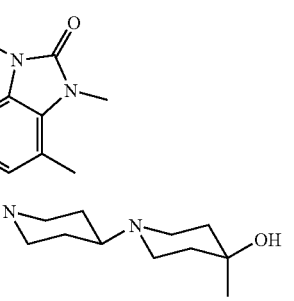 | (R)-2-(4-hydroxy-4-methyl-1,4'-bipiperidinyl-1'-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (437) 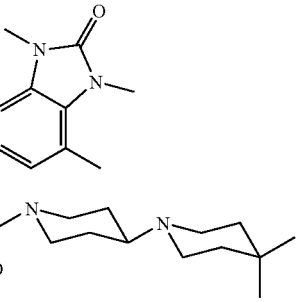 | (R)-2-(4,4-dimethyl-1,4'-bipiperidinyl-1'-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (438) 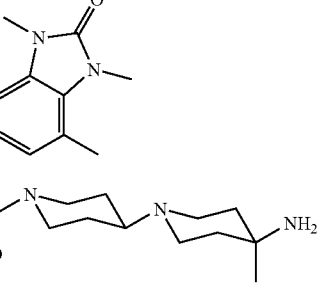 | (R)-2-(4-amino-4-methyl-1,4'-bipiperidinyl-1'-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |

-continued

| Structure | Name |
|---|---|
| (439) 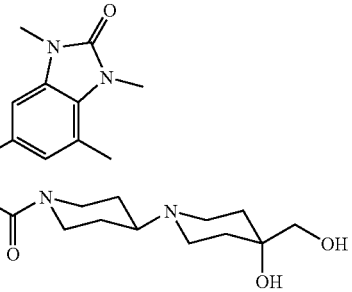 | (R)-2-(4-hydroxy-4-hydroxymethyl-1 4'-bipiperidinyl-1'-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (440) 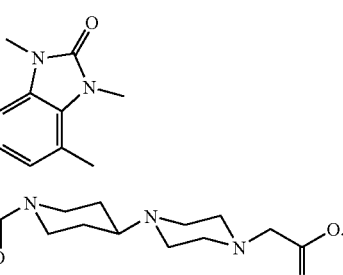 | (R)-2-(1'-ethoxycarbonylmethyl-4,4'-bipiperidinyl-1-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (441) 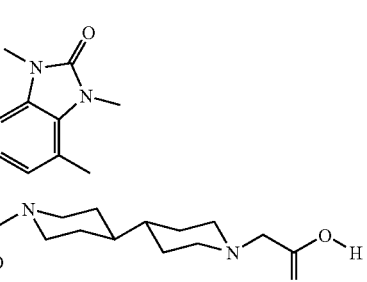 | (R)-2-(1'-carboxymethyl-4,4'-bipiperidinyl-1-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (442) 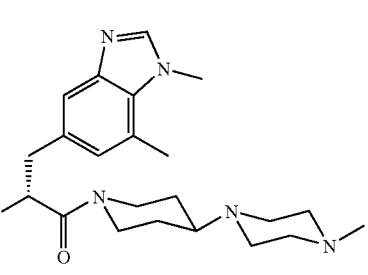 | (R)-1-(1,7-dimethyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (443) 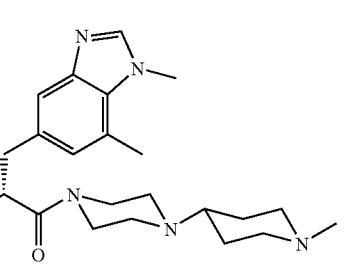 | (R)-1-(1,7-dimethyl-1H-benzimidazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

| Structure | Name |
|---|---|
| (444) 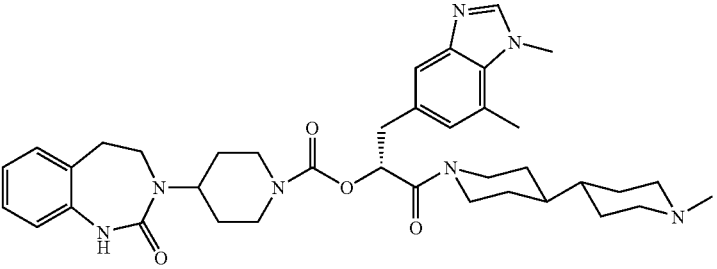 | (R)-1-(1,7-dimethyl-1H-benzimidazol-5-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (445) 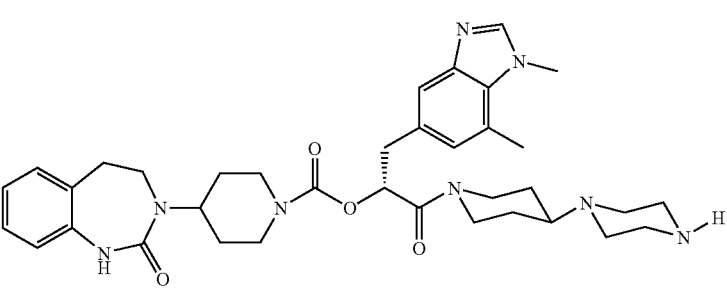 | (R)-1-(1,7-dimethyl-1H-benzimidazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (446) 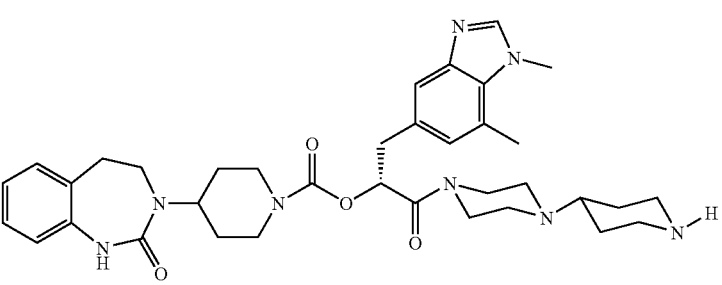 | (R)-1-(1,7-dimethyl-1H-benzimidazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (447) 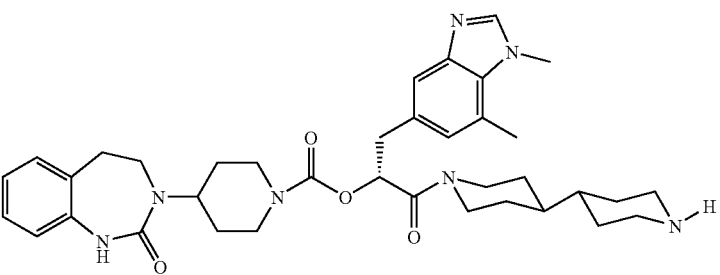 | (R)-2-4,4'-bipiperidinyl-1-yl-1-(1,7-dimethyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (448) 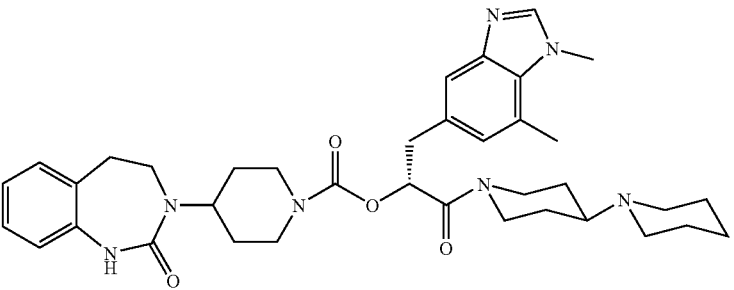 | (R)-2-1,4'-bipiperidinyl-1-yl-1-(1,7-dimethyl-1H-benzimidazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (449) 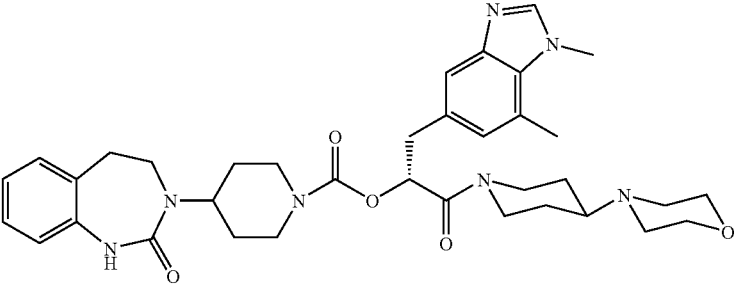 | (R)-1-(1,7-dimethyl-1H-benzimidazol-5-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (450) 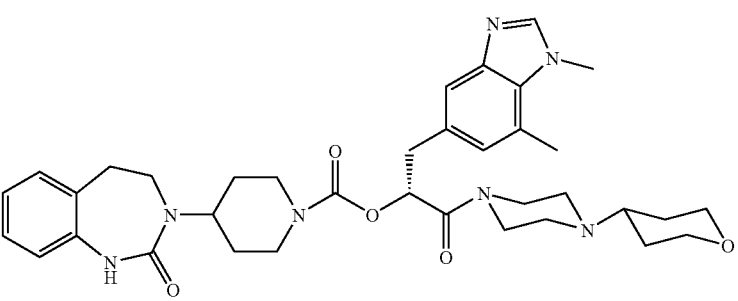 | (R)-1-(1,7-dimethyl-1H-benzimidazol-5-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (451) 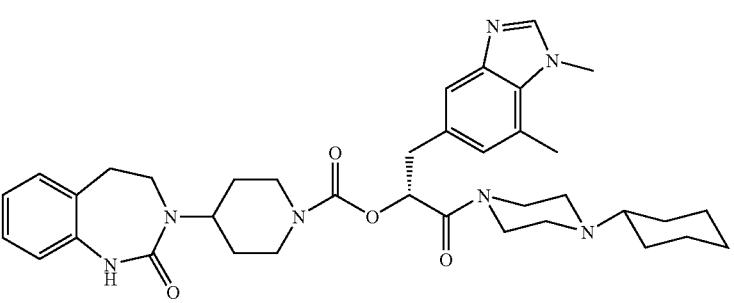 | (R)-2-(4-cyclohexyl-piperazin-1-yl)-1-(1,7-dimethyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (452) 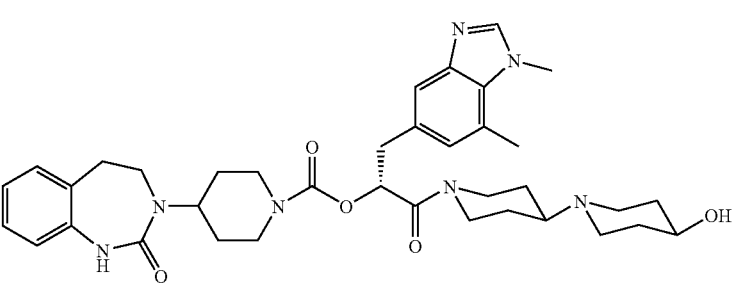 | (R)-1-(1,7-dimethyl-1H-benzimidazol-5-ylmethyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (453) 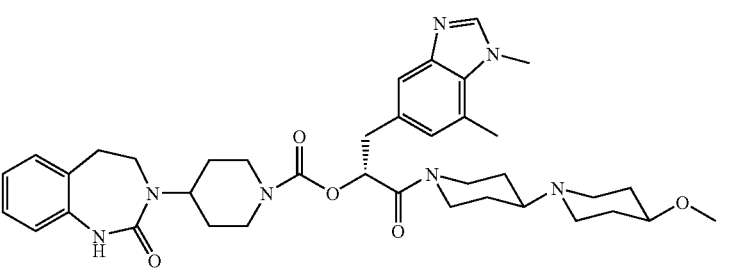 | (R)-1-(1,7-dimethyl-1H-benzimidazol-5-ylmethyl)-2-(4-methoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |

| Structure | Name |
|---|---|
| (454) | (R)-1-(1,7-dimethyl-1H-benzimidazol-5-ylmethyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (455) | (R)-1-(1,7-dimethyl-1H-benzimidazol-5-ylmethyl)-2-(4,4-dimethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (456) | (R)-2-(4-amino-4-methyl-1,4'-bipiperidinyl-1'-yl)-1-(1,7-dimethyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (457) | (R)-1-(1,7-dimethyl-1H-benzimidazol-5-ylmethyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (458) | (R)-1-(1,7-dimethyl-1H-benzimidazol-5-ylmethyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| Structure | Name |
|---|---|
| (459) 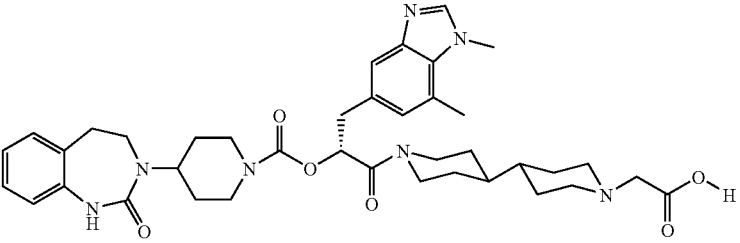 | (R)-2-(1'-carboxymethyl-4,4'-bipiperidinyl-1-yl)-1-(1,7-dimethyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (460) 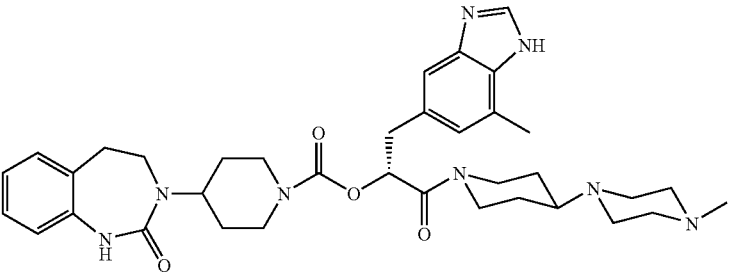 | (R)-1-(7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (461) 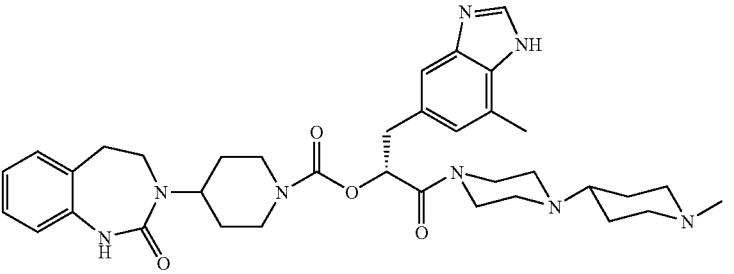 | (R)-1-(7-methyl-1H-benzimidazol-5-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (462) 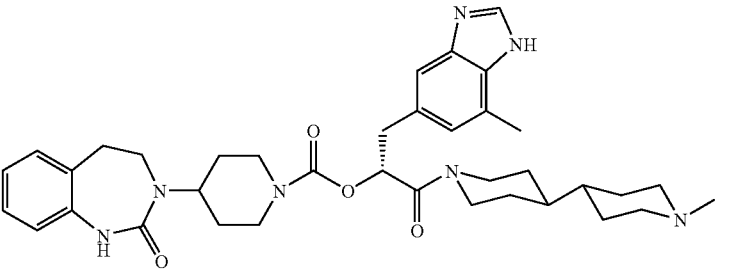 | (R)-1-(7-methyl-1H-benzimidazol-5-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (463) 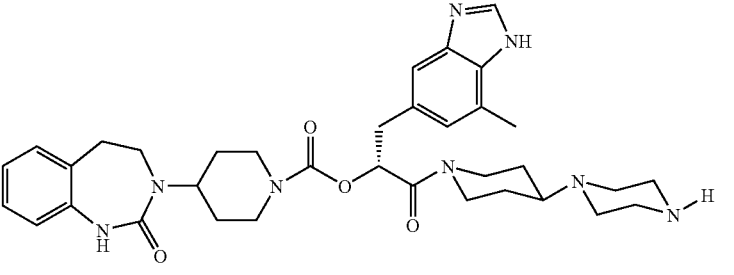 | (R)-1-(7-methyl-1H-benzimidazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (464) 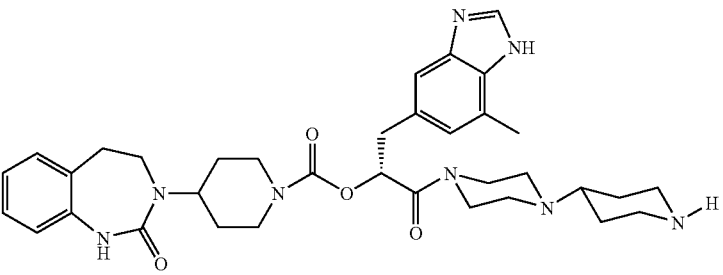 | (R)-1-(7-methyl-1H-benzimidazol-5-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (465) 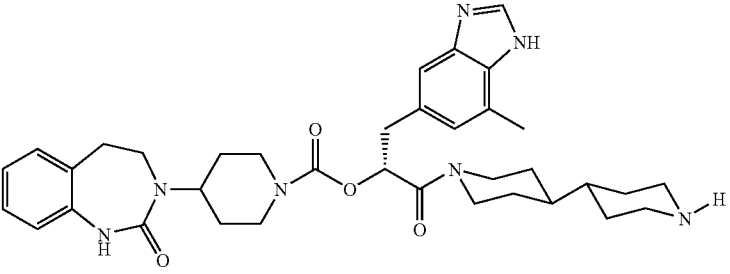 | (R)-2-4,4'-bipiperidinyl-1-yl-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (466) 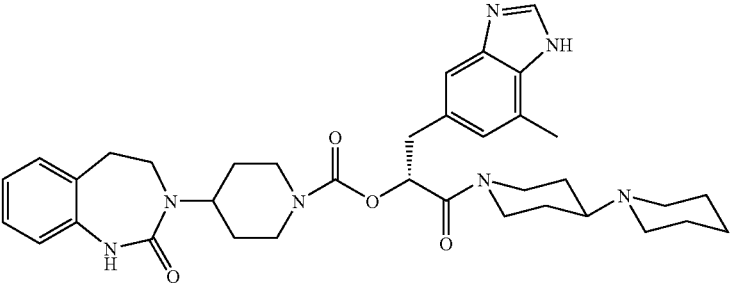 | (R)-2-1,4'-bipiperidinyl-1'-yl-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (467) 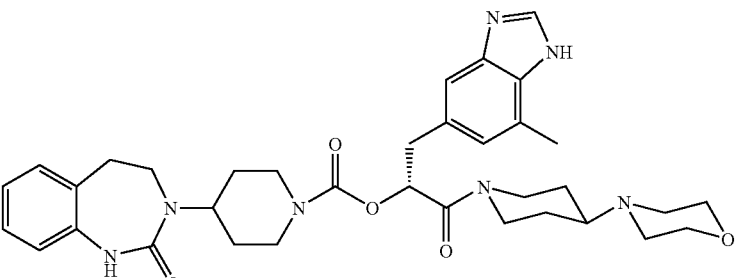 | (R)-1-(7-methyl-1H-benzimidazol-5-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (468) 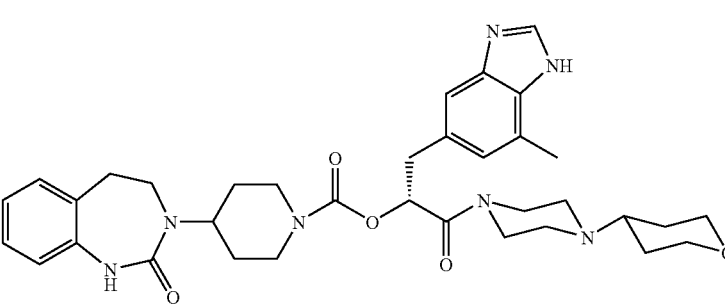 | (R)-1-(7-methyl-1H-benzimidazol-5-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |

-continued

| | Structure | Name |
|---|---|---|
| (469) | 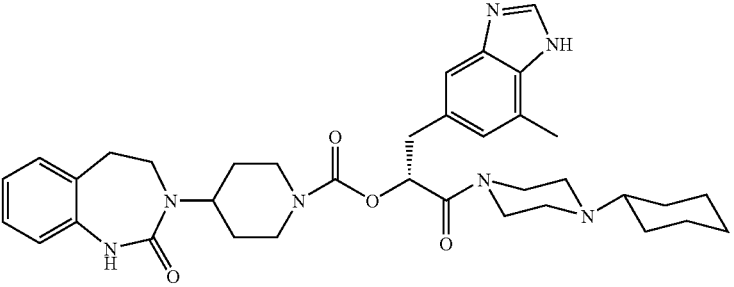 | (R)-2-(4-cyclohexyl-piperazin-1-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (470) | 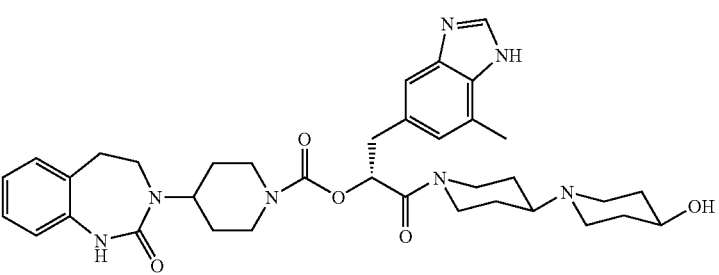 | (R)-2-(4-hydroxy-1,4'-bipiperidinyl-1'-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (471) | 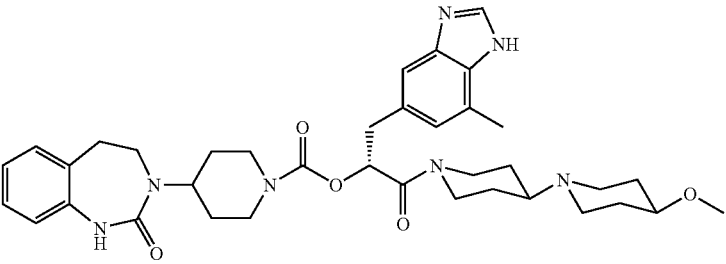 | (R)-2-(4-methoxy-1,4'-bipiperidinyl-1'-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (472) | 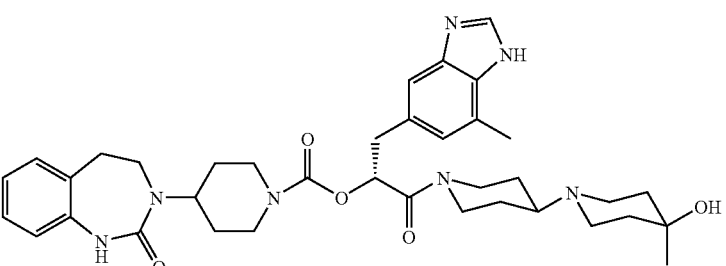 | (R)-2-(4-hydroxy-4-methyl-1,4'-bipiperidinyl-1'-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (473) | 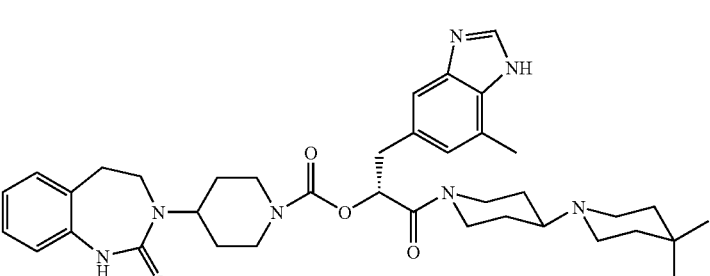 | (R)-2-(4,4-dimethyl-1,4'-bipiperidinyl-1'-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (474) 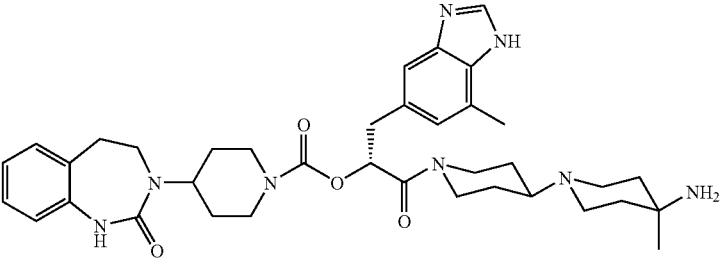 | (R)-2-(4-amino-4-methyl-1,4'-bipiperidinyl-1'-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (475) 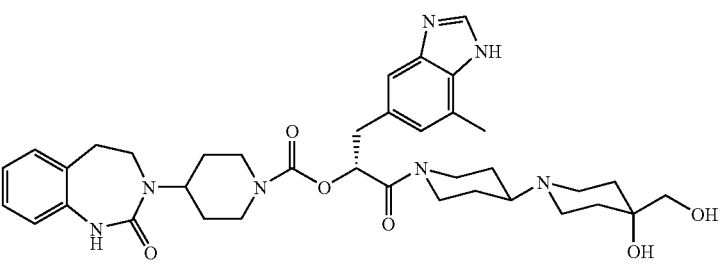 | (R)-2-(4-hydroxy-4-hydroxymethyl-1,4'-bi-piperidinyl-1'-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (476) 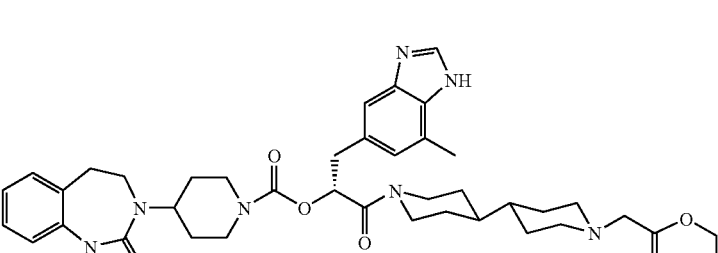 | (R)-2-(1'-ethoxycarbonylmethyl-4,4'-bipiperidinyl-1-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (477) 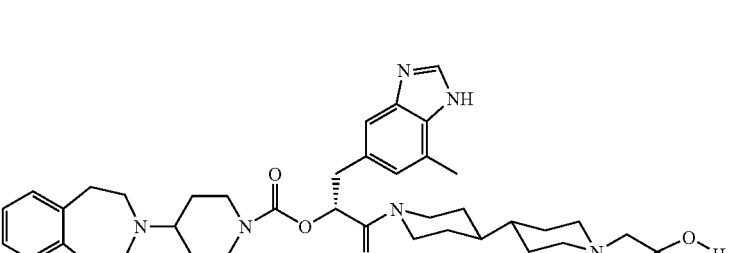 | (R)-2-(1'-carboxymethyl-4,4'-bipiperidinyl-1-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-i-carboxylate |
| (478) 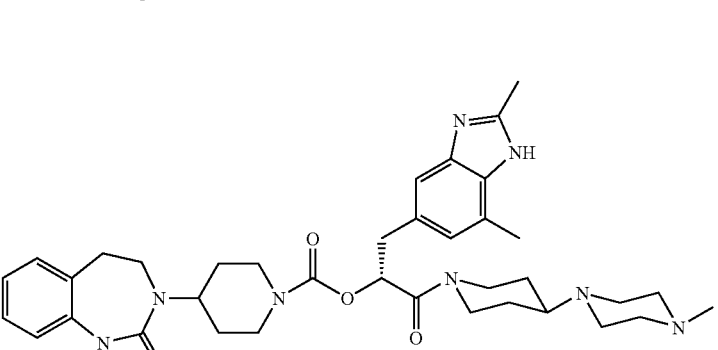 | (R)-1-(2,7-dimethyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| Structure | Name |
|---|---|
| (479) 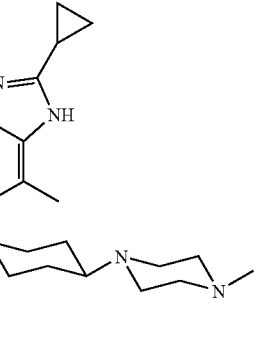 | (R)-1-(2-cyclopropyl-7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzo-diazepin-3-yl)-piperidine-1-carboxylate |
| (480) 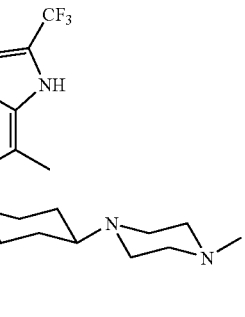 | (R)-2-[4-(4-methyl-piperazin-1-yl)-piperidin-1-yl]-1-(7-methyl-2-trifluoromethyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (481) 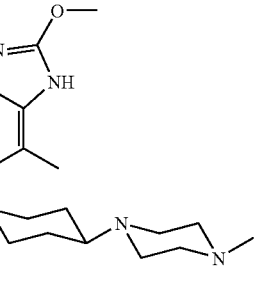 | (R)-1-(2-methoxy-7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzo-diazepin-3-yl)-piperidine-1-carboxylate |
| (482) 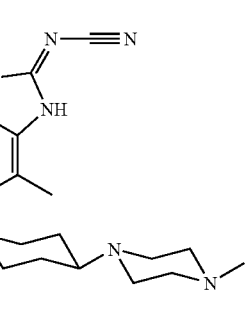 | (R)-1-{2-[(Z)-cyanimino]-7-methyl-2,3-dihydro-1H-benzimidazol-5-ylmethyl}-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (483) 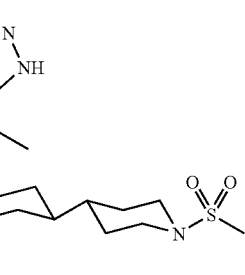 | (R)-1-(1H-indazol-5-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (484) | | (R)-2-(1'-methanesulphonyl-4,4'-bipiperidinyl-1-yl)-1-(1-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (485) | | (R)-2-(1'-methanesulphonyl-4,4'-bipiperidinyl-1-yl)-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (486) | | (R)-1-(1,7-dimethyl-1H-indazol-5-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (487) | | (R)-1-(7-chloro-1H-indazol-5-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (488) | | (R)-1-(7-chloro-1-methyl-1H-indazol-5-yl-methyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| Structure | Name |
|---|---|
| (489) 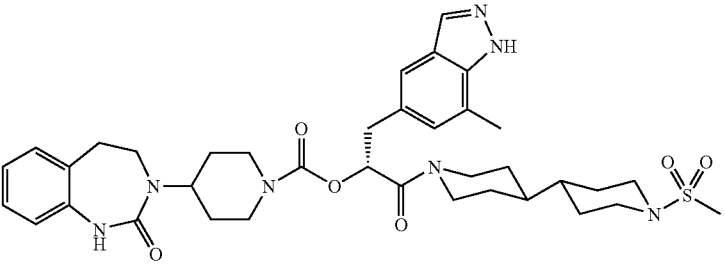 | (R)-2-(1'-methanesulphonyl-4,4'-bipiperidinyl-1-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (490) 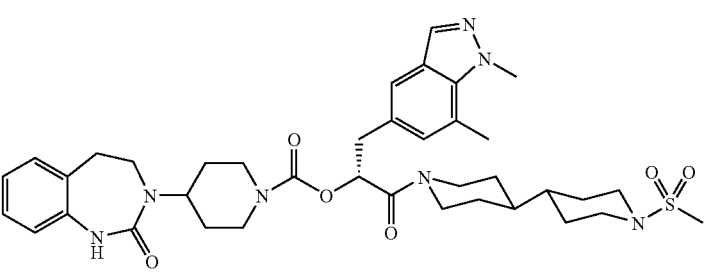 | (R)-1-(1,7-dimethyl-1H-benzimidazol-5-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (491) 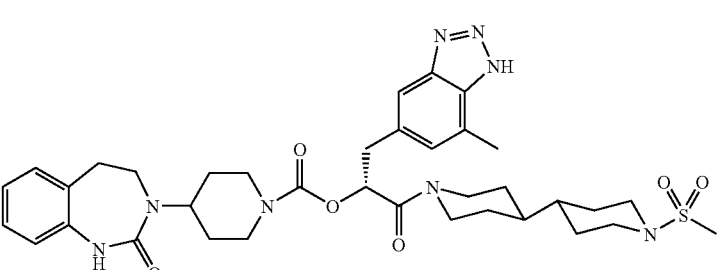 | (R)-2-(1'-methanesulphonyl-4,4'-bipiperidinyl-1-yl)-1-(7-methyl-1H-benzotriazol-5-ylmethyl)-2-oxo-ethyl 4-(2-oxo-1,2,4,5-tetrahydro-1,3-benzodiazepin-3-yl)-piperidine-1-carboxylate |
| (492) 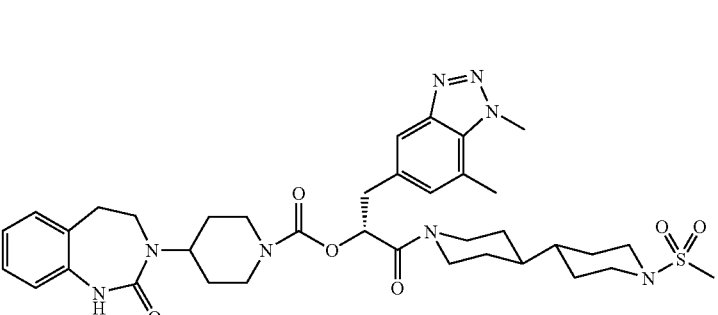 | (R)-1-(1,7-dimethyl-1H-benzotriazol-5-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (493) 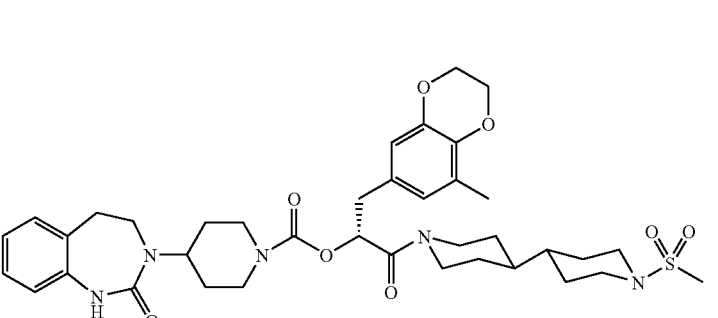 | (R)-2-(1'-methanesulphonyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |

| Structure | Name |
|---|---|
| (494) | (R)-1-(2,3-dihydro-1,4-benzodioxin-6-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (495) | (R)-2-(1'-methanesulphonyl-4,4'-bipiperidinyl-1-yl)-1-(5-methyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (496) | (R)-1-(4,5-dimethyl-3,4-dihydro-2H-1,4-benzoxazin-7-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (497) | (R)-2-(1'-methanesulphonyl-4,4'-bipiperidinyl-1-yl)-1-(8-methyl-2-oxo-1,2-dihydro-quinolin-6-ylmethyl)-2-oxo-ethyl 4-(2-oxo-1,2,4,5-tetrahydro-1,3-benzodiazepin-3-yl)-piperidine-1-carboxylate |
| (498) | (R)-1-(1,8-dimethyl-2-oxo-1,2-dihydro-quinolin-6-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (499) | | (R)-2-(1'-methanesulphonyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (500) | | (R)-2-(1'-methanesulphonyl-4,4'-bipiperidinyl-1-yl)-1-(7-methyl-2-oxo-2,3-dihydro-benzimidazol-5-ylmethyl)-2-oxo-ethyl 4-(2-oxo-1,2,4,5-tetrahydro-1,3-benzodiazepin-3-yl)-piperidine-1-carboxylate |
| (501) | | (R)-2-(1'-methanesulphonyl-4,4'-bipiperidinyl-1-yl)-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (502) | | (R)-2-(1'-methanesulphonyl-4,4'-bipiperidinyl-1-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (503) | | (R)-2-(1'-methanesulphonyl-4,4'-bipiperidinyl-1-yl)-2-oxo-1-quinoxalin-6-ylmethyl-ethyl 4-(2-oxo-1,2,4,5-tetrahydro-1,3-benzodiazepin-3-yl)-piperidine-1-carboxylate |

-continued

| Structure | Name |
|---|---|
| (504) 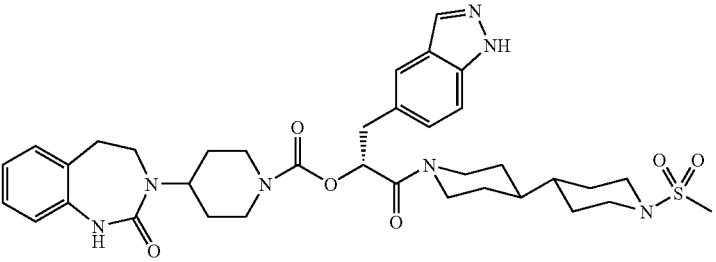 | (R)-1-(1H-indazol-5-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (505) 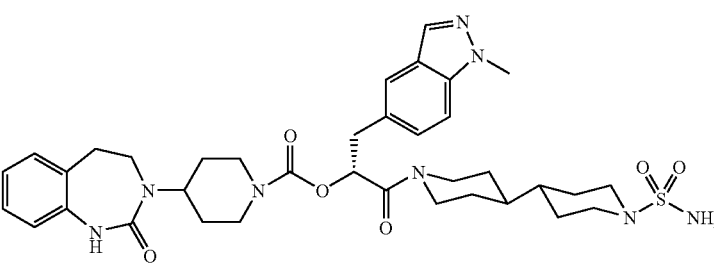 | (R)-1-(1-methyl-1H-indazol-5-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (506) 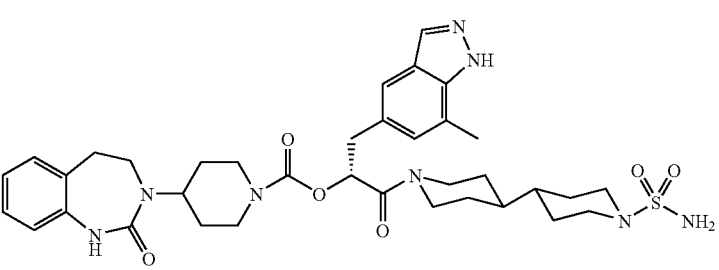 | (R)-1-(7-methyl-1H-indazol-5-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (507) 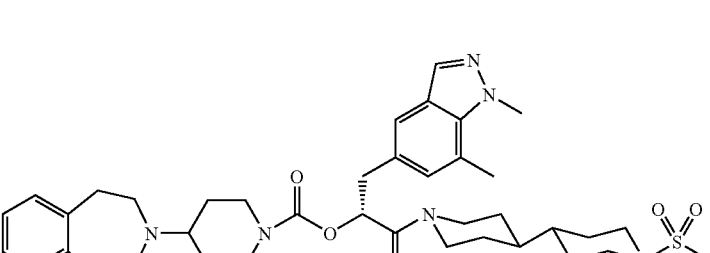 | (R)-1-(1,7-dimethyl-1H-indazol-5-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (508) 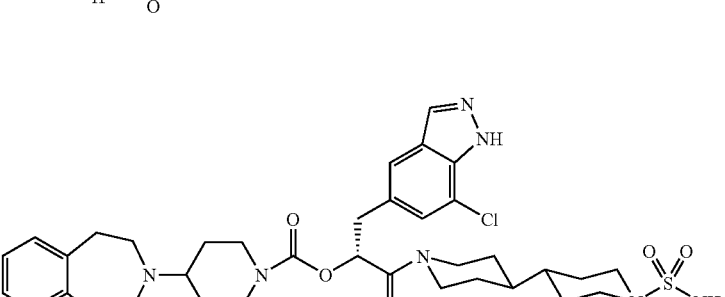 | (R)-1-(7-chloro-1H-indazol-5-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |

-continued

| Structure | Name |
|---|---|
| (509) 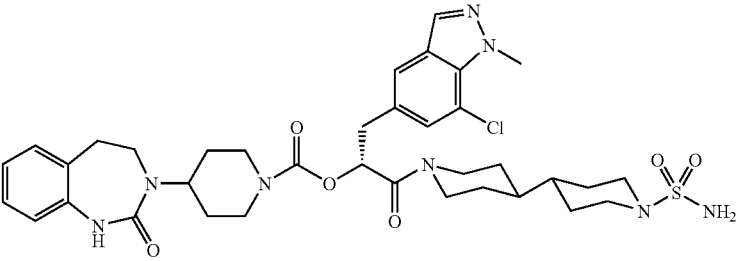 | (R)-1-(7-chloro-1-methyl-1H-indazol-5-yl-methyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (510) 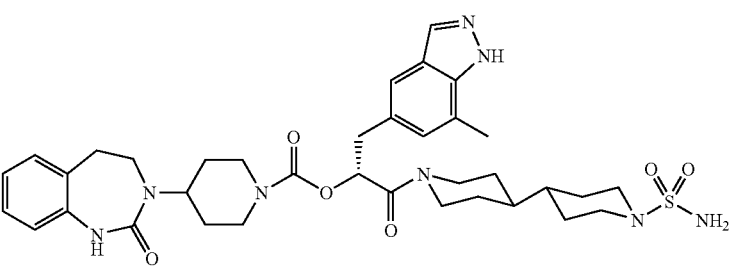 | (R)-1-(7-methyl-1H-benzimidazol-5-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (511) 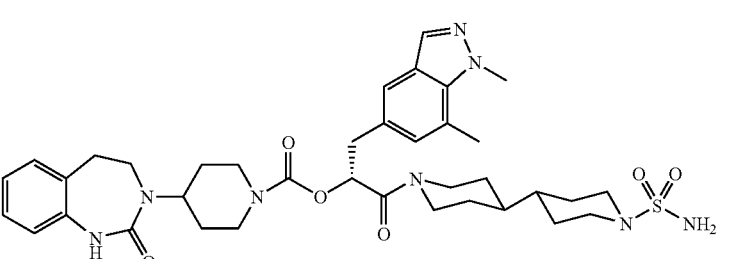 | (R)-1-(1,7-dimethyl-1H-benzimidazol-5-ylmethyl)-2-oxo-2-(1'-sulphamoyl-4,4'-bipiperidinyl-1-yl)-ethyl 4-(2-oxo-1,2,4,5-piperidine-1-carboxylate |
| (512) 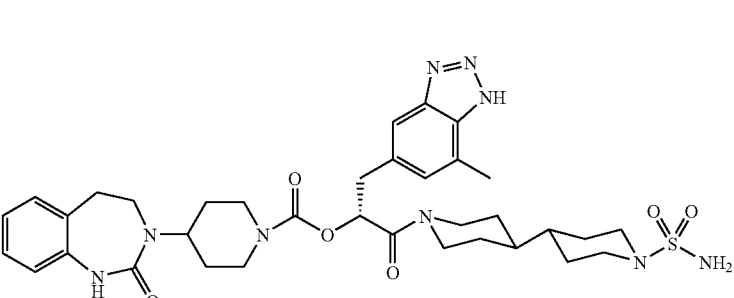 | (R)-1-(7-methyl-1H-benzotriazol-5-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (513) 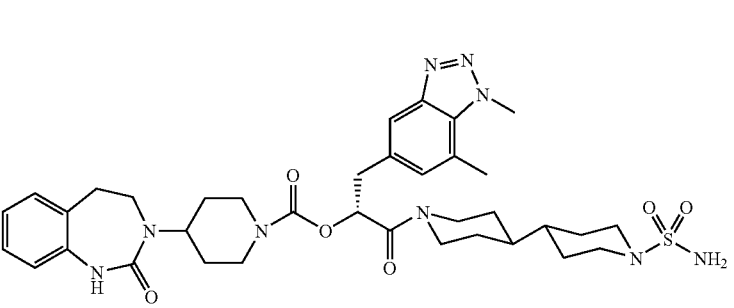 | (R)-1-(1,7-dimethyl-1H-benzotriazol-5-yl-methyl)-2-oxo-2-(1'-sulphamoyl-4-4'-bipiperidinyl-1-yl)-ethyl 4-(2-oxo-1,2,4,5-tetrahydro-1,3-benzodiazepin-3-yl)-piperidine-1-carboxylate |

-continued

| Structure | Name |
|---|---|
| (514) | (R)-1-(8-methyl-2,3-dihydro-1,4-benzodioxin-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (515) | (R)-1-(2,3-dihydro-1,4-benzodioxin-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (516) | (R)-1-(5-methyl-3,4-dihydro-2H-1,4-benzoxazin-7-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (517) | (R)-1-(4,5-dimethyl-3,4-dihydro-2H-1,4-benzoxazin-7-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (518) | (R)-1-(8-methyl-2-oxo-1,2-dihydro-quinolin-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |

-continued

| Structure | Name |
|---|---|
| (519) 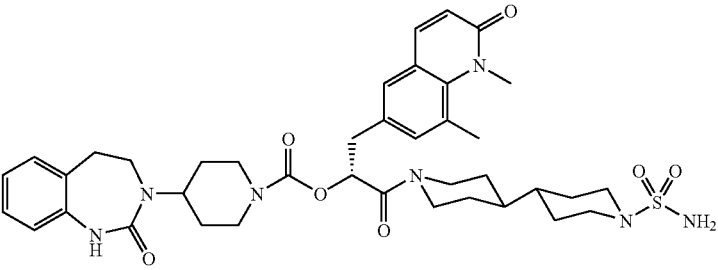 | (R)-1-(1,8-dimethyl-2-oxo-1,2-dihydro-quinolin-6-ylmethyl)-2-oxo-2-(1'-sulphamoyl-4,4'-bipiperidinyl-1-yl)-ethyl 4-(2-oxo-1,2,4,5-tetrahydro-1,3-benzo-diazepin-3-yl)-piperidine-1-carboxylate |
| (520) 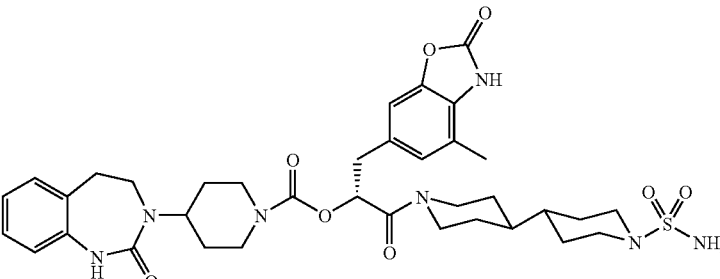 | (R)-1-(4-methyl-2-oxo-2,3-dihydro-benzoxazol-6-ylmethyl)-2-oxo-2-(1'-sulphamoyl-4,4'-bipiperidinyl-1-yl)-ethyl 4-(2-oxo-1,2,4,5-tetrahydro-1,3-benzo-diazepin-3-yl)-piperidine-1-carboxylate |
| (521) 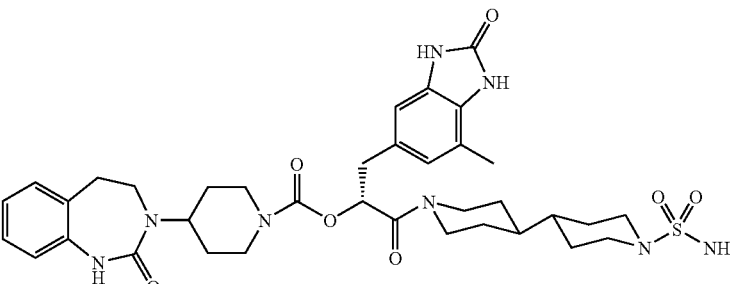 | (R)-1-(7-methyl-2-oxo-2,3-dihydro-1H-benzimidazol-5-ylmethyl)-2-oxo-2-(1'-sulphamoyl-4,4'-bipiperidinyl-1-yl)-ethyl 4-(2-oxo-1,2,4,5-tetrahydro-1,3-benzo-diazepin-3-yl)-piperidine-1-carboxylate |
| (522) 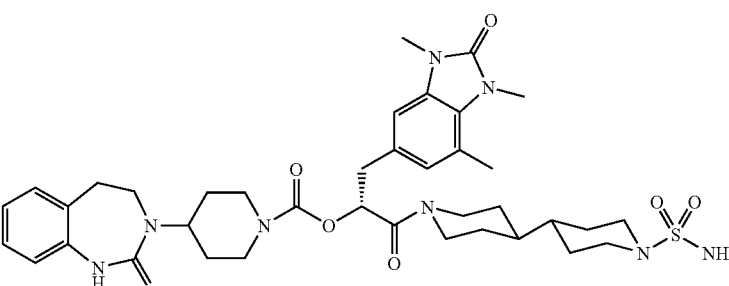 | (R)-2-oxo-2-(1'-sulphamoyl-4,4'-bipiperidinyl-1-yl)-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |
| (523) 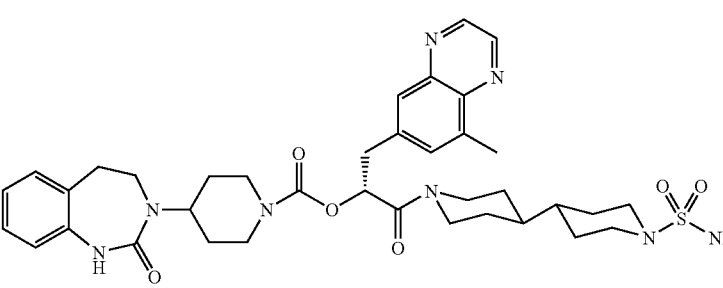 | (R)-1-(8-methyl-quinoxalin-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |

-continued

| Structure | Name |
|---|---|
| (524) 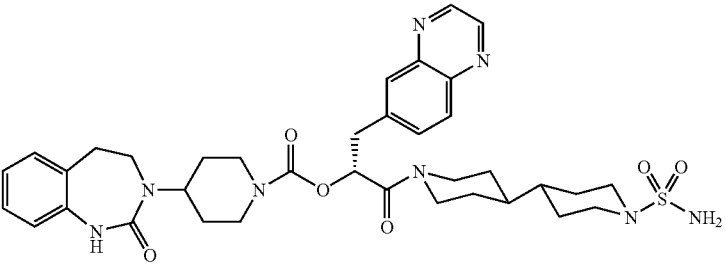 | (R)-2-oxo-1-quinoxalin-6-ylmethyl-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate |
| (525) 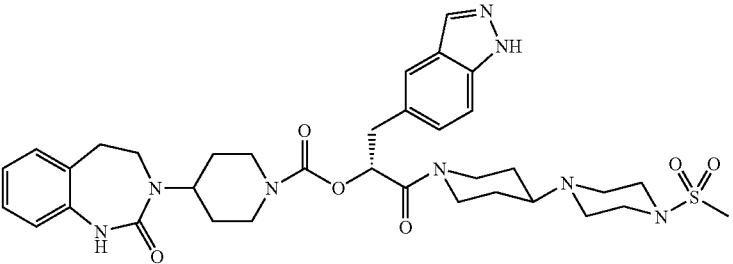 | (R)-1-(1H-indazol-5-ylmethyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (526) 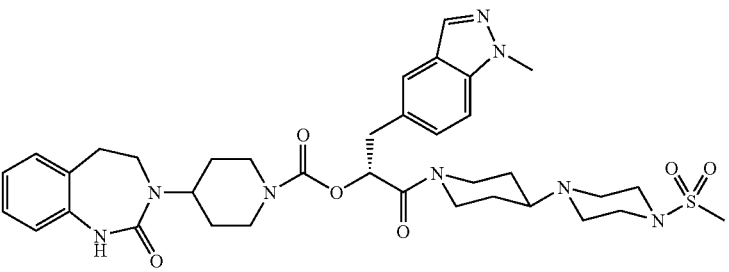 | (R)-2-[4-(4-methanesulphonyl-piperazin-1-yl)-piperidin-1-yl]-1-(1-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (527) 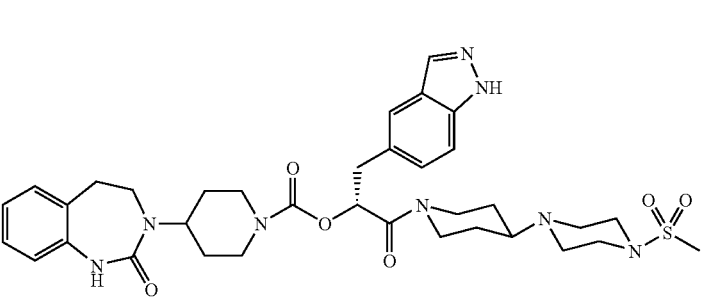 | (R)-2-[4-(4-methanesulphonyl-piperazin-1-yl)-piperidin-1-yl]-1-(7-methyl-1H-indazol-5-ylmethyl)-2-oxo-ethyl 4-(2-oxo-1,2,4,5-tetrahydro-1,3-benzodiazepin-3-yl)-piperidine-1-carboxylate |
| (528) 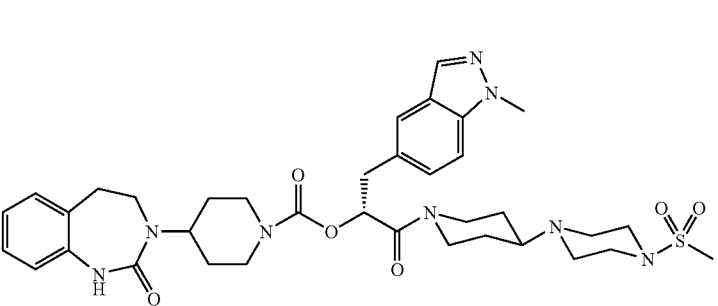 | (R)-1-(1,7-dimethyl-1H-indazol-5-ylmethyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

| Structure | Name |
|---|---|
| (529) 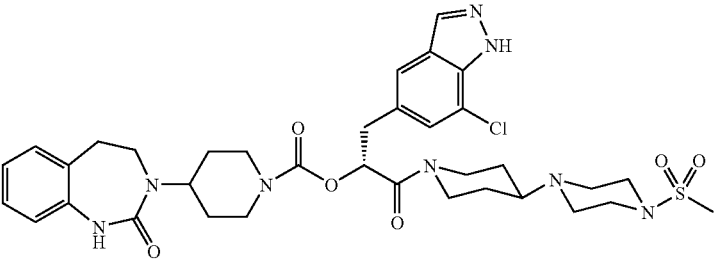 | 4-(2-oxo-1,2,4,5-tetrahydro-1,3-benzodi-(R)-1-(7-chloro-1H-indazol-5-ylmethyl)-2-[4-(4-methanesulphonyl-piperazin-1-yl)-piperidin-1-yl]-2-oxo-ethyl azepin-3-yl)-piperidine-1-carboxylate |
| (530) 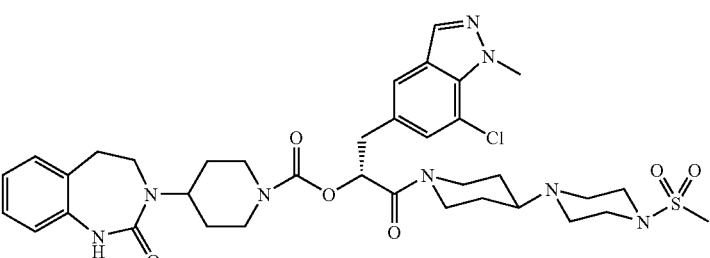 | (R)-1-(7-chloro-1-methyl-1H-indazol-5-yl-methyl)-2-[4-(4-methanesulphonyl-piperazin-1-yl)-piperidin-1-yl]-2-oxo-ethyl 4-(2-oxo-1,2,4,5-tetrahydro-1,3-benzodi-azepin-3-yl)-piperidine-1-carboxylate |
| (531) 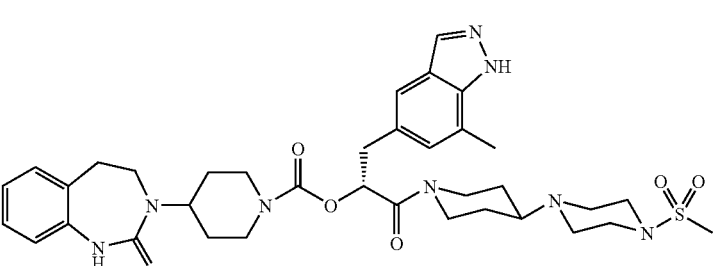 | (R)-2-[4-(4-methanesulphonyl-piperazin-1-yl)-piperidin-1-yl]-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (532) 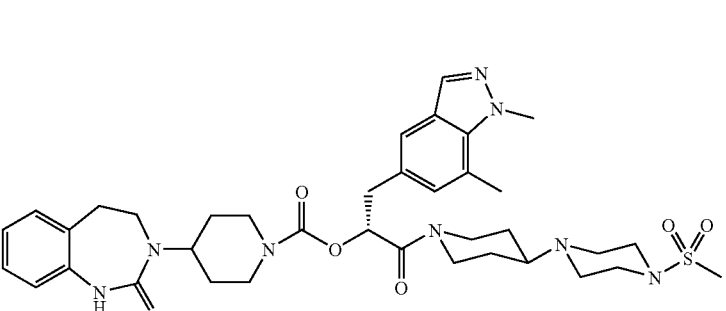 | (R)-1-(1,7-dimethyl-1H-benzimidazol-5-ylmethyl)-2-[4-(4-methanesulphonyl-piperazin-1-yl)-piperidin-1-yl]-2-oxo-ethyl 4-(2-oxo-1,2,4,5-tetrahydro-1,3-benzodi-azepin-3-yl)-piperidine-1-carboxylate |
| (533) 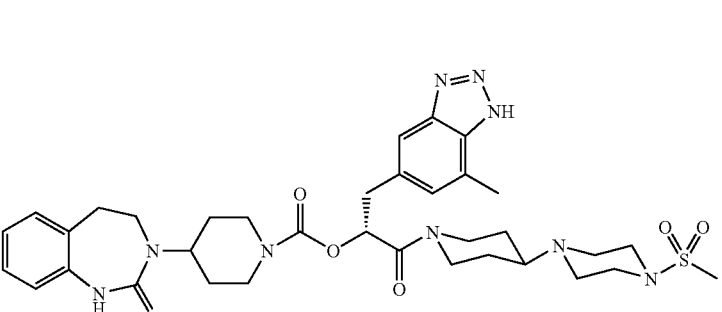 | (R)-2-[4-(4-methanesulphonyl-piperazin-1-yl)-piperidin-1-yl]-1-(7-methyl-1H-benzotriazol-5-ylmethyl)-2-oxo-ethyl 4-(2-oxo-1,2,4,5-tetrahydro-1,3-benzodiazepin-3-yl)-piperidine-1-carboxylate |

| | Structure | Name |
|---|---|---|
| (534) | 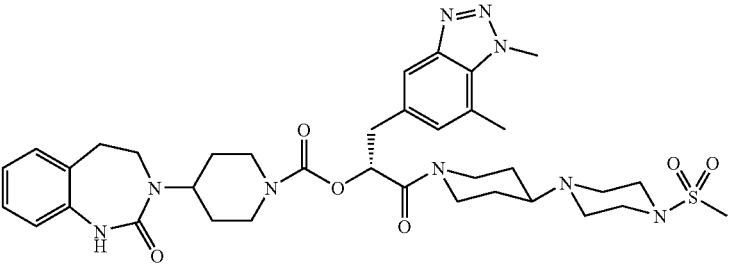 | (R)-1-(1,7-dimethyl-1H-benzotriazol-5-yl-methyl)-2-[4-(4-methanesulphonyl-piperazin-1-yl)-piperidin-1-yl]-2-oxo-ethyl 4-(2-oxo-1,2,4,5-tetrahydro-1,3-benzo0 diazepin-3-yl)-piperidine-1-carboxylate |
| (535) | 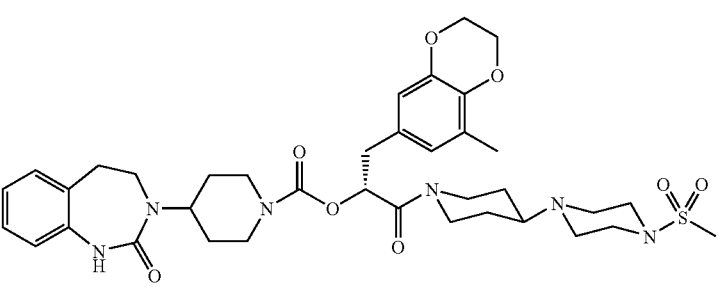 | (R)-2-[4-(4-methanesulphonyl-piperazin-1-yl)-piperidin-1-yl]-1-(8-methyl-2,3-dihydro-1,4-benzodioxin-6-ylmethyl)-2-oxo-ethyl 4-(2-oxo-1,2,4,5-tetrahydro-1,3-benzo-diazepin-3-yl)-piperidine-1-carboxylate |
| (536) | 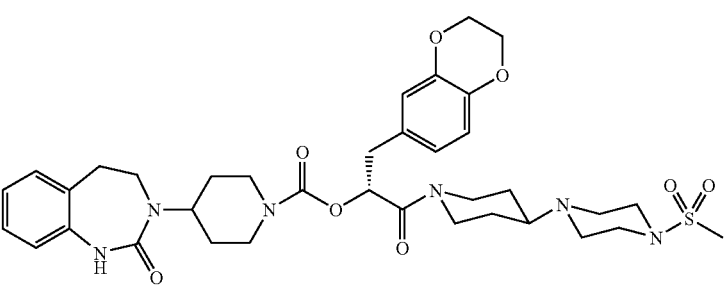 | (R)-1-(2,3-dihydro-1,4-benzodioxin-6-ylmethyl)-2-[4-(4-methanesulphonyl-piperazin-1-yl)-piperidin-1-yl]-2-oxo-ethyl 4-(2-oxo-1,2,4,5-tetrahydro-1,3-benzo-diazepin-3-yl)-piperidine-1-carboxylate |
| (537) | 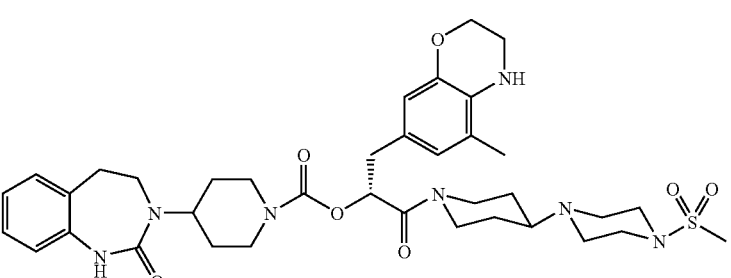 | (R)-2-[4-(4-methanesulphonyl-piperazin-1-yl)-piperidin-1-yl]-1-(5-methyl-3,4-dihydro-2H-1,4-benzoxazin-7-ylmethyl)-2-oxo-ethyl 4-(2-oxo-1,2.4,5-tetrahydro-1,3-benzo-diazepin-3-yl)-piperidine-1-carboxylate |
| (538) | 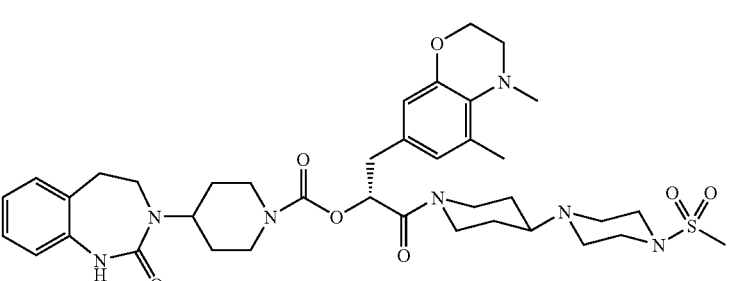 | (R)-1-(4,5-dimethyl-3,4-dihydro-2H-1,4-benzoxazin-7-ylmethyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |

-continued

| Structure | Name |
|---|---|
| (539) 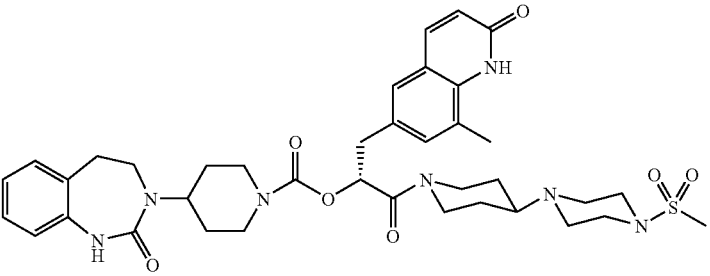 | (R)-2-[4-(4-methanesulphonyl-piperazin-1-yl)-piperidin-1-yl]-1-(8-methyl-2-oxo-1,2-di-hydro-quinolin-6-ylmethyl)-2-oxo-ethyl 4-(2-oxo-1,2,4,5-tetrahydro-1,3-benzo-diazepin-3-yl)-piperidine-1-carboxylate |
| (540) 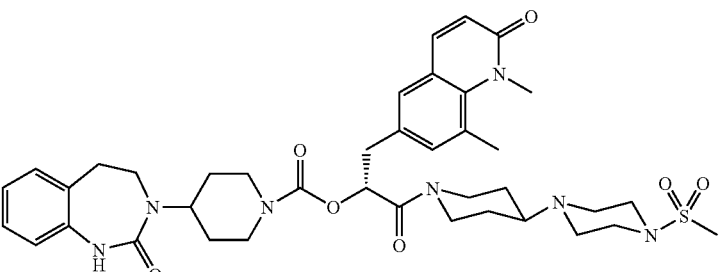 | (R)-1-(1,8-dimethyl-2-oxo-1,2-dihydro-quinolin-6-ylmethyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (541) 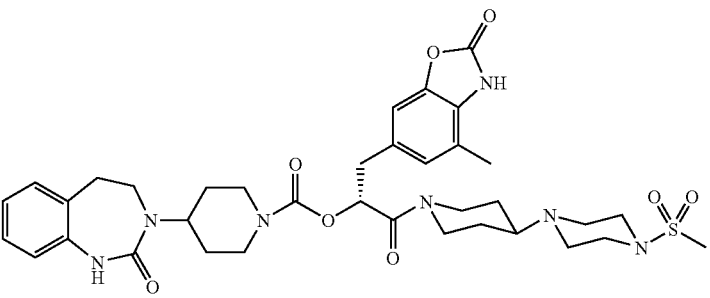 | (R)-2-[4-(4-methanesulphonyl-piperazin-1-yl)-piperidin-1-yl]-1-(4-methyl-2-oxo-2,3-dihydro-benzoxazol-6-ylmethyl)-2-oxo-ethyl 4-(2-oxo-1,2,4,5-tetrahydro-1,3-benzo-diazepin-3-yl)-piperidine-1-carboxylate |
| (542) 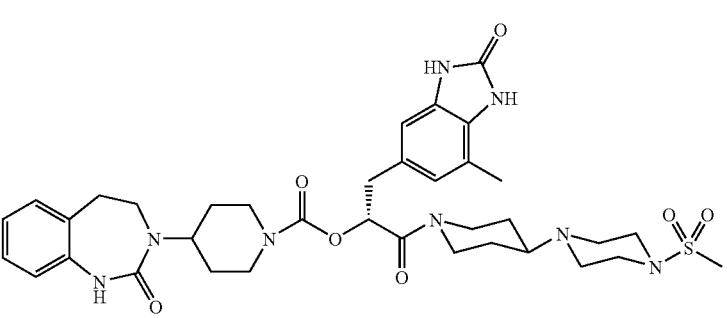 | (R)-2-[4-(4-methanesulphonyl-piperazin-1-yl)-piperidin-1-yl]-1-(7-methyl-2-oxo-2,3-di-hydro-1H-benzimidazol-5-ylmethyl)-2-oxo-ethyl 4-(2-oxo-1,2,4,5-tetrahydro-1,3-benzodiazepin-3-yl)-piperidine-1-carboxylate |
| (543) 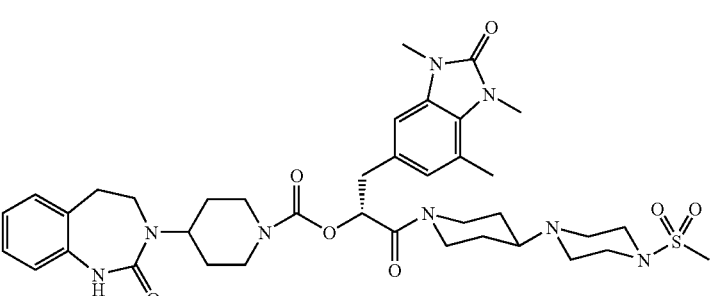 | (R)-2-[4-(4-methanesulphonyl-piperazin-1-yl)-piperidin-1-yl]-2-oxo-1-(1,3,7-trimethyl-2-oxo-2,3-dihydro-1H-benzimidazol-5-ylmethyl)-ethyl 4-(2-oxo-1,2,4,5-tetrahydro-1,3-benzodiazepin-3-yl)-piperidine-1-carboxylate |

-continued

| | Structure | Name |
|---|---|---|
| (544) | | (R)-2-[4-(4-methanesulphonyl-piperazin-1-yl)-piperidin-1-yl]-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (545) | | (R)-2-[4-(4-methanesulphonyl-piperazin-1-yl)-piperidin-1-yl]-2-oxo-1-quinoxalin-6-yl-methyl-ethyl 4-(2-oxo-1,2,4,5-tetrahydro-1,3-benzodiazepin-3-yl)-piperidine-1-carboxylate |
| (546) | | (R)-1-(4,5-dimethyl-3,4-dihydro-2H-1,4-benzoxazin-7-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (547) | | (R)-1-(4,5-dimethyl-3,4-dihydro-2H-1,4-benzoxazin-7-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |
| (548) | | (R)-1-(4,5-dimethyl-3,4-dihydro-2H-1,4-benzoxazin-7-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate |

| Structure | Name |
|---|---|
| (549) 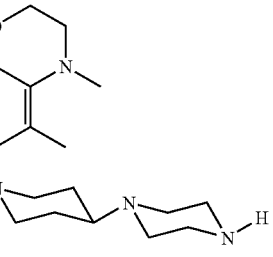 | (R)-1-(4,5-dimethyl-3,4-dihydro-2H-1,4-benzoxazin-7-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (550) 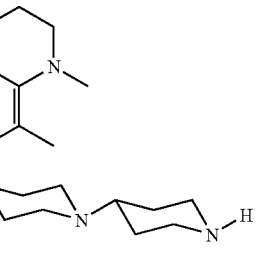 | (R)-1-(4,5-dimethyl-3,4-dihydro-2H-1,4-benzoxazin-7-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (551) 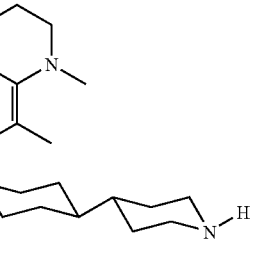 | (R)-2-4,4'-bipiperidinyl-1-yl-1-(4,5-dimethyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (552) 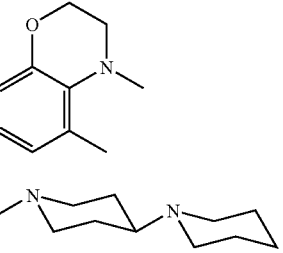 | (R)-2-1,4'-bipiperidinyl-1'-yl-1-(4,5-dimethyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (553) 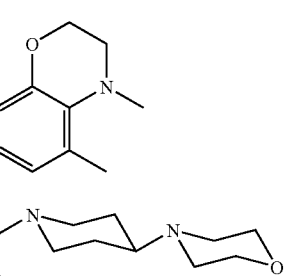 | (R)-1-(4,5-dimethyl-3,4-dihydro-2H-1,4-benzoxazin-7-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (554) 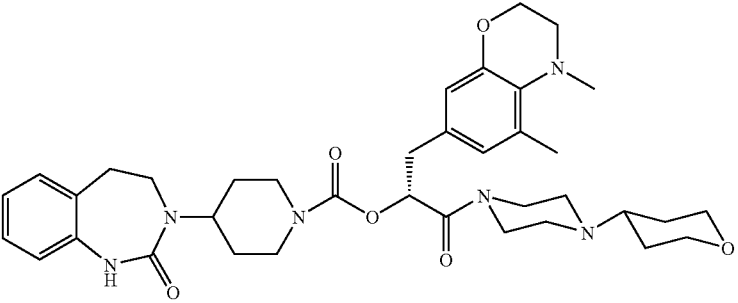 | (R)-1-(4,5-dimethyl-3,4-dihydro-2H-1,4-benzoxazin-7-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (555) 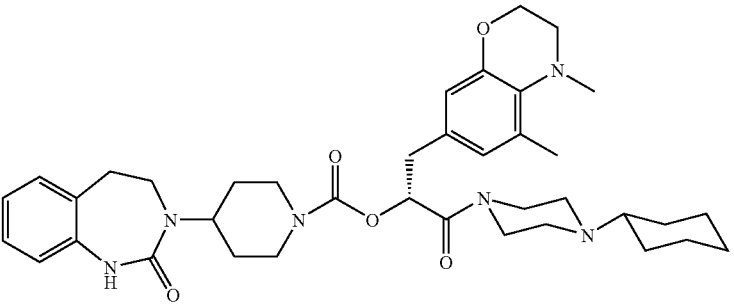 | (R)-2-(4-cyclohexyl-piperazin-1-yl)-1-(4,5-dimethyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (556) 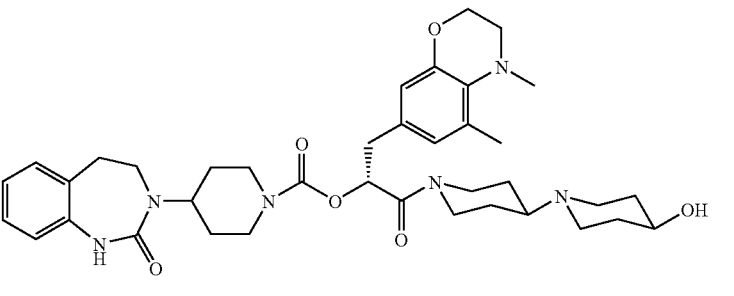 | (R)-1-(4,5-dimethyl-3,4-dihydro-2H-1,4-benzoxazin-7-ylmethyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (557) 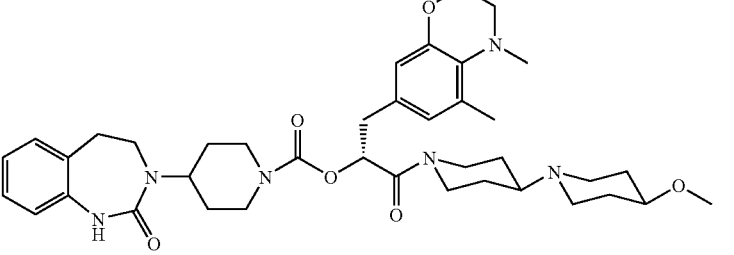 | (R)-1-(4,5-dimethyl-3,4-dihydro-2H-1,4-benzoxazin-7-ylmethyl)-2-(4-methoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (558) 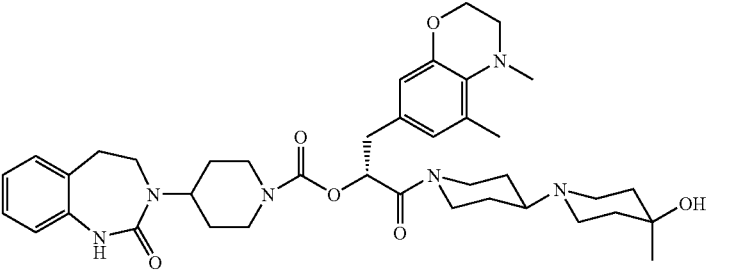 | (R)-1-(4,5-dimethyl-3,4-dihydro-2H-1,4-benzoxazin-7-ylmethyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (559) 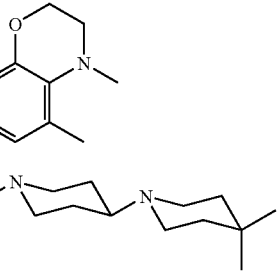 | (R)-2-(4,4-dimethyl-1,4'-bipiperidinyl-1'-yl)-1-(4,5-dimethyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (560) 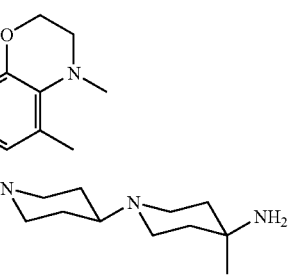 | (R)-2-(4-amino-4-methyl-1,4'-bipiperidinyl-1'-yl)-1-(4,5-dimethyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |
| (561) 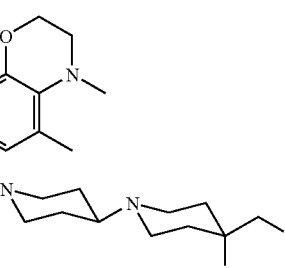 | (R)-1-(4,5-dimethyl-3,4-dihydro-2H-1,4-benzoxazin-7-ylmethyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate |
| (562) 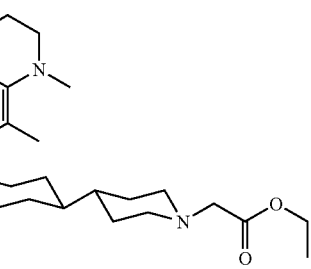 | (R)-1-(4,5-dimethyl-3,4-dihydro-2H-1,4-benzoxazin-7-ylmethyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate |
| (563) 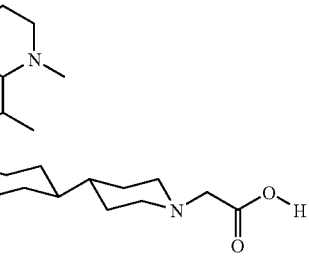 | (R)-2-(1'-carboxymethyl-4,4'-bipiperidinyl-1-yl)-1-(4,5-dimethyl-3,4-dihydro-2H-1,4-benzoxazin-7-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (564) 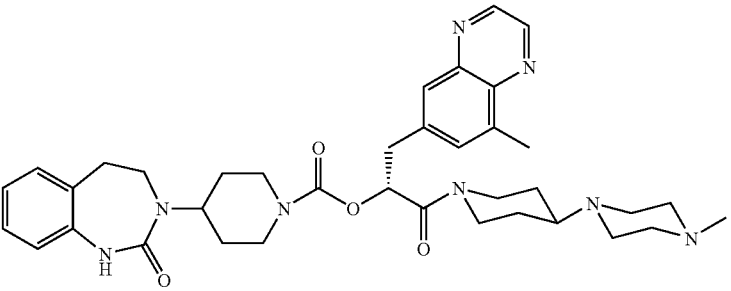 | (R)-2-[4-(4-methyl-piperazin-1-yl)-piperidin-1-yl]-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (565) 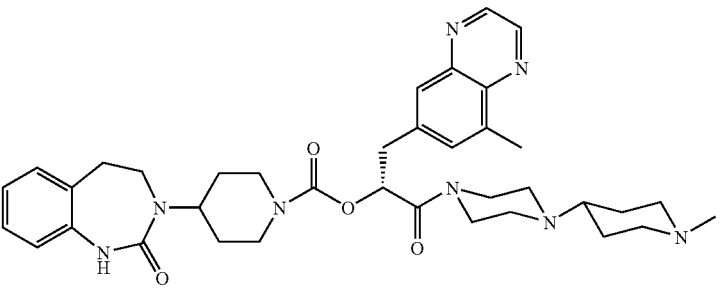 | (R)-2-[4-(1-methyl-piperidin-4-yl)-piperazin-1-yl]-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (566) 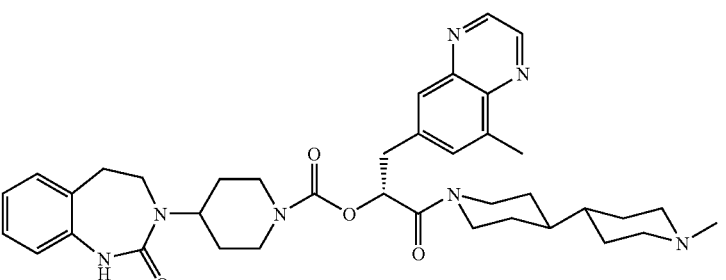 | (R)-2-(1'-methyl-4,4'-bipiperidinyl-1-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (567) 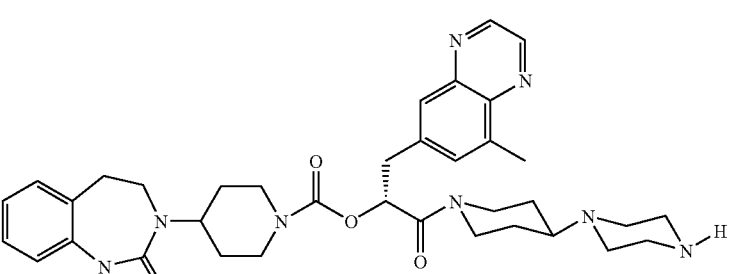 | (R)-1-(8-methyl-quinoxalin-6-ylmethyl)-2-oxo-2-(4-piperazin-1-yl-piperidin-1-yl)-ethyl 4-(2-oxo-1,2,4,5-tetrahydro-1,3-benzodiazepin-3-yl)piperidine-1-carboxylate |
| (568) 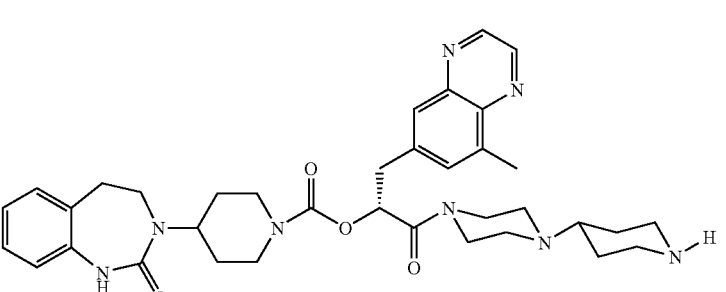 | (R)-1-(8-methyl-quinoxalin-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |

-continued

| Structure | Name |
|---|---|
| (569) 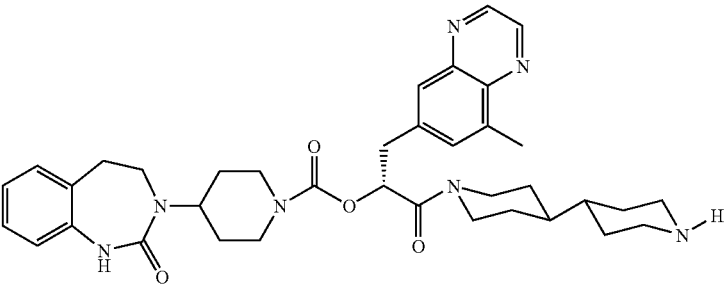 | (R)-2-4,4'-bipiperidinyl-1-yl-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (570) 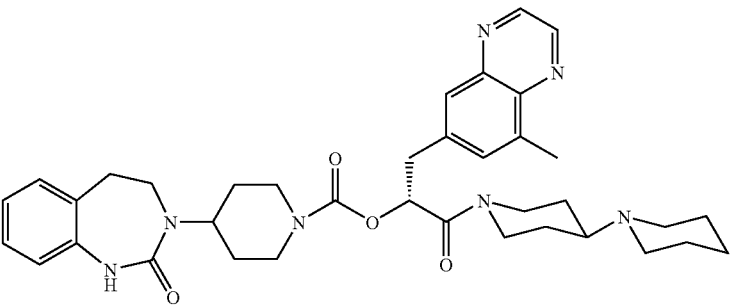 | (R)-2-1,4'-bipiperidinyl-1'-yl-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (571) 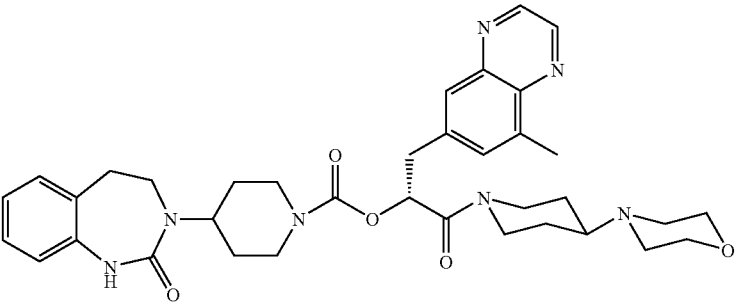 | (R)-1-(8-methyl-quinoxalin-6-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (572) 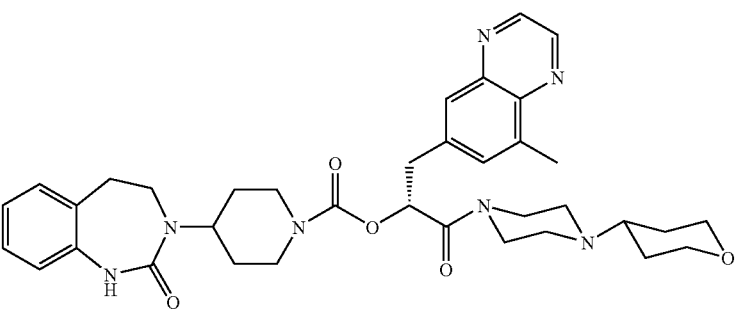 | (R)-1-(8-methyl-quinoxalin-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (573) 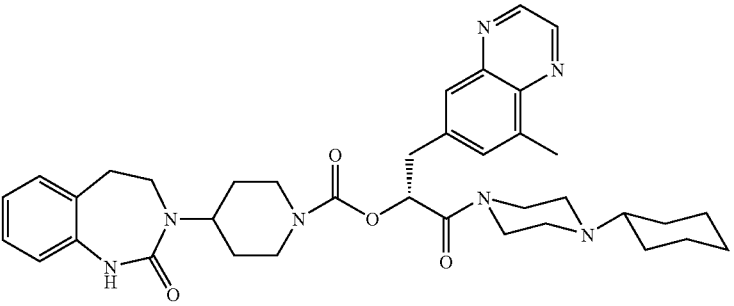 | (R)-2-(4-cyclohexyl-piperazin-1-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |

| | Structure | Name |
|---|---|---|
| (574) | | (R)-2-(4-hydroxy-1,4'-bipiperidinyl-1'-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (575) | | (R)-2-(4-methoxy-1,4'-bipiperidinyl-1'-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (576) | | (R)-2-(4-hydroxy-4-methyl-1,4'-bipiperidinyl-1'-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (577) | | (R)-2-(4,4-dimethyl-1,4'-bipiperidinyl-1'-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (578) | | (R)-2-(4-amino-4-methyl-1,4'-bipiperidinyl-1'-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (579) | carboxylate (R)-2-(4-hydroxy-4-hydroxymethyl-1,4'-bipiperidinyl-1'-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1- |
| (580) | (R)-2-(1'-ethoxycarbonylmethyl-4,4'-bipiperidinyl-1-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (581) | (R)-2-(1'-carboxymethyl-4,4'-bipiperidinyl-1-yl)-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate |
| (582) | (R)-1-(8-methyl-imidazo[1,2-a]pyridin-6-yl-methyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate |
| (583) | (R)-1-(8-methyl-imidazo[1,2-a]pyridin-6-yl-methyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate |

-continued

| Structure | Name |
|---|---|
| (584) | (R)-2-(1'-methyl-4,4'-bipiperidinyl-1-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (585) | (R)-1-(8-methyl-imidazo[1,2-a]pyridin-6-yl-methyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate |
| (586) | (R)-1-(8-methyl-imidazo[1,2-a]pyridin-6-yl-methyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate |
| (587) | (R)-2-4,4'-bipiperidinyl-1-yl-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (588) | (R)-2-1,4'-bipiperidinyl-1'-yl-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |

-continued

| | Structure | Name |
|---|---|---|
| (589) | 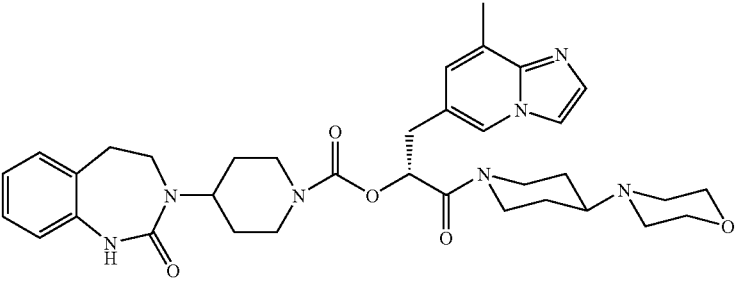 | (R)-1-(8-methyl-imidazo[1,2-a]pyridin-6-yl-methyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate |
| (590) | 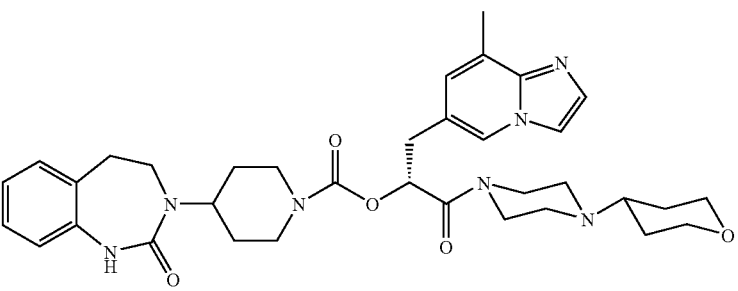 | (R)-1-(8-methyl-imidazo[1,2-a]pyridin-6-yl-methyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate |
| (591) | 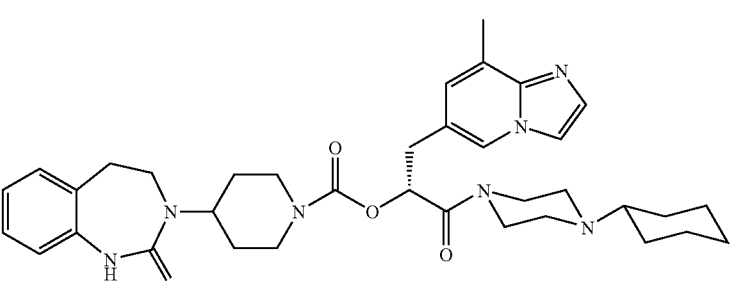 | (R)-2-(4-cyclohexyl-piperazin-1-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (592) | 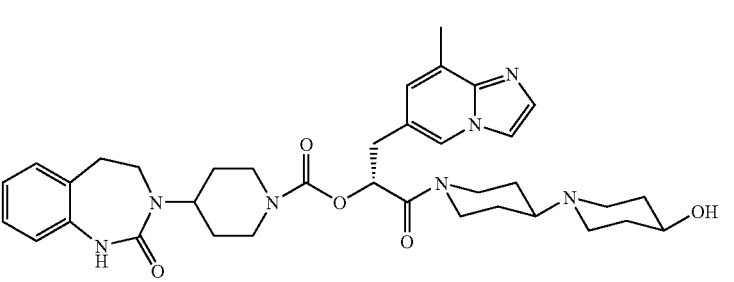 | (R)-2-(4-hydroxy-1,4'-bipiperidinyl-1'-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (593) | 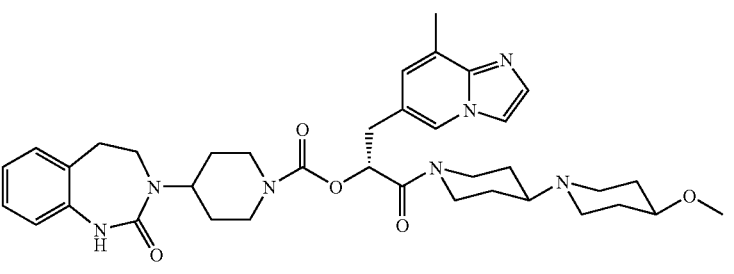 | (R)-2-(4-methoxy-1,4'-bipiperidinyl-1'-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (594) | (R)-2-(4-methoxy-1,4'-bipiperidinyl-1'-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (595) | (R)-2-(4-hydroxy-4-methyl-1,4'-bipiperidinyl-1'-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (596) | (R)-2-(4,4-dimethyl-1,4'-bipiperidinyl-1'-yl)-1-(8-methyl-imidazo[1,2-a]pyridin-6-yl-methyl)-2-oxo-ethyl 4-(2-oxo-1,2,4,5-tetrahydro-1,3-benzodiazepin-3-yl)-piperidine-1-carboxylate |
| (597) | (R)-2-(4-amino-4-methyl-1,4'-bipiperidinyl-1'-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (598) | (R)-2-(4-hydroxy-4-hydroxymethyl-1,4'-bipiperidinyl-1'-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (599) | (R)-2-(1'-ethoxycarbonylmethyl-4,4'-bipiperidinyl-1-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (600) 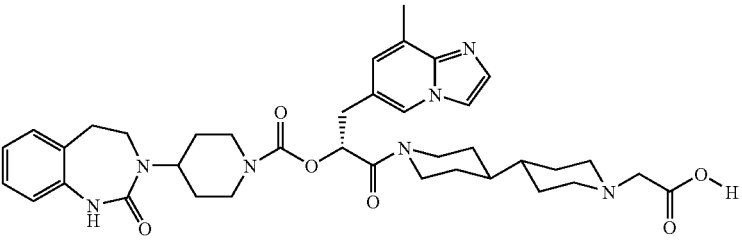 | (R)-2-(1'-carboxymethyl-4,4'-bipiperidinyl-1-yl)-1-(8-methyl-imidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate |
| (601) 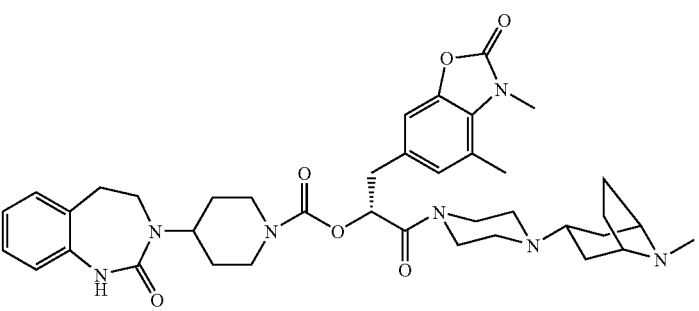 | (R)-1-(3,4-dimethyl-2-oxo-2,3-dihydro-benzoxazol-6-ylmethyl)-2-[4-(8-methyl-8-aza-bicyclo[3.2.1]oct-3-yl)-piperazin-1-yl]-2-oxo-ethyl 4-(2-oxo-1,2,4,5-tetrahydro-1,3-benzodiazepin-3-yl)-piperidine-1-carboxylate |
| (602) 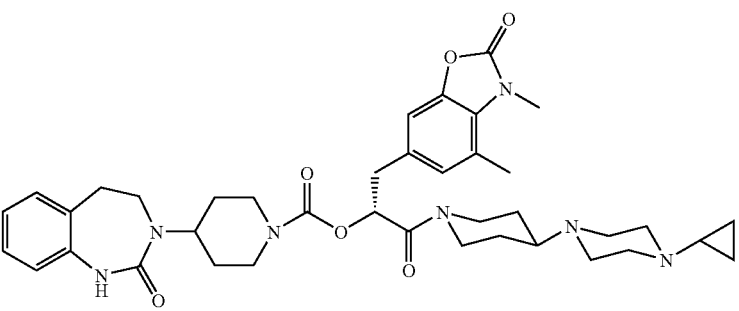 | (R)-2-[4-(4-cyclopropyl-piperazin-1-yl)-piperidin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate |
| (603) 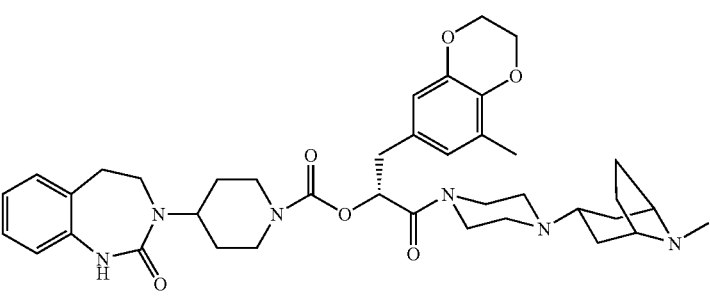 | (R)-2-[4-(8-methyl-8-aza-bicyclo[3.2.1]oct-3-yl)-piperazin-1-yl]-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (604) 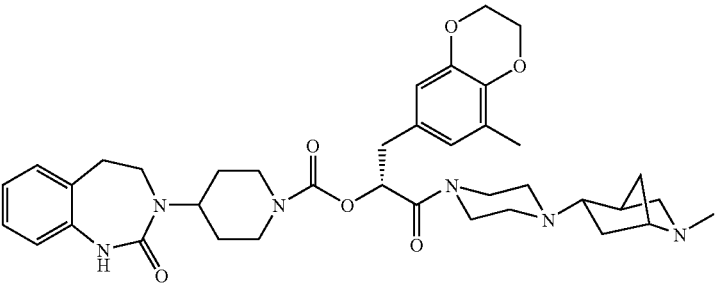 | (R)-2-[4-(5-methyl-2,5-diaza-bicyclo[2.2.1]-hept-2-yl)-piperidin-1-yl]-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |

-continued

| Structure | Name |
|---|---|
| (605) 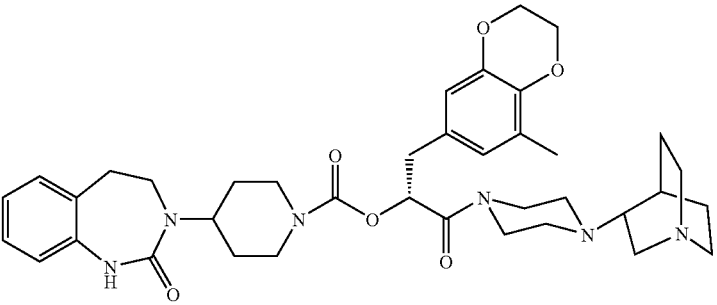 | (R)-2-[4-(1-aza-bicyclo[2.2.2]oct-3-yl)-piperazin-1-yl]-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate |
| (606) 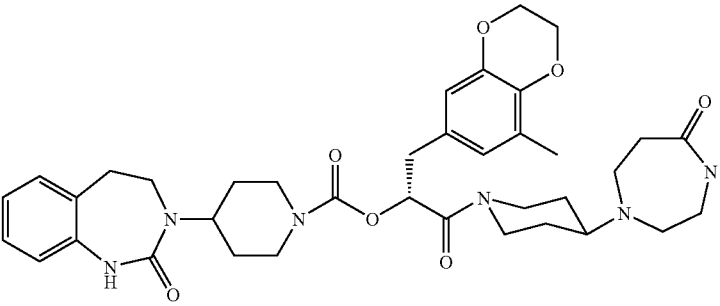 | (R)-1-(8-methyl-2,3-dihydro-1,4-benzodioxin-6-ylmethyl)-2-oxo-2-[4-(5-oxo-perhydro-1,4-diazepin-1-yl)-piperidin-1-yl]-ethyl 4-(2-oxo-1,2,4,5-tetrahydro-1,3-benzodiazepin-3-yl)-piperidine-1-carboxylate | the enantiomers, the diastereomers and the salts thereof, while the compounds (1) (R)-1-(7-methyl-1H-indazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (2) (R)-1-(4-amino-3-methyl-5-nitro-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (3) (R)-1-(3,4-diamino-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (4) (R)-1-(7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (5) (R)-2-4,4'-bipiperidinyl-1-yl-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate, (6) (R)-1-(7-methyl-1H-benzimidazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate, (7) (R)-1-(2,7-dimethyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (8) (R)-1-(7-methyl-2-oxo-2,3-dihydro-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (9) (R)-1-(2-cyclopropyl-7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate,

(10) (R)-2-[4-(4-methyl-piperazin-1-yl)-piperidin-1-yl]-1-(7-methyl-2-trifluoromethyl-1H-benzimidazol-5-ylmethyl)-2-oxo-ethyl 4-(2-oxo-1,2,4,5-tetrahydro-1,3-benzodiazepin-3-yl)-piperidine-1-carboxylate,

(11) (R)-1-(2-methoxy-7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate,

(12) (R)-2-[4-(4-methyl-piperazin-1-yl)-piperidin-1-yl]-1-(8-methyl-quinoxalin-6-yl-methyl)-2-oxo-ethyl 4-(2-oxo-1,2,4,5-tetrahydro-1,3-benzodiazepin-3-yl)-piperidine-1-carboxylate,

(13) (R)-1-{2-[(Z)-cyanimino]-7-methyl-2,3-dihydro-1H-benzimidazol-5-ylmethyl}-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate,

(14) (R)-1-(7-methyl-1H-benzotriazol-5-ylmethyl)-2-[4-(4-methyl-piperazin-1yl)-piperidin-1-yl]-2-oxo-ethyl 4-(2-oxo-1,2,4,5-tetrahydro-1,3-benzodiazepin-3-yl)-piperidine-1-carboxylate,

(15) (R)-2-(1'-methanesulphonyl-4,4'-bipiperidinyl-1-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate,

(16) (R)-1-(4-methyl-2-oxo-2,3-dihydro-benzoxazol-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate,

(17) (R)-1-(4-methyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate,

(18) (R)-2-(4-amino-4-methyl-1,4'-bipiperidinyl-1'-yl)-1-(4-methyl-2-oxo-2,3-dihydro-benzoxazol-6-ylmethyl)-2-

(19) (R)-1-(4-methyl-2-oxo-2,3-dihydro-benzoxazol-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate,

(20) (R)-2-(1'-methanesulphonyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(21) (R)-1-(3,4-dimethyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate,

(22) (R)-1-(3,4-dimethyl-2-oxo-2,3-dihydro-benzoxazol-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate,

(23) (R)-1-(3,4-dimethyl-2-oxo-2,3-dihydro-benzoxazol-6-ylmethyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate,

(24) (R)-1-(3,4-dimethyl-2-oxo-2,3-dihydro-benzoxazol-6-ylmethyl)-2-(4-hydroxy-1,4'-bipiperidinyl-1'-yl)-2-oxo-ethyl 4-(2-oxo-1,2,4,5-tetrahydro-1,3-benzodiazepin-3-yl)-piperidine-1-carboxylate,

(25) (R)-1-(3,4-dimethyl-2-oxo-2,3-dihydro-benzoxazol-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate,

(26) (R)-1-(3,4-dimethyl-2-oxo-2,3-dihydro-benzoxazol-6-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate,

(27) (R)-1-(3,4-dimethyl-2-oxo-2,3-dihydro-benzoxazol-6-ylmethyl)-2-[4-(8-methyl-8-aza-bicyclo[3.2.1]oct-3-yl)-piperazin-1-yl]-2-oxo-ethyl 4-(2-oxo-1,2,4,5-tetrahydro-1,3-benzodiazepin-3-yl)-piperidine-1-carboxylate,

(28) (R)-1-(3,4-dimethyl-2-oxo-2,3-dihydro-benzoxazol-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate,

(29) (R)-2-4,4'-bipiperidinyl-1-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(30) (R)-1-(3,4-dimethyl-2-oxo-2,3-dihydro-benzoxazol-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate,

(31) (R)-2-(4-amino-4-methyl-1,4'-bipiperidinyl-1'-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(32) (R)-1-(3,4-dimethyl-2-oxo-2,3-dihydro-benzoxazol-6-ylmethyl)-2-(1'-ethoxy-carbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate,

(33) (R)-2-(1'-carboxymethyl-4,4'-bipiperidinyl-1-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(34) (R)-2-1,4'-bipiperidinyl-1'-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(35) (R)-2-[4-(4-cyclopropyl-piperazin-1-yl)-piperidin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(36) (R)-2-(4-cyclohexyl-piperazin-1-yl)-1-(3,4-dimethyl-2-oxo-2,3-dihydro-benzoxazol-6-yl methyl)-2-oxo-ethyl 4-(2-oxo-1,2,4,5-tetrahydro-1,3-benzodiazepin-3-yl)-piperidine-1-carboxylate,

(37) (R)-1-(3,4-dimethyl-2-oxo-2,3-dihydro-benzoxazol-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate,

(38) (R)-1-(3,4-dimethyl-2-oxo-2,3-dihydro-benzoxazol-6-ylmethyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate,

(39) (R)-1-(2,3-dihydro-1,4-benzodioxin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate,

(40) (R)-1-(8-methyl-2,3-dihydro-1,4-benzodioxin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate,

(41) (R)-2-(1'-methyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(42) (R)-2-(4-hydroxy-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(43) (R)-1-(8-methyl-2,3-dihydro-1,4-benzodioxin-6-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate,

(44) (R)-1-(8-methyl-2,3-dihydro-1,4-benzodioxin-6-ylmethyl)-2-oxo-2-[4-(5-oxo-perhydro-1,4-diazepin-1-yl)-piperidin-1-yl]-ethyl 4-(2-oxo-1,2,4,5-tetrahydro-1,3-benzodiazepin-3-yl)-piperidine-1-carboxylate,

(45) (R)-2-(1'-ethoxycarbonylmethyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(46) (R)-1-(8-methyl-2,3-dihydro-1,4-benzodioxin-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate,

(47) (R)-2-1,4'-bipiperidinyl-1'-yl-1-(8-methyl-2,3-dihydro-1,4-benzodioxin-6-yl-methyl)-2-oxo-ethyl 4-(2-oxo-1,2,4,5-tetrahydro-1,3-benzodiazepin-3-yl)-piperidine-1-carboxylate,

(48) (R)-2-[4-(8-methyl-8-aza-bicyclo[3.2.1]oct-3-yl)-piperazin-1-yl]-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(49) (R)-2-[4-(5-methyl-2,5-diaza-bicyclo[2.2.1]hept-2-yl)-piperidin-1-yl]-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(50) (R)-2-[4-(1-aza-bicyclo[2.2.2]oct-3-yl)-piperazin-1-yl]-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(51) (R)-1-(8-methyl-2,3-dihydro-1,4-benzodioxin-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate,

(52) (R)-1-(8-methyl-2,3-dihydro-1,4-benzodioxin-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate,

(53) (R)-2-(1'-carboxymethyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(54) (R)-2-(4-amino-4-methyl-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(55) (R)-2-(1'-methanesulphonyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(56) (R)-2-[4-(4-methanesulphonyl-piperazin-1-yl)-piperidin-1-yl]-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate,

(57) (R)-1-(8-methyl-imidazo[1,5-a]pyridin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate,

(58) (R)-2-(1'-methyl-4,4'-bipiperidinyl-1-yl)-1-(8-methylimidazo[1,2-a]pyridin-6-ylmethyl)-2-oxo-ethyl 4-(2-oxo-1,2,4,5-tetrahydro-1,3-benzodiazepin-3-yl)-piperidine-1-carboxylate,

(59) (R)-1-(8-methyl-imidazo[1,2-a]pyridin-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, the enantiomers, the diastereomers and the salts thereof are of exceptional importance.

The compounds of general formula (I) are prepared by methods known in principle. The following processes have proved particularly suitable for preparing the compounds of general formula (I) according to the invention:

(a) In order to prepare compounds of general formula (I) wherein all the groups are as hereinbefore defined:

coupling a carboxylic acid of general formula

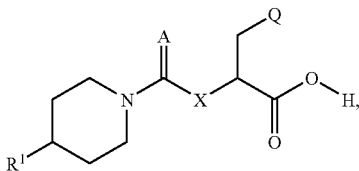

(III)

wherein all the groups are as hereinbefore defined, with an amine of general formula HNR²R³, wherein R² and R³ are as hereinbefore defined. Before the reaction, any carboxylic acid functions, primary or secondary amino functions or hydroxy functions present in a compound of formula (III) and/or in the groups R² and R³ of the amine of formula HNR²R³ may be protected by conventional protecting groups and after the reaction any protecting groups used may be cleaved using methods familiar to those skilled in the art.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N-N,N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (III) which is to be coupled and monoisobutyl carbonate is obtained, using isobutyl chlorocarbonate in the presence of bases such as 4-methylmorpholine or 4-ethylmorpholine. The preparation of this mixed anhydride and the coupling with amines are carried out in a one-pot process, using the above-mentioned solvents and at temperatures between −20 and +25° C., preferably 0° C. and +25° C.

(b) In order to prepare compounds of general formula (I) wherein all the groups are as hereinbefore defined:

coupling a compound of general formula

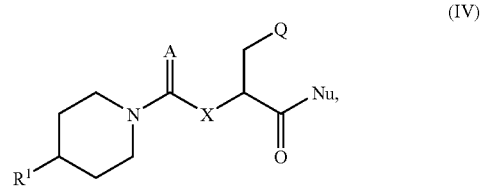

(IV)

with an amine of general formula HNR²R³, wherein all the groups are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group. Before the reaction any carboxylic acid functions, primary or secondary amino functions or hydroxy functions present in a compound of formula (IV) and/or in the groups $R^2$ and $R^3$ of the amine of formula $HNR^2R^3$ may be protected by conventional protecting groups and after the reaction any protecting groups used may be cleaved again using methods familiar to those skilled in the art.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2.2.2]octane or 1,8-diazabicyclo[5.4.0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula (I) according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Ra-cemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The needed as starting compounds hydroxycarboxylic acids of general formula (III) are obtained by reacting piperidines of general formula

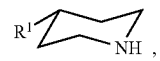
(V)

wherein $R^1$ is as hereinbefore defined, with carbonic acid derivatives of general is formula

(VI)

wherein $Y_1$ and $Y_2$ represent nucleofugic groups which may be identical or different, preferably the chlorine atom, the p-nitrophenoxy or trichloromethoxy group, if A denotes the oxygen atom, or the chlorine atom, if A denotes the sulphur atom, and with compounds of general formula

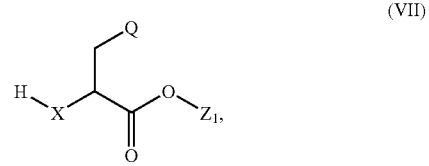
(VII)

wherein X and Q are as hereinbefore defined and $Z_1$ denotes a protective group for a carboxy group, for example a $C_{1-6}$-alkyl or benzyl group, while the alkyl groups may be straight-chain or branched and the benzyl group may be substituted by one or two methoxy groups. Preferably $Z_1$ is the methyl, ethyl, tert-butyl or benzyl group. Before the reaction any carboxylic acid functions, primary or secondary amino functions or hydroxy functions present in the group $R^1$ of a compound of formula (V) and/or in a compound of formula (VII) may be protected by conventional protecting groups and after the reaction any protecting groups used may be cleaved again by methods familiar to those skilled in the art.

In a first step the compounds of general formula (V) are reacted in a solvent, for example in dichloromethane, THF, pyridine or mixtures thereof, at a temperature from −20 to 50° C. in the presence of a base, for example triethylamine, pyridine or ethyidiisopropylamine, with the carbonic acid derivatives of general formula (VI). The resulting intermediate may be purified or reacted further without purification. The reaction of these intermediates with compounds of general formula (VII) is also carried out in one of the above-mentioned solvents, and at the temperatures specified above, in the presence of a base, such as triethylamine or pyridine, with or without the addition of an activating reagent, such as e.g. 4-dimethylaminopyridine. To activate them the compounds of general formula (VII) may also be deprotonated using a metal hydride, such as e.g. NaH or KH, while in this case the base or the activating reagent may be omitted.

The starting compounds of formula (V) and (VI) are either commercially obtainable, known from the literature or may be prepared by methods known from the literature.

If the group X in compounds of general formula (VII) denotes the oxygen atom, the hydroxycarboxylic acids of general formula

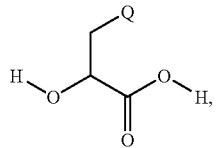
(VIII)

which are needed for the synthesis may be obtained from compounds of general formula

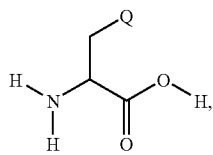
(IX)

while Q in both formulae is as hereinbefore defined.

By diazotising compounds of general formula (IX) with a suitable diazotising reagent, preferably sodium nitrite in an acid medium, it is possible to obtain the compounds of general formula (VIII). If enantiomerically pure compounds are used the corresponding enantiomerically pure hydroxycarboxylic acid compounds are obtained, the configuration being retained as the reaction proceeds.

An alternative method of obtaining compounds of general formula (VIII), if Q is not bound by a nitrogen atom, comprises reacting aldehydes of general formula (X) with N-acetylglycine in acetic anhydride as solvent in the presence of alkali metal acetate, preferably sodium or potassium acetate, at a suitable temperature, preferably at 80-130° C.

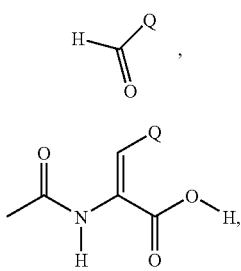
(X)

(XI)

The azlactones obtained as primary product are hydrolysed without being isolated to form the compounds of general formula (XI). By further reaction in the presence of aqueous inorganic acids, such as sulphur, phosphorus or hydrochloric acid, but preferably hydrochloric acid, compounds of general formula (XII) are obtained. These are then converted with suitable reducing agents into the compounds of general formula (VIII).

(XII)

Suitable reducing agents are alkali metal borohydrides, such as sodium or potassium borohydride. Other suitable reducing agents are chlorodialkylboranes, such as chlorodicyclohexylborane. If chiral chlorodialkylboranea, such as e.g. B-chlorodiisopinocampheylborane, are used, the compounds of general formula (VIII) may be isolated in enantiomerically pure form.

If Q is not bound by a nitrogen atom, another method of obtaining compounds of general formula (VIII) comprises alkylating compounds of formula

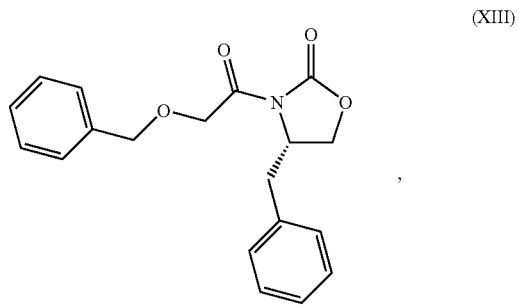
(XIII)

with compounds of general formula

(XIV)

wherein Hal denotes a chlorine, bromine or iodine atom, and Q is as hereinbefore defined, analogously to methods known from the literature (Michael T. Crimmins, Kyle A. Emmitte and Jason D. Katz, Org. Lett. 2, 2165-2167 [2000]). The diastereomeric products formed may then be separated by physicochemical methods, preferably by chromatographic methods or recrystallisation. The hydrolytic cleaving of the chiral auxiliary and cleaving of the benzyl protective group also provides a way of obtaining enantiomerically pure hydroxycarboxylic acid compounds of general formula (VII). The further reaction of compounds of general formula (VIII) to compounds of general formula (VII) is carried out in an alcoholic medium, preferably in methanol or ethanol, in the presence of a suitable acid, such as hydrochloric acid. Alternatively, the reaction may be carried out by reaction in alcoholic solvents, preferably methanol, with thionylchloride.

If the group X in compounds of general formula (VII) denotes the sulphur atom, the thiocarboxylic acids of general formula

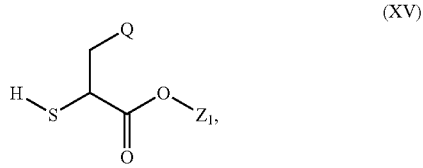

(XV)

needed for the synthesis, wherein Q is as hereinbefore defined and $Z_1$ denotes a protective group for a carboxy group as described in process (a), are obtained from compounds of general formula (VII) wherein X denotes the oxygen atom.

The corresponding alkylthiocarboxylic acid esters of these compounds may be obtained by Mitsunobu reaction of the compounds of general formula (VII) with $C_{1-6}$-alkylthiocarboxylic acids, while the alkyl chain may be straight-chain or branched but preferably denotes the methyl group. They may be hydrolysed by known methods to form the compounds of general formula (XV) (Bert Strijtveen and Richard M. Kellogg, J. Org. Chem. 51, 3664-3671 [1986]).

All the compounds of general formula (I) which contain primary or secondary amino, hydroxy or hydroxycarbonyl functions, are preferably obtained from precursors with protective groups. Examples of protective groups for amino functions include the benzyloxycarbonyl, 2-nitrobenzyloxycarbonyl, 4-nitro-benzyl-oxycarbonyl, 4-methoxy-benzyloxycarbonyl, 2-chloro-benzyloxycarbonyl, 3-chloro-benzyloxycarbonyl, 4-chloro-benzyloxycarbonyl, 4-biphenylyl-α,α-dimethyl-benzyl-oxycarbonyl or 3,5-dimethoxy-α,α-dimethyl-benzyloxycarbonyl group, a alkoxycarbonyl group with a total of 1 to 5 carbon atoms in the alkyl moiety, for example the methoxycarbonyl, ethoxycarbonyl, n-propoxycarbonyl, iso-propoxycarbonyl, n-butoxycarbonyl, 1-methylpropoxycarbonyl, 2-methylpropoxy-carbonyl or tert-butyloxycarbonyl group, the allyloxycarbonyl, 2,2,2-trichloro-(1,1-dimethylethoxy)carbonyl or 9-fluorenylmethoxycarbonyl group or a formyl, acetyl or trifluoracetyl group.

Examples of protective groups for hydroxy functions include the trimethylsilyl, triethylsilyl, triisopropyl, tert-butyldimethylsilyl or tert-butyldiphenylsilyl group, a tert-butyl, benzyl, 4-methoxybenzyl or 3,4-dimethoxybenzyl group.

Examples of protective groups for hydroxycarbonyl functions include an alkyl group with a total of 1 to 5 carbon atoms, for example the methyl, ethyl, n-propyl, isopropyl, n-butyl, tert-butyl, allyl, 2,2,2-trichloroethyl, benzyl or 4-methoxybenzyl group.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, if they contain a carboxylic acid function, the new compounds of formula (I) may be converted into the addition salts thereof with inorganic or organic bases, particularly, for pharmaceutical use, into their physiologically acceptable addition salts. Suitable bases for this include for example sodium hydroxide, potassium hydroxide, ammonia, cyclohexylamine, dicyclohexylamine, ethanolamine, diethanolamine and triethanolamine.

The present invention relates to racemates if the compounds of general formula (I) have only one chiral element. However, the application also includes the individual diastereomeric pairs of antipodes or mixtures thereof which are obtained if there is more than one chiral element in the compounds of general formula (I), as well as the individual optically active enantiomers of which the above-mentioned racemates are made up.

Also included in the subject matter of this invention are the compounds according to the invention, including the salts thereof, in which one or more hydrogen atoms, for example one, two, three, four or five hydrogen atoms, are replaced by deuterium.

The new compounds of general formula (I) and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 μl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 μl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 μM human CGRP-alpha during incubation.

The concentration binding curves are analysed using computer-aided non-linear curve matching.

The compounds mentioned hereinbefore show IC$_{50}$ values <10000 nM in the test described.

B. CGRP Antagonism in SK-N-MC cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 µl of 1 M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the $pA_2$ values of antagonistically acting substances are determined graphically.

The compounds of general formula I exhibit CGRP-antagonistic properties in the in vitro test model described, in a dosage range between $10^{-12}$ and $10^{-5}$ M.

In view of their pharmacological properties the compounds of general formula I and the salts thereof with physiologically acceptable acids are thus suitable for the acute and prophylactic treatment of headaches, particularly migraine or cluster headaches. Moreover, the compounds of general formula I also have a positive effect on the following diseases: non-insulin-dependent diabetes mellitus ("NIDDM"), complex regional pain syndrome (CRPS1), cardiovascular diseases, morphine tolerance, diarrhoea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and resultant reduced blood supply to the tissues, e.g. shock and sepsis. In addition, the compounds according to the invention have a general pain-relieving effect.

The symptoms of menopausal hot flushes caused by vasodilatation and increased blood flow in oestrogen-deficient women and hormone-treated patients with prostate carcinoma are favourably affected by the CGRP antagonists of the present application in a preventive and acute-therapeutic capacity, this therapeutic approach being distinguished from hormone replacement by the absence of side effects.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. antiemetics, prokinetics, neuroleptics, antidepressants, neurokinin antagonists, angiotensin receptor blockers (angiotensin II antagonists), iNOS inhibitors, AMPA antagonists, anticonvulsants, histamine-H1-receptor antagonists, antimuscarinics, β-blockers, α-agonists and α-antagonists, ergot alkaloids, mild analgesics, non-steroidal antiphlogistics, corticosteroids, calcium antagonists, 5-$HT_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, tenoxicam, zomepirac or the pharmaceutically acceptable salts thereof as well as meloxicam and other selective $COX_2$-inhibitors, such as for example rofecoxib and celecoxib.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, topiramate, riboflavin, montelukast, lisinopril, prochloroperazine, dexamethasone, flunarizine, dextropropoxyphene, meperidine, metoprolol, propranolol, nadolol, atenolol, clonidine, indoramin, carbamazepine, phenytoin, valproate, amitryptiline, lidocaine or diltiazem and other 5-$HT_{1B/1D}$-agonists such as, for example, almotriptan, avitriptan, donitriptan, eletriptan, frovatriptan, naratriptan, rizatriptan, sumatriptan and zolmitriptan.

The dosage of these active substances is expediently 1/5 of the lowest recommended dose to 1/1 of the normally recommended dose, i.e. for example 20 to 100 mg of sumatriptan.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

EXPERIMENTAL SECTION

As a rule, IR, $^1$H-NMR and/or mass spectra have been obtained for the compounds prepared.

Unless otherwise stated, the acid, base and salt solutions used for working up the reaction solutions are aqueous systems of the specified concentrations. Unless otherwise stated, $R_f$-values are obtained using ready-made silica gel TLC plates 60 F254 (E. Merck, Darmstadt, Item no. 1.05714) without chamber saturation.

The $R_f$-values determined under the heading Polygram are obtained using ready-made Polygram SIL G/$UV_{254}$ TLC films (coated with 0.2 mm silica gel) made by Messrs Macherey-Nagel (Düren, Item no. 805 021).

The $R_f$ values determined under the heading Polygram-Alox are obtained using ready-made Polygram Alox N/UV$_{254}$ TLC films (coated with 0.2 mm aluminium oxide) made by Messrs Macherey-Nagel (Düren, Item no. 802 021).

The ratios given for the eluants relate to units by volume of the solvent in question.

The units by volume specified for NH$_3$ refer to a concentrated solution of NH$_3$ in water.

For chromatographic purification, silica gel made by Millipore (MATREX™, 35-70 µm) is used.

For chromatographic purification, aluminium oxide 90 (standardised, E. Merck, Darmstadt, Item no. 1.01097) is used.

The HPLC data provided are measured using the parameters specified below:

Method A:

Analytical column: Zorbax column (Agilent Technologies), SB (Stable Bond) C18; 3.5 µm; 4.6×75 mm; column temperature: 30° C.; flow: 0.8 mL/min; injection volume: 5 µL; detection at 254 nm

| time (min) | percent by volume of water (with 0.1% formic acid) | percent by volume of acetonitrile (with 0.1% formic acid) |
| --- | --- | --- |
| 0 | 95 | 5 |
| 9 | 10 | 90 |
| 10 | 10 | 90 |
| 11 | 95 | 5 |

Method B:

Analytical column: Zorbax column (Agilent Technologies), SB (Stable Bond) C18; 3.5 µm; 4.6×75 mm; column temperature: 30° C.; flow: 1.6 mL/min; injection volume: 5 µL; detection at 254 nm

| time (min) | percent by volume of water (with 0.1% formic acid) | percent by volume of acetonitrile (with 0.1% formic acid) |
| --- | --- | --- |
| 0 | 95 | 5 |
| 4.5 | 10 | 90 |
| 5 | 10 | 90 |
| 5.5 | 90 | 10 |

In preparative HPLC purifications as a rule the same gradients are used as were used to collect the analytical HPLC data.

The products are collected under mass control and the fractions containing the product are combined and freeze-dried.

If no detailed information is given as to the configuration, it is not clear whether it is a pure enantiomer or whether partial or even complete racemisation has occurred.

The following abbreviations are used in the description of the experiments:
abs. absolute
Boc tert.-butoxycarbonyl
CDI N,N'-carbonyldiimidazole
CDT 1,1'-carbonyldi-(1,2,4-triazol)
Cyc cyclohexane
DCM dichloromethane
DMF N,N-dimethylformamide
EtOAc ethyl acetate
EtOH ethanol
semiconc. semiconcentrated
HCl hydrochloric acid
HOAc acetic acid
i. vac. in vacuo (in vacuo)
conc. concentrated
LiOH lithium hydroxide
MeOH methanol
NaCl sodium chloride
NaOH sodium hydroxide
NMP N-methyl-2-pyrrolidinone
PE petroleum ether
RT ambient temperature
TBME tert.-butylmethylether
TBTU 2-(1H-benzotriazol-1-yl)-1,1,3,3-tetramethyluronium-tetrafluoroborate
TFA trifluoroacetic acid
THF tetrahydrofuran A Preparation of the Intermediate Products Amine Component A1

3-piperazin-1-yl-1-aza-bicyclo[2.2.2]octane

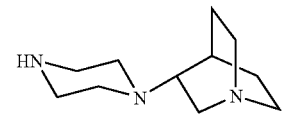

A1a) 3-(4-benzyl-piperazin-1-yl)-1-aza-bicyclo[2.2.2]octane

A solution of 5.0 g (30.0 mmol) 1-aza-bicyclo[2.2.2]octan-3-one (used as the hydrochloride salt) and 5.9 mL (33.3 mmol) N-benzylpiperazine in 300 mL DCM was stirred for 1 h at RT. While cooling with ice 10.0 g (65.9 mmol) sodium triacetoxyborohydride were added batchwise within 1 h and the reaction mixture was stirred overnight at RT. 15% K$_2$CO$_3$ solution was added and the mixture was stirred for 1 h at RT. The aqueous phase was separated off and the organic phase was dried over MgSO$_4$. After the desiccant and solvent had been eliminated the residue was purified by chromatography (silica gel, gradient DCM to MeOH/NH$_3$ 9:1).

Yield: 2.0 g (23% of theory) ESI-MS: (M+H)$^+$=286
R$_f$=0.35 (silica gel, DCM/Cyc/MeOH/NH$_3$ 70:15:15:2)

A1b) 3-piperazin-1-yl-1-aza-bicyclo[2.2.2]octane

A solution of 2.0 g (7.0 mmol) 3-(4-benzyl-piperazin-1-yl)-1-aza-bicyclo[2.2.2]-octane in 30 mL MeOH was combined with 400 mg 10% Pd/C and hydrogenated at 50° C. and 3 bar hydrogen pressure until the theoretical hydrogen uptake had occurred. The catalyst was filtered off and the filtrate was evaporated down i.vac.

Yield: 1.0 g (73% of theory) ESI-MS: (M+H)$^+$=196
R$_f$=0.13 (silica gel, DCM/MeOH/NH$_3$ 75:25:5)

Amine Component A2

[4,4']bipiperidinyl-1-sulphonic acid amide

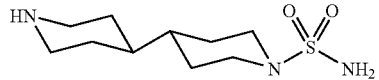

A2a) Carbobenzyloxysulphamoyl Chloride

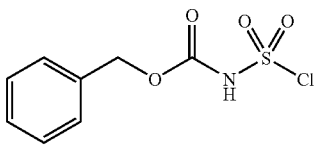

Under a nitrogen atmosphere a solution of 3.63 mL (35.0 mmol) benzylalcohol in 20 mL DCM was added dropwise to a solution of 5.0 g (35.3 mmol) chlorosulphonyl isocyanate in 20 mL DCM cooled to −10° C. and the reaction mixture was stirred for 1 h at this temperature. The reaction solution was evaporated down i.vac., the residue triturated with PE, suction filtered and dried.

Yield: 6.0 g (69% of theory)

A2b)

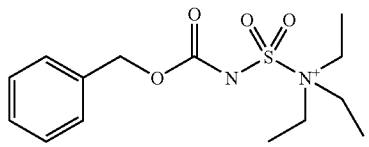

Under a nitrogen atmosphere a solution of 7.67 mL (55.0 mmol) triethylamine in 30 mL EtOAc was added dropwise at RT to a solution of 6.0 g (24.0 mmol) carbobenzyloxysulphamoyl chloride in 60 mL EtOAc and the reaction mixture was stirred for 2 h at RT. The precipitate was filtered and the filtrate was evaporated to dryness. The product was obtained as an oil, which was further reacted without purification.

Yield: 7.8 g (98% of theory)

A2c)

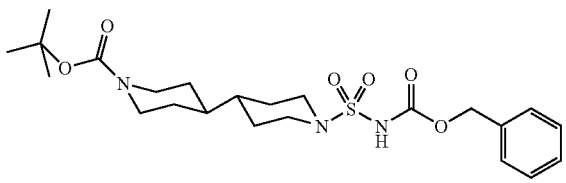

3.5 g (13.0 mmol) tert-butyl [4,4']bipiperidinyl-1-carboxylate were added to a solution of 6.2 g (18.7 mmol) of the crude product from Example A2b in 40 mL dry THF and the reaction mixture was refluxed for 3 h. It was evaporated down i.vac. and the residue was purified by chromatography (silica gel, gradient DCM/MeOH 50:1 to 30:1).

Yield: 4.5 g (72% of theory) ESI-MS: (M+H)$^+$=482 R$_f$=0.39 (Polygram-Alox, DCM/MeOH 50:1)

A2d)

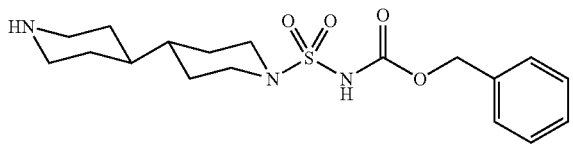

3.2 mL methanolic HCl (1.25 M) were added to a suspension of 1.68 g (3.49 mmol) Example A2c in 50 mL MeOH and the reaction mixture was stirred overnight at RT and for 2 h at 60° C. To complete the reaction a further 1 mL methanolic HCl were added and the mixture was again heated to 60° C. for 1 h. It was evaporated down i.vac., the residue was triturated with diethyl ether, the diethyl ether was decanted and the residue was dried. The product was obtained as the hydrochloride salt.

Yield: 1.51 g (98% of theory) ESI-MS: (M+H)$^+$=382

A2e) [4,4']bipiperidinyl-1-sulphonic acid amide 0.20 g 10% Pd/C were added to a suspension of 1.5 g (3.41 mmol) Example A2d in 40 mL MeOH and the reaction mixture was hydrogenated (for 3 h) at 50° C. and 3 bar hydrogen pressure until the theoretical hydrogen uptake had occurred. The catalyst was filtered off and the filtrate was evaporated to dryness. The product was obtained as the hydrochloride salt.

Yield: 0.85 g (88% of theory) ESI-MS: (M+H)$^+$=248

Amine Component A3

4-hydroxymethyl-[1,4']bipiperidinyl-4-ol

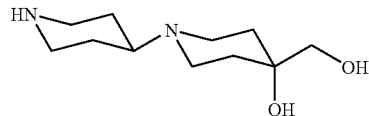

A3a) 1-benzyl-4-hydroxymethyl-piperidin-4-ol

A solution of 200 g AD-Mix-Alpha (Messrs Aldrich, Item no. 39,275-8) in 500 mL water and 300 mL tert-butanol was stirred for 20 min at RT, cooled to 0° C., combined with 13.7 g (144 mmol) methanesulphonic acid amide and 27.0 g (144 mmol) of 1-benzyl-4-methylene-piperidine and, after removal of the cooling bath, stirred for 22 h at RT. 59 g Na$_2$SO$_3$ were added to the reaction mixture and it was stirred for 1 h at RT. 2 L EtOAc and 500 mL saturated NaHCO$_3$ solution were added, the organic phase was separated off and dried over Na$_2$SO$_4$. After the desiccant and solvent had been eliminated the residue was dissolved in 150 mL EtOAc and filtered through Alox. The filtrate was discarded and the product was eluted from the Alox with 1 L MeOH. After the solvent had been eliminated the product was reacted further without purification.

Yield: 26.0 g (82% of theory) ESI-MS: (M+H)$^+$=222 retention time (HPLC): 1.4 min (method B)

A3b) 4-hydroxymethyl-piperidin-4-ol

A suspension of 26.0 g (117 mmol) 1-benzyl-4-hydroxymethyl-piperidin-4-ol and 5.0 g 10% Pd/C in 500 mL MeOH was hydrogenated at 50° C. and 3 bar hydrogen pressure until the theoretical hydrogen uptake had occurred (4 h). The catalyst was filtered off and washed with MeOH. After the solvent had been eliminated the residue was reacted further without purification.

Yield: 15.4 g (100% of theory) ESI-MS: (M+H)$^+$=132 retention time (HPLC): 0.5 min (method B)

A3c) 1'-benzyl-4-hydroxymethyl-[1,4']bipiperidinyl-4-ol

Under a nitrogen atmosphere a solution of 19.9 mL (111 mmol) 1-benzyl-piperidin-4-one, 14.6 g (111 mmol) 4-hydroxymethyl-piperidin-4-ol and 12.2 mL (222 mmol) is AcOH in 300 mL of a THF/MeOH mixture (2:1) was cooled to 0° C. and at this temperature 5.87 g (89 mmol) sodium cyanoborohydride was added batchwise. After the addition had ended the cooling bath was removed and the reaction mixture was stirred overnight at RT. 30 mL of 4 M HCl were added, the mixture was stirred for 1 h at RT and evaporated down i.vac. The residue was combined with 200 mL water and 100 mL 15% K₂CO₃ solution and extracted with 300 mL EtOAc. The organic phase was concentrated by evaporation, the residue was dissolved in 150 mL EtOH and acidified with methanolic HCl (1.25 M). The precipitate formed was filtered, washed with 100 mL EtOH and 100 mL diethyl ether and dried. The product was obtained as the bis-hydrochloride salt.

Yield: 9.6 g (23% of theory) ESI-MS: (M+H)⁺=305 R$_f$=0.25 (silica gel, DCM/MeOH/NH₃ 70:30:3)

A3d) 4-hydroxymethyl-[1,4']bipiperidinyl-4-ol

A suspension of 9.6 g (25.4 mmol, used as the bis-hydrochloride salt) of 1'-benzyl-4-hydroxymethyl-[1,4']bipiperidinyl-4-ol and 2.0 g 10% Pd/C in 300 mL MeOH was hydrogenated at 50° C. and 3 bar hydrogen pressure until the theoretical hydrogen uptake had occurred (2.5 h). The catalyst was filtered off, the filtrate was evaporated down i.vac., the residue was triturated with 200 mL diethyl ether, suction filtered, washed with 100 mL diethyl ether and dried. The product was obtained as the bis-hydrochloride salt.

Yield: 7.0 g (96% of theory) ESI-MS: (M+H)⁺=215

Example 1

(R)-1-(7-methyl-1H-indazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate through activated charcoal and evaporated down i.vac. The residue obtained was recrystallised from 70 mL EtOAc; the mother liquor obtained was evaporated down and the residue was purified by chromatography (silica gel, PE/EtOAc 2:1).

Yield: 6.9 g (67% of theory) ESI-MS: (M+H)⁺=161 R$_f$=0.5 (silica gel, PE/EtOAc 1:1)

1b) 7-methyl-1-(2-trimethylsilanyl-ethanesulphonyl)-1H-indazol-5-carbaldehyde 22.5 mL (160 mmol) triethylamine were added to a solution of 8.5 g (53.07 mmol) 7-methyl-1H-indazol-5-carbaldehyde in 250 mL DCM and then a solution of 15.96 g (79.5 mmol) 2-trimethylsilanyl-ethanesulphonyl chloride in 50 mL DCM was slowly added dropwise and the reaction solution was then stirred overnight at RT. It was evaporated down i.vac. and the residue was purified by chromatography (silica gel, PE/EtOAc 8:2).

Yield: 14.0 g (81% of theory) ESI-MS: (M+H)⁺=325 R$_f$=0.35 (silica gel, PE/EtOAc 8:2)

1c) (Z,E)-2-acetylamino-3-(7-methyl-1H-indazol-5-yl)-acrylic acid

A mixture of 14 g (43.15 mmol) 7-methyl-1-(2-trimethylsilanyl-ethanesulphonyl)-1H-indazol-5-carbaldehyde, 10.12 g (86.4 mmol) N-acetylglycine and 7.09 g (86.4 mmol) NaOAc in 60 mL acetic anhydride was refluxed for 3 h. The reaction mixture was cooled to approx 60° C. and combined dropwise with 40 mL water, stirred for 10 min at this temperature and then heated for 1 h to 95° C. The reaction solution was poured onto 500 mL water, extracted three times with in each case 300 mL EtOAc, the combined organic

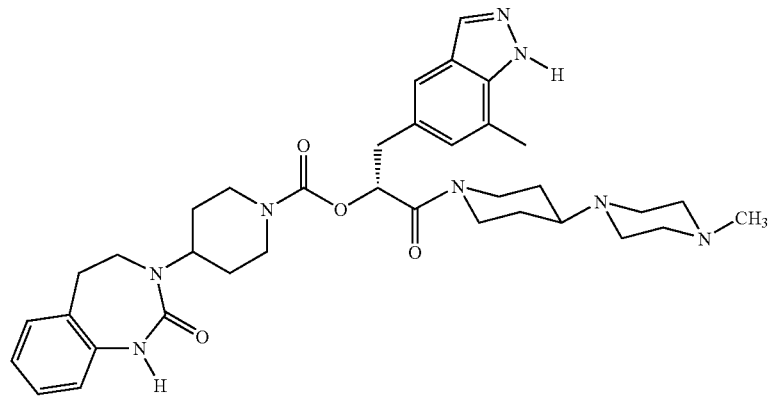

1a) 7-methyl-1H-indazol-5-carbaldehyde

Under an argon atmosphere 2.8 g (70 mmol, 55% in mineral oil) NaH were added batchwise to a solution of 13.5 g (64 mmol) 5-bromo-7-methyl-1H-indazole in 120 mL dry THF, while the temperature rose to approx 35° C. After 15 min the reaction mixture was cooled to −78° C. and within 30 min 100 mL sec. BuLi (140 mmol, 1.4 M in Cyc) were added dropwise. The mixture was kept for a further hour at this temperature, before a solution of 20 mL DMF in 20 mL dry THF was added (strongly exothermic reaction). The reaction mixture was stirred overnight at RT, cooled to 0° C. and 140 mL 2 M HCl was added dropwise under argon (strongly exothermic reaction). The acid solution was adjusted to pH 7-8 with solid NaHCO₃, combined with 500 mL water and extracted with 500 mL EtOAc. The organic phase was separated off, filtered phases were extracted twice with in each case 200 mL of 7% K₂CO₃ solution, the combined aqueous phases were acidified with conc. HCl and extracted three times more with 200 mL EtOAc. The combined organic phases were filtered through activated charcoal and evaporated down i.vac.

A mixture of the desired product and (Z,E)-2-acetylamino-3-(1-acetyl-7-methyl-1H-indazol-5-yl)-acrylic acid was obtained, which was further reacted without purification.

Yield: 2.1 g (19% of theory) ESI-MS: (M+H)⁺=260 retention time (HPLC): 4.2 min (method A)

(Z,E)-2-acetylamino-3-(1-acetyl-7-methyl-1H-indazol-5-yl)-acrylic acid

Yield: 2.1 g (16% of theory) ESI-MS: (M+H)⁺=302 retention time (HPLC): 5.8 min (method A)

1d) 3-(7-methyl-1H-indazol-5-yl)-2-oxo-propionic acid 70 mL 4 M HCl were added to a solution of 4.25 g of the above crude product in 40 mL NMP and the reaction mixture was heated for 3 h to a bath temperature of 100° C. The reaction solution was poured onto 400 mL water, extracted five times with in each case 200 mL EtOAc, the combined organic phases were washed twice with 300 mL water, dried over $Na_2SO_4$ and concentrated by evaporation i.vac.

Yield: 1.3 g (36% of theory) EI-MS: $(M)^+=218$ retention time (HPLC): 5.4 min (method A)

1e) ethyl (R)-2-hydroxy-3-(7-methyl-1H-indazol-5-yl)-propionate

A solution of 2.31 g (7.2 mmol) (1R)—B-chlorodiisopinocampheylborane in 20 mL THF was added dropwise within 30 min to a solution of 1.3 g (5.96 mmol) 3-(7-methyl-1H-indazol-5-yl)-2-oxo-propionic acid and 0.84 mL (7.2 mmol) triethylamine in 50 mL THF cooled to approx. −25° C. and the reaction mixture was kept for 1.5 h at this temperature and then heated to RT within another hour. The mixture was evaporated down i.vac., the residue was taken up in 100 mL 4 M ethanolic HCl and stirred overnight at RT. 200 mL EtOAc and 200 mL 15% $K_2CO_3$ solution were added, the organic phase was separated off and dried over $Na_2SO_4$. After the desiccant and solvent had been eliminated the residue was purified chromatographically by HPLC.

Yield: 0.45 g (30% of theory) ESI-MS: $(M+H)^+=249$ retention time (HPLC): 5.8 min (method A)

1f) tert.-butyl 5-((R)-2-ethoxycarbonyl-2-hydroxy-ethyl)-7-methyl-indazol-1-carboxylate A solution of 397 mg (1.82 mmo) Boc-anhydride in 5 mL DCM was slowly added dropwise to a solution of 450 mg (1.81 mmol) ethyl (R)-2-hydroxy-3-(7-methyl-1H-indazol-5-yl)-propionate, 55 mg (0.45 mmol) DMAP and 0.27 mL (1.82 mmol) triethylamine in 15 mL DCM and the reaction solution was stirred overnight at RT. The mixture was diluted with 50 mL DCM, washed with 10% citric acid and 15% $K_2CO_3$ solution and dried over $Na_2SO_4$. After the desiccant and solvent had been eliminated the residue was reacted further without purification.

Yield: 0.63 g (100% of theory) ESI-MS: $(2M+Na)+=719$ retention time (HPLC): 8.3 min (method A)

1g) 4-(2-oxo-1,2,4,5-tetrahydro-1,3-benzodiazerin-3-yl)-piperidine-1-carbonyl chloride 6 g (12.1 mmol) phosgene (20 percent by weight in toluene) were added to a solution of 2.5 g (10.2 mmol) 3-piperidin-4-yl-1,3,4,5-tetrahydro-1,3-benzodiazepin-2-one and 2.6 mL (14.9 mmol) ethyldiisopropylamine in 75 mL DCM cooled to 0° C. and the reaction mixture was stirred for 30 min at this temperature. It was allowed to warm up to RT, evaporated down i.vac. to approx. 50 mL and filtered through silica gel, the latter was washed with 200 mL DCM/EtOAc (1:1) and the combined filtrates were again evaporated down i.vac. The residue was stirred with diisopropylether, suction filtered and dried i.vac.

Yield: 2.42 g (77% of theory) $R_f=0.43$ (silica gel, DCM/EtOAc 1:1)

1h) tert.-butyl 5-{(R)-2-ethoxycarbonyl-2-[4-(2-oxo-1,2,4,5-tetrahydro-1,3-benzodiazepin-3-yl)-piperidine-1-carbonyloxy]-ethyl}-7-methyl-indazol-1-carboxylate Under a nitrogen atmosphere 92 mg (2.1 mmol, 55% in mineral oil) NaH were added batchwise to a solution of 632 mg (1.81 mmol) tert.-butyl 5-((R)-2-ethoxycarbonyl-2-hydroxy-ethyl)-7-methyl-indazol-1-carboxylate in 60 mL dry THF cooled to 0° C. and stirred for a further hour at this temperature. Subsequently 800 mg (1.82 mmol) 4-(2-oxo-1,2,4,5-tetrahydro-1,3-benzodiazepin-3-yl)-piperidine-1-carbonyl chloride were added batchwise while cooling and the reaction mixture was stirred overnight at RT.

It was evaporated down i.vac., combined with 200 mL 10% citric acid solution, extracted twice with 200 mL EtOAc, the combined organic phases were washed with 200 mL 15% $K_2CO_3$ solution and dried over $Na_2SO_4$. After the desiccant and solvent had been eliminated the residue was purified by chromatography (silica gel, EtOAc/PE 2:1).

Yield: 330 mg (29% of theory) ESI-MS: $(M+H)^+=620$ $R_f=0.45$ (silica gel, EtOAc/PE 2:1)

1i) tert.-butyl 5-{(R)-2-carboxy-2-[4-(2-oxo-1,2,4,5-tetrahydro-1,3-benzodiazepin-3-yl)-piperidine-1-carbonyloxy]-ethyl}-7-methyl-indazol-1-carboxylate A solution of 19.2 mg (0.8 mmol) lithium hydroxide hydrate in 10 mL water was added at RT to a solution of 330 mg (0.53 mmol) tert.-butyl 5-{(R)-2-ethoxycarbonyl-2-[4-(2-oxo-1,2,4,5-tetrahydro-1,3-benzodiazepin-3-yl)-piperidine-1-carbonyloxy]-ethyl}-7-methyl-indazol-1-carboxylate in 30 mL THF and the reaction mixture was stirred for 30 min at RT. It was evaporated down i.vac., the residue was taken up in 100 mL water, combined with 10% citric acid with stirring, extracted twice with 100 mL DCM and the combined organic phases were dried over $Na_2SO_4$. After the desiccant and solvent had been eliminated the residue was reacted further without purification.

Yield: 440 mg (crude) ESI-MS: $(M+H)^+=592$ retention time (HPLC): 8.2 min (method A)

1k) tert.-butyl 7-methyl-5-{(R)-3-[4-(4-methyl-piperazin-1-yl)-piperidin-1-yl]-3-oxo-2-[4-(2-oxo-1,2,4,5-tetrahydro-1,3-benzodiazepin-3-yl)-piperidine-1-carbonyloxy]-propyl}-indazol-1-carboxylate A solution of 440 mg tert.-butyl 5-{(R)-2-carboxy-2-[4-(2-oxo-1,2,4,5-tetrahydro-1,3-benzodiazepin-3-yl)-piperidine-1-carbonyloxy]-ethyl}-7-methyl-indazol-1-carboxylate, 256 mg (0.8 mmol) TBTU, 146 μL (1.0 mmol) triethylamine and 147 mg (0.8 mmol) 1-methyl-4-piperidin-4-yl-piperazine in 8 mL DMF was stirred for 2 h at RT. The reaction solution was filtered through an injection filter and purified directly by HPLC without any further working up. The fractions containing the product were combined, evaporated down i.vac., made alkaline with 15% $K_2CO3$ solution, extracted three times with 30 mL DCM, the combined organic phases were dried over $Na_2SO_4$ and the solvent was eliminated i. vac.

Yield: 160 mg (28% of theory) ESI-MS: $(M+H)^+=757$ retention time (HPLC): 6.6 min (method A)

1l) (R)-1-(7-methyl-1H-indazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate A solution of 160 mg (0.21 mmol) tert.-butyl 7-methyl-5-{(R)-3-[4-(4-methyl-piperazin-1-yl)-piperidin-1-yl]-3-oxo-2-[4-(2-oxo-1,2,4,5-tetrahydro-1,3-benzodiazepin-3-yl)-piperidine-1-carbonyloxy]-propyl}-indazol-1-carboxylate in 10 mL 1 M HCl was stirred for 1 h at RT. To complete the reaction the mixture was heated to 50° C. for 10 min and stirred for a further hour at RT. The mixture was combined with 15% $K_2CO_3$ solution, extracted three times with in each case 30 mL DCM and the combined organic phases were dried over $Na_2SO_4$. After the desiccant and solvent had been eliminated the residue was triturated with 30 mL diisopropylether, suction filtered, washed with 10 mL diisopropylether again and dried in the air.

Yield: 100 mg (72% of theory) ESI-MS: $(M+H)^+=657$ retention time (HPLC): 4.9 min (method A)

Example 2

(R)-1-(4-amino-3-methyl-5-nitro-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

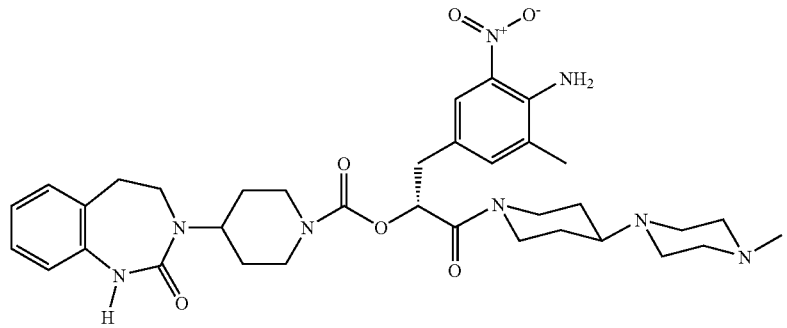

2a) methyl (Z,E)-2-acetylamino-3-(4-amino-methyl-5-nitro-phenyl)-acrylate 0.7 g (2.9 mmol) Pd(OAc)$_2$ and 0.9 g (2.9 mmol) tri-o-tolyl-phosphane were added under an argon atmosphere to a solution of 9.0 g (39.0 mmol) 4-bromo-2-methyl-6-nitro-phenylamine and 10.0 g (69.9 mmol) methyl 2-acetylamino-acrylate in 100 mL acetonitrile and 100 mL triethylamine. The reaction mixture was stirred for 24 h at a bath temperature of 90° C., evaporated down i.vac., the residue was combined with 200 mL water and 200 mL EtOAc and the precipitate was filtered off. The crystals were dissolved by refluxing in 500 mL MeOH, filtered off hot and the filtrate was evaporated to dryness i.vac.

Yield: 8.0 g (70% of theory) ESI-MS: (M+H)$^+$=294

2b) 3-(4-amino-3-methyl-5-nitro-phenyl)-2-oxo-propionic acid 60 mL of a 4 M HCl were metered into a solution of 8.0 g (53.1 mmol) methyl (Z,E)-2-acetylamino-3-(4-amino-methyl-5-nitro-phenyl)-acrylate in 60 mL 1,4-dioxane, refluxed for 3 h with stirring, the reaction solution was evaporated down i.vac. and the residue was combined with ice. The precipitate was filtered off, washed with ice water and dried.

Yield: 6.5 g (95% of theory) EI-MS: (M)+=238

2c) (R)-3-(4-amino-3-methyl-5-nitro-phenyl)-2-hydroxy-propionic acid

Under a nitrogen atmosphere a solution of 12.0 g (37.4 mmol) (1R)—B-chlorodiisopinocampheylborane in 40 mL THF was added dropwise within 15 min to a solution of 6.5 g (26.0 mmol) 3-(4-amino-3-methyl-5-nitro-phenyl)-2-oxo-propionic acid and 4.5 mL (32.4 mmol) triethylamine in 100 mL THF cooled to −35° C. and the reaction solution was stirred overnight at RT. Then the reaction solution was carefully combined with 60 mL of 1 M NaOH and 150 mL diethyl ether at 5° C. and stirred for 15 min. The organic phase was separated off, extracted three times with 40 mL 1 M NaOH and once with 40 mL water. The combined aqueous phases were acidified with semiconc. HCl while cooling with an ice bath and extracted twice with in each case 120 mL EtOAc. The combined organic phases were dried over Na$_2$SO$_4$ and evaporated down i.vac. The crude product was obtained, which was further reacted without purification.

Yield: 6.0 g (67% of theory)

2d) methyl (R)-3-(4-amino-3-methyl-5-nitro-phenyl)-2-hydroxy-propionate

While cooling with ice/acetone, 4.0 mL (54.8 mmol) SOCl$_2$ and at 0° C. 6.0 g (17.5 mmol) (R)-3-(4-amino-3-methyl-5-nitro-phenyl)-2-hydroxy-propionic acid in 10 mL MeOH were slowly added dropwise to 90 mL MeOH. The reaction solution was stirred for 1 h at 0° C. and for 1 h at RT and then evaporated down i.vac. The residue was combined with EtOAc, washed with saturated NaHSO$_4$ solution and dried over Na$_2$SO$_4$. After the desiccant and solvent had been eliminated the residue was purified by chromatography (silica gel, gradient DCM/MeOH 100:1 to 50:1).

Yield: 3.4 g (76% of theory) ESI-MS: (M+H)$^+$=255 R$_f$=0.43 (Polygram, DCM/MeOH 50:1)

2e) (R)-2-(4-amino-3-methyl-5-nitro-phenyl)-1-methoxy-carbonyl-ethyl 4-(2-oxo-1,2,4,5-tetrahydro-1,3-benzodiazepin-3-yl)-piperidine-1-carboxylate Under a nitrogen atmosphere 1.8 g (14.7 mmol) 4-dimethylaminopyridine in 25 mL pyridine were first combined with 2.7 g (13.4 mmol) 4-nitro-phenyl chloroformate while cooling with an ice bath, stirred for 30 min at RT, then combined with 3.4 g (13.2 mmol) methyl (R)-3-(4-amino-3-methyl-5-nitro-phenyl)-2-hydroxy-propionate in 15 mL pyridine, stirred again for 2 h at RT, and then combined with 3.5 g (14.3 mmol) 3-piperidin-4-yl-1,3,4,5-tetrahydro-1,3-benzodiazepin-2-one and stirred for 5 h at RT. After the reaction had ended the reaction mixture was evaporated down i.vac., the residue was combined with EtOAc, the organic phase was washed with 10% KHSO$_4$ solution and saturated NaHSO$_4$ solution and dried over Na$_2$SO$_4$. After the desiccant and solvent had been eliminated the residue was purified by chromatography (silica gel, DCM/MeOH 25:1).

Yield: 3.7 g (50% of theory) ESI-MS: (M+H)$^+$=526 R$_f$=0.42 (Polygram, DCM/MeOH 25:1)

2f) (R)-2-(4-amino-3-methyl-5-nitro-phenyl)-1-carboxy-ethyl 4-(2-oxo-1,2,4,5-tetrahydro-1,3-benzodiazepin-3-yl)-piperidine-1-carboxylate A solution of 120 mg (5.0 mmol) LiOH in 5 mL water was metered into a solution of 1.0 g (1.8 mmol) (R)-2-(4-amino-3-methyl-5-nitro-phenyl)-1-methoxy-carbonyl-ethyl 4-(2-oxo-1,2,4,5-tetrahydro-1,3-benzodiazepin-3-yl)-piperidine-1-carboxylate in 10 mL THF, the reaction solution was stirred for 4 h at RT and then evaporated down i.vac. The residue was combined with 30 mL water, washed with 30 mL diethyl ether, acidified with 4 M HCl while cooling with an ice bath and stirred for 30 min at RT. The precipitate was filtered off, washed with water and dried.

Yield: 0.79 g (81% of theory) ESI-MS: (M−H)$^-$=510

2g) (R)-1-(4-amino-3-methyl-5-nitro-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate A solution of 780 mg (1.5 mmol) (R)-2-(4-amino-3-methyl-5-nitro-phenyl)-1-carboxy-ethyl 4-(2-oxo-1,2,4,5-tetrahydro-1,3-benzodiazepin-3-yl)-piperidine-1-carboxylate, 520 mg (1.6 mmol) TBTU, 350 μL (2.1 mmol) ethyldiisopropylamine in 30 mL THF and 5 mL DMF was stirred for 1 h at RT, then combined with 300 mg (1.6 mmol) 1-methyl-4-piperidin-4-yl-piperazine and stirred for 4 h at RT. The reaction solution was combined with 100 mL semisaturated NaHCO₃ solution and extracted twice with 50 mL EtOAc. The organic phases were dried over Na₂SO₄, filtered and evaporated down i.vac. The residue was dissolved in a little DCM, combined with diethyl ether, the precipitate was suction filtered and dried.

Yield: 1.0 g (97% of theory) ESI-MS: (M+H)⁺=677 R$_f$=0.46 (Polygram-Alox, DCM/MeOH 25:1)

Example 2.1

(R)-1-(3,4-diamino-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

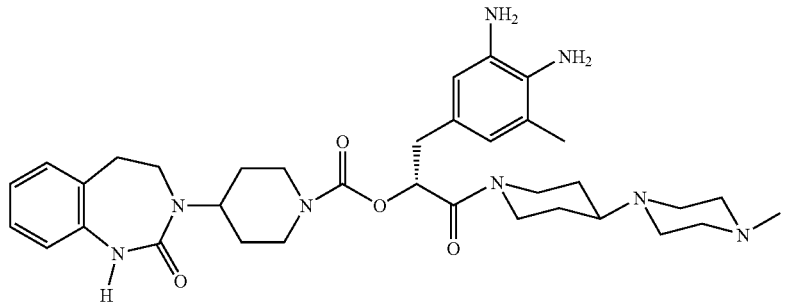

260 mg (0.37 mmol) (R)-1-(4-amino-3-methyl-5-nitro-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate were dissolved in 25 mL THF and combined with 130 mg 10% Pd/C. The mixture was hydrogenated for 4.5 h in a Parr apparatus at 50° C. under 50 psi hydrogen pressure. Then the catalyst was filtered off, the filtrate was evaporated down i.vac., the residue was dissolved in a little DCM, combined with diethyl ether, the precipitate was suction filtered and dried.

Yield: 180 mg (75% of theory) ESI-MS: (M+H)⁺=647 retention time (HPLC): 4.3 min (method A)

Example 2.2

(R)-1-(7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

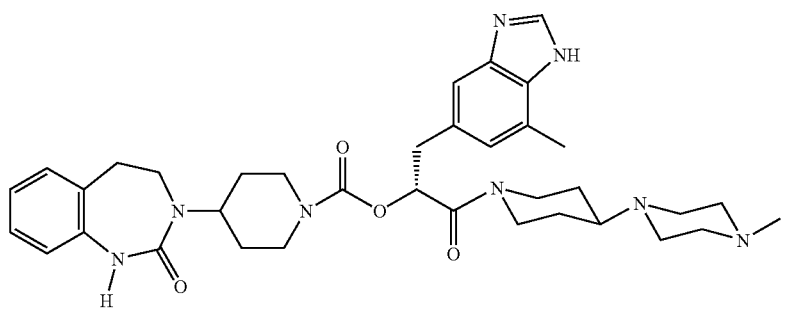

110 mg (0.16 mmol) (R)-1-(4-amino-3-methyl-5-nitrobenzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate were dissolved in 10 mL THF, combined with 1 mL formic acid and 30 mg 10% Pd/C. The mixture was hydrogenated for 1 h in a Parr apparatus at RT and 50 psi hydrogen pressure and for 1.75 h at 50° C. and 50 psi hydrogen pressure. Then the catalyst was filtered off, the filtrate was evaporated down i.vac., the residue was dissolved in 5 mL formic acid, refluxed for 1 h and then evaporated down i.vac. The residue was combined with water, made alkaline with $Na_2CO_3$ solution, extracted with DCM and the organic phase was dried over $Na_2SO_4$. After the desiccant and solvent had been eliminated the residue was purified by chromatography (Alox, gradient DCM/MeOH 30:1 to 20:1).

Yield: 40 mg (39% of theory) ESI-MS: $(M+H)^+=655$ $R_f=0.28$ (Polygram-Alox, DCM/MeOH 25:1)

Example 2.3

(R)-2-4,4'-bipiperidinyl-1-yl-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate methoxycarbonyl-2-(7-methyl-1H-benzimidazol-5-yl)-ethyl 4-(2-oxo-1,2,4,5-tetrahydro-1,3-benzodiazepin-3-yl)-piperidine-1-carboxylate in 12 mL THF and the reaction solution was stirred overnight at RT. The residue was combined with 1 mL 4 M HCl and evaporated to dryness i.vac.

Yield: 980 g (100% of theory) ESI-MS: $(M+H)^+=492$ 2.3c) (R)-2-(1'-benzyl-4,4'-bipiperidinyl-1-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate A solution of 120 mg (0.22 mmol) (R)-1-carboxy-2-(7-methyl-1H-benzimidazol-5-yl)-ethyl 4-(2-oxo-1,2,4,5-tetrahydro-1,3-benzodiazepin-3-yl)-piperidine-1-carboxylate, 85 mg (0.27 mmol) TBTU and 50 µL (0.36 mmol) triethylamine in 10 mL THF and 1 mL DMF was stirred for 1 h at RT, then combined with 80 mg (0.31 mmol) 1-benzyl-[4,4']bipiperidinyl and stirred overnight at RT. The reaction solution was combined with 1 mL saturated $Na_2CO_3$ solution and extracted with 100 mL EtOAc. The organic phase was dried

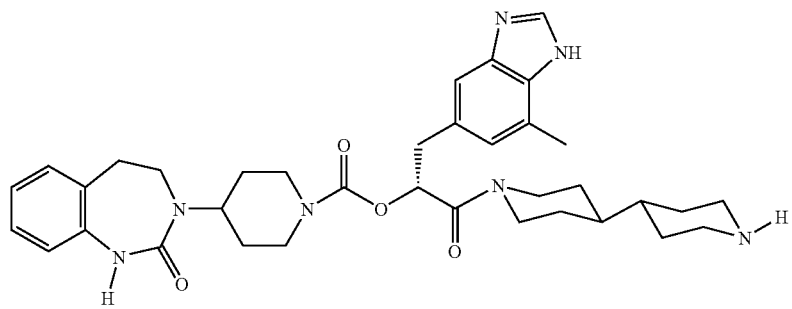

2.3a) (R)-1-methoxycarbonyl-2-(7-methyl-1H-benzimidazol-5-yl)-ethyl 4-(2-oxo-1,2,4,5-tetrahydro-1,3-benzodiazepin-3-yl)-piperidine-1-carboxylate 1.2 g (2.3 mmol) (R)-2-(4-amino-3-methyl-5-nitro-phenyl)-1-methoxycarbonyl-ethyl 4-(2-oxo-1,2,4,5-tetrahydro-1,3-benzodiazepin-3-yl)-piperidine-1-carboxylate were dissolved in 50 mL formic acid and combined with 300 mg 10% Pd/C. The mixture was hydrogenated for 2 h in a Parr apparatus at 60° C. and 50 psi hydrogen pressure. Then the catalyst was filtered off, the filtrate was evaporated down i.vac. and the residue was purified by chromatography (Alox, gradient DCM/MeOH 40:1 to 30:1). Yield: 880 mg (76% of theory) ESI-MS: $(M+H)^+=506$ $R_f=0.40$ (Polygram-Alox, DCM/MeOH 25:1)

2.3b) (R)-1-carboxy-2-(7-methyl-1H-benzimidazol-5-yl)-ethyl 4-(2-oxo-1,2,4,5-tetrahydro-1,3-benzodiazepin-3-yl)-piperidine-1-carboxylate A solution of 96 mg (4.0 mmol) LiOH in 5 mL water was added dropwise to a solution of 910 mg (1.8 mmol) (R)-1- over $Na_2SO_4$, filtered and evaporated down i.vac. The residue was purified via HPLC, the fractions containing the product were combined and evaporated to dryness i.vac.

Yield: 75 mg (42% of theory) ESI-MS: $(M+H)^+=732$ 2.3d) (R)-2-4,4'-bipiperidinyl-1-yl-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate 75 mg (0.09 mmol) (R)-2-(1'-benzyl-4,4'-bipiperidinyl-1-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate were dissolved in 10 mL MeOH and combined with 30 mg 10% Pd/C. The mixture was hydrogenated for 2 h in a Parr apparatus at 50° C. and 50 psi hydrogen pressure. Then the catalyst was filtered off and the filtrate was evaporated down i.vac.

Yield: 48 mg (81% of theory) ESI-MS: $(M+H)^+=642$ retention time (HPLC): 4.6 min (method A)

Example 2.4

(R)-1-(7-methyl-1H-benzimidazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

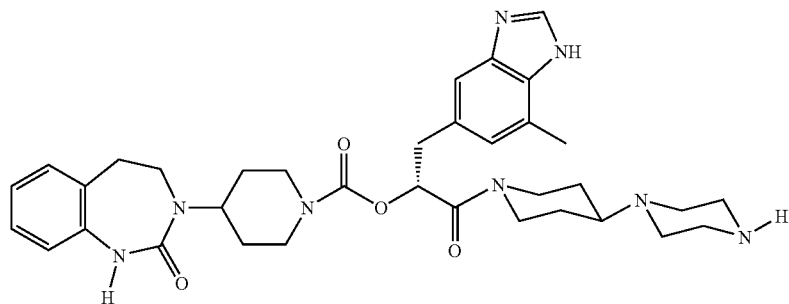

2.4a) (R)-2-[4-(4-benzyl-piperazin-1-yl)-piperidin-1-yl]-1-(7-methyl-1H-benzimidazol-5-ylmethyl)-2-oxo-ethyl 4-(2-oxo-1,2,4,5,-tetrahydro-1,3-benzodiazepin-3-yl)-piperidine-1-carboxylate A solution of 120 mg (0.22 mmol) (R)-1-carboxy-2-(7-methyl-1H-benzimidazol-5-yl)-ethyl 4-(2-oxo-1,2,4,5-tetrahydro-1,3-benzodiazepin-3-yl)-piperidine-1-carboxylate, 85 mg (0.27 mmol) TBTU and 120 µL (0.86 mmol) triethylamine in 10 mL THF and 1 mL DMF was stirred for 1 h at RT, then combined with 90 mg (0.27 mmol) 1-benzyl-4-piperidin-4-yl-piperazine (used as the bishydrochloride salt) and stirred overnight at RT. The reaction solution was combined with 1 mL semisaturated NaHCO₃ solution and extracted with 100 mL EtOAc. The organic phase was dried over Na₂SO₄, filtered and evaporated down i.vac.

Yield: 67 mg (42% of theory)

2.4b) (R)-1-(7-methyl-1H-benzimidazol-5-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate 67 mg (0.08 mmol) (R)-2-[4-(4-benzyl-piperazin-1-yl)-piperidin-1-yl]-1-(7-methyl-1H-benzimidazol-5-ylmethyl)-2-oxo-ethyl 4-(2-oxo-1,2,4,5,-tetrahydro-1,3-benzodiazepin-3-yl)-piperidine-1-carboxylate were dissolved in 10 mL MeOH and combined with 30 mg 10% Pd/C. The mixture was hydrogenated for 3 h in a Parr apparatus at 50° C. and 50 psi hydrogen pressure. Then the catalyst was filtered off and the filtrate was evaporated down i.vac. The residue was purified by HPLC, the fractions containing the product were combined and lyophilised.

Yield: 18 mg (34% of theory) ESI-MS: (M–H)⁻=641
retention time (HPLC): 4.1 min (method A)

Example 2.5

(R)-1-(2,7-dimethyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

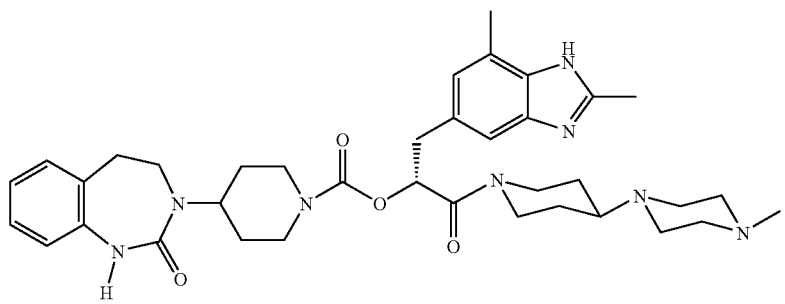

A solution of 120 mg (0.16 mmol) (R)-1-(3,4-diamino-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate were refluxed in 2 mL AcOH for 2 h and then evaporated down i.vac. The residue was purified by HPLC, the fractions containing the product were combined and lyophilised.

Yield: 59 mg (56% of theory) ESI-MS: $(M+H)^+=671$
retention time (HPLC): 4.3 min (method A)

Example 2.6

(R)-1-(7-methyl-2-oxo-2,3-dihydro-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

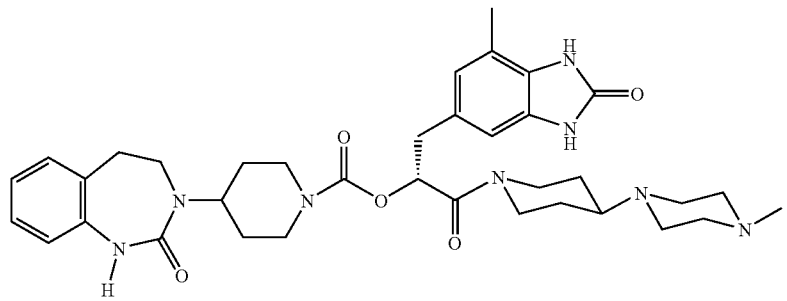

120 mg (0.17 mmol) (R)-1-(4-amino-3-methyl-5-nitrobenzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate were dissolved in 10 mL THF and combined with 30 mg 10% Pd/C. The mixture was hydrogenated for 2 h in a Parr apparatus at 50° C. and 50 psi hydrogen pressure, the catalyst was filtered off and the filtrate was evaporated down i.vac. The residue was dissolved in 10 mL 1,4-dioxane, combined with 30 mg (0.18 mmol) CDT, refluxed for 2 h and then evaporated to dryness i.vac. The residue was purified by chromatography (Alox, DCM/MeOH 9:1), the fractions containing the product were combined, evaporated down i.vac., dissolved in MeOH, combined with diethyl ether, the precipitate was suction filtered and dried.

Yield: 95 mg (82% of theory) ESI-MS: $(M+H)^+=673$ $R_f=0.57$ (Polygram-Alox, DCM/MeOH 9:1)

Example 2.7

(R)-1-(2-cyclopropyl-7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

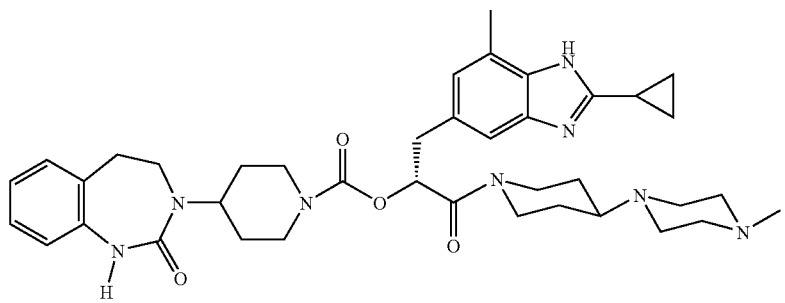

A solution of 120 mg (0.16 mmol) (R)-1-(3,4-diamino-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate in 1 mL DMF was combined with 20 μL (0.27 mmol) cyclopropanecarbaldehyde and stirred for 2 days at RT. The residue was purified by HPLC, the fractions containing the product were combined and lyophilised.

Yield: 85 mg (73% of theory) ESI-MS: (M+H)$^+$=697 retention time (HPLC): 4.4 min (method A)

Example 2.8

(R)-2-[4-(4-methyl-piperazin-1-yl)-piperidin-1-yl]-1-(7-methyl-2-trifluoromethyl-1H-benzimidazol-5-ylmethyl)-2-oxo-ethyl 4-(2-oxo-1,2,4,5-tetrahydro-1,3-benzodiazepin-3-yl)-piperidine-1-carboxylate

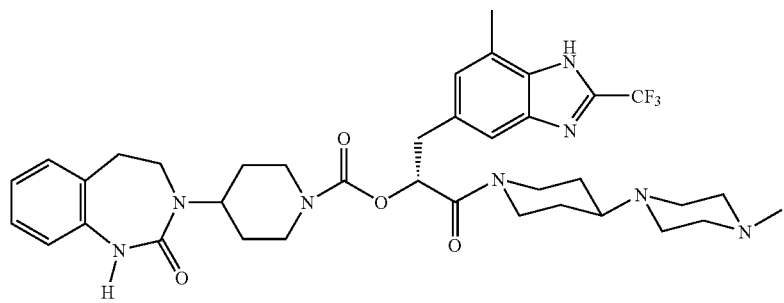

A solution of 120 mg (0.16 mmol) (R)-1-(3,4-diamino-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate in 1 mL DMF was combined with 30 mg (0.26 mmol) trifluoroacetaldehyde and 3 drops of TFA and stirred for 2 h at 100° C. The residue was purified by HPLC, the fractions containing the product were combined and lyophilised.

Yield: 39 mg (34% of theory) ESI-MS: (M+H)$^+$=725 retention time (HPLC): 5.5 min (method A)

Example 2.9

(R)-1-(2-methoxy-7-methyl-1H-benzimidazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

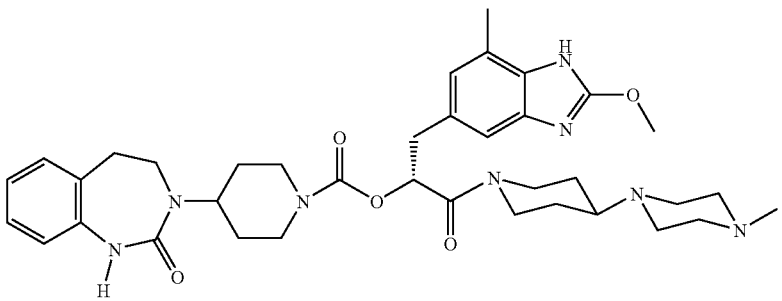

A solution of 115 mg (0.15 mmol) (R)-1-(3,4-diamino-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate in 0.5 mL MeOH was combined with 200 mg (1.47 mmol) tetramethoxymethane and 10 mg p-toluenesulphonic acid and refluxed for 4 h. The residue was purified by HPLC, the fractions containing the product were combined and lyophilised. The product was obtained as the formate salt.

Yield: 50 mg (45% of theory) ESI-MS: (M+H)⁺=687 retention time (HPLC): 4.8 min (method A)

Example 2.10

(R)-2-[4-(4-methyl-piperazin-1-yl)-piperidin-1-yl]-1-(8-methyl-quinoxalin-6-ylmethyl)-2-oxo-ethyl 4-(2-oxo-1,2,4,5-tetrahydro-1,3-benzodiazepin-3-yl)-piperidine-1-carboxylate

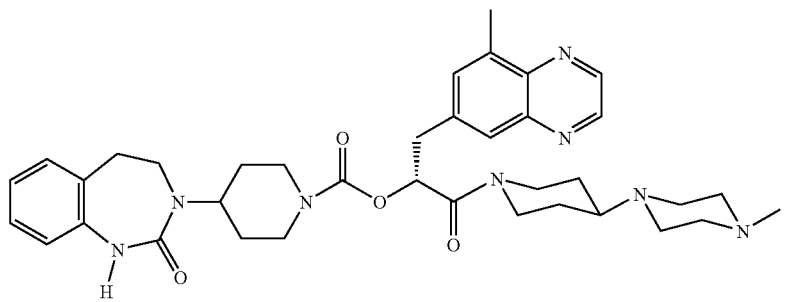

Under a nitrogen atmosphere a solution of 120 mg (0.16 mmol) 4-(2-oxo-1,2,4,5-tetrahydro-1,3-benzodiazepin-3-yl)-piperidine-1-carboxylate (R)-1-(3,4-diamino-5-methyl-benzyl)-2-[4-(4-methyl-piperazin-1-yl)-piperidin-1-yl]-2-oxo-ethyl in 20 mL THF was combined with 20 µL (40% in water, 0.78 mmol) Glyoxal and 300 mg Na$_2$SO$_4$, stirred for 20 h at RT, filtered and evaporated down i.vac. The residue was purified by HPLC, the fractions containing the product were combined and lyophilised.

Yield: 72 mg (68% of theory) ESI-MS: (M+H)⁺=669 retention time (HPLC): 5.3 min (method A)

Example 2.11

(R)-1-{2-[(Z)-cyanimino]-7-methyl-2,3-dihydro-1H-benzimidazol-5-ylmethyl}-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

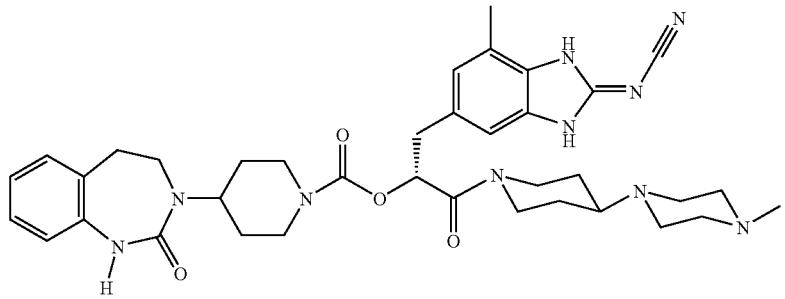

A solution of 120 mg (0.16 mmol) (R)-1-(3,4-diamino-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate in 10 mL THF was combined with 60 mg (0.25 mmol) diphenylcyanocarbonimidate and refluxed for 2 h with stirring. Then EtOAc and saturated NaHCO$_3$ solution was added, the phases were separated and the organic phase was dried over Na$_2$SO$_4$. After the desiccant and solvent had been eliminated the residue was purified by chromatography (Alox, DCM/MeOH 25:1 to 8:1). The fractions containing the product were combined, evaporated down i.vac., dissolved in a little MeOH, combined with diethyl ether, and the precipitate was suction filtered and dried.

Yield: 28 mg (22% of theory) ESI-MS: (M+H)$^+$=697
R$_f$=0.24 (Polygram-Alox, DCM/MeOH 25:1)

Example 2.12

(R)-1-(7-methyl-1H-benzotriazol-5-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate 120 mg (0.17 mmol) (R)-1-(4-amino-3-methyl-5-nitro-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate were dissolved in 10 mL MeOH and combined with 30 mg 10% Pd/C. The mixture was hydrogenated for 1 h in a Parr apparatus at 50° C. at 50 psi hydrogen pressure. Then the catalyst was filtered off, the filtrate was combined with 2.5 mL 20% ACOH and 15 mg (0.22 mmol) sodium nitrite in 0.5 mL water and stirred for 2 h at RT. The reaction solution was made alkaline with NaHCO$_3$ solution, extracted with DCM and the organic phase was dried over Na$_2$SO$_4$. After the desiccant and solvent had been eliminated the residue was purified by chromatography (Alox, gradient DCM/MeOH 25:1 to 5:1).

Yield: 22 mg (19% of theory) ESI-MS: (M+H)$^+$=658
R$_f$=0.25 (Polygram-Alox, DCM/MeOH 25:1)

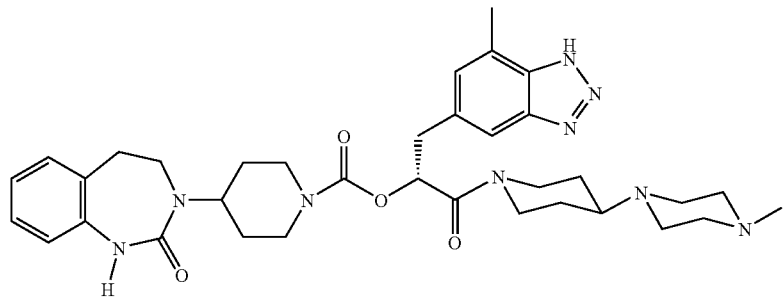

Example 2.13

(R)-2-(1'-methanesulphonyl-4,4'-bipiperidinyl-1-yl)-1-(7-methyl-1H-benzimidazol-5-ylmethyl)-2-oxo-ethyl 4-(2-oxo-1,2,4,5-tetrahydro-1,3-benzodiazepin-3-yl)-piperidine-1-carboxylate

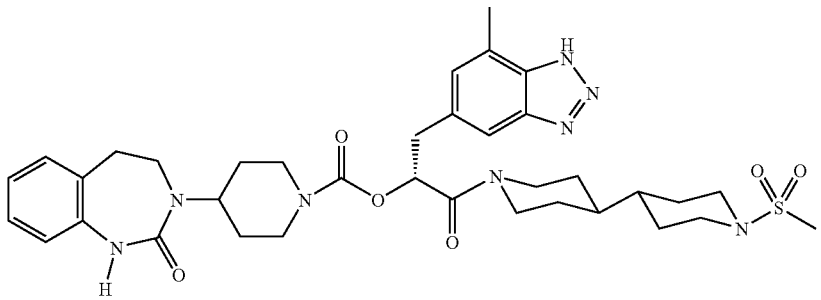

A solution of 120 mg (0.22 mmol) (R)-1-carboxy-2-(7-methyl-1H-benzimidazol-5-yl)-ethyl 4-(2-oxo-1,2,4,5-tetrahydro-1,3-benzodiazepin-3-yl)-piperidine-1-carboxylate, 80 mg (0.25 mmol) TBTU, 40 µL (0.29 mmol) triethylamine and 80 mg (0.33 mmol) 1-methanesulphonyl-[4,4']bipiperidinyl in 1.5 mL DMF was stirred overnight at RT. The reaction mixture was purified by HPLC without working up. The fractions containing the product were combined and lyophilised.

Yield: 67 mg (42% of theory) ESI-MS: $(M+H)^+=720$
retention time (HPLC): 5.9 min (method A)

Example 3

(R)-1-(4-methyl-2-oxo-2,3-dihydro-benzoxazol-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

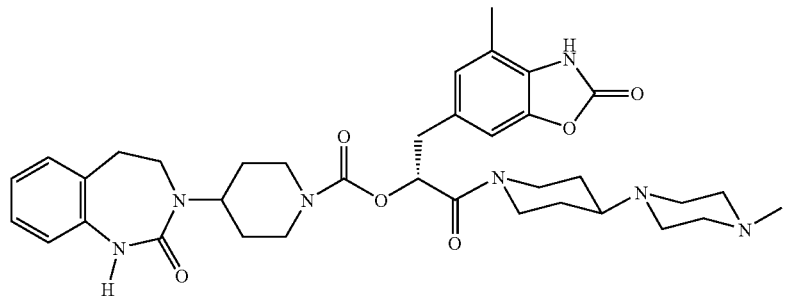

3a) 4-methyl-3H-benzoxazol-2-one 76.0 g (0.45 mol) CDI in 1 L DCM were added dropwise at 0° C. to a solution of 50.0 g (0.39 mol) 5-amino-m-cresol and 210 mL (1.2 mol) in 1 L DCM. After the end of the reaction the reaction mixture was combined with 250 mL water, the organic phase was separated off and washed twice with 250 mL 1 M $KHSO_4$ solution and 250 mL water and dried over $MgSO_4$. After the desiccant and solvent had been eliminated the residue obtained was dissolved in 200 mL EtOAc, refluxed, combined with 100 mL PE, slowly cooled to RT, the precipitate formed was suction filtered and dried.

Yield: 39.2 g (67% of theory) ESI-MS: $(M+H)^+=150$
$R_f=0.65$ (silica gel, $DCM/Cyc/MeOH/NH_3$ 70:15:15:2)

3b) 6-bromo-4-methyl-3H-benzoxazol-2-one 35.8 g (199.1 mmol) N-bromosuccinimide were added to a solution of 29.5 g (197.8 mmol) 4-methyl-3H-benzoxazol-2-one in 200 mL AcOH and stirred overnight at RT. The reaction solution was combined with 800 mL water, stirred for 15 min at RT, the precipitate was suction filtered, washed with water and dried at 60° C. in the vacuum drying cupboard.

Yield: 43.0 g (95% of theory) ESI-MS: $(M+H)^+=226/228$ (Br) $R_f=0.35$ (silica gel, $DCM/Cyc/MeOH/NH_3$ 70:15:15:2)

3c) methyl (Z,E)-2-acetylamino-3-(4-methyl-2-oxo-2,3-dihydro-benzoxazol-6-yl)-acrylate Under a nitrogen atmosphere 5.4 g (23.9 mmol) $Pd(OAc)_2$ and 7.5 g (24.0 mmol) tri-o-tolyl-phosphane were added to a solution of 38.3 g (168.0 mmol) 6-bromo-4-methyl-3H-benzoxazol-2-one and 28.0 g (191.7 mmol) methyl 2-acetylamino-acrylate in 800 mL acetonitrile and 480 mL triethylamine, the reaction mixture was stirred for 18 h at 80° C. and then evaporated down i.vac. The residue was is combined with 100 mL water and 50 mL EtOAc and the precipitate was filtered off. The crystals were dissolved in MeOH/DCM 1:1 at reflux temperature, combined with activated charcoal, filtered off and the filtrate was evaporated to dryness.

Yield: 31.2 g (64% of theory) ESI-MS: $(M+H)^+=291$
$R_f=0.38$ (silica gel, $DCM/Cyc/MeOH/NH_3$ 70:15:15:2)

3d) 3-(4-methyl-2-oxo-2,3-dihydro-benzoxazol-6-yl)-2-oxo-propionic acid 160 mL 4 M HCl were added to a solution of 31.2 g (107.5 mmol) methyl (Z,E)-2-acetylamino-3-(4-methyl-2-oxo-2,3-dihydro-benzoxazol-6-yl)-acrylate in 320 mL 1,4-dioxane and the reaction solution was refluxed for 5 h. The mixture was evaporated down i. vac., the precipitate was filtered off, washed with water and dried at 60° C. in the vacuum drying cupboard.

Yield: 24.9 g (98% of theory) ESI-MS: $(M+H)^+=236$
$R_f=0.38$ (silica gel, $DCM/Cyc/MeOH/NH_3$ 70:15:15:2)

3e) (R)-2-hydroxy-3-(4-methyl-2-oxo-2,3-dihydro-benzoxazol-6-yl)-propionic acid

Under a nitrogen atmosphere a solution of 60.0 g (187.1 mmol) (1R)—B-chlorodiisopinocampheylborane in 200 mL THF was added dropwise within 15 min to a solution of 24.9 g (105.9 mmol) 3-(4-methyl-2-oxo-2,3-dihydro-benzoxazol-6-yl)-2-oxo-propionic acid and 20.0 mL (143.9 mmol) triethylamine in 400 mL THF cooled to −35° C. and the reaction solution was stirred overnight at RT. Then the reaction solution was carefully made alkaline with 1 M NaOH at 5° C., combined with 400 mL EtOAc and stirred for 15 min. The organic phase was separated off, extracted twice with 100 mL 1 M NaOH and with 100 mL water. The combined aqueous phases were acidified with semiconc. HCl and extracted twice with 150 mL EtOAc. The combined organic phases were dried over $MgSO_4$ and evaporated down i.vac.

Yield: 20.8 g (83% of theory) ESI-MS: $(M+H)^+=238$
$R_f=0.10$ (silica gel, $DCM/Cyc/MeOH/NH_3$ 70:15:15:2)

3f) methyl (R)-2-hydroxy-3-(4-methyl-2-oxo-2,3-dihydro-benzoxazol-6-yl)-propionate 23.0 g (97.0 mmol) (R)-2-hydroxy-3-(4-methyl-2-oxo-2, 3-dihydro-benzoxazol-6-yl)-propionic acid were dissolved in 200 mL methanolic HCl (1.3 M), stirred overnight at RT and then evaporated down i.vac. The residue was combined with 200 mL EtOAc, washed with 15% $K_2CO_3$ solution and the organic phase was dried over $Na_2SO_4$. After the desiccant and solvent had been eliminated the residue was combined with DIPE, the crystals were filtered off and dried at 50° C. in the vacuum drying cupboard.

Yield: 14.6 g (60% of theory) ESI-MS: $(M+H)^+=252$
$R_f=0.44$ (silica gel, $DCM/Cyc/MeOH/NH_3$ 70:15:15:2)

3g) (R)-1-carboxy-2-(4-methyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate Under a nitrogen atmosphere 4.1 g (20.1 mmol) 4-nitrophenyl chloroformate in 20 mL THF were metered into 40 mL pyridine at a bath temperature of 60° C. within 10 min, stirred for 5 min, then 5.0 g (19.9 mmol) methyl (R)-2-hydroxy-3-(4-methyl-2-oxo-2,3-dihydro-benzoxazol-6-yl)-propionate and 20 mL pyridine were added and the reaction mixture was stirred for 1.5 h at 60° C. The reaction solution was combined with 4.9 g (20.0 mmol) 3-piperidin-4-yl-1,3,4,5-tetrahydro-1,3-benzodiazepin-2-one and stirred for 2 h at 100 C. After the reaction had ended 150 mL EtOAc was added, the mixture was washed three times with 70 mL 1 M KHSO$_4$ solution and 12 times with 50 mL 15% K$_2$CO$_3$ solution and the organic phase was dried over MgSO$_4$. After the desiccant and solvent had been eliminated the residue was dissolved in 60 mL THF, combined with 250 mg LiOH in 10 mL water and the reaction mixture was stirred for 3 h at RT. The THF was eliminated i.vac., the aqueous residue was mixed with 60 mL TBME, insoluble constituents were filtered off, the organic phase was separated off and the aqueous phase was acidified with 1 M HCl. After 1 h at RT the precipitate formed was suction filtered, washed with water and dried at 60° C. in the vacuum drying cupboard.

Yield: 2.5 g (25% of theory) ESI-MS: (M−H)$^−$=507 R$_f$=0.10 (silica gel, DCM/Cyc/MeOH/NH$_3$ 70:15:15:2)

3h) (R)-1-(4-methyl-2-oxo-2,3-dihydro-benzoxazol-6-ylmethyl-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate A solution of 510 mg (1.0 mmol) (R)-1-carboxy-2-(4-methyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 365 mg (1.12 mmol) TBTU, 230 µL (1.31 mmol) ethyldiisopropylamine in 80 mL THF was stirred for 30 min at RT, then combined with 210 mg (1.12 mmol) 1-methyl-4-piperidin-4-yl-piperazine and stirred for 22 h at RT. To complete the reaction the mixture was again combined with 100 mg (0.3 mmol) TBTU and 50 mg (0.27 mmol) 1-methyl-4-piperidin-4-yl-piperazine and 40 mL THF and stirred for a further 4 h at RT. The reaction solution was diluted with 250 mL EtOAc and extracted twice with 60 mL saturated NaHCO$_3$ solution. The organic phase was dried over Na$_2$SO$_4$, filtered and evaporated down i.vac. The residue was purified by chromatography (Alox, DCM/MeOH 50:1 to 25:1), the fractions containing the product were combined, evaporated down i.vac., combined with diethyl ether, filtered off and dried.

Yield: 440 mg (65% of theory) ESI-MS: (M+H)$^+$=674 R$_f$=0.46 (Polygram-Alox, DCM/MeOH 25:1)

Example 3.1

(R)-1-(4-methyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

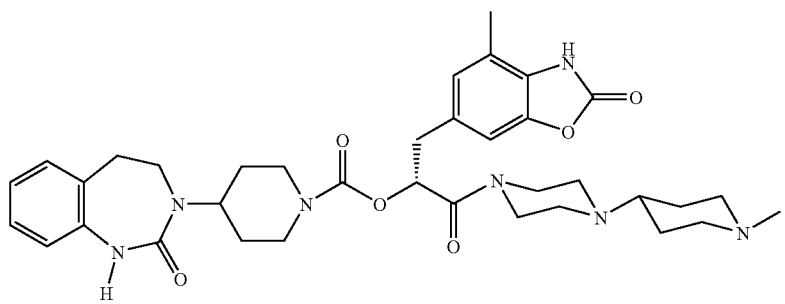

A solution of 510 mg (1.0 mmol) (R)-1-carboxy-2-(4-methyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate, 370 mg (1.11 mmol) TBTU, 230 µL (1.31 mmol) ethyldiisopropylamine in 60 mL THF was stirred for 30 min at RT, then combined with 210 mg (1.12 mmol) 1-(1-methyl-piperidin-4-yl)-piperazine and stirred for 22 h at RT. To complete the reaction the mixture was again combined with 80 mg (0.24 mmol) TBTU, 50 µL (0.28 mmol) ethyldiisopropylamine, 50 mg (0.27 mmol) 1-(1-methyl-piperidin-4-yl)-piperazine and 40 mL THF and stirred for a further 2 days at RT. The reaction solution was combined with 10 mL LiOH solution (0.5 M) and stirred for 30 min at RT. Then it was diluted with 250 mL EtOAc and extracted twice with 60 mL saturated NaHCO$_3$ solution. The organic phase was dried over Na$_2$SO$_4$, filtered and evaporated down i.vac. The residue was purified by chromatography (Alox, DCM/MeOH 50:1 to 25:1), the fractions containing the product were combined, evaporated down i.vac., combined with diethyl ether, filtered off and dried.

Yield: 420 mg (62% of theory) ESI-MS: (M+H)$^+$=674 R$_f$=0.40 (Polygram-Alox, DCM/MeOH 25:1)

Example 3.2

(R)-2-(4-amino-4-methyl-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

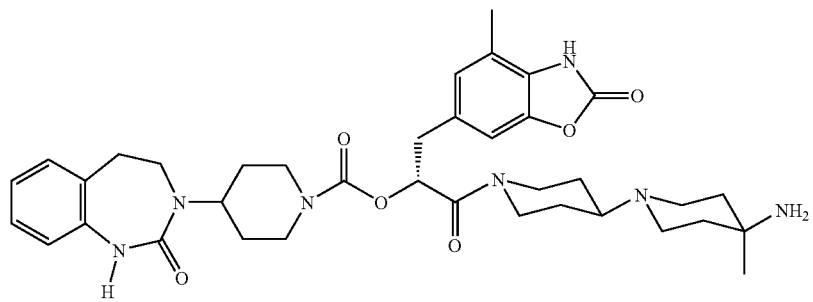

A solution of 80 mg (0.16 mmol) (R)-1-carboxy-2-(4-methyl-2-oxo-2,3-dihydro-benzoxazol-6-yl)-ethyl 4-(2-oxo-1,2,4,5-tetrahydro-1,3-benzodiazepin-3-yl)-piperidine-1-carboxylate, 58 mg (0.18 mmol) TBTU, 140 μL (1.0 mmol) triethylamine and 59 mg (0.16 mmol) tert.-butyl (4-methyl-[1,4']bipiperidinyl-4-yl)-carbamate (used as the bis-hydrochloride salt) in 1.8 mL DMF was stirred overnight at RT. The reaction mixture was purified by HPLC, the fractions containing the product were combined and lyophilised.

The coupling product was taken up in 4 mL DCM, combined with 0.5 mL TFA and the reaction mixture was shaken for 5 h at RT and overnight without a seal, during which time the DCM evaporated off. The residue was combined with 2 mL 15% $K_2CO_3$ solution and extracted twice with 2 mL DCM. The solvent from the combined organic phases was allowed to evaporate off overnight, the residue was taken up in 1 mL DMF and the crude product was purified by HPLC. The fractions containing the product were combined and lyophilised.

Yield: 42 mg (36% of theory) ESI-MS: $(M+H)^+$=688 retention time (HPLC): 4.5 min (method A)

Example 3.3

(R)-1-(4-methyl-2-oxo-2,3-dihydro-benzoxazol-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate

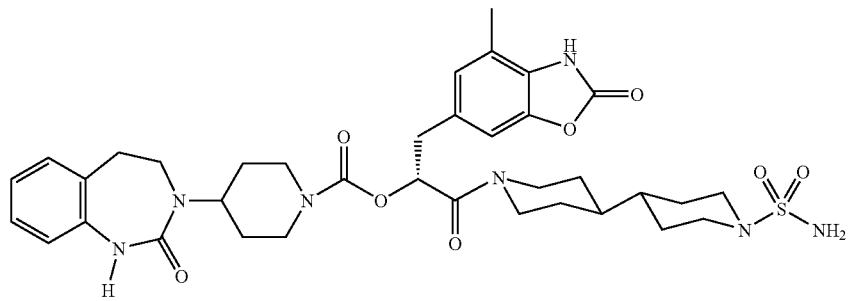

A solution of 73 mg (0.14 mmol) (R)-1-carboxy-2-(4-methyl-2-oxo-2,3-dihydrobenz-oxazol-6-yl)-ethyl 4-(2-oxo-1,2,4,5-tetrahydro-1,3-benzodiazepin-3-yl)-piperidine-1-carboxylate, 51 mg (0.16 mmol) TBTU, 42 μL (0.3 mmol) triethylamine and 41 mg (0.14 mmol) [4,4']bipiperidinyl-1-sulphonic acid amide (used as the hydrochloride salt) in 1.8 mL DMF was stirred overnight at RT. The reaction mixture was purified by HPLC, the fractions containing the product were combined and lyophilised.

Yield: 22 mg (21% of theory) ESI-MS: (M+H)⁺=738 retention time (HPLC): 3.5 min (method B)

Example 3.4

(R)-2-(1'-methanesulphonyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

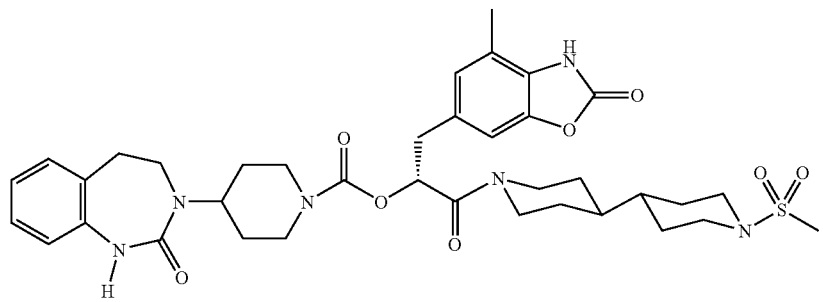

A solution of 110 mg (0.22 mmol) (R)-1-carboxy-2-(4-methyl-2-oxo-2,3-dihydrobenz-oxazol-6-yl)-ethyl 4-(2-oxo-1,2,4,5-tetrahydro-1,3-benzodiazepin-3-yl)-piperidine-1-carboxylate, 80 mg (0.25 mmol) TBTU and 50 µL (0.29 mmol) ethyldiisopropylamine in 10 mL THF was stirred for 50 min at RT. Then 60 mg (0.24 mmol) 1-methanesulphonyl-[4,4']bipiperidinyl was added. The reaction mixture was stirred overnight at RT. It was diluted with 50 mL EtOAc, extracted twice with 30 mL 15% K₂CO₃ solution and the organic phase was dried over MgSO₄. After the desiccant and solvent had been eliminated the residue was triturated with water, suction filtered and purified by chromatography (silica gel, gradient DCM to DCM/MeOH/NH₃ 50:45:5).

Yield: 80 mg (50% of theory) ESI-MS: (M+H)⁺=737 R$_f$=0.38 (silica gel, DCM/Cyc/MeOH/NH₃ 70:15:15:2)

Example 4

(R)-1-(3,4-dimethyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate 4a) 3,4-dimethyl-3H-benzoxazol-2-one A solution of 10.0 g (67.0 mmol) 4-methyl-3H-benzoxazol-2-one in 200 mL THF was combined with 8.0 g (70.6 mmol) potassium-tert.-butoxide, stirred for 30 min at RT, then combined with 7.0 mL (110.3 mmol) iodomethane and stirred overnight at RT. The reaction mixture was combined with 100 mL EtOAc, washed twice with 50 mL saturated NaCl solution, the organic phase was dried over MgSO₄, filtered and evaporated to dryness i.vac. The residue was combined with PE/EtOAc 2:1, the precipitate was suction filtered and dried at 60° C. in the vacuum drying cupboard.

Yield: 9.0 g (82% of theory) ESI-MS: (M+H)⁺=164 R$_f$=0.56 (silica gel, PE/EtOAc 2:1)

4b) 6-bromo-3,4-dimethyl-3H-benzoxazol-2-one

To a solution of 9.0 g (55.2 mmol) 3,4-dimethyl-3H-benzoxazol-2-one in 50 mL AcOH were added 11.0 g (60.0 mmol) N-bromosuccinimide and the reaction mixture was stirred overnight at RT. The reaction solution was combined with 300 mL water, stirred for 15 min at RT, the precipitate was suction filtered, washed with water and dried at 60° C. in the vacuum drying cupboard.

Yield: 12.7 g (95% of theory) ESI-MS: (M+H)⁺=242/244 (Br) R$_f$=0.52 (silica gel, PE/EtOAc 2:1)

4c) methyl (Z,E)-2-acetylamino-3-(3,4-dimethyl-2-oxo-2,3-dihydro-benzoxazol-6-yl)-acrylate Under a nitrogen atmosphere 1.8 g (8.0 mmol) Pd(OAc)₂ and 2.5 g (8.0 mmol) tri-o-tolyl-phosphane were added to a solution of 13.2 g (54.5 mmol) 6-bromo-3,4-dimethyl-3H-benzoxazol-2-one and 9.0 g (61.6 mmol) methyl 2-acetylamino-acrylate in 250 mL acetonitrile and 160 mL triethylamine and the reaction mixture was stirred for 18 h at 80° C.

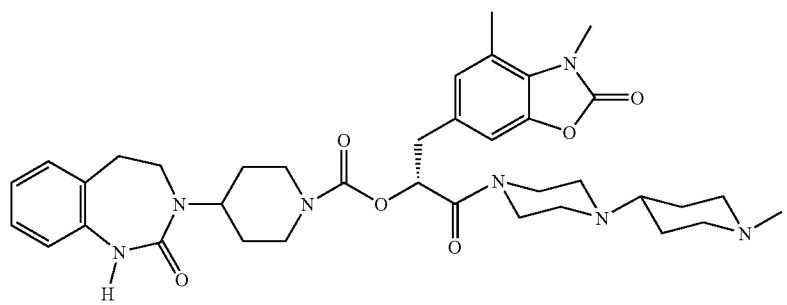

The reaction solution was evaporated down i.vac., the residue was combined with 100 mL water and 50 mL EtOAc and the precipitate was filtered off. The latter was dissolved in MeOH/DCM (1:1), combined with activated charcoal, filtered off and the filtrate was evaporated to dryness.

Yield: 8.7 g (52% of theory) ESI-MS: $(M+H)^+=305$
$R_f=0.47$ (silica gel, DCM/Cyc/MeOH/NH$_3$ 70:15:15:2)

4d) 3-(3,4-dimethyl-2-oxo-2,3-dihydro-benzoxazol-6-yl)-2-oxo-propionic acid 40 mL 4 M HCl were added to a solution of 8.7 g (28.6 mmol) methyl (Z,E)-2-acetylamino-3-(3,4-dimethyl-2-oxo-2,3-dihydro-benzoxazol-6-yl)-acrylate in 80 mL 1,4-dioxane and the reaction solution was refluxed for 5 h and then left overnight at RT. It was evaporated down i.vac., the precipitated product was filtered off, washed with water and dried at 60° C. in the vacuum drying cupboard.

Yield: 6.6 g (93% of theory) ESI-MS: $(M+H)^+=250$
$R_f=0.13$ (silica gel, DCM/Cyc/MeOH/NH$_3$ 70:15:15:2)

4e) (R)-3-(3,4-dimethyl-2-oxo-2,3-dihydro-benzoxazol-6-yl)-2-hydroxy-propionic acid Under a nitrogen atmosphere a solution of 15.0 g (46.8 mmol) (1R)—B-chlorodiisopinocampheylborane in 50 mL THF was added dropwise within 15 min to a solution of 6.6 g (26.5 mmol) 3-(3,4-dimethyl-2-oxo-2,3-dihydro-benzoxazol-6-yl)-2-oxo-propionic acid and 5.0 mL (36.0 mmol) triethylamine in 100 mL THF cooled to −35° C. and the reaction solution was stirred overnight at RT. Then at 5° C. the mixture was combined with 60 mL 1 M NaOH and 100 mL EtOAc, stirred for 15 min, the organic phase was separated off and extracted twice with 30 mL 1 M NaOH and with 40 mL water. The combined aqueous phases were acidified with semiconc. HCl and extracted twice with 100 mL EtOAc. The combined organic phases were dried over MgSO$_4$ and evaporated down i.vac.

Yield: 3.4 g (51% of theory) ESI-MS: $(M+H)^+=252$
$R_f=0.13$ (silica gel, DCM/Cyc/MeOH/NH$_3$ 70:15:15:2)

4f) methyl (R)-3-(3,4-dimethyl-2-oxo-2,3-dihydro-benzoxazol-6-yl)-2-hydroxy-propionate 3.4 g (13.5 mmol) (R)-3-(3,4-dimethyl-2-oxo-2,3-dihydro-benzoxazol-6-yl)-2-hydroxy-propionic acid were dissolved in 40 mL methanolic HCl (1.3 M) and the reaction mixture was stirred overnight at RT. It was evaporated down i.vac., the residue was taken up in 200 mL EtOAc, washed with 15% K$_2$CO$_3$ solution and the organic phase was dried over Na$_2$SO$_4$. After the desiccant and solvent had been eliminated the residue was reacted further without purification.

Yield: 2.5 g (70% of theory) ESI-MS: $(M+H)^+=266$
$R_f=0.54$ (silica gel, DCM/Cyc/MeOH/NH$_3$ 70:15:15:2)

4g) (R)-1-carboxy-2-(3,4-dimethyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate Under a nitrogen atmosphere a solution of 2.0 g (10.0 mmol) 4-nitrophenyl chloroformate in 10 mL THF was added at 60° C. within 10 min to 20 mL pyridine and stirred for 10 min. Then a solution of 2.5 g (9.4 mmol) methyl (R)-3-(3,4-dimethyl-2-oxo-2,3-dihydro-benzoxazol-6-yl)-2-hydroxy-propionate in 10 mL pyridine was added, the mixture was stirred for a further 2.5 h at 60° C. and then combined with 2.5 g (10.0 mmol) 3-piperidin-4-yl-1,3,4,5-tetrahydro-1,3-benzodiazepin-2-one. The reaction solution was stirred for 3 h at 100° C. After the end of the reaction the reaction mixture was evaporated down i.vac., combined with 150 mL EtOAc, the organic phase was washed three times with 40 mL 1 M KHSO$_4$ solution and 12 times with 30 mL 15% K$_2$CO$_3$ solution and dried over MgSO$_4$. After the desiccant and solvent had been eliminated the residue was dissolved in 60 mL THF, combined with 250 mg LiOH in 10 mL water and the reaction mixture was stirred for 3 h at RT. The THF was eliminated i.vac., the aqueous phase was diluted with 60 mL EtOAc, filtered to remove the insoluble constituents and the organic phase was separated off. The aqueous phase was acidified with 15 mL 1 M HCl, extracted three times with 50 mL EtOAc and the combined organic phases were dried over MgSO$_4$. After the desiccant and solvent had been eliminated the residue was dissolved at 80° C. in 30 mL isopropanol. The solution was left to cool slowly overnight, the precipitate was suction filtered, washed with isopropanol and dried at 60° C. in the vacuum drying cupboard.

Yield: 1.1 g (22% of theory) ESI-MS: $(M+H)^+=523$
$R_f=0.31$ (silica gel, DCM/Cyc/MeOH/NH$_3$ 70:15:15:2)

4h) (R)-1-(3,4-dimethyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate A solution of 80 mg (0.15 mmol) (R)-1-carboxy-2-(3,4-dimethyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 52 mg (0.16 mmol) TBTU, 24 μL (0.17 mmol) triethylamine and 30 mg (0.16 mmol) 1-(1-methylpiperidin-4-yl)-piperazine in 1.5 mL DMF was stirred overnight at RT. The reaction mixture was purified by HPLC, the fractions containing the product were combined and lyophilised.

Yield: 70 mg (66% of theory) ESI-MS: $(M+H)^+=688$
$R_f=0.36$ (silica gel, DCM/Cyc/MeOH/NH$_3$ 70:15:15:2)

The following compounds were prepared analogously from in each case 80 mg (Examples 4.1 and 4.2) or in each case 100 mg (Examples 4.3 to 4.6) of (R)-1-carboxy-2-(3,4-dimethyl-2-oxo-2,3-dihydro-benzoxazol-6-yl)-ethyl 4-(2-oxo-1,2,4,5-tetrahydro-1,3-benzodiazepin-3-yl)-piperidine-1-carboxylate and the corresponding amount of amine:

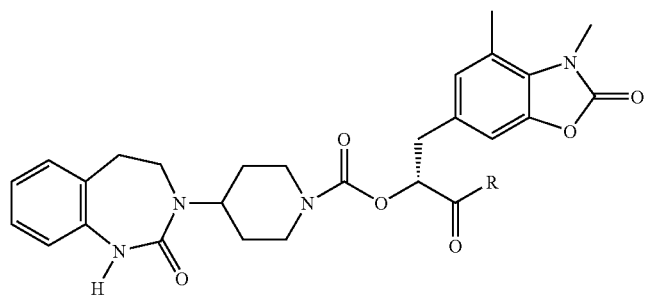
| Example | R | Yield (%) | Mass spectrum | $R_f$ (silica gel, DCM/MeOH/Cyc/NH$_3$ 70:15:15:2) |
|---|---|---|---|---|
| 4.1 | *-N(piperidine)-N(piperidine)-CH$_3$ | 62 | 688 [M + H]$^+$ | 0.32 |
| 4.2 | *-N(piperidine)-cyclohexyl-N-CH$_3$ | 52 | 687 [M + H]$^+$ | 0.33 |
| 4.3 | *-N(piperidine)-N(piperidine)-CH$_2$-Ph | 44 | 764 [M + H]$^+$ | 0.43 |
| 4.4 | *-N(piperidine)-cyclohexyl-N-CH$_2$-Ph | 29 | 763 [M + H]$^+$ | 0.49 |
| 4.5 | *-N(piperidine)-N(piperidine)-CH$_2$-pyridyl | 44 | 764 [M + H]$^+$ | 0.38 |
| 4.6 | *-N(piperidine)-N(piperidine)=N-OH | 49 | 689 [M + H]$^+$ | 0.43 |

Example 4.7

(R)-1-(3,4-dimethyl-2-oxo-2,3-dihydro-benzoxazol-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate

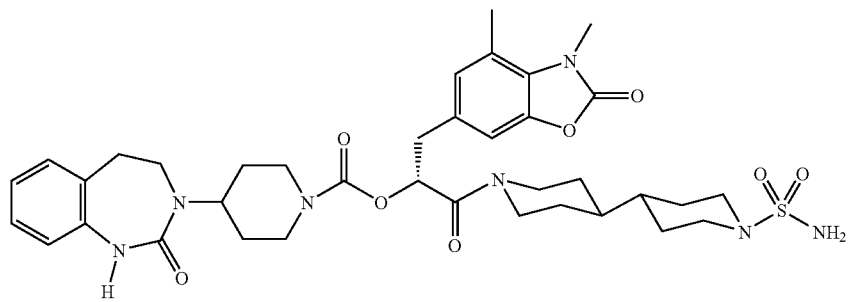

A solution of 75 mg (0.14 mmol) (R)-1-carboxy-2-(3,4-dimethyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate, 51 mg (0.16 mmol) TBTU, 42 µL (0.30 mmol) triethylamine and 41 mg (0.14 mmol) [4,4']bipiperidinyl-1-sulphonic acid amide (used as the hydrochloride salt) in 2 mL DMF were stirred overnight at RT. The reaction mixture was purified by HPLC, the fractions containing the product were combined and lyophilised.

Yield: 31 mg (29% of theory) ESI-MS: (M+H)$^+$=752 retention time: 3.7 min (method B)

The following compounds were prepared analogously from in each case 83 mg (R)-1-carboxy-2-(3,4-dimethyl-2-oxo-2,3-dihydro-benzoxazol-6-yl)-ethyl 4-(2-oxo-1,2,4,5-tetrahydro-1,3-benzodiazepin-3-yl)-piperidine-1-carboxylate and the corresponding amount of amine:

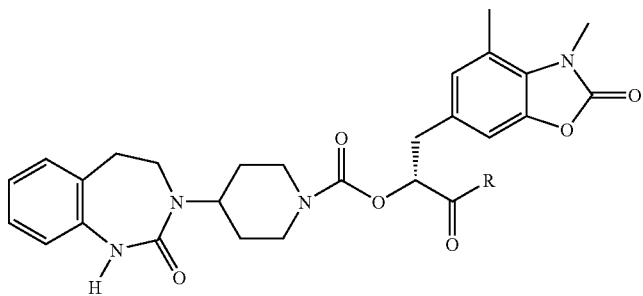

| Example | R | Yield (%) | Mass spectrum | retention time HPLC (method) |
|---|---|---|---|---|
| 4.8 | ![structure] | 72 | 751 [M + H]$^+$ | 3.9 min (B) |
| 4.9 | ![structure] | 52 | 714 [M + H]$^+$ | 2.5 min (B) |

Example 4.10

(R)-1-(3,4-dimethyl-2-oxo-2,3-dihydro-benzoxazol-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

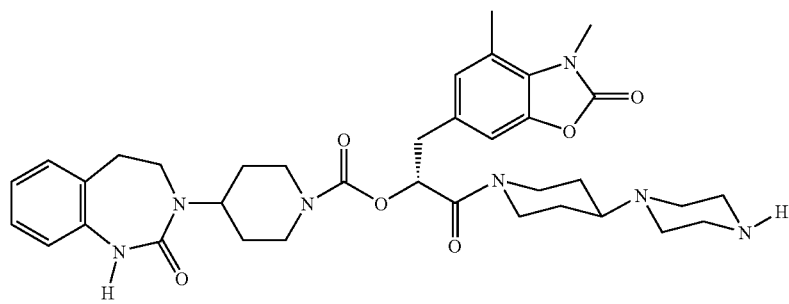

60 mg (0.08 mmol) (R)-2-[4-(4-benzyl-piperazin-1-yl)-piperidin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate (Example 4.3) were dissolved in 20 mL MeOH and combined with 10 mg 10% Pd/C. The mixture was hydrogenated at 50° C. and 3 bar hydrogen pressure until the theoretical hydrogen uptake had occurred. Then the catalyst was filtered off, the filtrate was evaporated to dryness i. vac., the residue was combined with MeOH and water and lyophilised.

Yield: 50 mg (94% of theory) ESI-MS: (M+H)$^+$=674
$R_f$=0.33 (silica gel, DCM/Cyc/MeOH/NH$_3$ 70:15:15:2)

Example 4.11

(R)-2-4,4'-bipiperidinyl-1-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate Analogously to Example 4.10 the product was obtained from 40 mg (0.05 mmol) (R)-2-(1'-benzyl-4,4'-bipiperidinyl-1-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate (Example 4.4).

Yield: 35 mg (99% of theory) ESI-MS: (M+H)$^+$=673
$R_f$=0.29 (silica gel, DCM/Cyc/MeOH/NH$_3$ 70:15:15:2)

Example 4.12

(R)-1-(3,4-dimethyl-2-oxo-2,3-dihydro-benzoxazol-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

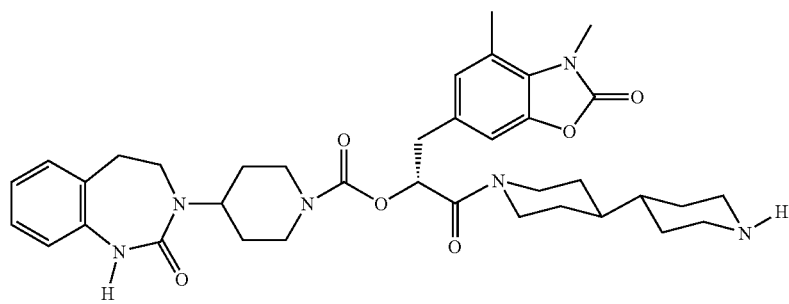

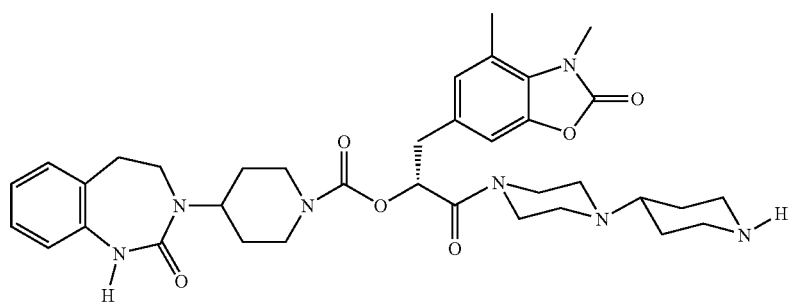

Analogously to Example 4.10 the product was obtained from 60 mg (0.08 mmol) (R)-2-[4-(1-benzyl-piperidin-4-yl)-piperazin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate (Example 4.5).

Yield: 45 mg (85% of theory) ESI-MS: $(M+H)^+=674$
$R_f=0.22$ (silica gel, DCM/Cyc/MeOH/NH$_3$ 70:15:15:2)

Example 4.13

(R)-2-(4-amino-4-methyl-1,4'-bipiperidinyl-1'-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate combined and lyophilised. The residue obtained was dissolved in 4 mL DCM, combined with 0.5 mL TFA and the reaction solution was stirred for 5 h at RT. The DCM was left to evaporate off overnight, the residue was combined with 2 mL 15% K$_2$CO$_3$ solution and extracted twice with 2 mL DCM. After the solvent had been eliminated the residue was taken up in 1 mL DMF and purified by HPLC. The fractions containing the product were combined and lyophilised.

Yield: 40 mg (35% of theory) ESI-MS: $(M+H)^+=702$
retention time (HPLC): 4.6 min (method A)

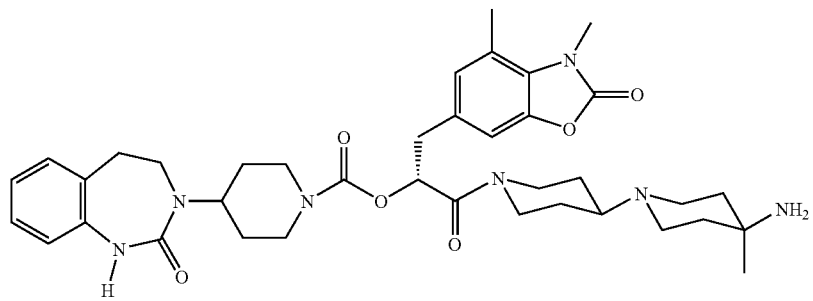

A solution of 80 mg (0.15 mmol) (R)-1-carboxy-2-(3,4-dimethyl-2-oxo-2,3-dihydrobenz-oxazol-6-yl)-ethyl 4-(2-oxo-1,2,4,5,-tetrahydro-1,3-benzodiazepin-3-yl)-piperidine-1-carboxylate, 58 mg (0.18 mmol) TBTU, 140 µL (1.00 mmol) triethylamine and 59 mg (0.16 mmol) tert.-butyl (4-methyl-[1,4']bipiperidinyl-4-yl)-carbamate in 1.8 mL DMF were stirred overnight at RT. The reaction mixture was purified by HPLC, the fractions containing the product were

Example 4.14

(R)-1-(3,4-dimethyl-2-oxo-2,3-dihydro-benzoxazol-6-ylmethyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate

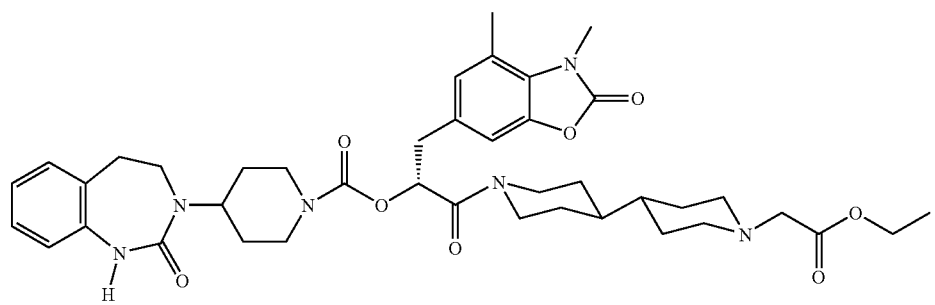

Analogously to Example 4 h the product was obtained from 200 mg (0.38 mmol) (R)-1-carboxy-2-(3,4-dimethyl-2-oxo-2,3-dihydro-benzoxazol-6-yl)-ethyl 4-(2-oxo-1,2,4,5-tetrahydro-1,3-benzodiazepin-3-yl)-piperidine-1-carboxylate and 110 mg (0.43 mmol) ethyl [4,4']bipiperidinyl-1-yl-acetate.

Yield: 60 mg (21% of theory) ESI-MS: (M+H)$^+$=759
R$_f$=0.54 (silica gel, DCM/Cyc/MeOH/NH$_3$ 70:15:15:2)

Example 4.15

(R)-2-(1'-carboxymethyl-4,4'-bipiperidinyl-1-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

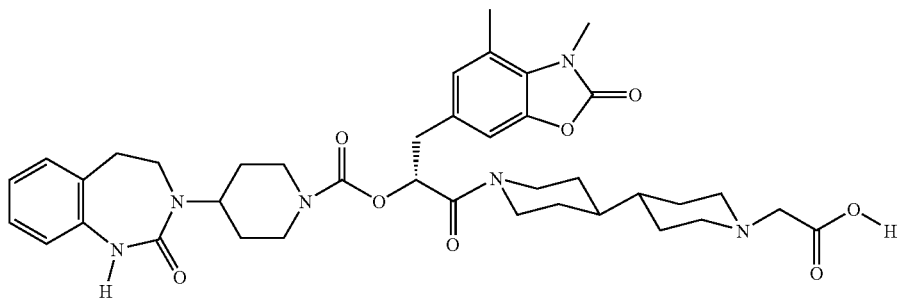

A solution of 4 mg (0.16 mmol) LIOH in 3 mL water was added to a solution of 60 mg (0.08 mmol) (R)-1-(3,4-dimethyl-2-oxo-2,3-dihydro-benzoxazol-6-ylmethyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate (Example 4.14) in 6 mL THF and the reaction mixture was stirred for 14 h at RT. The mixture was combined with 1 M HCl until an acid reaction was produced, evaporated down i.vac., the residue was taken up in a little DMF and the crude product was purified by HPLC. The fractions containing the product were combined and lyophilised.

Yield: 20 mg (35% of theory) ESI-MS: (M−H)$^-$=729
R$_f$=0.43 (silica gel, DCM/Cyc/MeOH/NH$_3$ 70:15:15:2)

Example 4.16

(R)-2-1,4'-bipiperidinyl-1'-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate

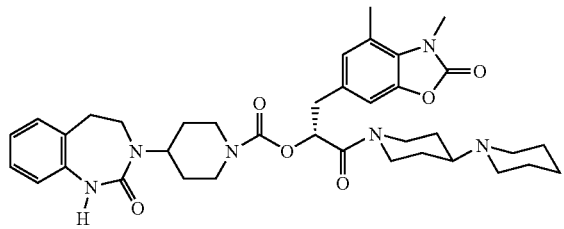

A solution of 70 mg (0.13 mmol) (R)-1-carboxy-2-(3,4-dimethyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate, 50 mg (0.16 mmol) TBTU, 25 µL (0.18 mmol) triethylamine and 59 mg (0.16 mmol) [1,4']bipiperidinyl in 1.0 mL DMF were shaken overnight at RT. The reaction mixture was purified by HPLC without any further working up, the fractions containing the product were combined and lyophilised.

Yield: 68 mg (75% of theory) ESI-MS: (M+H)$^+$=673
R$_f$=0.78 (silica gel, DCM/Cyc/MeOH/NH$_3$ 70:15:15:2)

The following compounds were prepared analogously from in each case 70 mg (R)-1-carboxy-2-(3,4-dimethyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate and the corresponding amount of amine:

| Example | R | Yield (%) | Mass spectrum | $R_f$ (silica gel, DCM/MeOH/Cyc/NH$_3$ 70:15:15:2) |
|---|---|---|---|---|
| 4.17 | *-N(piperidine)-N(piperazine)-N-cyclopropyl | 37 | 714 [M + H]$^+$ | 0.32 |
| 4.18 | *-N(piperidine)-N(piperidine) | 50 | 673 [M + H]$^+$ | 0.65 |
| 4.19 | *-N(piperidine)-N(tetrahydropyran) | 77 | 675 [M + H]$^+$ | 0.63 |
| 4.20$^a$ | *-N(piperidine)-N(cyclohexane with OH, OH) | 31 | 719 [M + H]$^+$ | 0.49 |

$^a$use of 4 eq. of triethylamine, as the amine component was used as the bis-hydrochloride salt

Example 5

(R)-1-(2,3-dihydro-1,4-benzodioxin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

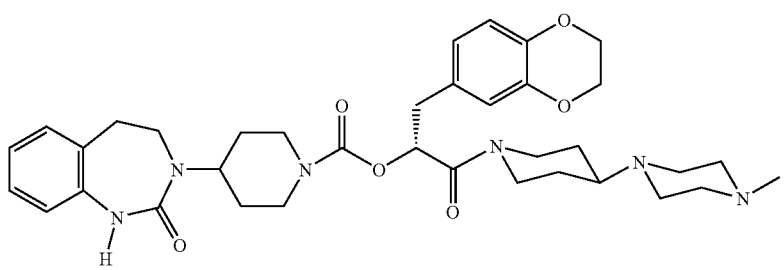

5a) (Z,E)-2-acetylamino-3-(2,3-dihydro-1,4-benzodioxin-6-yl)-acrylic acid

A suspension of 15.0 g (91.4 mmol) 2,3-dihydro-1,4-benzodioxin-6-carbaldehyde, 16.0 g (137 mmol) N-acetylglycine and 11.2 g (137 mmol) NaOAc in 50 mL acetic anhydride was heated to 120° C. in the oil bath for 4 h. After cooling 35 mL water were slowly added and the reaction mixture was stirred for 1 h at 80° C. The cooled solution was poured onto 350 mL water and combined with 150 mL toluene. A further 200 mL water were added, the phases were separated and the aqueous phase was again extracted with toluene. The aqueous phase was combined with 500 mL DCM and the phases were again separated. After standing for some time at RT a precipitate was deposited from the aqueous phase, and it was filtered off and dried. The organic phase was evaporated down to approx. 100 mL and left at RT. The precipitate formed was also filtered and dried. The two product fractions were combined.

Yield: 9.3 g (38% of theory) ESI-MS: (M+H)⁺=264

5b) 3-(2,3-dihydro-1,4-benzodioxin-6-yl)-2-oxo-propionic acid 110 mL 4 M HCl were added to a boiling solution of 9.25 g (35.1 mmol) (Z,E)-2-acetylamino-3-(2,3-dihydro-1,4-benzodioxin-6-yl)-acrylic acid in 100 mL isopropanol, the reaction mixture was refluxed for 2 h, combined with another 40 mL of 4 M HCl, refluxed for a further 4 h and left overnight at RT. The precipitate formed was filtered and dried at 60° C. The product was reacted further without purification.

Yield: 4.6 g (59% of theory) ESI-MS: (M−H)⁻=221

5c) (R)-3-(2,3-dihydro-1,4-benzodioxin-6-yl)-2-hydroxy-propionic acid

A solution of 12.4 g (23.0 mmol) (1R)—B-chlorodiisopinocampheylborane in 50 mL THF was added dropwise within 30 min to a solution of 4.6 g (20.7 mmol) 3-(2,3-dihydro-1,4-benzodioxin-6-yl)-2-oxo-propionic acid and 3.14 mL (23.0 mmol) triethylamine in 150 mL THF cooled to −35° C. and the reaction mixture was kept for 1 h at this temperature and for 4 h at RT. To complete the reaction a solution of 5.0 g (9.3 mmol) (1R)—B-chlorodiisopinocampheylborane in 50 mL THF was added and the reaction mixture was stirred overnight at RT. THF was removed i.vac. and the crude product (2.0 g) was reacted further without purification.

ESI-MS: (M+H)⁺=225 retention time (HPLC): 5.1 min (method A)

5d) methyl (R)-3-(2,3-dihydro-1,4-benzodioxin-6-yl)-2-hydroxy-propionate 2.0 g of the crude product from Example 5c were dissolved in 150 mL methanolic HCl (1.25 M) and the reaction mixture was stirred for 70 h at RT. The solvent was eliminated i.vac., the residue was taken up in 50 mL EtOAc and 50 mL saturated K₂CO₃ solution, the organic phase was separated off and the solvent was removed. The crude product was then purified by HPLC.

Yield: 0.23 g (5% of theory over 2 steps) ESI-MS: (M+H)⁺=239 retention time (HPLC): 6.0 min (method A)

5e) (R)-1-carboxy-2-(2,3-dihydro-1,4-benzodioxin-6-yl)-ethyl 4-(2-oxo-1,2,4,5-tetrahydro-1,3-benzodiazerin-3-yl)-piperidine-1-carboxylate Under a nitrogen atmosphere 55 mg (55% in mineral oil, 1.2 mmol) sodium hydride were added to a solution of 230 mg (0.97 mmol) methyl (S)-3-(2,3-dihydro-1,4-benzodioxin-6-yl)-2-hydroxy-propionate in 25 mL THF at 0° C., the reaction mixture was stirred for 30 min, then combined with 424 mg (0.97 mmol) 4-(2-oxo-1,2,4,5-tetrahydro-1,3-benzodiazepin-3-yl)-piperidine-1-carbonyl chloride and stirred overnight at RT. The reaction mixture was evaporated to dryness i.vac. and the residue was combined with 20 mL EtOAc and 20 mL 10% citric acid solution. The phases were separated, the aqueous phase was extracted again with 20 mL EtOAc and the combined organic phases were washed with 15% K₂CO₃ solution. The aqueous phase was separated off, combined with 4 M HCL, the precipitate formed was suction filtered and dried.

Yield: 35 mg (7% of theory) ESI-MS: (M+H)⁺=496 retention time (HPLC): 7.3 min (method A)

5f) (R)-1-(2,3-dihydro-1,4-benzodioxin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate A solution of 35 mg (0.07 mmol) (R)-1-carboxy-2-(2,3-dihydro-1,4-benzodioxin-6-yl)-ethyl 4-(2-oxo-1,2,4,5-tetrahydro-1,3-benzodiazepin-3-yl)-piperidine-1-carboxylate, 25 mg (0.08 mmol) TBTU, 11 µL (0.08 mmol) triethylamine and 14 mg (0.08 mmol) 1-methyl-4-piperidin-4-yl-piperazine in 1 mL DMF was stirred overnight at RT. The reaction mixture was purified by HPLC, the fractions containing the product were combined and lyophilised.

Yield: 30 mg (64% of theory) ESI-MS: (M+H)⁺=661 retention time (HPLC): 5.4 min (method A)

Example 6

(R)-1-(8-methyl-2,3-dihydro-1,4-benzodioxin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

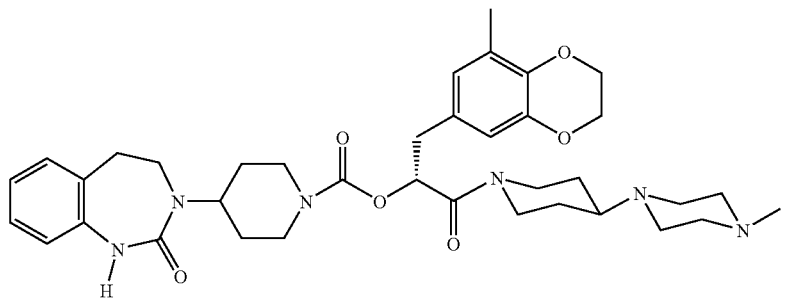

6a) 3,4-dihydroxy-5-methyl-benzoic acid

Under a nitrogen atmosphere 50.0 g (0.25 mol) 3,4-dimethoxy-5-methyl-benzoic acid and 170 g pyridine-hydrochloride were stirred for 2 h at a bath temperature of 160° C. The reaction mixture was poured onto 1 L citric acid solution and extracted with 1 L EtOAc. The organic phase was washed with 1 L water, dried and evaporated down i.vac.

Yield: 38.5 g (90% of theory) ESI-MS: (M−H)⁻=167 retention time (HPLC): 4.2 min (method A)

6b) methyl 3,4-dihydroxy-5-methyl-benzoate

A solution of 41.5 g (0.25 mol) 3,4-dihydroxy-5-methyl-benzoic acid in 500 mL methanolic HCl (1.25 M) was stirred overnight at RT. It was evaporated down i.vac., the residue was combined with DIPE, the precipitate was filtered off and dried in the vacuum drying cupboard.

Yield: 36.0 g (80% of theory) ESI-MS: $(M+H)^+=183$ retention time (HPLC): 5.9 min (method A)

6c) methyl 8-methyl-2,3-dihydro-1,4-benzodioxin-6-carboxylate

A mixture of 34.0 g (0.19 mol) methyl 3,4-dihydroxy-5-methyl-benzoate, 77.12 g (0.56 mol) $K_2CO_3$ and 32.1 mL (0.37 mol) dibromoethane in 500 mL acetonitrile was refluxed for 6 h. The solid was filtered off, washed with 100 mL acetonitrile and the filtrate was evaporated to dryness i.vac. The residue was combined with 500 mL water and 500 mL EtOAc, the phases were separated, the organic phase was dried and evaporated to dryness i. vac. The residue was combined with 120 mL DIPE, the precipitate was suction filtered, washed with 50 mL DIPE and dried.

Yield: 32.5 g (84% of theory) ESI-MS: $(M+H)^+=209$ retention time (HPLC): 4.2 min (method B)

6d) 8-methyl-2,3-dihydro-1,4-benzodioxin-6-carboxylic acid

A solution of 6.65 g (0.28 mol) LiOH in 100 mL water was metered into a solution of 33.60 g (0.16 mol) methyl 8-methyl-2,3-dihydro-1,4-benzodioxin-6-carboxylate in 200 mL THF and the reaction solution was stirred overnight at RT. To complete the reaction 150 mL 6 M NaOH were added and the mixture was stirred for a further 2 h at 50° C. The reaction mixture was evaporated down i.vac, the residue was combined with THF, acidified with conc. HCl while cooling with ice, the precipitate was filtered off, washed with 150 mL water and dried at 60° C. in the circulating air dryer.

Yield: 31.1 g (99% of theory) ESI-MS: $(M+H)^+=195$ retention time (HPLC): 3.3 min (method B)

6e) (8-methyl-2,3-dihydro-1,4-benzodioxin-6-yl)-methanol

A solution of 31.0 g (0.16 mol) 8-methyl-2,3-dihydro-1,4-benzodioxin-6-carboxylic acid in 500 mL THF was combined with 29.2 g (0.18 mol) CDI, stirred for 2 h at 40° C. and then added dropwise to a solution of 18.14 g (0.48 mol) sodium borohydride in 200 mL water at approx. 20° C. After the addition had ended the mixture was stirred for 2 h at RT, then acidified with semiconc. HCl while being cooled, combined with 300 mL water and 600 mL EtOAc, the phases were separated and the organic phase was dried. After the desiccant and solvent had been eliminated the residue was purified by chromatography (silica gel, PE/EtOAc 2:1).

Yield: 25.8 g (90% of theory) ESI-MS: $(M-H_2O+H)^+=163$ $R_f=0.55$ (silica gel, PE/EtOAc 1:1)

6f) 8-methyl-2,3-dihydro-1,4-benzodioxin-6-carbaldehyde 73.9 g (0.85 mol) manganese dioxide were added batchwise to a solution of 25.8 g (0.14 mol) (8-methyl-2,3-dihydro-1,4-benzodioxin-6-yl)-methanol in 300 mL DCM while cooling with an ice bath and the reaction solution was stirred overnight at RT. The precipitate was filtered off, washed with 100 mL DCM and the filtrate was evaporated to dryness i.vac.

Yield: 23.6 g (93% of theory) ESI-MS: $(2M+Na)^+=179$ $R_f=0.75$ (silica gel, PE/EtOAc 1:1)

6g) (Z,E)-2-acetylamino-3-(8-methyl-2,3-dihydro-1,4-benzodioxin-6-yl)-acrylic acid A mixture of 15.0 g (0.08 mol) 8-methyl-2,3-dihydro-1,4-benzodioxin-6-carbaldehyde, 14.9 g (0.13 mol) N-acetylglycine and 10.4 g (0.13 mol) NaOAc in 60 mL acetic anhydride was stirred for 5 h at a bath temperature of 120° C. The reaction mixture was cooled to 60° C. and combined dropwise with 40 mL water, then heated to 80° C. again for 1.5 h. The reaction solution was poured onto 200 mL water and 100 mL toluene, combined with 200 mL EtOAc, stirred for 30 min at RT, the precipitate was suction filtered, washed with 100 mL EtOAc and dried.

Yield: 11.0 g (47% of theory) ESI-MS: $(M-H)^-=276$ $R_f=0.1$ (silica gel, DCM/MeOH/$NH_3$ 80:20:2)

6h) 3-(8-methyl-2,3-dihydro-1,4-benzodioxin-6-yl)-2-oxo-propionic acid 60 mL 4 M HCl were metered into a solution of 11.0 g (39.7 mmol) (Z,E)-2-acetylamino-3-(8-methyl-2,3-dihydro-1,4-benzodioxin-6-yl)-acrylic acid in 120 mL 1,4-dioxane and the reaction solution was refluxed for 2 h. Then it was evaporated down i.vac, the residue was combined with 100 mL water, the precipitate was filtered off, washed with water and dried at 50° C. in the vacuum drying cupboard.

Yield: 9.2 g (98% of theory) ESI-MS: $(M-H)^-=235$ retention time (HPLC): 3.5 min (method B)

6i) (R)-2-hydroxy-3-(8-methyl-2,3-dihydro-1,4-benzodioxin-6-yl)-propionic acid

Under a nitrogen atmosphere a solution of 15.1 g (47.0 mmol) (1R)—B-chlorodiisopinocampheylborane in 50 mL THF was added dropwise within 15 min to a solution of 9.2 g (38.9 mmol) 3-(8-methyl-2,3-dihydro-1,4-benzodioxin-6-yl)-2-oxo-propionic acid and 5.4 mL (39.0 mmol) triethylamine in 100 mL THF cooled to −35° C. and the reaction mixture was stirred for 1 h at RT. After the end of the reaction the reaction solution was evaporated down i.vac., combined with 200 mL 1 M NaOH and 150 mL TBME, stirred, the aqueous phase was separated off, acidified with 2 M HCl and extracted twice with 250 mL EtOAc. The combined organic phases were dried, filtered through activated charcoal and evaporated down i.vac.

Yield: quantitative ESI-MS: $(M-H)^-=237$ retention time (HPLC): 2.8 min (method B)

6j) methyl (R)-2-hydroxy-3-(8-methyl-2,3-dihydro-1,4-benzodioxin-6-yl)-propionate 11.3 g (47.4 mmol) (R)-2-hydroxy-3-(8-methyl-2,3-dihydro-1,4-benzodioxin-6-yl)-propionic acid were dissolved in 250 mL methanolic HCl (1.3 M), stirred overnight at RT and then evaporated down i.vac. The product was reacted further without purification.

Yield: 10.3 g (86% of theory) ESI-MS: $(M+H)^+=253$ retention time (HPLC): 3.4 min (method B)

6k) (R)-1-(methoxycarbonyl-2-(8-methyl-2,3-dihydro-1,4-benzodioxin-6-yl)-ethyl 4-(2-oxo-1,2,4,5-tetrahydro-1,3-benzodiazepin-3-yl)-piperidine-1-carboxylate Under a nitrogen atmosphere 4.0 g (19.8 mmol) 4-nitrophenyl chloroformate in 10 mL THF was added dropwise to a solution of 2.7 g (21.8 mmol) dimethyl-aminopyridine in 20 mL pyridine while cooling with an ice bath, the cooling bath was removed and the mixture was stirred for 30 min at RT. While cooling again to 0° C., 5.0 g (19.8 mmol) methyl (R)-2-hydroxy-3-(8-methyl-2,3-dihydro-1,4-benzodioxin-6-yl)-propionate in 10 mL pyridine were added, the cooling bath was removed and the mixture was stirred for 2 h at RT. The reaction solution was combined with 5.3 g (21.8 mmol) 3-piperidin-4-yl-1,3,4,5-tetrahydro-1,3-benzodiazepin-2-one and stirred for 20 h at RT. After the end of the reaction the reaction mixture was evaporated down i.vac., combined with 150 mL EtOAc, the organic phase was washed with 1 M $KHSO_4$ and saturated $K_2CO_3$ solution and dried over $Na_2SO_4$. After the desiccant and solvent had been eliminated the residue was purified by chromatography (silica gel, EtOAc).

Yield: 5.2 g (50% of theory) ESI-MS: $(M+H)^+=524$ retention time (HPLC): 4.4 min (method B)

6l) (R)-1-carboxy-2-(8-methyl-2,3-dihydro-1,4-benzodioxin-6-yl)-ethyl 4-(2-oxo-1,2,4,5-tetrahydro-1,3-benzodiazepin-3-yl)-piperidine-1-carboxylate 151 mg (6.3 mmol) LiOH in 50 mL water were metered into a solution of 2.2 g (4.2 mmol) (R)-1-(methoxycarbonyl-2-(8-methyl-2,3-dihydro-1,4-benzodioxin-6-yl)-ethyl 4-(2-oxo-1,2,4,5-tetrahydro-1,3-benzodiazepin-3-yl)-piperidine-1-carboxylate in 50 mL THF and the reaction mixture was stirred for 2 h at RT. After the end of the reaction the mixture was evaporated to dryness i.vac. The residue was combined with 100 mL water and 100 mL EtOAc, the aqueous phase was separated off, acidified with 2 M HCl, extracted with 200 mL EtOAc and the organic phase was dried. After the desiccant and solvent had been eliminated the residue was evaporated to dryness i.vac. and reacted further without purification.

Yield: 1.9 g (86% of theory) ESI-MS: $(M+H)^+$=510 retention time (HPLC): 3.9 min (method A)

6m) (R)-1-(8-methyl-2,3-dihydro-1,4-benzodioxin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate A solution of 80 mg (0.16 mmol) (R)-1-carboxy-2-(8-methyl-2,3-dihydro-1,4-benzodioxin-6-yl)-ethyl 4-(2-oxo-1,2,4,5-tetrahydro-1,3-benzodiazepin-3-yl)-piperidine-1-carboxylate, 51 mg (0.16 mmol) TBTU, 42 µL (0.30 mmol) triethylamine and 29 mg (0.16 mmol) 1-methyl-4-piperidin-4-yl-piperazine in 1 mL DMF was stirred overnight at RT. The reaction mixture was purified by HPLC, the fractions containing the product were combined and lyophilised.

Yield: 60 mg (57% of theory) ESI-MS: $(M+H)^+$=675 retention time (HPLC): 5.0 min (method A)

The following compounds were prepared analogously from in each case 80 mg (R)-1-carboxy-2-(8-methyl-2,3-dihydro-1,4-benzodioxin-6-yl)-ethyl 4-(2-oxo-1,2,4,5-tetrahydro-1,3-benzodiazepin-3-yl)-piperidine-1-carboxylate and the corresponding amount of amine:

| Example | R | Yield (%) | Mass spectrum | HPLC retention time (method) |
|---|---|---|---|---|
| 6.1 | | 72 | 674 [M + H]⁺ | 5.4 min (A) |
| 6.2 | | 68 | 676 [M + H]⁺ | 5.2 min (A) |
| 6.3 | | 67 | 662 [M + H]⁺ | 5.2 min (A) |
| 6.4 | | 69 | 689 [M + H]⁺ | 5.2 min (A) |
| 6.5 | | 44 | 746 [M + H]⁺ | 5.6 min (A) |

-continued
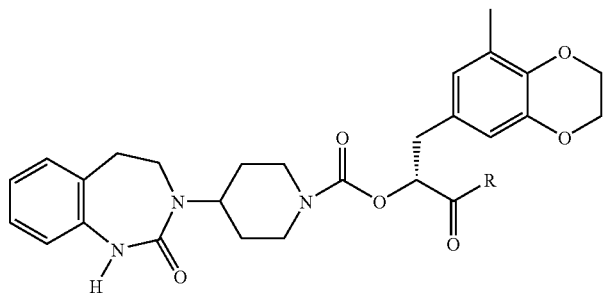
| Example | R | Yield (%) | Mass spectrum | HPLC retention time (method) |
|---|---|---|---|---|
| 6.6 | *-N(piperidine)-N(piperidine)-N-Me | 68 | 675 [M + H]+ | 4.6 min (A) |
| 6.7 | *-N(piperidine)-cyclohexyl | 77 | 660 [M + H]+ | 5.4 min (A) |
| 6.8 | *-N(piperidine)-N-tropane-Me | 65 | 701 [M + H]+ | 2.7 min (B) |
| 6.9 | *-N(piperidine)-N-diazabicyclo-Me | 74 | 687 [M + H]+ | 3.0 min (B) |
| 6.10 | *-N(piperidine)-quinuclidine | 20 | 687 [M + H]+ | 4.2 min (B) |
| 6.11 | *-N(piperidine)-N(piperidine)-C(O)O-CH2-Ph | 72 | 795 [M + H]+ | 6.1 min (A) |
| 6.12 | *-N(piperidine)-N(piperidine)-C(O)O-CH2-Ph | 33 | 795 [M + H]+ | 6.0 min (A) |

Example 6.13

(R)-1-(8-methyl-2,3-dihydro-1,4-benzodioxin-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

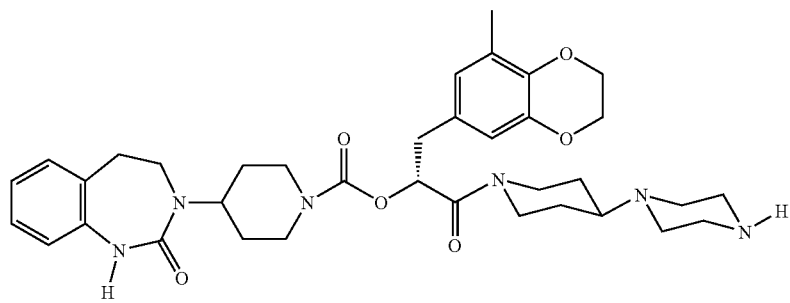

35 mg (0.04 mmol) benzyl 4-(1-{(R)-3-(8-methyl-2,3-dihydro-1,4-benzodioxin-6-yl)-2-[4-(2-oxo-1,2,4,5-tetrahydro-1,3-benzodiazepin-3-yl)-piperidine-1-carbonyloxy]-propionyl}-piperidin-4-yl)-piperazin-1-carboxylate (Example 6.12) were dissolved in 10 mL MeOH and combined with 50 mg 10% Pd/C. The mixture was hydrogenated at 50° C. and 3 bar hydrogen pressure until the theoretical hydrogen uptake had occurred (for 3 h). Then the catalyst was filtered off, the filtrate was evaporated to dryness i.vac., the residue was taken up in 2 mL DMF and purified by HPLC. The fractions containing the product were combined and lyophilised.

Yield: 15 mg (52% of theory) ESI-MS: $(M+H)^+=661$
retention time (HPLC): 2.8 min (method A)

Example 6.14

(R)-1-(8-methyl-2,3-dihydro-1,4-benzodioxin-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

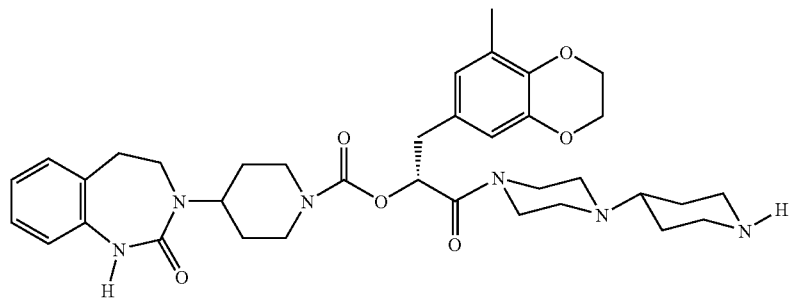

Analogously to Example 6.13 the product was obtained from 85 mg (0.11 mmol) (R)-1-(8-methyl-2,3-dihydro-1,4-benzodioxin-6-ylmethyl)-2-[4-(1-benzyloxy-carbonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 6.11).

Yield: 50 mg (52% of theory) ESI-MS: $(M+H)^+=661$
retention time (HPLC): 2.6 min (method A)

Example 6.15

(R)-2-(1'-carboxymethyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate

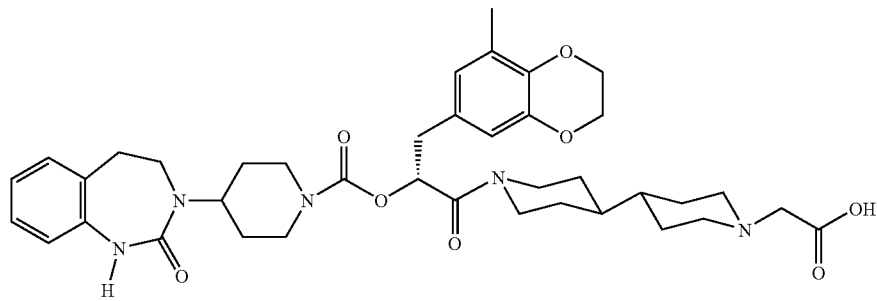

A solution of 1.4 mg (0.06 mmol) LiOH in 0.5 mL water was added to a solution of 28 mg (0.04 mmol) (R)-2-(1'-ethoxycarbonylmethyl-4,4'-bipiperidinyl-1-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate (Example 6.5) in 0.5 mL THF and the reaction solution was stirred for 3 h at RT. The reaction mixture was purified by HPLC without any further working up. The fractions containing the product were combined and lyophilised.

Yield: 23 mg (85% of theory) ESI-MS: (M+H)$^+$=718 retention time (HPLC): 3.2 min (method B)

Example 6.16

(R)-2-(4-amino-4-methyl-1,4'-bipiperidinyl-1'-yl)-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate

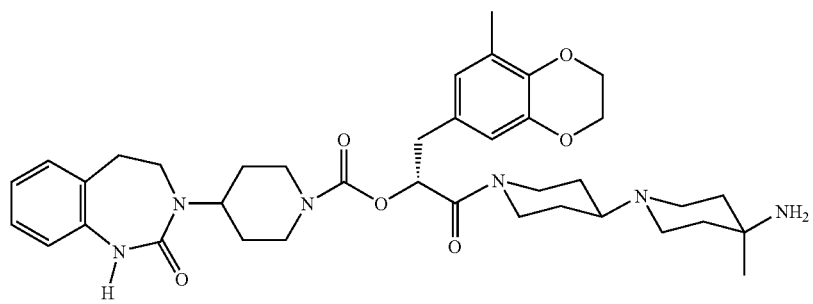

Analogously to Example 3.2 the product was obtained from 80 mg (0.16 mmol) (R)-1-carboxy-2-(8-methyl-2,3-dihydro-1,4-benzodioxin-6-yl)-ethyl 4-(2-oxo-1,2,4,5-tetrahydro-1,3-benzodiazepin-3-yl)-piperidine-1-carboxylate and 59 mg (0.16 mmol) tert.-butyl (4-methyl-[1,4']bipiperidinyl-4-yl)-carbamate (used as the bis-hydrochloride salt).

Yield: 50 mg (43% of theory) ESI-MS: (M+H)$^+$=689 retention time (HPLC): 4.9 min (method A)

Example 6.17

(R)-2-(1'-methanesulphonyl-4,4'-bipiperidinyl-1-yl)-1-(8-methyl-2,3-dihydro-1,4-benzodioxin-6-yl methyl)-2-oxo-ethyl 4-(2-oxo-1,2,4,5-tetrahydro-1,3-benzodiazepin-3-yl)-piperidine-1-carboxylate

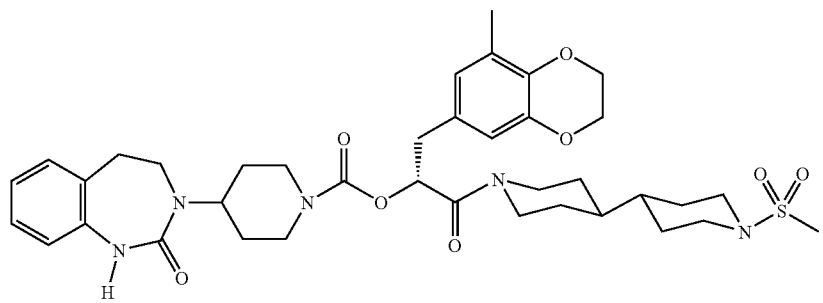

Analogously to Example 6m the product was obtained from 80 mg (0.16 mmol) (R)-1-carboxy-2-(8-methyl-2,3-dihydro-1,4-benzodioxin-6-yl)-ethyl 4-(2-oxo-1,2,4,5-tetrahydro-1,3-benzodiazepin-3-yl)-piperidine-1-carboxylate and 39 mg (0.16 mmol) 1-methanesulphonyl-[4,4']bipiperidinyl.

Yield: 90 mg (78% of theory) ESI-MS: $(M+H)^+=738$
retention time (HPLC): 4.2 min (method B)

Example 6.18

(R)-2-[4-(4-methanesulphonyl-piperazin-1-yl)-piperidin-1-yl]-1-(8-methyl-2,3-dihydro-1,4-benzodioxin-6-ylmethyl)-2-oxo-ethyl 4-(2-oxo-1,2,4,5-tetrahydro-1,3-benzodiazepin-3-yl)-piperidine-1-carboxylate

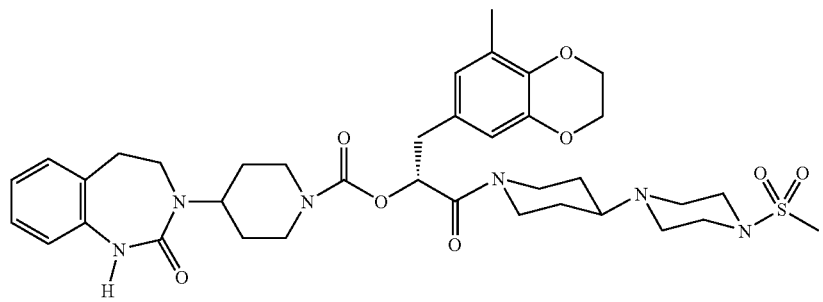

Analogously to Example 6m the product was obtained from 80 mg (0.16 mmol) (R)-1-carboxy-2-(8-methyl-2,3-dihydro-1,4-benzodioxin-6-yl)-ethyl 4-(2-oxo-1,2,4,5-tetrahydro-1,3-benzodiazepin-3-yl)-piperidine-1-carboxylate and 40 mg 1-methanesulphonyl-4-piperidin-4-yl-piperazine.

Yield: 52 mg (45% of theory) ESI-MS: $(M+H)^+=739$
retention time (HPLC): 3.1 min (method B)

Example 7

(R)-1-(8-methyl-imidazo[1,5-a]pyridin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

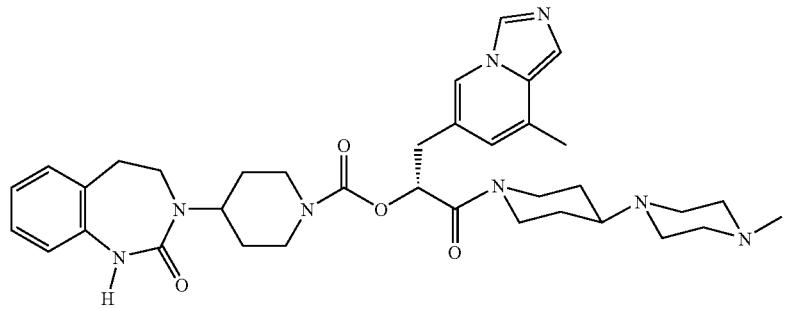

7a) methyl (Z,E)-2-acetylamino-3-(6-amino-5-methyl-pyridin-3-yl)-acrylate

Under a nitrogen atmosphere 6.58 g (7.19 mmol) tris-(dibenzylideneacetone)-palladium were added to a mixture of 33.6 g (180 mmol) 5-bromo-3-methyl-pyridin-2-ylamine, 28.9 g (198 mmol) methyl 2-acetylamino-acrylate, 4.42 g (14.4 mmol) tri-o-tolyl-phosphane and 30.9 mL (180 mmol) ethyldiisopropylamine in 500 mL butyronitrile and the reaction mixture was heated to 110° C. for 17 h. The reaction solution was evaporated down i.vac. and the residue was stirred with approx. 500 mL water. The precipitate was filtered, recrystallised from acetonitrile and dried. The aqueous mother liquor was evaporated down and the residue was purified by chromatography (silica gel, EtOAc/MeOH/NH$_3$ 90:10:1). The fractions containing the product were evaporated down, the residue was triturated with a little acetonitrile, filtered, dried and combined with the above product fraction.

Yield: 16.6 g (37% of theory) ESI-MS: (M+H)$^+$=250 R$_f$=0.46 (silica gel, EtOAc/MeOH/NH$_3$ 90:10:1)

7b) 3-(6-amino-5-methyl-pyridin-3-yl)-2-oxo-propionic acid 230 mL 4 M HCl were added to a solution of 15.57 g (62.46 mmol) methyl (Z,E)-2-acetylamino-3-(6-amino-5-methyl-pyridin-3-yl)-acrylate in 250 mL 1,4-dioxane, the reaction mixture was refluxed for 1.5 h and stirred for a further 16 h at RT. It was evaporated down i.vac., the residue was triturated with EtOAc/DIPE (1:1), filtered and dried in the circulating air dryer. The product was obtained as the hydrochloride salt.

Yield: 14.4 g (100% of theory) ESI-MS: (M+H)$^+$=195 retention time (HPLC): 2.7 min (method A)

7c) methyl (R)-3-(6-amino-5-methyl-pyridin-3-yl)-2-hydroxy-propionate

A mixture of 13.8 g (59.9 mmol) 3-(6-amino-5-methyl-pyridin-3-yl)-2-oxo-propionic acid and 17.5 mL (125.7 mmol) triethylamine in 140 mL THF was cooled to −35° C. under an argon atmosphere. Then a solution of 40.3 g (126 mmol) (1 R)-B-chlorodiisopinocampheylborane in 210 mL THF was added dropwise so that the reaction temperature remained between −35° C. and −25° C.; the reaction mixture was kept for 3 h at this temperature before being combined at 0-5° C. with 150 mL of 1 M NaOH and being stirred for 2 h at RT. 200 mL TBME were added, the organic phase was separated off and acidified with 200 mL 2 M HCl. The aqueous phase was separated off, evaporated down, the residue was taken up in THF/MeOH (1:1), filtered and the filtrate was then evaporated down. The crude product thus obtained (12.5 g) was dissolved in 300 mL MeOH, combined dropwise with 4.3 mL (59.3 mmol) SOCl$_2$ while cooling with ice and stirred for a further 2 h at RT. The mixture was evaporated down i. vac. and the residue was purified by chromatography (silica gel, EtOAc/MeOH/NH$_3$ 90:10:1).

Yield: 5.62 g (45% of theory) ESI-MS: (M+H)$^+$=211 retention time (HPLC): 2.4 min (method A)

7d) methyl (R)-2-hydroxy-3-(8-methyl-imidazo[1.5-a]pyridin-6-yl)-propionate

A solution of 800 mg (3.81 mmol) methyl (R)-3-(6-amino-5-methyl-pyridin-3-yl)-2-hydroxy-propionate and 1.6 mL (12.6 mmol, 50% in water) chloroacetaldehyde in 16 mL MeOH was refluxed for 2 h under a nitrogen atmosphere. It was evaporated down i.vac., the residue was taken up in 100 mL DCM, extracted with 10 mL saturated NaHCO$_3$ solution, the organic phase was separated off and dried over Na$_2$SO$_4$. After the desiccant and solvent had been eliminated the residue was purified by chromatography (Alox, DCM/MeOH 40:1).

Yield: 610 mg (68% of theory) ESI-MS: (M+H)$^+$=235 R$_f$=0.57 (Polygram-Alox, DCM/MeOH 25:1)

7e) (R)-1-methoxycarbonyl-2-(8-methyl-imidazo[1.5-a]pyridin-6-yl)-ethyl 4-(2-oxo-1,2,4,5-tetrahydro-1,3-benzodiazepin-3-yl)-piperidine-1-carboxylate Analogously to Example 6k the product was obtained from 685 mg (2.92 mmol) methyl (R)-2-hydroxy-3-(8-methyl-imidazo[1,5-a]pyridin-6-yl)-propionate and 800 mg (3.26 mmol) 3-piperidin-4-yl-1,3,4,5-tetrahydro-1,3-benzodiazepin-2-one, and purified by chromatography (first purification: Alox, gradient DCM/MeOH 50:1 to 40:1; second purification: silica gel, DCM/MeOH 15:1).

Yield: 570 mg (39% of theory) ESI-MS: (M+H)$^+$=506

7f) (R)-1-carboxy-2-(8-methyl-imidazo[1.5-a]pyridin-6-yl)-ethyl 4-(2-oxo-1.2.4.5-tetrahydro-1.3-benzodiazepin-3-yl)-piperidine-1-carboxylate A solution of 40.0 mg (1.67 mmol) LiOH in 15 mL water was added to a solution of 560 mg (1.11 mmol) (R)-1-methoxycarbonyl-2-(8-methyl-imidazo[1,5-a]pyridin-6-yl)-ethyl 4-(2-oxo-1,2,4,5-tetrahydro-1,3-benzodiazepin-3-yl)-piperidine-1-carboxylate in 20 mL THF and the reaction mixture was stirred for 1 h at RT. It was evaporated down i.vac., the residue was taken up in 30 mL water auf and acidified with ACOH. The precipitate was filtered and dried.

Yield: 700 mg (100% of theory, product contained AcOH) ESI-MS: (M+H)$^+$=492

7g) (R)-1-(8-methyl-imidazo[1.5-a]pyridin-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate A solution of 115 mg (0.18 mmol) (R)-1-carboxy-2-(8-methyl-imidazo[1,5-a]pyridin-6-yl)-ethyl 4-(2-oxo-1,2,4,5-tetrahydro-1,3-benzodiazepin-3-yl)-piperidine-1-carboxylate, 70 mg (0.22 mmol) TBTU and 40 μL (0.29 mmol) triethylamine in 10 mL THF and 1 mL DMF was stirred for 1 h at RT. Then 50 mg (0.27 mmol) 1-methyl-4-piperidin-4-yl-piperazine were added and the reaction mixture was stirred overnight at RT. To complete the reaction another 70 mg TBTU and 50 mg 1-methyl-4-piperidin-4-yl-piperazine were added, the mixture was stirred for a further 65 h at RT and again combined with 70 mg TBTU, 50 mg 1-methyl-4-piperidin-4-yl-piperazine, 40 μL triethylamine and 1 mL DMF and stirred overnight at RT. 10 mL semisaturated NaHCO$_3$ solution were added to the reaction mixture, it was extracted twice with 30 mL EtOAc and the combined organic phases were dried over Na$_2$SO$_4$. After the desiccant and solvent had been eliminated the residue was purified by HPLC. The fractions containing the product were combined and lyophilised.

Yield: 49 mg (29% of theory) ESI-MS: (M+H)$^+$=657 retention time (HPLC): 2.0 min (method B)

The following compounds were prepared analogously from in each case 115 mg of (R)-1-carboxy-2-(8-methyl-imidazo[1,5-a]pyridin-6-yl)-ethyl 4-(2-oxo-1,2,4,5-tetrahydro-1,3-benzodiazepin-3-yl)-piperidine-1-carboxylate and the corresponding amount of amine:

The following Examples describe the preparation of pharmaceutical formulations which contain as active substance any desired compound of general formula (I):

Example I

Capsules for Powder Inhalation Containing 1 mg of Active Ingredient

| Composition: 1 capsule for powder inhalation contains: | |
| --- | --- |
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

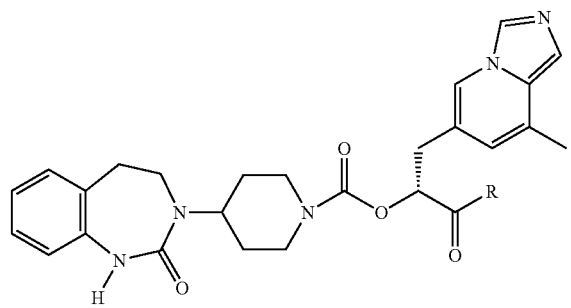

| Example | R | Yield (%) | Mass spectrum | HPLC retention time (method) |
| --- | --- | --- | --- | --- |
| 7.1 | | 63 | 656 [M + H]$^+$ | 2.2 min (B) |
| 7.2 | | 41 | 657 [M + H]$^+$ | 1.9 min (B) |

Example II

Inhalable Solution for Respimat® containing 1 mg of Active Ingredient

| Composition: 1 puff contains: | |
|---|---|
| active ingredient | 1.0 mg |
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

Example III

Inhalable Solution for Nebulisers Containing 1 mg of Active Ingredient

| Composition: 1 vial contains: | |
|---|---|
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-operated Metering Aerosol Containing 1 mg of Active Ingredient

| Composition: 1 puff contains: | |
|---|---|
| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient

| Composition: | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI

Injectable Solution Containing 5 mg of Active Substance Per 5 ml

| Composition: | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

Example VII

Injectable Solution Containing 100 mg of Active Substance Per 20 ml

| Composition: | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

Example VIII

Lyophilisate Containing 10 mg of Active Substance

| Composition: | |
|---|---|
| Active substance | 10 mg |
| Mannitol | 300 mg |
| human serum albumin | 20 mg |

Preparation:

Mannitol is dissolved in water for injections (Wfl); human serum albumin is added; active ingredient is dissolved with heating; made up to specified volume with Wfl; transferred into vials; freeze-dried.

| Solvent for lyophilisate: | |
|---|---|
| Polysorbate 80 = Tween 80 | 20 mg |
| mannitol | 200 mg |
| water for injections ad | 10 ml |

Preparation:
Polysorbate 80 and mannitol are dissolved in water for injections (Wfl); transferred into ampoules.

Example IX

Tablets Containing 20 mg of Active Substance

| Composition: | |
|---|---|
| active substance | 20 mg |
| lactose | 120 mg |
| maize starch | 40 mg |
| magnesium stearate | 2 mg |
| Povidone K 25 | 18 mg |

Preparation:
Active substance, lactose and maize starch are homogeneously mixed; granulated with an aqueous solution of Povidone; mixed with magnesium stearate; compressed in a tablet press; weight of tablet 200 mg.

Example X

Capsules Containing 20 mg Active Substance

| Composition: | |
|---|---|
| active substance | 20 mg |
| maize starch | 80 mg |
| highly dispersed silica | 5 mg |
| magnesium stearate | 2.5 mg |

Preparation:
Active substance, maize starch and silica are homogeneously mixed; mixed with magnesium stearate; the mixture is packed into size for 3 hard gelatine capsules in a capsule filling machine.

Example XI

Suppositories Containing 50 mg of Active Substance

| Composition: | |
|---|---|
| active substance | 50 mg |
| hard fat (Adeps solidus) q.s. ad | 1700 mg |

Preparation:
Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance Per 1 ml

| Composition: | |
|---|---|
| active substance | 10 mg |
| mannitol | 50 mg |
| human serum albumin | 10 mg |
| water for injections ad | 1 ml |

Preparation:
Mannitol is dissolved in water for injections (Wfl); human serum albumin is added; active ingredient is dissolved with heating; made up to specified volume with Wfl; transferred into ampoules under nitrogen gas.

What is claimed is:
1. A compound of the formula

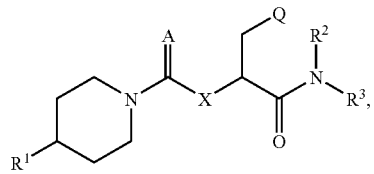

(I)

wherein
A denotes an oxygen or sulphur atom,
X denotes an oxygen or sulphur atom,
Q denotes 2-oxo-dihydrobenzoxazolyl,
$R^1$ denotes 2-oxo-1,2,4,5-tetrahydro-1,3,bezodiazepinyl,
$R^2$ denotes the hydrogen atom, a phenylmethyl group or a $C_{2-7}$-alkyl group which may be substituted in the ω position by a cyclo-$C_{3-7}$-alkyl, cyclo-$C_{3-7}$-alkenyl, phenyl, pyridinyl, diazinyl, hydroxy, amino, $C_{1-6}$-alkylamino, di-($C_{1-6}$-alkyl)-amino, $C_{3-6}$-alkenylamino, di-($C_{3-6}$-alkenyl)amino, $C_{3-6}$-alkynylamino, di-($C_{3-6}$-alkynyl)amino, hydroxycarbonyl, $C_{1-6}$-alkoxycarbonyl, aminocarbonyl, aminocarbonylamino, $C_{1-6}$-alkylcarbonylamino, $C_{2-6}$-alkenylcarbonylamino, $C_{2-6}$-alkynylcarbonylamino, 4-morpholinyl, [bis-(2-hydroxyethyl)] amino, 4-($C_{1-6}$-alkyl)-1-piperazinyl or 4-(ω-hydroxy-$C_{2-7}$-alkyl)-1-piperazinyl group,
a phenyl or pyridinyl group, while the phenyl, pyridinyl and diazinyl groups mentioned in the above definitions of $R^2$ or contained as substituents may additionally be mono- di- or trisubstituted in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkyl-amino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonylamino-$C_{1-3}$-alkyl, aminocarbonyl, $C_{1-3}$-alkyl-aminocarbonyl, di-($C_{1-3}$-alkyl)-aminocarbonyl, cyano, aminosulphonyl, $C_{1-3}$-alkyl-aminosulphonyl, di-($C_{1-3}$-alkyl)-aminosulphonyl, $C_{1-3}$-alkyl-thio, $C_{1-3}$-alkyl-sulphinyl or $C_{1-3}$-alkyl-sulphonyl and the substituents may be identical or different,
$R^3$ denotes the hydrogen atom or a $C_{1-3}$-alkyl group substituted by a phenyl or pyridinyl group, while the $C_{1-3}$-alkyl group may be connected to an alkyl group contained in R² or a phenyl or pyridyl ring contained in R² including the nitrogen atom to which R² and R³ are bound, forming a 4- to 7-membered ring, or R² and R³ together with the enclosed nitrogen atom denote a group of general formula

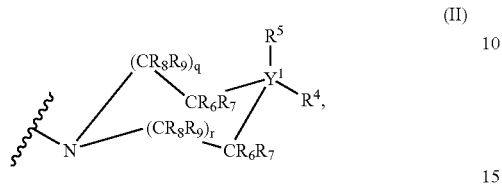

(II)

wherein $Y^1$ denotes the carbon atom or, if $R^5$ denotes a pair of free electrons, it may also denote the nitrogen atom, q and r, if $Y^1$ denotes the carbon atom, denote the numbers 0, 1 or 2, or q and r, if $Y^1$ denotes the nitrogen atom, denote the numbers 1 or 2, $R^4$ denotes the hydrogen atom, an amino, $C_{1-4}$-alkyl-amino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$-alkyl-amino)-$C_{2-7}$-alkyl, aminoiminomethyl, aminocarbonylamino, $C_{1-4}$-alkyl-aminocarbonylamino, di-($C_{1-4}$-alkyl)-aminocarbonylamino, $C_{1-4}$-alkyl-aminocarbonyl-$C_{1-4}$-alkyl-amino, di-($C_{1-4}$-alkyl)-aminocarbonyl-$C_{1-4}$-alkyl-amino, phenylaminocarbonylamino, aminocarbonyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{3-6}$-alkenoxycarbonyl, $C_{3-6}$-alkynoxycarbonyl, $C_{1-6}$-alkoxycarbonyl-$C_{1-3}$-alkyl, $C_{1-6}$-alkenoxycarbonyl-$C_{1-3}$-alkyl, $C_{1-6}$-alkynoxycarbonyl-$C_{1-3}$-alkyl or hydroxycarbonyl-$C_{1-3}$-alkyl group, a phenyl, pyridinyl, diazinyl, 1-naphthyl, 2-naphthyl, pyridinylcarbonyl or phenylcarbonyl group which may be mono- di- or trisubstituted in each case in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-4}$-alkyl-aminocarbonyl, di-($C_{1-4}$-alkyl)-aminocarbonyl, cyano, aminosulphonyl, $C_{1-4}$-alkyl-aminosulphonyl, di-($C_{1-4}$-alkyl)-aminosulphonyl, $C_{1-4}$-alkyl-thio, $C_{1-4}$-alkyl-sulphinyl or $C_{1-4}$-alkyl-sulphonyl and the substituents may be identical or different, a heterocycle selected from a 4- to 10-membered azacycloalkyl group, a 6- to 10-membered oxaza-, thiaza-, S,S-dioxothiaza- and diazacycloalkyl group as well as a 6- to 10-membered azabicycloalkyl group, a 1-alkyl-4-piperidinylcarbonyl or 4-alkyl-1-piperazinylcarbonyl group, while the above-mentioned mono- and bicyclic heterocycles are bound to $Y^1$ in formula (II) by a nitrogen or a carbon atom, in the above-mentioned mono- and bicyclic heterocycles a methyne group not directly linked to a nitrogen, oxygen or sulphur atom may be substituted by a fluorine atom and a methylene group not directly linked to a nitrogen, oxygen or sulphur atom may be substituted by one or two fluorine atoms, the above-mentioned mono- and bicyclic heterocycles as well as the 1-($C_{1-6}$-alkyl)-4-piperidinylcarbonyl- and 4-($C_{1-6}$-alkyl)-1-piperazinylcarbonyl group in the ring may be mono- to tetra-substituted by hydroxy, $C_{1-6}$-alkyl or hydroxy-$C_{1-3}$-alkyl groups, or, optionally additionally, may be monosubstituted by a cyclo-$C_{3-7}$-alkyl, hydroxy-$C_{3-7}$-cycloalkyl, cyclo-$C_{3-7}$-alkenyl, cyclo-$C_{3-7}$-alkyl-$C_{1-3}$-alkyl, phenyl-$C_{1-3}$-alkyl, pyridyl-$C_{1-3}$-alkyl, $C_{1-6}$-alkylcarbonyl, $C_{1-6}$-alkylcarbonyl-$C_{1-3}$-alkyl, hydroxy, $C_{1-6}$-alkoxy, amino, $C_{1-4}$-alkylamino, di-($C_{1-4}$-alkyl)amino, phenylcarbonyl, pyridinylcarbonyl, $C_{1-6}$-alkoxycarbonyl, hydroxycarbonyl-carbonyl, $C_{1-6}$-alkoxycarbonyl-carbonyl, hydroxycarbonyl-$C_{1-3}$-alkyl, $C_{1-6}$-alkoxycarbonyl-$C_{1-3}$-alkyl, hydroxycarbonyl-$C_{1-3}$-alkylcarbonyl, $C_{1-6}$-alkoxycarbonyl-$C_{1-3}$-alkylcarbonyl, aminocarbonyl, $C_{1-4}$-alkylaminocarbonyl, di-($C_{1-4}$-alkyl)aminocarbonyl, aminosulphonyl, $C_{1-4}$-alkylaminosulphonyl, di-($C_{1-4}$-alkyl)aminosulphonyl, $C_{1-3}$-alkylsulphonyl, cyclo-$C_{3-7}$-alkylsulphonyl, aminocarbonyl-$C_{1-3}$-alkyl, $C_{1-4}$-alkylaminocarbonyl-$C_{1-3}$-alkyl, di-($C_{1-4}$-alkyl)aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl group, by a cyclo-$C_{3-7}$-alkyl-carbonyl, azacyclo-$C_{4-7}$-alkyl-carbonyl, diazacyclo-$C_{5-7}$-alkyl-carbonyl or oxazacyclo-$C_{5-7}$-alkyl-carbonyl group optionally $C_{1-3}$-alkyl-substituted in the ring, while the substituents may be identical or different and may be bound to a cyclic carbon or cyclic nitrogen atom, while the phenyl and pyridinyl groups contained in the groups given as definitions of $R^4$ hereinbefore may in turn be mono-, di- or trisubstituted by halogen atoms, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-3}$-alkyl-aminocarbonyl, di-$C_{1-4}$-alkyl-aminocarbonyl, cyano, aminosulphonyl, $C_{1-4}$-alkyl-aminosulphonyl, di-($C_{1-4}$-alkyl)-aminosulphonyl, $C_{1-3}$-alkyl-thio, $C_{1-3}$-alkyl-sulphinyl or $C_{1-3}$-alkyl-sulphonyl, while the substituents may be identical or different, or, if $Y^1$ denotes the carbon atom, $R^4$ may denote the hydroxycarbonyl, aminomethyl, $C_{1-4}$-alkyl-aminomethyl or di-($C_{1-4}$-alkyl)-aminomethyl group, $R^5$ denotes a hydrogen atom or a hydroxy group, a $C_{1-4}$-alkyl group, while an unbranched alkyl group in the ω position may be substituted by a phenyl, pyridinyl, diazinyl, amino, $C_{1-4}$-alkylamino, di-($C_{1-4}$-alkyl)-amino, 4-$C_{1-4}$-alkyl-1-piperazinyl or 4-morpholinyl group, a $C_{1-6}$-alkoxycarbonyl, cyano or aminocarbonyl group or, if $Y^1$ denotes a nitrogen atom, $R^5$ also denotes a pair of free electrons, or, if $Y^1$ denotes the carbon atom, $R^5$ also denotes the fluorine atom, or $R^4$ together with $R^5$ and $Y^1$ denotes a 4- to 7-membered cycloaliphatic ring wherein a methylene group may be replaced by an —NH—, —N($C_{1-4}$-alkyl)-, —N($C_{3-4}$-alkenyl)-, —N($C_{3-4}$-alkynyl)-, —N(cyclo-$C_{3-7}$-alkyl)-, —N($C_{3-7}$-cycloalkyl-$C_{1-3}$-alkyl)-, —N(hydroxycarbonyl-$C_{1-3}$-alkyl)- or —N($C_{1-6}$-alkoxycarbonyl-$C_{1-3}$-alkyl)- group, while a hydrogen atom bound to a nitrogen atom in one of the groups defined for $R^4$ hereinbefore may be replaced by a protective group, $R^6$ and $R^7$, which may be identical or different, in each case denote a hydrogen atom, a $C_{1-4}$-alkyl group or, if $Y^1$ denotes a carbon atom, also denote the fluorine atom, an amino, $C_{1-4}$-alkylamino or di-($C_{1-4}$-alkyl)-amino group, while the two $C_{1-4}$-alkyl groups may be joined together to form a ring and $R^8$ and $R^9$, which may be identical or different, in each case denote a hydrogen atom or a $C_{1-3}$-alkyl group, or a tautomer or salt thereof.

2. A compound of the formula (I) according to claim 1, wherein

A denotes an oxygen or sulphur atom,

X denotes an oxygen or sulphur atom, $R^2$ denotes the hydrogen atom, a phenylmethyl group or a $C_{2-7}$-alkyl group which may be substituted in the ω position by a cyclo-$C_{3-7}$-alkyl, cyclo-$C_{3-7}$-alkenyl, phenyl, pyridinyl, diazinyl, hydroxy, amino, $C_{1-6}$-alkylamino, di-($C_{1-6}$-alkyl)-amino, $C_{3-6}$-alkenylamino, di-($C_{3-6}$-alkenyl)amino, $C_{3-6}$-alkynylamino, di-($C_{3-6}$-alkynyl)amino, hydroxycarbonyl, $C_{1-6}$-alkoxycarbonyl, aminocarbonyl, aminocarbonylamino, $C_{1-6}$-alkylcarbonylamino, $C_{2-6}$-alkenylcarbonylamino, $C_{2-6}$-alkynylcarbonylamino, 4-morpholinyl, [bis-(2-hydroxyethyl)]amino, 4-($C_{1-6}$-alkyl)-1-piperazinyl or 4-(ω-hydroxy-$C_{2-7}$-alkyl)-1-piperazinyl group, a phenyl or pyridinyl group, while the phenyl, pyridinyl and diazinyl groups mentioned in the groups defined for $R^2$ hereinbefore or contained as substituents may additionally be mono-, di- or trisubstituted in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkyl-amino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonylamino-$C_{1-3}$-alkyl, aminocarbonyl, $C_{1-3}$-alkyl-aminocarbonyl, di-($C_{1-3}$-alkyl)-aminocarbonyl, cyano, aminosulphonyl, $C_{1-3}$-alkyl-aminosulphonyl, di-($C_{1-3}$-alkyl)-aminosulphonyl, $C_{1-3}$-alkylthio, $C_{1-3}$-alkylsulphinyl or $C_{1-3}$-alkylsulphonyl and the substituents may be identical or different, $R^3$ denotes the hydrogen atom or a $C_{1-3}$-alkyl group substituted by a phenyl or pyridinyl group, while the $C_{1-3}$-alkyl group may be connected to an alkyl group contained in $R^2$ or a phenyl or pyridyl ring contained in $R^2$ including the nitrogen atom to which $R^2$ and are bound, forming a 4- to 7-membered ring, or $R^2$ and $R^3$ together with the enclosed nitrogen atom denote a group of general formula

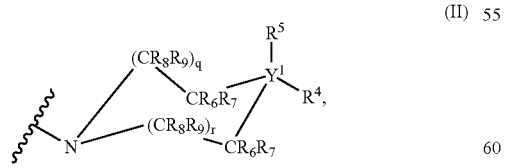

(II)

wherein $Y^1$ denotes the carbon atom or, if $R^5$ denotes a pair of free electrons, $Y^1$ may also denote the nitrogen atom, q and r, if $Y^1$ denotes the carbon atom, denote the numbers 0, 1 or 2, or q and r, if $Y^1$ denotes the nitrogen atom, denote the numbers 1 or 2, $R^4$ denotes the hydrogen atom, an amino, $C_{1-4}$-alkylamino, di-($C_{1-4}$-alkyl)-alkylamino, $C_{1-6}$-alkyl, cyclo-$C_{3-7}$-alkyl, cyclo-$C_{3-7}$-alkenyl, amino-$C_{2-7}$-alkyl, $C_{1-4}$-alkyl-amino-$C_{2-7}$-alkyl, di-($C_{1-4}$-alkyl-amino)-$C_{2-7}$-alkyl, aminoiminomethyl, aminocarbonylamino, $C_{1-4}$-alkyl-aminocarbonylamino, di-($C_{1-4}$-alkyl)-aminocarbonylamino, $C_{1-4}$-alkyl-aminocarbonyl-$C_{1-4}$-alkyl-amino, di-($C_{1-4}$-alkyl)-aminocarbonyl-$C_{1-4}$-alkyl-amino, phenylaminocarbonylamino, aminocarbonyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{3-6}$-alkenoxycarbonyl, $C_{3-6}$-alkynoxycarbonyl, $C_{1-6}$-alkoxycarbonyl-$C_{1-3}$-alkyl, $C_{1-6}$-alkenoxycarbonyl-$C_{1-3}$-alkyl, $C_{1-6}$-alkynoxycarbonyl-$C_{1-3}$-alkyl or hydroxycarbonyl-$C_{1-3}$-alkyl group, a phenyl, pyridinyl, diazinyl, 1-naphthyl, 2-naphthyl, pyridinylcarbonyl or phenylcarbonyl group which may be mono-, di- or trisubstituted in the carbon skeleton in each case by halogen, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-4}$-alkyl-aminocarbonyl, di-($C_{1-4}$-alkyl)-aminocarbonyl, cyano, aminosulphonyl, $C_{1-4}$-alkyl-aminosulphonyl, di-($C_{1-4}$-alkyl)-aminosulphonyl, $C_{1-4}$-alkyl-thio, $C_{1-4}$-alkyl-sulphinyl or $C_{1-4}$-alkyl-sulphonyl, and the substituents may be identical or different, a heterocycle selected from a 4-to 10-membered azacycloalkyl group, a 6-to 10-membered oxaza, thiaza- and diazacycloalkyl group as well as a 6-to 10-membered azabicycloalkyl group, a 1-alkyl-4-piperidinylcarbonyl or 4-alkyl-1-piperazinylcarbonyl group, while the above-mentioned mono- and bicyclic heterocycles are bound to $Y^1$ by a nitrogen or a carbon atom in formula (II), in the above-mentioned mono- and bicyclic heterocycles a methyne group not directly linked to a nitrogen, oxygen or sulphur atom may be substituted by a fluorine atom and a methylene group not directly linked to a nitrogen, oxygen or sulphur atom may be substituted by one or two fluorine atoms, the above-mentioned mono- and bicyclic heterocycles as well as the 1-($C_{1-6}$-alkyl)-4-piperidinylcarbonyl and 4-($C_{1-6}$-alkyl)-1-piperazinylcarbonyl group in the ring may be mono- to tetra-substituted by $C_{1-6}$-alkyl groups, or may optionally additionally be monosubstituted by a cyclo-$C_{3-7}$-alkyl, cyclo-$C_{3-7}$-alkenyl, cyclo-$C_{3-7}$-alkyl-$C_{1-3}$-alkyl, phenyl-$C_{1-3}$-alkyl, pyridyl-$C_{1-3}$-alkyl, $C_{1-6}$-alkyl-carbonyl, hydroxy, $C_{1-6}$-alkoxy, amino, $C_{1-4}$-alkylamino, di-($C_{1-4}$-alkyl)amino, phenylcarbonyl, pyridinylcarbonyl, hydroxycarbonyl, hydroxycarbonyl-$C_{1-3}$-alkyl, $C_{1-6}$-alkoxycarbonyl, $C_{1-6}$-alkoxycarbonyl-$C_{1-3}$-alkyl, aminocarbonyl, $C_{1-4}$-alkylaminocarbonyl, di-($C_{1-4}$-alkyl)aminocarbonyl or $C_{1-3}$-alkylsulphonyl group, by a cyclo-$C_{3-7}$-alkyl-carbonyl, azacyclo-$C_{4-7}$-alkyl-carbonyl, diazacyclo-$C_{5-7}$-alkyl-carbonyl or oxazacyclo-$C_{5-7}$-alkyl-carbonyl group optionally $C_{1-3}$-alkyl-substituted in the ring, while the substituents may be identical or different and may be bound to a cyclic carbon or cyclic nitrogen atom, while the phenyl and pyridinyl groups contained in the groups mentioned for $R^4$ hereinbefore may in turn be mono-, di- or trisubstituted by halogen atoms, by $C_{1-3}$-alkyl, $C_{2-3}$-alkenyl, $C_{2-3}$-alkynyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkyl-amino-$C_{1-3}$-alkyl, di-($C_{1-4}$-alkyl)-amino-$C_{1-3}$-alkyl, $C_{1-4}$-alkylcarbonylamino, $C_{1-4}$-alkylcarbonylamino-$C_{1-3}$-alkyl, aminocarbonyl, $C_{1-3}$-alkyl-aminocarbonyl, di-$C_{1-4}$-alkyl-aminocarbonyl, cyano, aminosulphonyl, $C_{1-4}$-alkyl-aminosulphonyl, di-($C_{1-4}$-alkyl)-aminosulphonyl, $C_{1-3}$-alkyl-thio, $C_{1-3}$-alkyl-sulphinyl or $C_{1-3}$-alkyl-sulphonyl, while the substituents may be identical or different, or, if $Y^1$ denotes the carbon atom, $R^4$ may denote the hydroxycarbonyl, aminomethyl, $C_{1-4}$-alkyl-aminomethyl or di-($C_{1-4}$-alkyl)-aminomethyl group, $R^5$ denotes a hydrogen atom, a $C_{1-4}$-alkyl group, while an unbranched alkyl group may be substituted in the ω position by a phenyl, pyridinyl, diazinyl, amino, $C_{1-4}$-alkylamino, di-($C_{1-4}$-alkyl)-amino, 4-$C_{1-4}$-alkyl-1-piperazinyl or 4-morpholinyl group, a $C_{1-6}$-alkoxycarbonyl, cyano or aminocarbonyl group or, if $Y^1$ denotes a nitrogen atom, $R^5$ may denote a pair of free electrons, or, if $Y^1$ denotes the carbon atom, $R^5$ may denote the fluorine atom, or $R^4$ together with $R^5$ and $Y^1$ denote a 4- to 7-membered cycloaliphatic ring wherein a methylene group may be replaced by a —NH—, —N($C_{1-4}$-alkyl)-, —N($C_{3-4}$-alkenyl)-, —N($C_{3-4}$-alkynyl)-, —N(cyclo-$C_{3-7}$-alkyl)- or —N($C_{3-7}$-cycloalkyl-$C_{1-3}$-alkyl) group, while a hydrogen atom bound to a nitrogen atom in one of the groups defined for $R^4$ hereinbefore may be replaced by a protective group, $R^6$ and $R^7$, which may be identical or different, in each case denote a hydrogen atom, a $C_{1-4}$-alkyl group or, if $Y^1$ denotes a carbon atom, the fluorine atom, a $C_{1-4}$-alkylamino or di-($C_{1-4}$-alkyl)-amino group, while the two $C_{1-4}$-alkyl groups may be joined together to form a ring and $R^8$ and $R^9$, which may be identical or different, in each case denote a hydrogen atom or a $C_{1-3}$-alkyl group.

3. A compound of the formula (I) according to claim 1, wherein

A, X, Q and $R^1$ are defined as in claim 1 and $R^2$ denotes the hydrogen atom or a phenylmethyl group or a $C_{2-7}$-alkyl group which may be substituted in the ω position by a cyclo-$C_{3-7}$-alkyl, cyclo-$C_{3-7}$-alkenyl, phenyl, pyridinyl, hydroxy, amino, $C_{1-6}$-alkylamino, di-($C_{1-6}$-alkyl)-amino, hydroxycarbonyl, $C_{1-6}$-alkoxycarbonyl, aminocarbonyl, aminocarbonylamino, $C_{1-6}$-alkylamino, 4-morpholinyl group, while the phenyl and pyridinyl groups mentioned in the groups defined hereinbefore for $R^2$ or contained as substituents may additionally be mono-, di- or trisubstituted in the carbon skeleton by halogen, by $C_{1-3}$-alkyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonyl-$C_{1-3}$-alkylamino, aminocarbonyl, $C_{1-3}$-alkylaminocarbonyl or di-($C_{1-3}$-alkyl)-aminocarbonyl groups and the substituents may be identical or different, $R^3$ denotes the hydrogen atom or a $C_{1-3}$-alkyl group or $R^2$ and $R^3$ together with the enclosed nitrogen atom denote a group of general formula

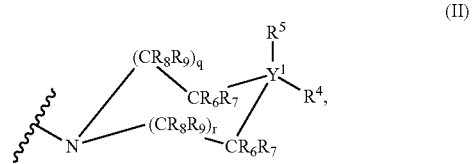

(II)

wherein $Y^1$ denotes the carbon atom or, if $R^5$ denotes a pair of free electrons, $Y^1$ may also be the nitrogen atom, q and r, if $Y^1$ denotes the carbon atom, denote the numbers 0 or 1 or q and r, if $Y^1$ denotes the nitrogen atom, denote the numbers 1 or 2, $R^4$ denotes the hydrogen atom, an amino, $C_{1-4}$-alkylamino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group, a phenyl, pyridinyl or diazinyl group which may be substituted in each case by a halogen, by a $C_{1-3}$-alkyl, $C_{1-3}$-alkoxy, hydroxy, amino, $C_{1-4}$-alkyl-amino, di-($C_{1-4}$-alkyl)-amino-amino-$C_{1-3}$-alkyl, $C_{1-4}$-alkyl-amino-$C_{1-3}$-alkyl, di-($C_{1-4}$-alkyl)-amino-$C_{1-3}$-alkyl group, a heterocycle selected from a 4- to 7-membered azacycloalkyl group, a 6- to 7-membered oxaza, S,S-dioxothiaza or diazacycloalkyl group and a 7- to 9-membered azabicycloalkyl group, while the above-mentioned mono- and bicyclic heterocycles are bound to $Y^1$ in formula (II) by a nitrogen or a carbon atom, in the above-mentioned mono- and bicyclic heterocycles a methylene group not directly linked to a nitrogen, oxygen or sulphur atom may be substituted by one or two fluorine atoms and the above-mentioned mono- and bicyclic heterocycles may be mono- or disubstituted by hydroxy, $C_{1-3}$-alkyl or hydroxy-$C_{1-3}$-alkyl groups or may be monosubstituted by a benzyl, cyclo-$C_{3-6}$-alkyl, hydroxycyclo-$C_{3-6}$-alkyl, cyclo-$C_{3-6}$-alkyl-$C_{1-3}$-alkyl, $C_{1-4}$-alkylcarbonyl, $C_{1-4}$-alkylcarbonyl-$C_{1-3}$-alkyl, hydroxy, $C_{1-4}$-alkoxy, amino, $C_{1-4}$-alkylamino, di-($C_{1-4}$-alkyl)-amino, $C_{1-3}$-alkoxycarbonyl, hydroxycarbonyl-carbonyl, $C_{1-3}$-alkoxycarbonyl-carbonyl, hydroxycarbonyl-$C_{1-3}$-alkyl, $C_{1-3}$-alkoxycarbonyl-$C_{1-3}$-alkyl, hydroxycarbonyl-$C_{1-3}$-alkylcarbonyl, $C_{1-3}$-alkoxycarbonyl-$C_{1-3}$-alkylcarbonyl, aminosuiphonyl, $C_{1-4}$-alkylaminosulphonyl, di-($C_{1-4}$-alkyl)-aminosulphonyl, $C_{1-3}$-alkylsulphonyl, cyclo-$C_{3-7}$-alkylsulphonyl, aminocarbonyl-$C_{1-3}$-alkyl, $C_{1-4}$-alkylaminocarbonyl-$C_{1-3}$-alkyl, di-($C_{1-4}$-alkyl)-aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl groups, or, if $Y^1$ denotes the carbon atom, $R^4$ may also denote the hydroxycarbonyl, aminomethyl, $C_{1-4}$-alkyl-aminomethyl or di-($C_{1-4}$-alkyl)-aminomethyl group, $R^5$ denotes a hydrogen atom, a $C_{1-3}$-alkyl group or, if $Y^1$ denotes a nitrogen atom, also denotes a pair of free electrons, $R^6$ and $R^7$, which may be identical or different, in each case denote a hydrogen atom, a $C_{1-3}$-alkyl group or, if $Y^1$ denotes a carbon atom, they may also denote an amino, $C_{1-3}$-alkylamino or di-($C_{1-3}$-alkyl)-amino group, while the two $C_{1-3}$-alkyl groups may be joined together to form a ring and $R^8$ and $R^9$, which may be identical or different, in each case denote a hydrogen atom or a $C_{1-3}$-alkyl group, while, unless otherwise stated, all the alkyl, alkenyl and alkynyl groups mentioned or contained in the groups defined hereinbefore may be straight- chain or branched, every methyne group contained in the groups defined hereinbefore may be substituted by a fluorine atom, each methylene group may be substituted by up to 2 fluorine atoms and each methyl group may be substituted by up to 3 fluorine atoms and two alkyl and alkenyl groups bound to a nitrogen atom may be joined together forming a 4- to 7-membered, saturated or unsaturated heterocyclic ring, all the aromatic and heteroaromatic groups mentioned or contained in the groups defined hereinbefore may additionally be mono-, di- or trisubstituted by halogen, by cyano or hydroxy groups and the substituents may be identical or different, or a tautomer or salt thereof.

4. A compound of the formula (I) according to claim 1, wherein

A, X, Q and $R^1$ are defined as in claim 1 and $R^2$ denotes the hydrogen atom or a phenylmethyl group or a $C_{2-7}$-alkyl group which may be substituted in the w position by a cyclo-$C_{3-7}$-alkyl, cyclo-$C_{3-7}$-alkenyl, phenyl, pyridinyl, hydroxy, amino, $C_{1-6}$-alkylamino, di-($C_{1-6}$-alkyl)-amino, hydroxycarbonyl, $C_{1-6}$-alkoxycarbonyl, aminocarbonyl, aminocarbonylamino, $C_{1-6}$-alkylamino, 4-morpholinyl group, while the phenyl and pyridinyl groups mentioned in the groups defined hereinbefore for $R^2$ or contained as substituents may additionally be mono-, di- or trisubstituted in the carbon skeleton by halogen, by $C_{1-3}$-alkyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino, $C_{1-3}$-alkylcarbonyl-$C_{1-3}$-alkylamino, aminocarbonyl, $C_{1-3}$-alkylaminocarbonyl or di-($C_{1-3}$-alkyl)-aminocarbonyl groups and the substituents may be identical or different, $R^3$ denotes the hydrogen atom or a $C_{1-3}$-alkyl group or $R^2$ and $R^3$ together with the enclosed nitrogen atom denote a group of general formula

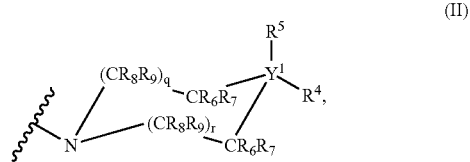

(II)

wherein $Y^1$ denotes the carbon atom or, if $R^5$ denotes a pair of free electrons, may also represent the nitrogen atom, q and r, if $Y^1$ denotes the carbon atom, denote the numbers 0 or 1 or q and r, if $Y^1$ denotes the nitrogen atom, denote the numbers 1 or 2, $R^4$ denotes the hydrogen atom, an amino, $C_{1-4}$-alkylamino, di-($C_{1-4}$-alkyl)-alkylamino, $C_{1-6}$-alkyl, cyclo-$C_{3-7}$-alkyl, cyclo-$C_{3-7}$-alkenyl, amino-$C_{2-7}$-alkyl, $C_{1-4}$-alkyl-amino-$C_{2-7}$-alkyl, di-($C_{1-4}$-alkyl-amino)-$C_{2-7}$-alkyl, $C_{1-4}$-alkyl-aminocarbonyl, di-($C_{1-4}$-alkyl)-aminocarbonyl, aminocarbonyl-$C_{1-3}$-alkyl, $C_{1-4}$-alkyl-aminocarbonyl-$C_{1-3}$-alkyl, di-($C_{1-4}$-alkyl)-aminocarbonyl-$C_{1-3}$-alkyl, aminocarbonylamino-$C_{1-3}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group, a phenyl, pyridinyl or diazinyl group which may be substituted in each case by a halogen, by a $C_{1-3}$-alkyl, $C_{1-3}$-alkoxy, hydroxy, amino, $C_{1-4}$-alkylamino, di-($C_{1-4}$-alkyl)-amino, amino-$C_{1-3}$-alkyl, $C_{1-4}$-alkylamino-$C_{1-3}$-alkyl, di-($C_{1-4}$-alkyl)-amino-$C_{1-3}$-alkyl group, a heterocycle selected from a 4- to 7-membered azacycloalkyl group, a 6- to 7-membered oxaza or diazacycloalkyl group and a 7- to 9-membered azabicycloalkyl group, while the above-mentioned mono- and bicyclic heterocycles are bound to $Y^1$ in formula (II) by a nitrogen or a carbon atom, in the above-mentioned mono- and bicyclic heterocycles a methylene group not directly linked to a nitrogen, oxygen or sulphur atom may be substituted by one or two fluorine atoms and the above-mentioned mono- and bicyclic heterocycles may be mono- or polysubstituted, for example mono- to trisubstituted, by $C_{1-3}$-alkyl groups or monosubstituted by a benzyl, cyclo-$C_{3-6}$-alkyl, cyclo-$C_{3-6}$-alkyl-$C_{1-3}$-alkyl, $C_{1-4}$-alkylcarbonyl, hydroxy, $C_{1-4}$-alkoxy, amino, $C_{1-4}$-alkylamino, di-($C_{1-4}$-alkyl)-amino, hydroxycarbonyl, $C_{1-3}$-alkoxycarbonyl, hydroxycarbonyl-$C_{1-3}$-alkyl, $C_{1-3}$-alkoxycarbonyl-$C_{1-3}$-alkyl or $C_{1-3}$-alkylsulphonyl group, or also, if $Y^1$ denotes the carbon atom, $R^4$ may denote the hydroxycarbonyl, aminomethyl, $C_{1-4}$-alkylaminomethyl or di-($C_{1-4}$-alkyl)-aminomethyl group, $R^5$ denotes a hydrogen atom, a $C_{1-3}$-alkyl group or, if $Y^1$ denotes a nitrogen atom, also a pair of free electrons, $R^6$ and $R^7$, which may be identical or different, in each case represent a hydrogen atom, a $C_{1-3}$-alkyl group or also, if $Y^1$ denotes a carbon atom, a $C_{1-3}$-alkylamino or di-($C_{1-3}$-alkyl)-amino group, while the two $C_{1-3}$-alkyl groups may be joined together to form a ring and $R^8$ and $R^9$, which may be identical or different, in each case represent a hydrogen atom or a $C_{1-3}$-alkyl group, while, unless otherwise stated, all the alkyl, alkenyl and alkynyl groups mentioned or contained in the groups defined hereinbefore may be straight-chain or branched, every methyne group contained in the groups defined hereinbefore may be substituted by a fluorine atom, each methylene group may be substituted by up to 2 fluorine atoms and each methyl group may be substituted by up to 3 fluorine atoms and two alkyl and alkenyl groups bound to a nitrogen atom may be joined together forming a 4- to 7-membered, saturated or unsaturated heterocyclic ring, all the aromatic and heteroaromatic groups mentioned or contained in the groups defined hereinbefore may additionally be mono-, di- or trisubstituted by halogen, by cyano or hydroxy groups and the substituents may be identical or different, or a tautomer or salt thereof.

5. A compound of the formula (I) according to claim 1, wherein A, X, Q and $R^1$ are defined as in claim 1 and $R^2$ denotes the hydrogen atom or a phenylmethyl group or a $C_{2-7}$-alkyl group which may be substituted in the w position by a phenyl, amino, $C_{1-6}$-alkylamino, di-($C_{1-6}$-alkyl)-amino group, while the phenyl and phenylmethyl group mentioned hereinbefore may additionally be mono- or disubstituted at an aromatic carbon atom by halogen, by $C_{1-3}$-alkyl, $C_{1-3}$-alkoxy, amino-$C_{1-3}$-alkyl, $C_{1-3}$-alkylamino-$C_{1-3}$-alkyl or di-($C_{1-3}$-alkyl)-amino-$C_{1-3}$-alkyl groups and the substituents may be identical or different, $R^3$ denotes the hydrogen atom or a $C_{1-3}$-alkyl group or $R^2$ and $R^3$ together with the enclosed nitrogen atom denote a group of general formula

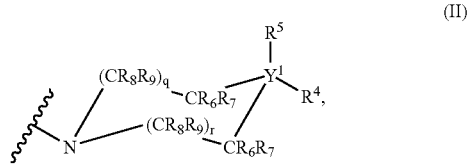

(II)

wherein $Y^1$ denotes the carbon atom or, if $R^5$ denotes a pair of free electrons, may also represent the nitrogen atom, q and r, if $Y^1$ denotes the carbon atom, denote the numbers 0 or 1 or q and r, if $Y^1$ denotes the nitrogen atom, denote the numbers 1 or 2, $R^4$ denotes the hydrogen atom, an amino, $C_{1-4}$-alkyl-amino, di-($C_{1-4}$-alkyl)-alkylamino, $C_{1-6}$-alkyl, a cyclo-$C_{3-7}$-alkyl or cyclo-$C_{3-7}$-alkenyl group optionally substituted by a hydroxycarbonyl, $C_{1-6}$-alkoxycarbonyl, hydroxycarbonyl-$C_{1-3}$-alkyl or $C_{1-6}$-alkoxycarbonyl-$C_{1-3}$-alkyl group, an amino-$C_{2-7}$-alkyl, $C_{1-4}$-alkyl-amino-$C_{2-7}$-alkyl, di-($C_{1-4}$- alkyl-amino)-$C_{2-7}$-alkyl, $C_{1-6}$-alkoxycarbonyl, $C_{1-6}$-alkoxycarbonyl-$C_{1-3}$-alkyl or hydroxycarbonyl-$C_{1-3}$-alkyl group, a phenyl or pyridyl group which may be substituted in each case by a halogen, by a $C_{1-3}$-alkyl, $C_{1-3}$-alkoxy, amino, $C_{1-4}$-alkyl-amino, di-($C_{1-4}$-alkyl) -amino group, a heterocycle selected from a 6- to 7-membered azacycloalkyl group, a 6- to 7-membered S,S, dioxothiaza- and diazacycloalkyl group and a 7- to 9-membered azabicycloalkyl group, while the above-mentioned mono- and bicyclic heterocycles are bound to $Y^1$ in formula (II) by a nitrogen or a carbon atom, in the above-mentioned mono- and bicyclic heterocycles a methylene group not directly linked to a nitrogen, oxygen or sulphur atom may be substituted by one or two fluorine atoms and the above-mentioned mono- and bicyclic heterocycles may be mono- or disubstituted by a hydroxy, $C_{1-3}$-alkyl or hydroxy-$C_{1-3}$-alkyl group, by a benzyl, cyclo-$C_{3-6}$-alkyl, hydroxy-$C_{3-6}$-cycloalkyl, cyclo-$C_{3-6}$-alkyl-$C_{1-3}$-alkyl, $C_{1-3}$-alkylcarbonyl-$C_{1-3}$-alkyl, amino, $C_{1-4}$-alkylamino or di-($C_{1-4}$-alkyl)-amino, hydroxycarbonyl-carbonyl, $C_{1-6}$-alkoxycarbonyl-carbonyl, hydroxycarbonyl-$C_{1-3}$-alkylcarbonyl, $C_{1-3}$-alkoxycarbonyl-$C_{1-3}$-alkylcarbonyl, aminosulphonyl, $C_{1-4}$-alkylaminosulphonyl, di-($C_{1-4}$-alkyl)-aminosulphonyl, cyclo-$C_{3-7}$-alkylsulphonyl, aminocarbonyl-$C_{1-3}$-alkyl, $C_{1-4}$-alkylaminocarbonyl-$C_{1-3}$-alkyl, di-($C_{1-4}$-alkyl)-aminocarbonyl-$C_{1-3}$-alkyl, hydroxyaminocarbonyl-$C_{1-3}$-alkyl, $C_{1-3}$-alkoxyaminocarbonyl-$C_{1-3}$-alkyl or hydroxy-($C_{1-3}$-alkyl)-aminocarbonyl-$C_{1-3}$-alkyl groups, or, if $Y^1$ denotes the carbon atom, $R^4$ may denote the hydroxycarbonyl, aminomethyl, $C_{1-4}$-alkyl-aminomethyl or di-($C_{1-4}$-alkyl)-aminomethyl group, $R^5$ denotes a hydrogen atom or, if $Y^1$ denotes a nitrogen atom, it may also denote a pair of free electrons, $R^6$ and $R^7$, which may be identical or different, in each case represent a hydrogen atom, a $C_{1-3}$-alkyl group or, if $Y^1$ denotes a carbon atom, may also represent a $C_{1-3}$-alkylamino or di-($C_{1-3}$-alkyl)-amino group, while the two $C_{1-3}$-alkyl groups may be joined together to form a ring and $R^8$ and $R^9$, which may be identical or different, in each case represent a hydrogen atom or a $C_{1-3}$-alkyl group, or a tautomer or salt thereof.

6. A compound of the formula (I) according to claim 1, wherein

A, X, Q and $R^1$ are defined as in claim 1 and $R^2$ denotes a phenylmethyl group or a $C_{2-7}$-alkyl group which may be substituted in the ω position by a phenyl, amino, $C_{1-6}$-alkylamino, di-($C_{1-6}$-alkyl)-amino group, while the above-mentioned phenyl and phenylmethyl group may be substituted at an aromatic carbon atom by an amino-$C_{1-3}$-alkyl, $C_{1-3}$-alkylamino-$C_{1-3}$-alkyl or di-($C_{1-3}$-alkyl)-amino-$C_{1-3}$-alkyl group, $R^3$ denotes the hydrogen atom or a $C_{1-3}$-alkyl group or $R^2$ and $R^3$ together with the enclosed nitrogen atom denote a group of general formula

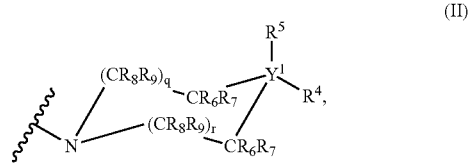

(II)

wherein $R^6$ and $R^7$ in each case denote a hydrogen atom or a dimethylamino group, $R^8$ and $R^9$ in each case denote the hydrogen atom and (a) $Y^1$ denotes the carbon atom, q and r denote the numbers 0 or 1, $R^4$ denotes the hydrogen atom, a phenyl, pyridinyl or pyrimidinyl group which may be substituted in each case by a halogen, by an amino, methylamino, dimethylamino, methyl or methoxy group, a hydroxy, 2-diethylaminoethyl, amino, methylamino, dimethylamino, diethylamino, pyrrolidin-1-yl, piperidin-1-yl, 4-amino-piperidin-1-yl, 4-methylamino-piperidin-1-yl, 4-dimethylamino-piperidin-1-yl, 4-hydroxymethyl-piperidin-1-yl, 4-hydroxy-piperidin-1-yl, 4-methoxy-piperidin-1-yl, 4-hydroxy-4-methyl-piperidin-1-yl, 4-hydroxy-4-trifluoromethyl-piperidin-1-yl, 4-ethyl-4-hydroxy-piperidin-1-yl, 4,4-dimethylpiperidin-1-yl, 4-amino-4-methyl-piperidin-1-yl, 4-hydroxy-4-hydroxymethyl-piperidini-yl, 3-amino-piperidin-1-yl, 3-methylamino-piperidin-1-yl, 3-dimethylamino-piperidin-1-yl, perhydro-azepin-1-yl, perhydro-1,4-diazepin-1-yl, 4-methyl-perhydro-1,4-diazepin-1-yl, 1-methyl-piperidin-4-yl, piperidin-4-yl, 1-ethylpiperidin-4-yl, 1-(2-hydroxyethyl)-piperidin-4-yl, 1-cyclopropyl-piperidin-4-yl, 1-cyclopropylmethyl-piperidin-4-yl, 1-hydroxycarbonylmethyl-piperidin-4-yl, 1-ethoxycarbonylmethyl-piperidin-4-yl, 1-hydroxycarbonylethyl-piperidin-4-yl, 1-ethoxycarbonylethyl-piperidin-4-yl, 1-hydroxycarbonylethylcarbonyl-piperidin-4-yl, 1-ethoxycarbonylethylcarbonyl-piperidin-4-yl, 1-methylsulphonyl-piperidin-4-yl, 1-aminosulphonyl-piperidin-4-yl, 1-hydroxycarbamoylmethyl-piperidin-4-yl, 1-(hydroxy-methyl-carbamoyl) -piperidin-4-yl, 1-(methoxycarbamoyl-methyl)-piperidin-4-yl, piperazin-1-yl, 4-methyl-piperazin-1-yl, 4-methylsulphonyl-piperazin-1-yl, 4-aminosulphonyl-piperazin-1-yl, 4-cyclopropylmethyl-piperazin-1-yl, 4-ethyl-piperazin-1-yl, 4-(2-hydroxyethyl)-piperazin-1-yl, 4-cyclopropyl-piperazin-1-yl, 4-hydroxycarbonylmethyl-piperazin-1-yl, 4-ethoxycarbonylmethyl-piperazin-1-yl, 4-hydroxycarbonylethyl-piperazin-1-yl, 4-ethoxycarbonylethyl-piperazin-1-yl, 4-hydroxycarbonylethylcarbonyl-piperidin-1-yl, 4-ethoxycarbonylethylcarbonyl-piperazin-1-yl, 1,2-dimethyl-piperazin-1-yl, 3-methyl-piperazin-1-yl, 3,4,5-trimethyl-piperazin-1-yl, 3,5-dimethyl-piperazin-1-yl, 3,3,4-trimethyl-piperazin-1-yl, 3,3-dimethyl-piperazin-1-yl, 3,3,4,5,5-pentamethyl-piperazin-1-yl, 3,3,5,5-tetramethyl-piperazin-1-yl, morpholin-4-yl, 4,4-difluoro-piperidin-1-yl, 8-methyl-8-aza-bicyclo[3.2.1]oct-3-yl, 8-aza-bicyclo[3.2.1]oct-3-yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-hydroxycarbonylmethyl-piperidin-4-yl or 4-hydroxycarbonylmethyl-piperazin-1-yl group, and $R^5$ denotes a hydrogen atom, or (b) $Y^1$ denotes a nitrogen atom, q and r denote the numbers 1 or 2, $R^4$ denotes the hydrogen atom, a phenyl, pyridinyl or pyrimidinyl group which may be substituted in each case by a halogen, by an amino, methylamino, dimethylamino, methyl or methoxy group, a methyl, ethyl, isopropyl, cyclopropyl, cyclopentyl, cyclohexyl, cycloheptyl, cyclopropylmethyl, 2-diethylamino-propyl, 1-quinuclidin-3-yl, piperidin-4-yl, 1-methyl-piperidin-4-yl, 1-ethyl-piperidin-4-yl, 1-(2-hydroxyethyl)-piperidin-4-yl, 1-cyclopropyl-piperidin-4-yl, 1-cyclopropylmethyl-piperidin-4-yl, 1-hydroxycarbonylmethyl-piperidin-4-yl, 1-ethoxycarbonylmethyl-piperidin-4-yl, 1-hydroxycarbonylethyl-piperidin-4-yl, 1-ethoxycarbonylethyl-piperidin-4-yl, 1-hydroxycarbonylethylcarbonyl-piperidin-4-yl, 1-ethoxycarbonylethylcarbonyl-piperidin-4-yl, 1-ethoxycarbonylmethyl-piperidin-4-yl, 1-methylsulphonyl-piperidin-4-yl, 1-aminosul phonyl-piperidin-4-yl, tetrahydropyran-4-yl, 8-methyl-8-aza-bicyclo[3.2.1]oct-3-yl, 5-methyl-2,5-diaza-bicyclo[2.2.1]hept-2-yl or 1-aza-bicyclo[2.2.2]oct-3-yl group and $R^5$ denotes a pair of free electrons, or a tautomer or salt thereof.

7. A compound of the formula (I) according to claim 1, wherein

A, X, Q and $R^1$ are defined as in claim 1 and $R^2$ denotes a phenylmethyl group or a $C_{2-7}$-alkyl group which may be substituted in the ω position by a phenyl, amino, $C_{1-6}$-alkylamino, di-($C_{1-6}$-alkyl)-amino group, while the phenyl and phenylmethyl group mentioned hereinbefore may be substituted at an aromatic carbon atom by an amino-$C_{1-3}$-alkyl, $C_{1-3}$-alkylamino-$C_{1-3}$-alkyl or di-($C_{1-3}$-alkyl)-amino-$C_{1-3}$-alkyl group, $R^3$ denotes the hydrogen atom or a $C_{1-3}$-alkyl group or $R^2$ and $R^3$ together with the enclosed nitrogen atom denote a group of general formula

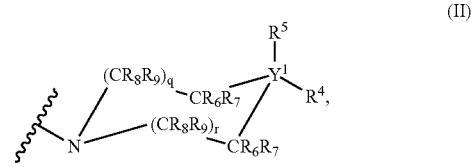

wherein $R^6$ and $R^7$ in each case denote a hydrogen atom or a dimethylamino group, $R^8$ and $R^9$ in each case denote the hydrogen atom and (a) $Y^1$ denotes the carbon atom, q and r denote the numbers 0 or 1, $R^4$ denotes the hydrogen atom, a phenyl, pyridinyl or pyrimidinyl group which may be substituted in each case by a halogen, by an amino, methylamino, dimethylamino, methyl or methoxy group, a hydroxy, 2-diethylaminoethyl, amino, methylamino, dimethylamino, diethylamino, pyrrolidin-1-yl, piperidin-1-yl, 4-amino-piperidin-1-yl, 4-methylamino-piperidin-1-yl, 4-dimethylamino-piperidin-1-yl, 3-amino-piperidin-1-yl, 3-methylamino-piperidin-1-yl, 3-dimethylamino-piperidin-1-yl, perhydro-azepin-1-yl, perhydro-1,4-diazepin-1-yl, 4-methyl-perhydro-1,4-diazepin-1-yl, 1-methyl-piperidin-4-yl, piperidin-4-yl, 1-ethylpiperidin-4-yl, 1-cyclopropyl-piperidin-4-yl, 1-cyclopropylmethyl-piperidin-4-yl, piperazin-1-yl, 4-methyl-piperazin-1-yl, 4-cyclopropylmethyl-piperazin-1-yl, 4-ethyl-piperazin-1-yl, 4-cyclopropyl-piperazin-1-yl, 1,2-dimethyl-piperazin-1-yl, 3-methyl-piperazin-1-yl, 3,4,5-trimethyl-piperazin-1-yl, 3,5-dimethyl-piperazin-1-yl, 3,3,4-trimethyl-piperazin-1-yl, 3,3-dimethyl-piperazin-1-yl, 3,3,4,5,5-pentamethyl-piperazin-1-yl, 3,3,5,5-tetramethyl-piperazin-1-yl, morpholin-4-yl, 4,4-difluoro-piperidin-1-yl, 8-methyl-8-aza-bicyclo[3.2.1]oct-3-yl, 8-aza-bicyclo[3.2.1]oct-3-yl, azetidin-1-yl, 1-(methoxycarbonylmethyl)-piperidin-4-yl, 1-(ethoxycarbonylmethyl)-piperidin-4-yl, 4-(ethoxycarbonylmethyl)-piperazin-1-yl, 1-hydroxycarbonylmethyl-piperidin-4-yl or 4-hydroxycarbonylmethyl-piperazin-1-yl group, and $R^5$ denotes a hydrogen atom, or (b) $Y^1$ denotes a nitrogen atom, q and r denote the numbers 1 or 2, $R^4$ denotes the hydrogen atom, a phenyl, pyridinyl or pyrimidinyl group which may be substituted in each case by a halogen, by an amino, methylamino, dimethylamino, methyl or methoxy group, a methyl, ethyl, isopropyl, cyclopropyl, cyclopropylmethyl, 2-diethylamino-propyl, 1-quinuclidin-3-yl, 1-piperidin-4-yl, 1-methyl-piperidin-4-yl, 1-ethyl-piperidin-4-yl, 1-cyclopropyl-piperidin-4-yl, 1-cyclopropylmethyl-piperidin-4-yl, 1-hydroxycarbonylmethyl-piperidin-4-yl or 1-ethoxycarbonylmethyl-piperidin-4-yl group and $R^5$ denotes a pair of free electrons, or a tautomer or salt thereof.

8. A compound of the formula (I) according to claim 1, wherein

A and X in each case denote an oxygen atom, $R^2$ denotes the hydrogen atom, a phenylmethyl group or a $C_{2-7}$-alkyl group which may be substituted in the ω position by a cyclo-$C_{3-7}$-alkyl, cyclo-$C_{3-7}$-alkenyl, phenyl, pyridinyl, diazinyl, hydroxy, amino, $C_{1-6}$-alkylamino, di-($C_{1-6}$-alkyl)-amino, $C_{3-6}$-alkenylamino, di- ($C_{3-6}$-alkenyl)amino, $C_{3-6}$-alkynylamino, di-($C_{3-6}$-alkynyl)amino, hydroxycarbonyl, $C_{1-6}$-alkoxycarbonyl, aminocarbonyl, aminocarbonylamino, $C_{1-6}$-alkylcarbonylamino, $C_{2-6}$-alkenylcarbonylamino, $C_{2-6}$-alkynylcarbonylamino, 4-morpholinyl, [bis-(2-hydroxyethyl)]amino, 4-($C_{1-6}$-alkyl)-1-piperazinyl or 4-(ω-hydroxy-$C_{2-7}$-alkyl)-1-piperazinyl group, a phenyl or pyridinyl group, while the phenyl, pyridinyl and diazinyl groups mentioned in the groups defined for $R^2$ hereinbefore or contained as substituents may additionally be mono-, di- or trisubstituted in the carbon skeleton by halogen, by $C_{1-3}$-alkyl, $C_{2-3}$-alkenyl, $C_{2-3}$-alkynyl, $C_{1-3}$-alkoxy, hydroxy, amino, $C_{1-3}$-alkylamino, di-($C_{1-3}$-alkyl)-amino, amino-$C_{1-3}$-alkyl, $C_{1-3}$-alkyl-amino-$C_{1-3}$-alkyl, di-($C_1$ 3-alkyl)-amino-$C_{1-3}$-alkyl, $C_{1-3}$-alkylcarbonylamino, $C_{1-3}$-alkylcarbonylamino-$C_{1-3}$-alkyl, aminocarbonyl, $C_{1-3}$-alkyl-aminocarbonyl, di-($C_{1-3}$-alkyl)-aminocarbonyl, cyano, aminosulphonyl, $C_{1-3}$-alkyl-aminosulphonyl, di-($C_{1-3}$-alkyl)-aminosulphonyl, $C_{1-3}$-alkylthio, $C_{1-3}$-alkylsulphinyl or $C_{1-3}$-alkylsulphonyl and the substituents may be identical or different, $R^3$ denotes the hydrogen atom or a $C_{1-3}$-alkyl group substituted by a phenyl or pyridinyl group, while the $C_{1-3}$-alkyl group may be connected to an alkyl group contained in $R^2$ or a phenyl or pyridyl ring contained in $R^2$ including the nitrogen atom to which $R^2$ and are bound, forming a 4- to 7-membered ring, or $R^2$ and $R^3$ together with the enclosed nitrogen atom denote a group of general formula

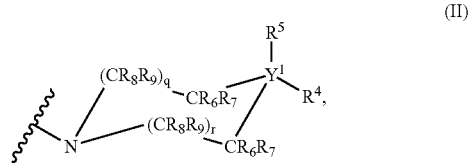

(II)

wherein $Y^1$ denotes the carbon atom or, if $R^5$ denotes a pair of free electrons, $Y^1$ may also denote the nitrogen atom, q and r, if $Y^1$ denotes the carbon atom, denote the numbers 0, 1 or 2, or q and r, if $Y^1$ denotes the nitrogen atom, denote the numbers 1 or 2, while the heterocycles mentioned hereinbefore under Ri may additionally be monosubstituted in the carbon skeleton by a methoxy group, and all the aromatic and heteroaromatic groups and parts of molecules mentioned or contained in the groups defined under $R^1$ may additionally be mono-, di- or trisubstituted by halogen atoms or by cyano or hydroxy groups and the substituents may be identical or different, or a tautomer or salt thereof.

9. A compound of the formula (I) according to claim 1, wherein

A and X in each case denote an oxygen atom, or a tautomer or salt thereof.

10. A compound of the formula (I) according to claim 1, wherein

A and X in each case denote an oxygen atom, $R^3$ denotes the hydrogen atom or a $C_{1-3}$-alkyl group or $R^2$ and $R^3$ together with the enclosed nitrogen atom denote a group of general formula

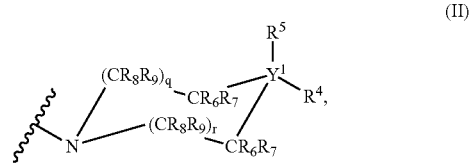

(II)

wherein $R^6$ and $R^7$ in each case denote a hydrogen atom or a dimethylamino group, $R^8$ and $R^9$ in each case denote the hydrogen atom and (a) $Y^1$ denotes the carbon atom, q and r denote the numbers 0 or 1, $R^4$ denotes the hydrogen atom, a phenyl, pyridinyl or pyrimidinyl group which may be substituted in each case by a halogen, by an amino, methylamino, dimethylamino, methyl or methoxy group, a hydroxy, 2-diethylamino-ethyl, amino, methylamino, dimethylamino, diethylamino, pyrrolidin-1-yl, piperidin-1-yl, 4-amino-piperidin-1-yl, 4-methylamino-piperidin-1-yl, 4-dimethylamino-piperidin-1-yl, 4-hydroxymethyl-piperidin-1-yl, 4-hydroxy-piperidin-1-yl, 4-methoxy-piperidin-1-yl, 4-hydroxy-4-methyl-piperidin-1-yl, 4-hydroxy-4-trifluoromethyl-piperidin-1-yl, 4-ethyl-4-hydroxy-piperidin-1-yl, 4,4-dimethylpiperidin-1-yl, 4-amino-4-methyl-piperidin-1-yl, 4-hydroxy-4-hydroxymethyl-piperidinl-yl, 3-amino-piperidin-1-yl, 3-methylamino-piperidin-1-yl, 3-dimethylamino-piperidin-1-yl, perhydro-azepin-1-yl, perhydro-1,4-diazepin-1-yl, 4-methyl-perhydro-1,4-diazepin-1-yl, 1-methyl-piperidin-4-yl, piperidin-4-yl, 1-ethylpiperidin-4-yl, 1-(2-hydroxyethyl)-piperidin-4-yl, 1-cyclopropyl-piperidin-4-yl, 1-cyclopropylmethyl-piperidin-4-yl, 1-hydroxycarbonylmethyl-piperidin-4-yl, 1-ethoxycarbonylmethyl-piperidin-4-yl, 1-hydroxycarbonylethyl-piperidin-4-yl, 1-ethoxycarbonylethyl-piperidin-4-yl, 1-hydroxycarbonylethylcarbonyl-piperidin-4-yl, 1-ethoxycarbonylethylcarbonyl-piperidin-4-yl, 1-methylsulphonyl-piperidin-4-yl, 1-aminosulphonyl-piperidin-4-yl, 1-hydroxycarbamoylmethyl-piperidin-4-yl, 1-(hydroxy-methyl-carbamoyl)-piperidin-4-yl, 1-(methoxycarbamoyl-methyl)-piperidin-4-yl, piperazin-1-yl, 4-methyl-piperazin-1-yl, 4-methylsulphonyl-piperazin-1-yl, 4-aminosulphonyl-piperazin-1-yl, 4-cyclopropylmethyl-piperazin-1-yl, 4-ethyl-piperazin-1-yl, 4-(2-hydroxyethyl)-piperazin-1-yl, 4-cyclopropyl-piperazin-1-yl, 4-hydroxycarbonyl-methyl-piperazin-1-yl, 4-ethoxycarbonylmethyl-piperazin-1-yl, 4-hydroxycarbonylethyl-piperazin-1-yl, 4-ethoxycarbonylethyl-piperazin-1-yl, 4-hydroxycarbonylethylcarbonyl-piperazin-1-yl, 4-ethoxycarbonylethylcarbonyl-piperazin-1-yl, 1,2-dimethyl-piperazin-1-yl, 3-methyl-piperazin-1-yl, 3,4,5-trimethyl-piperazin-1-yl, 3,5-dimethyl-piperazin-1-yl, 3,3,4-trimethyl-piperazin-1-yl, 3,3-dimethyl-piperazin-1-yl, 3,3,4,5,5-pentam ethyl-piperazin-1-yl, 3,3,5,5-tetramethyl-piperazin-1-yl, morpholin-4-yl, 4,4-difluoro-piperidin-1-yl, 8-methyl-8-aza-bicyclo[3.2.1]oct-3-yl, 8-aza-bicyclo[3.2.1]oct-3-yl, azetidin-1-yl, 1-(methoxycarbonylmethyl)-piperidin-4-yl, 1-(ethoxycarbonylmethyl)-piperidin-4-yl, 4-(ethoxycarbonylmethyl)- piperazin-1-yl, 1-hydroxycarbonylmethyl-piperidin-4-yl or 4-hydroxycarbonylmethyl-piperazin-1-yl group, and R⁵ denotes a hydrogen atom, or (b) Y¹ denotes a nitrogen atom, q and r denote the numbers 1 or 2, R⁴ denotes the hydrogen atom, a phenyl, pyridinyl or pyrimidinyl group which may be substituted in each case by a halogen, by an amino, methylamino, dimethylamino, methyl or methoxy group, a methyl, ethyl, isopropyl, cyclopropyl, cyclopentyl, cyclohexyl, cycloheptyl, cyclopropylmethyl, 2-diethylamino-propyl, 1-quinuclidin-3-yl, piperidin-4-yl, 1-methyl-piperidin-4-yl, 1-ethyl-piperid in-4-yl, 1-(2-hydroxyethyl)-piperidin-4-yl, 1-cyclopropyl-piperidin-4-yl, 1-cyclopropylmethyl-piperidin-4-yl, 1-hydroxycarbonylmethyl-piperidin-4-yl, 1-ethoxycarbonylmethyl-piperidin-4-yl, 1-hydroxycarbonylethyl-piperidin-4-yl, 1-ethoxycarbonylethyl-piperidin-4-yl, 1-hydroxycarbonylethylcarbonyl-piperidin-4-yl, 1-ethoxycarbonylethylcarbonyl-piperidin-4-yl, 1-ethoxycarbonylmethyl-piperidin-4-yl, 1-methylsul phonyl-piperidin-4-yl, 1-aminosulphonyl-piperidin-4-yl, tetrahydropyran-4-yl, 8-methyl-8-azabicyclo[3.2.1]oct-3-yl, 5-methyl-2,5-diaza-bicyclo[2.2.1]hept-2-yl or 1-aza-bicyclo[2.2.2]oct-3-yl group and R⁵ denotes a pair of free electrons, or a tautomer or salt thereof.

11. A compound of the formula (I) according to claim 1 selected from the group consisting of:

(R)-1-(4-methyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, (R)-1-(4-methyl-2-oxo-2,3-dihydro-benzoxazol-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (R)-2-(1'-methyl-4,4'-bipiperidinyl-1-yl)-1-(4-methyl-2-oxo-2,3-dihydro-benzoxazol-6-yl-methyl)-2-oxo-ethyl 4-(2-oxo-1,2,4,5-tetrahydro-1,3-benzodiazepin-3-yl)-piperidine-1-carboxylate, (R)- 1-(4-methyl-2-oxo-2,3-dihydro-benzoxazol-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate, (R)-1-(4-methyl-2-oxo-2,3-dihydro-benzoxazol-6-ylmethyl)-2-oxo-2-(4-piperazin-1-yl-piperidin-1-yl-ethyl 4-(2-oxo-1,2,4,5-tetrahydro-1,3-benzodiazepin-3-yl)-piperidine-1-carboxylate, (R)-2-4,4'-bipiperidinyl-1-yl-1-(4-methyl-2-oxo-2,3-dihydro-benzoxazol-6-ylmethyl)-2-oxo-ethyl 4-(2-oxo-1, 2,4,5-tetrahydro-1,3-benzodiazepin-3-yl)-piperidine-1-carboxylate, (R)-2-1,4'-bipiperidinvl-1'-yl-1-(4-methyl-2-oxo-2,3-dihydro-benzoxazol-6-ylmethyl)-2-oxo-ethyl 4-(2-oxo-1, 2,4,5-tetrahydro-1,3-benzodiazepin-3-yl)-piperidine-1-carboxylate, (R)-1-(4-methyl-2-oxo-2,3-dihydro-benzoxazol-6-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate, (R)- 1-(4-methyl-2-oxo-2,3-dihydro-benzoxazol-6-ylmethyl)-2-oxo-2-(4-perhydro- 1,4-diazepin-1-yl-piperidin-1-yl)-ethyl 4-(2-oxo-1,2,4,5-tetrahydro-1,3-benzodiazepin-3-yl)-piperidine-1-carboxylate, 4-(2-oxo-1,2,4,5-tetrahydro-1,3-benzodi(R)-1-(4-methyl-2-oxo-2,3-dihydro-benzoxazol-6-ylmethyl)-2-(4-morpholin-4-yl-piperidin-1-yl)-2-oxo-ethyl azepin-3-yl)-piperidine-1-carboxylate, (R)- 1-(4-methyl-2-oxo-2,3-dihydro-benzoxazol-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate, (R)-2-(4-cyclohexyl-piperazin-1-yl)-1-(4-methyl-2-oxo-2, 3-dihydro-benzoxazol-6-yl-methyl)-2-oxo-ethyl 4-(2-oxo-1,2,4,5-tetrahydro-1,3-benzodiazepin-3-yl)-piperidine-1-carboxylate, (R)-2-(4-hydroxy-1,4'-bipiperidinvl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-2-(4-methoxy-1,4'-bipiperidinyl-1'-yl)-1-(4-methyl-2-oxo-2,3-dihydro-benzoxazol-6-yl-methyl)-2-oxo-ethyl 4-(2-oxo-1,2,4,5-tetrahydro-1,3-benzodiazepin-3-yl)-piperidine-1-carboxylate, (R)-2-(4-hydroxy-4-methyl-1,4'-bipiperidinvl-1'-yl)-1-(4-methyl-2-oxo-2,3-dihydro-benz-oxazol-6-ylmethyl)-2-oxo-ethyl 4-(2-oxo-1,2,4,5-tetrahydro-1,3-benzodiazepin-3-yl)-piperidine-1-carboxylate, (R)-2-(4,4-dimethyl-1,4'-bipiperidinvl-1'-yl)-1-(4-methyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-2-(4-amino-4-methyl-1,4'-bipiperidinyl-1'-yl)-1-(4-methyl-2-oxo-2,3-dihydro-benz-oxazol-6-ylmethyl)-2-oxo-ethyl 4-(2-oxo-1,2,4,5-tetrahydro-1,3-benzodiazepin-3-yl)-piperidine-1-carboxylate, (R)-2-(4-hydroxy-4-hydroxymethyl-1,4'-bipiperidinyl-1'-yl)-1-(4-methyl-2-oxo-2,3-dihydro-benzoxazol-6-ylmethyl)-2-oxo-ethyl 4-(2-oxo-1,2,4,5-tetrahydro- 1,3-benzodiazepin-3-yl)-piperidine-1-carboxylate, (R)-2-(1'-ethoxycarbonylmethyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro- 1,3-benzodiazepin-3-yl)-piperidine -1-carboxylate, (R)-2-(1'-carboxymethyl-4,4'-bipiperidinyl-1-yl)-1-(4-methyl-2-oxo-2,3-dihydro-benzoxazol-6-ylmethyl)-2-oxo-ethyl 4-(2-oxo-1,2,4,5-tetrahydro- 1,3-benzodiazepin-3-yl)-piperidine-1-carboxylate, (R)-1-(3,4-dimethyl-2-oxo-2,3-dihydro-benzoxazol-6-ylmethyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine -1-carboxylate, (R)-1-(3,4-dimethyl-2-oxo-2,3-dihydro-benzoxazol-6-ylmethyl)-2-(1'-methyl-4,4'-bipiperidinyl -1-yl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate, (R)-2-4,4'-bipiperidinyl-1-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-2-1,4'-bipiperidinyl-1'-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-[4-(4-methyl-perhydro-1,4-diazepin-1-yl)-piperidin-1-yl]-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-oxo-2-(4-perhydro-1,4-diazepin-1-yl-piperidin-1-yl)-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate, (R)-2-(4-cyclohexyl-piperazin-1-yl-1-(3,4-dimethyl-2-oxo-2,3-dihydro-benzoxazol-6-yl-methyl)-2-oxo-ethyl 4-(2-oxo-1,2,4,5-tetrahydro-1,3-benzodiazepin-3-yl)-piperidine-1-carboxylate, (R)-2-(4-cycloheptyl-piperazin-1-yl)-1-(3,4-dimethyl-2-oxo-2,3-dihydro-benzoxazol-6-yl-methyl)-2-oxo-ethyl 4-(2-oxo-1,2,4,5-tetrahydro-1,3-benzodiazepin-3-yl)-piperidine-1-carboxylate, (R)-2-(4-cyclopentyl-piperazin-1-yl)-1-(3,4-dimethyl-2-oxo-2,3-dihydro-benzoxazol-6-yl-methyl)-2-oxo-ethyl 4-(2-oxo-1,2,4,5-tetrahydro-1,3-benzodiazepin-3-yl)-piperidine-1-carboxylate, (R)-2-(4,4-dimethyl-1,4'-bipiperidinyl-1'-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-(4-hydroxy-1,4'-bi-piperidinyl-1'-yl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate, (R)1-(3,4-dimethyl-2-oxo-2,3-dihydro-benzoxazol-6-ylmethyl)-2-(4-ethyl-4-hydroxy1,4'-bipiperidinyl-1'-yl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-(4-hydroxy-4-trifluoromethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-[1'-(2-hydroxy-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-{4-[1-(2-hydroxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-{4-[4-(2-hydroxy-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate, (R)-2-(4-amino-4-methyl-1,4'-bipiperidinyl-1'-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-(4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-(1'-methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-[4-(4-methanesulphonyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-[4-(1-methanesulphonyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-oxo-2-[4-(4-sulphamoyl-piperazin-1-yl)-piperidin-1-yl]-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-oxo-2-[4-(1-sulphamoyl-piperidin-4-yl)-piperazin-1-yl]-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate, (R)-2-(1'-carboxymethyl-4,4'-bipiperidinyl-1-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-[4-(4-ethoxycarbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (R)-2-[4-(4-carboxymethyl-piperazin-1-yl)-piperidin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-[4-(1-ethoxycarbonylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, (R)-2-[4-(1-carboxymethyl-piperidin-4-yl)-piperazin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate, (R)-1-(3,4-dimethyl-2-oxo-2,3-dihydro-benzoxazol-6-ylmethyl)-2-[1'-(2-ethoxycarbonylethyl)-4,4'-bipiperidinyl-1-yl]-2-oxo-ethyl 4-(2-oxo-1,2,4,5-tetrahydro-1,3-benzodiazepin-3-yl) -piperidine-1-carboxylate, (R)-2-[1'-(2-carboxy-ethyl)-4,4'-bipiperidinyl-1-yl]-1-(3,4-dimethyl-2-oxo-2,3-dihydro-benzoxazol -6-ylmethyl)-2-oxo-ethyl 4-(2-oxo-1,2,4,5-tetrahydro-1,3-benzodiazepin-3-yl)-piperidine -1-carboxylate, (R)-1-(3,4-dimethyl-2-oxo-2,3-dihydro-benzoxazol-6-ylmethyl)-2-{4-[1-(2-ethoxycarbonylethyl) -piperidin-4-yl]-piperazin-1-yl}-2-oxo-ethyl 4-(2-oxo-1,2,4,5-tetrahydro-1,3-benzodiazepin-3-yl) -piperidine-1-carboxylate, (R)-2-{4-[1-(2-carboxy-ethyl)-piperidin-4-yl]-piperazin-1-yl}-1-(3,4-dimethyl-2-oxo-2,3-dihydro-benzoxazol-6-ylmethyl)-2-oxo-ethyl 4-(2-oxo-1,2,4 ,5-tetrahydro-1,3-benzodi -azepin-3-yl)-piperidine-1-carboxylate, (R)-1-(3,4-dimethyl-2-oxo-2,3-dihydro-benzoxazol-6-ylmethyl)-2-{4-[4-(2-ethoxycarbonylethyl) -piperazin-1-yl]-piperidin-1-yl}-2-oxo-ethyl 4-(2-oxo-1,2,4,5-tetrahydro-1,3-benzodiazepin-3-yl) -piperidine-1-carboxylate, (R)-2-{4-[4-(2-carboxy-ethyl)-piperazin-1-yl]-piperidin-1-yl}-1-(3,4-dimethyl-2-oxo-2,3-dihydro -benzoxazol-6-ylmethyl)-2-oxo-ethyl 4-(2-oxo-1,2,4,5-tetrahydro-1,3-benzodiazepin -3-yl)-piperidine-1-carboxylate, (R)-1-(3,4-dimethyl-2-oxo-2,3-dihydro-benzoxazol-6-ylmethyl)-2-[1'-(3-ethoxycarbonyl-propionyl) -4,4'-bipiperidinyl-1-yl]-2-oxo-ethyl 4-(2-oxo-1,2,4,5-tetrahydro-1,3-benzodiazepin -3-yl)-piperidine-1-carboxylate, (R)-2-[1'-(3-carboxy-propionyl)-4,4'-bipiperidinyl-1-yl]-1-(3,4-dimethyl-2-oxo-2,3-dihydro-benzoxazol -6-ylmethyl)-2-oxo-ethyl 4-(2-oxo-1,2,4,5-tetrahydro- 1,3-benzodiazepin-3-yl)-piperidine -1-carboxylate, (R)-1-(3,4-dimethyl-2-oxo-2,3-dihydro-benzoxazol-6-ylmethyl)-2-{4-[4-(3-ethoxycarbonyl-propionyl)-piperazin-1-yl]-piperidin-1-yl}-2-oxo-ethyl 4-(2-oxo-1,2,4, 5-tetrahydro-1,3-benzodiazepin -3-yl)-piperidine-1-carboxylate, (R)-2-{4-[4-(3-carboxy-propionyl)-piperazin-1-yl]-piperidin-1-yl}-1-(3,4-dimethyl-2-oxo-2,3-dihydro -benzoxazol-6-ylmethyl)-2-oxo-ethyl 4-(2-oxo-1,2,4,5-tetrahydro-1,3-benzodiazepin -3-yl)-piperidine-1-carboxylate, (R)-1-(3,4-dimethyl-2-oxo-2,3-dihydro-benzoxazol-6-ylmethyl)-2-{4-[1-(3-ethoxycarbonyl-propionyl) -piperidin-4-yl]-piperazin-1-yl}-2-oxo-ethyl 4-(2-oxo-1,2,4, 5-tetrahydro-1,3-benzodiazepin-3-yl) -piperidine-1-carboxylate, (R)-2-{4-[1-(3-carboxy-propionyl)-piperidin-4-yl]-piperazin-1-yl}1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin -3-yl)-piperidine-1-carboxylate, (R)-1-(3,4-dimethyl-2-oxo-2,3-dihydro-benzoxazol-6-ylmethyl)-2-(1'-hydroxycarbamoylmethyl -4,4'-bipiperidinyl-1-yl)-2-oxo-ethyl 4-(2-oxo-1,2,4,5-tetrahydro-1,3-benzodiazepin -3-yl)-piperidine-1-carboxylate, (R)-1-(3,4-dimethyl-2-oxo-2,3-dihydro-benzoxazol-6-ylmethyl)-2-{1'-[(hydroxy-methylcarbamoyl) -methyl]-4,4'-bipiperidinyl-1-yl}-2-oxo-ethyl 4-(2-oxo-1,2,4,5-tetrahydro-1,3-benzodiazepin-3-yl) -piperidine-1-carboxylate, (R)-1-(3,4-dimethyl-2-oxo-2,3-dihydro-benzoxazol-6-ylmethyl)-2-[1'-(methoxycarbamoyl-methyl) -4,4'-bipiperidinyl-1-yl]-2-oxo-ethyl 4-(2-oxo-1,2,4,5-tetrahydro-1,3-benzodiazepin -3-yl)-piperidine-1-carboxylate, (R)-1-(4-methyl-2-oxo-2,3-dihydro-benzoxazol-6-ylmethyl)-2-oxo-2-(1'-sulphamoyl-4,4'-bipiperidinyl-1-yl)-ethyl 4-(2-oxo-1,2,4,5-tetrahydro-1,3-benzodiazepin-3-yl)-piperidine-1-carboxylate, (R)-2-[4-(4-methanesulphonyl-piperazin-1-yl)-piperidin-1-yl]-1-(4-methyl-2-oxo-2,3-dihydro -benzoxazol-6-ylmethyl)-2-oxo-ethyl 4-(2-oxo-1,2,4,5-tetrahydro-1,3-benzodiazepin -3-yl)-piperidine-1-carboxylate, (R)-1-(3,4-dimethyl-2-oxo-2,3-dihydro-benzoxazol-6-ylmethyl)-2-[4-(8-methyl-8-aza-bicyclo [3.2.1]oct-3-yl)-piperazin-1-yl]-2-oxo-ethyl 4-(2-oxo-1,2,4,5-tetrahydro-1,3-benzodiazepin -3-yl)-piperidine-1-carboxylate, (R)-2-[4-(4-cyclopropyl-piperazin-1-yl)-piperidin-1-yl]-1-(3,4-dimethyl-2-oxo-2,3-dihydro -benzoxazol-6-ylmethyl)-2-oxo-ethyl 4-(2-oxo-1,2,4,5-tetrahydro- 1,3-benzodiazepin-3-yl)-piperidine -1-carboxylate, or a salt thereof.

12. A compound of the formula (I) according to claim 1 selected from the group consisting of:

(16) (R)-1-(4-methyl-2-oxo-2,3-dihydro-benzoxazol-6-ylmethyl)-2-[4-(4-methyl-piperazin-1-yl) -piperidin-1-yl]-2-oxo-ethyl 4-(2-oxo-1,2,4,5-tetrahydro-1,3-benzodiazepin-3-yl) -piperidine-1-carboxylate,

(17) (R)-1-(4-methyl-2-oxo-2,3-dihydro-benzoxazol-6-ylmethyl)-2-[4-(1-methyl-piperidin-4-yl) -piperazin-1-yl]-2-oxo-ethyl 4-(2-oxo-1,2,4,5-tetrahydro-1,3-benzodiazepin-3-yl)- piperidine-1-carboxylate,

(18) (R)-2-(4-amino-4-methyl-1,4'-bipiperidinyl-1'-yl)-1-(4-methyl-2-oxo-2,3-dihydro-benzoxazol -6-ylmethyl)-2-oxo-ethyl 4-(2-oxo-1,2,4 ,5-tetrahydro- 1,3-benzodiazepin-3-yl)-piperidine-1-carboxylate,

(19) (R)-1-(4-methyl-2-oxo-2,3-dihydro-benzoxazol-6-ylmethyl)-2-oxo-2-(1'-sulphamoyl -4,4'-bipiperidinyl-1-yl)-ethyl 4-(2-oxo-1,2,4,5-tetrahydro-1,3-benzodiazepin-3-yl) -piperidine-1-carboxylate,

(20) (R)-2-(1'-methanesulphonyl-4,4'-bipiperidinyl-1-yl) 1-(4-methyl-2-oxo-2,3-dihydro-benzoxazol -6-ylmethyl)-2-oxo-ethyl 4-(2-oxo-1,2,4 ,5-tetrahydro- 1,3-benzodiazepin-3-yl)-piperidine-1-carboxylate,

(21) (R)-1-(3,4-dimethyl-2-oxo-2,3-dihydro-benzoxazol-6-ylmethyl)-2-[4-( 1-methyl-piperidin -4-yl)-piperazin-1-yl]-2-oxo-ethyl 4-(2-oxo-1,2,4,5-tetrahydro-1,3-benzodiazepin -3-yl)-piperidine-1-carboxylate,

(22) (R)-1-(3,4-dimethyl-2-oxo-2,3-dihydro-benzoxazol-6-ylmethyl)-2-[4-(4-methyl-piperazin -1-yl)-piperidin-1-yl]-2-oxo-ethyl 4-(2-oxo-1,2,4,5-tetrahydro-1,3-benzodiazepin -3-yl)-piperidine-1-carboxylate,

(23) (R)-1-(3,4-dimethyl-2-oxo-2,3-dihydro-benzoxazol-6-ylmethyl)-2-(1'-methyl-4,4'-bipiperidinyl -1-yl)-2-oxo-ethyl 4-(2-oxo-1,2,4,5-tetrahydro-1,3-benzodiazepin-3-yl) -piperidine-1-carboxylate,

(24) (R)-1-(3,4-dimethyl-2-oxo-2,3-dihydro-benzoxazol-6-ylmethyl)-2-(4-hydroxy-1,4'-bipiperidinyl -1'-yl)-2-oxo-ethyl 4-(2-oxo-1,2,4,5-tetrahydro-1,3-benzodiazepin-3-yl) -piperidine-1-carboxylate,

(25) (R)-1-(3,4-dimethyl-2-oxo-2,3-dihydro-benzoxazol-6-ylmethyl)-2-oxo-2-(1 sulphamoyl-4,4'-bipiperidinyl-1-yl)-ethyl 4-(2-oxo-1,2,4,5-tetrahydro-1,3-benzodiazepin -3-yl)-piperidine-1-carboxylate,

(26) (R)-1-(3,4-dimethyl-2-oxo-2,3-dihydro-benzoxazol-6-ylmethyl)-2-(1 methanesulphonyl-4,4'-bipiperidinyl-1-yl)-2-oxo-ethyl 4-(2-oxo-1,2,4,5-tetrahydro-1,3-benzodiazepin-3-yl)-piperidine-1-carboxylate,

(27) (R)-1-(3,4-dimethyl-2-oxo-2,3-dihydro-benzoxazol-6-ylmethyl)-2-[4-(8-methyl-8-aza -bicyclo[3.2.1]oct-3-yl)-piperazin-1-yl]-2-oxo-ethyl 4-(2-oxo-1,2,4,5-tetrahydro-1,3-benzodiazepin-3-yl)-piperidine-1-carboxylate,

(28) (R)-1-(3,4-dimethyl-2-oxo-2,3-dihydro-benzoxazol-6-ylmethyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate,

(29) (R)-2-4,4'-bipiperidinyl-1-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(30) (R)-1-(3,4-dimethyl-2-oxo-2,3-dihydro-benzoxazol-6-ylmethyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate,

(31) (R)-2-(4-amino-4-methyl-1,4'-bipiperidinyl-1'-yl)-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(32) (R)-1-(3,4-dimethyl-2-oxo-2,3-dihydro-benzoxazol-6-ylmethyl)-2-(1'-ethoxy-carbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate,

(33) (R)-2-(1'-carboxymethyl-4,4'-bipiperidinyl-1-yl)1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(34) (R)-2-1,4'-bipiperidinyl-1'-yl-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(35) (R)-2-[4-(4-cyclopropyl-piperazin-1-yl)-piperidin-1-yl]-1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(36) (R)-2-(4-cyclohexyl-piperazin-1-yl)1-(3,4-dimethyl-2-oxo-2,3-dihydro-benzoxazol-6-ylmethyl)-2-oxo-ethyl 4-(2-oxo-1,2,4,5-tetrahydro-1,3-benzodiazepin-3-yl)-piperidine-1-carboxylate,

(37) (R)-1-(3,4-dimethyl-2-oxo-2,3-dihydro-benzoxazol-6-ylmethyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate,

(38) (R)-1-(3,4-dimethyl-2-oxo-2,3-dihydro-benzoxazol-6-ylmethyl)-2-(4-hydroxy-4-hydroxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate, or a salt thereof.

13. A physiologically acceptable salt of a compound of the formula I according to claim 1.

14. A pharmaceutical composition comprising a compound of the formula I according to claim 1 together with one or more inert carriers and/or diluents.

15. A method for treating headaches, migraine or cluster headaches, which comprises administering to a host in need of such treatment a therapeutically effective amount of a compound of the formula I in accordance with claim 1.

* * * * *